US012643958B2

(12) United States Patent
Ehrlich et al.

(10) Patent No.: US 12,643,958 B2
(45) Date of Patent: Jun. 2, 2026

(54) METHODS OF TREATING AN EYE DISORDER

(71) Applicant: KODIAK SCIENCES INC., Palo Alto, CA (US)

(72) Inventors: Jason Ehrlich, Palo Alto, CA (US); Pablo Velazquez-Martin, Palo Alto, CA (US); Joel Naor, Palo Alto, CA (US); Daniel Victor Perlroth, Palo Alto, CA (US); Hong Liang, Palo Alto, CA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 0 days.

(21) Appl. No.: 18/504,723

(22) Filed: Nov. 8, 2023

(65) Prior Publication Data

US 2024/0084043 A1 Mar. 14, 2024

Related U.S. Application Data

(62) Division of application No. 17/066,856, filed on Oct. 9, 2020, now Pat. No. 11,912,784.

(60) Provisional application No. 62/971,738, filed on Feb. 7, 2020, provisional application No. 62/935,434, filed on Nov. 14, 2019, provisional application No. 62/913,567, filed on Oct. 10, 2019.

(51) Int. Cl.

| | |
|---|---|
| ***A61K 39/395*** | (2006.01) |
| ***A61K 9/00*** | (2006.01) |
| ***A61K 47/58*** | (2017.01) |
| ***A61K 47/68*** | (2017.01) |
| ***A61P 27/02*** | (2006.01) |
| ***C07K 16/22*** | (2006.01) |
| ***C07K 17/08*** | (2006.01) |
| *A61K 39/00* | (2006.01) |

(52) U.S. Cl.

CPC ............ *C07K 17/08* (2013.01); *A61K 9/0019* (2013.01); *A61K 9/0048* (2013.01); *A61K 47/605* (2017.08); *A61K 47/6845* (2017.08); *A61P 27/02* (2018.01); *A61K 2039/505* (2013.01); *A61K 2039/54* (2013.01); *A61K 2039/545* (2013.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 4,609,707 | A | 9/1986 | Nowinski et al. |
| 4,634,664 | A | 1/1987 | Oestberg |
| 4,634,666 | A | 1/1987 | Engleman et al. |
| 4,683,195 | A | 7/1987 | Mullis et al. |
| 4,683,202 | A | 7/1987 | Mullis |
| 4,754,065 | A | 6/1988 | Levenson et al. |
| 4,757,006 | A | 7/1988 | Toole, Jr. et al. |
| 4,777,127 | A | 10/1988 | Suni et al. |
| 4,800,159 | A | 1/1989 | Mullis et al. |
| 4,816,567 | A | 3/1989 | Cabilly et al. |
| 4,868,112 | A | 9/1989 | Toole, Jr. |
| 4,892,538 | A | 1/1990 | Aebischer et al. |
| 5,013,556 | A | 5/1991 | Woodle et al. |
| 5,047,335 | A | 9/1991 | Paulson et al. |
| 5,162,218 | A | 11/1992 | Schultz |
| 5,198,349 | A | 3/1993 | Kaufman |
| 5,219,740 | A | 6/1993 | Dusty et al. |
| 5,225,539 | A | 7/1993 | Winter |
| 5,250,421 | A | 10/1993 | Kaufman et al. |
| 5,252,713 | A | 10/1993 | Morgan, Jr. et al. |
| 5,278,299 | A | 1/1994 | Wong et al. |
| 5,283,187 | A | 2/1994 | Aebischer et al. |
| 5,336,603 | A | 8/1994 | Capon et al. |
| 5,422,120 | A | 6/1995 | Kim et al. |
| 5,510,261 | A | 4/1996 | Goochee et al. |
| 5,530,101 | A | 6/1996 | Queen et al. |

(Continued)

FOREIGN PATENT DOCUMENTS

| | | |
|---|---|---|
| AU | 2010330727 | 12/2010 |
| AU | 2011239434 | 4/2015 |

(Continued)

OTHER PUBLICATIONS

Awwad et al. (2020). Eur J Pharm Biopharm. 153:130-149.*
U.S. Appl. No. 09/253,689 filed Filed Feb. 20, 1999, Fung et al.
"Bevacizumab in Severe or Critical Patients With COVID-19 Pneumonia", ClinicalTrials.gov (studysponsored by Qilu Hospital of Shandong University) first posted Feb. 19, 2020 (last updated Sep. 14, 2020), in 4 pages. URL: https://clinicaltrials.gov/ct2/show/NCT04275414.
"Facts About Diabetic Eye Disease", National Eye Institute,https://nei.nih.gov/health/diabetic/retinopathy, publication reviewed Sep. 2015, accessed Mar. 27, 2018, in 7 pages.

(Continued)

*Primary Examiner* — Christine J Saoud
*Assistant Examiner* — Jon M Lockard
(74) *Attorney, Agent, or Firm* — KNOBBE, MARTENS, OLSON & BEAR, LLP

(57) ABSTRACT

Provided herein are methods of treating eye disorders by administering an anti-VEGF antibody and/or conjugate to a subject having an eye disorder. The anti-VEGF antibody of the present disclosure may be an anti-VEGF antibody conjugate that includes a polymeric moiety that extends the half-life/effectiveness/properties of the antibody when administered to a subject. A method of the present disclosure includes administering one or more doses of an anti-VEGF antibody conjugate to a subject (e.g., human or other mammalian patient) in need of treating an eye disorder, where the anti-VEGF antibody conjugate may be administered less frequently than a standard anti-VEGF therapy to treat the eye disorder.

29 Claims, 69 Drawing Sheets

Specification includes a Sequence Listing.

(56) References Cited

U.S. PATENT DOCUMENTS 5,545,806 A 8/1996 Lonberg et al.
5,565,332 A 10/1996 Hoogenboom et al.
5,569,825 A 10/1996 Lonberg et al.
5,580,859 A 12/1996 Felgner et al.
5,585,089 A 12/1996 Queen et al.
5,624,821 A 4/1997 Winter et al.
5,625,126 A 4/1997 Lonberg et al.
5,633,425 A 5/1997 Lonberg et al.
5,661,016 A 8/1997 Lonberg et al.
5,663,425 A 9/1997 Detroit et al.
5,681,746 A 10/1997 Bodner et al.
5,733,743 A 3/1998 Johnson et al.
5,733,873 A 3/1998 Osterberg et al.
5,741,923 A 4/1998 Driver et al.
5,763,548 A 6/1998 Matyjaszewski et al.
5,770,429 A 6/1998 Lonberg et al.
5,789,487 A 8/1998 Matyjaszewski et al.
5,789,650 A 8/1998 Lonberg et al.
5,807,937 A 9/1998 Matyjaszewski et al.
5,814,318 A 9/1998 Lonberg et al.
5,814,482 A 9/1998 Dubensky, Jr. et al.
5,834,597 A 11/1998 Tso et al.
5,837,242 A 11/1998 Holliger et al.
5,858,657 A 1/1999 Winter et al.
5,859,205 A 1/1999 Adair et al.
5,863,551 A 1/1999 Woerly
5,871,907 A 2/1999 Winter et al.
5,872,218 A 2/1999 Wolf et al.
5,874,299 A 2/1999 Lonberg et al.
5,877,218 A 3/1999 Herzig et al.
5,877,397 A 3/1999 Lonberg et al.
5,882,644 A 3/1999 Chang et al.
5,919,766 A 7/1999 Osterberg et al.
5,945,491 A 8/1999 Matyjaszewski et al.
5,981,786 A 11/1999 Kitano et al.
6,111,022 A 8/2000 Matyjaszewski et al.
6,121,371 A 9/2000 Matyjaszewski et al.
6,124,411 A 9/2000 Matyjaszewski et al.
6,156,884 A 12/2000 Ahlem et al.
6,162,882 A 12/2000 Matyjaszewski et al.
6,270,993 B1 8/2001 Shibuya et al.
6,344,050 B1 2/2002 Chen
6,348,554 B1 2/2002 Roos et al.
6,376,471 B1 4/2002 Lawrence, III et al.
6,383,486 B1 5/2002 Davis-Smyth et al.
6,407,187 B1 6/2002 Matyjaszewski et al.
6,407,213 B1 6/2002 Carter et al.
6,413,942 B1 7/2002 Felgner et al.
6,436,908 B1 8/2002 Koch et al.
6,512,060 B1 1/2003 Matyjaszewski et al.
6,538,091 B1 3/2003 Matyjaszewski et al.
6,541,580 B1 4/2003 Matyjaszewski et al.
6,554,853 B2 4/2003 Chen
6,555,593 B1 4/2003 Hoyle et al.
6,583,272 B1 6/2003 Bailon
6,624,262 B2 9/2003 Matyjaszewski et al.
6,624,821 B1 9/2003 Shin et al.
6,627,314 B2 9/2003 Matyjaszewski et al.
6,632,926 B1 10/2003 Chen et al.
6,657,043 B1 12/2003 Guerret et al.
6,703,528 B2 3/2004 Hagiya et al.
6,730,822 B1 5/2004 Ivarie et al.
6,737,056 B1 5/2004 Presta
6,759,491 B2 7/2004 Matyjaszewski et al.
6,780,428 B2 8/2004 Ranger et al.
6,781,030 B1 8/2004 Baguisi et al.
6,790,919 B2 9/2004 Matyjaszewski et al.
6,833,349 B2 12/2004 Xia et al.
6,852,816 B2 2/2005 Lewis et al.
6,870,033 B1 3/2005 Hsei et al.
6,881,557 B2 4/2005 Foote
6,884,879 B1 4/2005 Baca et al.
6,887,962 B2 5/2005 Matyjaszewski et al.
6,964,859 B2 11/2005 Rajbhandary et al.
6,979,556 B2 12/2005 Simmons et al.
6,992,176 B2 1/2006 Reiter et al.
7,019,082 B2 3/2006 Matyjaszewski et al.
7,049,373 B2 5/2006 Matyjaszewski et al.
7,052,691 B2 5/2006 Sleeman et al.
7,056,455 B2 6/2006 Matyjaszewski et al.
7,056,509 B2 6/2006 Thorpe et al.
7,060,269 B1 6/2006 Baca et al.
7,060,271 B2 6/2006 Ramakrishnan et al.
7,064,166 B2 6/2006 Matyjaszewski et al.
7,070,959 B1 7/2006 Papadopoulos et al.
7,071,159 B2 7/2006 Kendall et al.
7,122,636 B1 10/2006 Hsei et al.
7,125,938 B2 10/2006 Matyjaszewski et al.
7,157,530 B2 1/2007 Matyjaszewski et al.
7,169,901 B2 1/2007 Baca et al.
7,200,990 B2 4/2007 Gabrielsson et al.
7,214,776 B2 5/2007 Hsei et al.
7,291,721 B2 11/2007 Giles-Komar et al.
7,297,334 B2 11/2007 Baca et al.
7,300,653 B2 11/2007 Wiegand et al.
7,300,990 B2 11/2007 Lewis et al.
7,303,748 B2 12/2007 Wiegand et al.
7,306,799 B2 12/2007 Wiegand et al.
7,332,581 B2 2/2008 Presta
7,345,027 B2 3/2008 Tolentino et al.
7,348,424 B2 3/2008 Miyazawa et al.
7,351,411 B2 4/2008 Holash et al.
7,354,578 B2 4/2008 Kandel et al.
7,354,579 B2 4/2008 Holash et al.
7,354,580 B2 4/2008 Cedarbaum
7,354,581 B2 4/2008 Cedarbaum et al.
7,354,582 B2 4/2008 Yung et al.
7,365,166 B2 4/2008 Baca et al.
7,374,757 B2 5/2008 Papadopoulos et al.
7,374,762 B2 5/2008 Amphlett et al.
7,375,193 B2 5/2008 Baca et al.
7,375,234 B2 5/2008 Sharpless et al.
7,378,095 B2 5/2008 Cao et al.
7,491,390 B2 2/2009 Law et al.
7,494,649 B2 2/2009 Amphlett et al.
7,501,120 B2 3/2009 Amphlett et al.
7,507,405 B2 3/2009 Hsei et al.
7,514,080 B2 4/2009 Amphlett et al.
7,521,541 B2 4/2009 Eigenbrot et al.
7,531,172 B2 5/2009 Stahl et al.
7,560,112 B2 7/2009 Chen et al.
7,569,655 B2 8/2009 Pacetti et al.
7,608,261 B2 10/2009 Furfine et al.
7,612,182 B2 11/2009 Giles-Komar et al.
7,632,921 B2 12/2009 Pan et al.
7,662,387 B2 2/2010 Law et al.
7,667,004 B2 2/2010 Zhong et al.
7,695,716 B2 4/2010 Drachman et al.
7,740,844 B2 6/2010 Hong et al.
7,740,850 B2 6/2010 Zhu et al.
7,745,394 B2 6/2010 Doronina et al.
7,750,138 B2 7/2010 Fang et al.
7,754,208 B2 7/2010 Ledbetter et al.
7,754,681 B2 7/2010 Feng
7,754,855 B1 7/2010 Cox, III et al.
7,758,859 B2 7/2010 Fuh et al.
7,759,472 B2 7/2010 Shima et al.
7,842,789 B2 11/2010 Hsei et al.
7,855,178 B2 12/2010 Alitalo et al.
7,893,173 B2 2/2011 Matyjaszewski et al.
7,910,098 B2 3/2011 Fuh et al.
7,919,099 B2 4/2011 Tahara et al.
7,928,072 B2 4/2011 Scaria et al.
7,955,597 B2 6/2011 Giles-Komar et al.
8,003,097 B2 8/2011 Schroeter et al.
8,007,798 B2 8/2011 Ashkenazi et al.
8,007,799 B2 8/2011 Van Bruggen et al.
8,008,453 B2 8/2011 Gegg et al.
8,034,905 B2 10/2011 Kavlie et al.
8,048,418 B2 11/2011 Noguera-Troise et al.
8,092,797 B2 1/2012 Fuh et al.
8,092,803 B2 1/2012 Furfine et al.
8,101,177 B2 1/2012 Fuh et al.
8,110,546 B2 2/2012 Dix et al.

(56) References Cited

U.S. PATENT DOCUMENTS

| | | | |
|---|---|---|---|
| 8,124,076 | B2 | 2/2012 | Solomon et al. |
| 8,147,830 | B2 | 4/2012 | Johnson et al. |
| 8,163,726 | B2 | 4/2012 | Wen et al. |
| 8,187,597 | B2 | 5/2012 | Shima et al. |
| 8,206,707 | B2 | 6/2012 | Shima et al. |
| 8,211,864 | B2 | 7/2012 | Ambati et al. |
| 8,216,571 | B2 | 7/2012 | Ramachandra et al. |
| 8,216,575 | B2 | 7/2012 | Yu |
| 8,231,907 | B2 | 7/2012 | Lillard et al. |
| 8,236,312 | B2 | 8/2012 | Park et al. |
| RE43,672 | E | 9/2012 | Chan et al. |
| 8,268,314 | B2 | 9/2012 | Baehner et al. |
| 8,273,353 | B2 | 9/2012 | Davis-Smyth et al. |
| 8,309,532 | B2 | 11/2012 | Feinstein et al. |
| 8,318,169 | B2 | 11/2012 | Trogden et al. |
| 8,324,169 | B2 | 12/2012 | Quinn |
| 8,329,866 | B2 | 12/2012 | Rosendahl et al. |
| 8,349,325 | B2 | 1/2013 | Brophy et al. |
| 8,388,963 | B2 | 3/2013 | Vrignaud et al. |
| 8,455,622 | B2 | 6/2013 | McDonagh et al. |
| 8,486,397 | B2 | 7/2013 | Bagri et al. |
| 8,492,527 | B2 | 7/2013 | Fuh et al. |
| 8,506,962 | B2 | 8/2013 | Trogden et al. |
| 8,512,699 | B2 | 8/2013 | Fuh et al. |
| 8,546,345 | B2 | 10/2013 | Tolentino et al. |
| 8,557,246 | B2 | 10/2013 | Martínez Escribano et al. |
| 8,571,802 | B2 | 10/2013 | Robinson et al. |
| 8,614,235 | B2 | 12/2013 | Robinson et al. |
| 8,632,774 | B2 | 1/2014 | Misher et al. |
| 8,658,633 | B2 | 2/2014 | Poulaki et al. |
| 8,663,639 | B2 | 3/2014 | Dor et al. |
| 8,685,397 | B2 | 4/2014 | Shima et al. |
| 8,691,226 | B2 | 4/2014 | Chiu et al. |
| 8,703,130 | B2 | 4/2014 | Baehner et al. |
| 8,703,133 | B2 | 4/2014 | Chen et al. |
| 8,765,432 | B2 | 7/2014 | Charles |
| 8,785,385 | B2 | 7/2014 | Stout et al. |
| 8,790,647 | B2 | 7/2014 | Greenwood et al. |
| 8,802,129 | B2 | 8/2014 | Whitcup et al. |
| 8,815,236 | B2 | 8/2014 | Burke et al. |
| 8,822,645 | B2 | 9/2014 | Ghayur et al. |
| 8,834,884 | B2 | 9/2014 | Trogden et al. |
| 8,846,021 | B2 | 9/2014 | Charles |
| 8,864,869 | B2 | 10/2014 | Kurisu et al. |
| 8,883,157 | B1 | 11/2014 | Clube |
| 8,883,519 | B1 | 11/2014 | Perez et al. |
| 8,911,768 | B2 | 12/2014 | Whitcup et al. |
| 8,926,972 | B2 | 1/2015 | Zhou et al. |
| 8,945,552 | B2 | 2/2015 | Baehner et al. |
| 8,956,600 | B2 | 2/2015 | Shih et al. |
| 8,962,804 | B2 | 2/2015 | Williams |
| 8,969,526 | B2 | 3/2015 | Baehner et al. |
| 8,986,692 | B2 | 3/2015 | Li et al. |
| 9,029,508 | B2 | 5/2015 | Ghayur et al. |
| 9,045,551 | B2 | 6/2015 | Gu et al. |
| 9,079,953 | B2 | 7/2015 | Harding et al. |
| 9,125,940 | B2 | 9/2015 | Ma et al. |
| 9,149,427 | B2 | 10/2015 | Ling et al. |
| 9,163,093 | B2 | 10/2015 | Gu et al. |
| 9,217,039 | B2 | 12/2015 | Pedersen et al. |
| 9,220,631 | B2 | 12/2015 | Sigg et al. |
| 9,226,917 | B2 | 1/2016 | Strong et al. |
| 9,241,906 | B2 | 1/2016 | Freeman et al. |
| 9,254,338 | B2 | 2/2016 | Yancopoulos |
| 9,265,827 | B2 | 2/2016 | Wiegand et al. |
| 9,273,113 | B2 | 3/2016 | Davis-Smyth et al. |
| 9,334,324 | B2 | 5/2016 | Choo et al. |
| 9,353,177 | B2 | 5/2016 | Fuh et al. |
| 9,388,239 | B2 | 7/2016 | Baldi et al. |
| 9,409,990 | B2 | 8/2016 | Zhang |
| 9,416,180 | B1 | 8/2016 | Clube |
| 9,416,210 | B2 | 8/2016 | Emrick et al. |
| 9,421,256 | B2 | 8/2016 | Kavlie et al. |
| 9,428,575 | B2 | 8/2016 | Lai et al. |
| 9,567,403 | B2 | 2/2017 | Wu et al. |
| 9,575,067 | B2 | 2/2017 | Kosmeder et al. |
| 9,650,443 | B2 | 5/2017 | Song et al. |
| 9,650,444 | B2 | 5/2017 | Wiegand et al. |
| 9,657,084 | B2 | 5/2017 | Ke et al. |
| 9,669,069 | B2 | 6/2017 | Yancopoulos |
| 9,682,144 | B2 | 6/2017 | Thorin et al. |
| 9,695,233 | B2 | 7/2017 | Duerr et al. |
| 9,708,390 | B2 | 7/2017 | Sivakumar et al. |
| 9,708,396 | B2 | 7/2017 | Baehner et al. |
| 9,708,397 | B2 | 7/2017 | Greenwood et al. |
| 9,815,893 | B2 | 11/2017 | Akamatsu |
| 9,822,174 | B2 | 11/2017 | Doh et al. |
| 9,840,553 | B2 | 12/2017 | Perlroth et al. |
| 9,850,514 | B2 | 12/2017 | Laird et al. |
| 9,914,770 | B2 | 3/2018 | Shandilya et al. |
| 9,931,330 | B2 | 4/2018 | Zarnitsyn et al. |
| 9,937,129 | B2 | 4/2018 | Freeman et al. |
| 9,943,573 | B2 | 4/2018 | Constable et al. |
| 9,944,720 | B2 | 4/2018 | Gu et al. |
| 9,962,333 | B2 | 5/2018 | Gailard et al. |
| 10,004,788 | B2 | 6/2018 | Constable et al. |
| 10,035,850 | B2 | 7/2018 | Gekkieva et al. |
| 10,072,075 | B2 * | 9/2018 | Koenig .................. A61K 47/61 |
| 10,106,605 | B2 | 10/2018 | Ghosh et al. |
| 10,130,681 | B2 | 11/2018 | Yancopoulos |
| 10,184,010 | B2 | 1/2019 | Lee et al. |
| 10,208,124 | B2 | 2/2019 | Le Bouteiller et al. |
| 10,208,355 | B2 | 2/2019 | Bais et al. |
| 10,240,207 | B2 | 3/2019 | Yu et al. |
| 10,259,862 | B2 | 4/2019 | Carter et al. |
| 10,363,290 | B2 | 7/2019 | Perlroth et al. |
| 10,406,226 | B2 | 9/2019 | Dix et al. |
| 10,407,510 | B2 | 9/2019 | Kelley et al. |
| 10,421,984 | B2 | 9/2019 | Laird et al. |
| 10,456,466 | B2 | 10/2019 | Fang et al. |
| 10,456,470 | B2 | 10/2019 | Bais et al. |
| 10,464,992 | B2 | 11/2019 | Furfine et al. |
| 10,519,226 | B2 | 12/2019 | Rau et al. |
| 10,526,382 | B2 | 1/2020 | Bel Aiba et al. |
| 10,548,998 | B2 | 2/2020 | Bradbury et al. |
| 10,568,951 | B2 | 2/2020 | Sigl |
| 10,702,608 | B2 | 7/2020 | Charles et al. |
| 10,828,345 | B2 | 11/2020 | Yancopoulos |
| 10,857,205 | B2 | 12/2020 | Yancopoulos |
| 10,857,231 | B2 | 12/2020 | Yancopoulos |
| 10,888,601 | B2 | 1/2021 | Yancopoulos |
| 11,066,465 | B2 | 7/2021 | Perlroth et al. |
| 11,071,771 | B2 | 7/2021 | Perlroth et al. |
| 11,155,610 | B2 | 10/2021 | Perlroth et al. |
| 11,584,790 | B2 | 2/2023 | Perlroth et al. |
| 11,590,235 | B2 | 2/2023 | Charles et al. |
| 11,819,531 | B2 | 11/2023 | Charles et al. |
| 11,912,784 | B2 | 2/2024 | Ehrlich et al. |
| 12,071,476 | B2 | 8/2024 | Jacobson et al. |
| 12,214,044 | B2 | 2/2025 | Charles et al. |
| 12,466,879 | B2 | 11/2025 | Perlroth et al. |
| 2002/0032315 | A1 | 3/2002 | Baca et al. |
| 2002/0044937 | A1 | 4/2002 | Birnstiel et al. |
| 2002/0091082 | A1 | 7/2002 | Aiello |
| 2003/0113335 | A1 | 6/2003 | Li et al. |
| 2003/0143596 | A1 | 7/2003 | Bentley et al. |
| 2003/0171320 | A1 | 9/2003 | Guyer |
| 2003/0204022 | A1 | 10/2003 | Kennedy et al. |
| 2003/0235536 | A1 | 12/2003 | Blumberg et al. |
| 2004/0010376 | A1 | 1/2004 | Luo et al. |
| 2004/0063881 | A1 | 4/2004 | Lewis et al. |
| 2004/0091490 | A1 | 5/2004 | Johnson et al. |
| 2004/0247588 | A1 | 12/2004 | Johnson et al. |
| 2004/0253596 | A1 | 12/2004 | Pawlak et al. |
| 2004/0266688 | A1 | 12/2004 | Nayak |
| 2005/0009988 | A1 | 1/2005 | Harris et al. |
| 2005/0041080 | A1 | 2/2005 | Hall et al. |
| 2005/0074497 | A1 | 4/2005 | Schultz |
| 2005/0100500 | A1 | 5/2005 | Kishita |
| 2005/0100550 | A1 | 5/2005 | Trikha et al. |
| 2005/0112061 | A1 | 5/2005 | Holash et al. |
| 2005/0112088 | A1 | 5/2005 | Zhao et al. |
| 2005/0118651 | A1 | 6/2005 | Basi et al. |
| 2005/0123501 | A1 | 6/2005 | Lews |

(56) References Cited

U.S. PATENT DOCUMENTS

| | | | |
|---|---|---|---|
| 2005/0136049 | A1 | 6/2005 | Ledbetter et al. |
| 2005/0159556 | A1 | 7/2005 | Lewis et al. |
| 2005/0164301 | A1 | 7/2005 | Kolkman et al. |
| 2005/0180945 | A1 | 8/2005 | Chaikof et al. |
| 2005/0214286 | A1 | 9/2005 | Epstein et al. |
| 2005/0220880 | A1 | 10/2005 | Lewis et al. |
| 2005/0239088 | A1 | 10/2005 | Shepard et al. |
| 2005/0276796 | A1 | 12/2005 | Tomatsu et al. |
| 2005/0281822 | A1 | 12/2005 | Cedarbaum et al. |
| 2005/0281861 | A1 | 12/2005 | Hughes et al. |
| 2005/0282233 | A1 | 12/2005 | Eriksson et al. |
| 2006/0058234 | A1 | 3/2006 | Daly et al. |
| 2006/0067930 | A1 | 3/2006 | Adams et al. |
| 2006/0069203 | A1 | 3/2006 | Lewis et al. |
| 2006/0135714 | A1 | 6/2006 | Lewis et al. |
| 2006/0165804 | A1 | 7/2006 | Lewis et al. |
| 2006/0167230 | A1 | 7/2006 | Koga et al. |
| 2006/0182783 | A1 | 8/2006 | Hughes et al. |
| 2006/0193830 | A1 | 8/2006 | Hauswirth et al. |
| 2006/0216789 | A1 | 9/2006 | Blake et al. |
| 2006/0217285 | A1 | 9/2006 | Destarac |
| 2006/0231107 | A1 | 10/2006 | Glickman et al. |
| 2006/0234347 | A1 | 10/2006 | Harding et al. |
| 2006/0234437 | A1 | 10/2006 | Harding et al. |
| 2007/0037183 | A1 | 2/2007 | Edwards et al. |
| 2007/0037214 | A1 | 2/2007 | Luo et al. |
| 2007/0037760 | A1 | 2/2007 | Tolentino et al. |
| 2007/0041967 | A1 | 2/2007 | Jung et al. |
| 2007/0059302 | A1 | 3/2007 | Baca et al. |
| 2007/0059336 | A1 | 3/2007 | Hughes et al. |
| 2007/0071756 | A1 | 3/2007 | Peyman |
| 2007/0111279 | A1 | 5/2007 | Rosenberg |
| 2007/0134244 | A1 | 6/2007 | Slakter et al. |
| 2007/0141104 | A1 | 6/2007 | Hauenstein |
| 2007/0167526 | A1 | 7/2007 | Zhang et al. |
| 2007/0190058 | A1 | 8/2007 | Shams |
| 2007/0196374 | A1 | 8/2007 | Baca et al. |
| 2007/0258976 | A1 | 11/2007 | Ward et al. |
| 2007/0264236 | A1 | 11/2007 | Yang |
| 2007/0265203 | A1 | 11/2007 | Eriksson et al. |
| 2008/0008736 | A1 | 1/2008 | Glauser |
| 2008/0070855 | A1 | 3/2008 | Gills |
| 2008/0096923 | A1 | 4/2008 | Girach |
| 2008/0124450 | A1 | 5/2008 | Pacetti |
| 2008/0147175 | A1 | 6/2008 | Pacetti et al. |
| 2008/0147178 | A1 | 6/2008 | Pacetti et al. |
| 2008/0152654 | A1 | 6/2008 | Reich et al. |
| 2008/0152661 | A1 | 6/2008 | Rozema et al. |
| 2008/0167600 | A1 | 7/2008 | Peyman |
| 2008/0187534 | A1 | 8/2008 | Baca et al. |
| 2008/0187966 | A1 | 8/2008 | Simmons |
| 2008/0199464 | A1 | 8/2008 | Plowman et al. |
| 2008/0214439 | A1 | 9/2008 | Grabstein et al. |
| 2008/0226629 | A1 | 9/2008 | Baca et al. |
| 2008/0241102 | A1 | 10/2008 | Hersel et al. |
| 2008/0242587 | A1 | 10/2008 | Kim et al. |
| 2008/0248030 | A1 | 10/2008 | Folkman et al. |
| 2008/0268051 | A1 | 10/2008 | Hughes et al. |
| 2008/0269318 | A1 | 10/2008 | Romano |
| 2008/0292628 | A1 | 11/2008 | Hui |
| 2008/0311134 | A1 | 12/2008 | Junutula et al. |
| 2009/0053137 | A1 | 2/2009 | Moore |
| 2009/0053217 | A1 | 2/2009 | Blank et al. |
| 2009/0053786 | A1 | 2/2009 | Kao et al. |
| 2009/0060906 | A1 | 3/2009 | Barry et al. |
| 2009/0061533 | A1 | 3/2009 | Minami |
| 2009/0092664 | A1 | 4/2009 | Mumper et al. |
| 2009/0098139 | A1 | 4/2009 | Katz et al. |
| 2009/0104259 | A1 | 4/2009 | Tolentino et al. |
| 2009/0117103 | A1 | 5/2009 | Devalaraja et al. |
| 2009/0220504 | A1 | 9/2009 | Chuntharapai et al. |
| 2009/0226441 | A1 | 9/2009 | Yan et al. |
| 2009/0249503 | A1 | 10/2009 | Rosendahl |
| 2009/0285826 | A1 | 11/2009 | Bonnel et al. |
| 2009/0324679 | A1 | 12/2009 | Ippoliti et al. |
| 2010/0059541 | A1 | 3/2010 | Hsu |
| 2010/0086551 | A1 | 4/2010 | Olwill et al. |
| 2010/0098730 | A1 | 4/2010 | Lowman et al. |
| 2010/0111942 | A1 | 5/2010 | Shima et al. |
| 2010/0111963 | A1 | 5/2010 | Shams |
| 2010/0129375 | A1 | 5/2010 | Junge et al. |
| 2010/0150911 | A1 | 6/2010 | Caiado De Castro et al. |
| 2010/0151566 | A1 | 6/2010 | Lamdan Ordas et al. |
| 2010/0158850 | A1 | 6/2010 | Baker, Jr. et al. |
| 2010/0166700 | A1 | 7/2010 | Charles |
| 2010/0233079 | A1 | 9/2010 | Jakob et al. |
| 2010/0247515 | A1 | 9/2010 | Steward et al. |
| 2010/0254995 | A1 | 10/2010 | Steward et al. |
| 2010/0260668 | A1 | 10/2010 | Ghayur et al. |
| 2010/0260760 | A1 | 10/2010 | Blank et al. |
| 2010/0278896 | A1 | 11/2010 | Khaw et al. |
| 2010/0291065 | A1 | 11/2010 | Kabanov et al. |
| 2011/0033378 | A1 | 2/2011 | Dimasi et al. |
| 2011/0047103 | A1 | 2/2011 | Swamy et al. |
| 2011/0052575 | A1 | 3/2011 | Baca et al. |
| 2011/0054031 | A1 | 3/2011 | McNamara et al. |
| 2011/0059080 | A1 | 3/2011 | Cornfeld et al. |
| 2011/0064738 | A1 | 3/2011 | Blank et al. |
| 2011/0069176 | A1 | 3/2011 | Lin et al. |
| 2011/0076278 | A1 | 3/2011 | Khodadoust |
| 2011/0076279 | A1 | 3/2011 | Ramachandra et al. |
| 2011/0081342 | A1 | 4/2011 | Baca et al. |
| 2011/0104069 | A1 | 5/2011 | Xu et al. |
| 2011/0110932 | A1 | 5/2011 | Patel |
| 2011/0117189 | A1 | 5/2011 | Mazzone et al. |
| 2011/0159608 | A1 | 6/2011 | Graham |
| 2011/0165648 | A1 | 7/2011 | Campange et al. |
| 2011/0177074 | A1 | 7/2011 | Sivakumar et al. |
| 2011/0189174 | A1 | 8/2011 | Shafiee et al. |
| 2011/0200593 | A1 | 8/2011 | Shima et al. |
| 2011/0213105 | A1 | 9/2011 | Jakubowski et al. |
| 2011/0262432 | A1 | 10/2011 | Plouet et al. |
| 2011/0263827 | A1 | 10/2011 | Ghayur et al. |
| 2011/0305689 | A1 | 12/2011 | Kim |
| 2012/0003641 | A1 | 1/2012 | Graham et al. |
| 2012/0006716 | A1 | 1/2012 | Frey et al. |
| 2012/0009185 | A1 | 1/2012 | Shams |
| 2012/0014957 | A1 | 1/2012 | Ghayur et al. |
| 2012/0070428 | A1 | 3/2012 | Chan et al. |
| 2012/0076787 | A1 | 3/2012 | Adamson et al. |
| 2012/0100136 | A1 | 4/2012 | Patel et al. |
| 2012/0100166 | A1 | 4/2012 | Roschke et al. |
| 2012/0128626 | A1 | 5/2012 | Smith |
| 2012/0134993 | A1 | 5/2012 | Pan et al. |
| 2012/0135070 | A1 | 5/2012 | Kros et al. |
| 2012/0141573 | A1 | 6/2012 | Ling et al. |
| 2012/0156202 | A1 | 6/2012 | Shantha et al. |
| 2012/0164079 | A1 | 6/2012 | Sharma |
| 2012/0213705 | A1 | 8/2012 | Dimasi et al. |
| 2012/0244147 | A1 | 9/2012 | Theuer et al. |
| 2012/0258108 | A1 | 10/2012 | Ghayur et al. |
| 2012/0263722 | A1 | 10/2012 | Ghayur et al. |
| 2012/0276083 | A1 | 11/2012 | Junge et al. |
| 2012/0282211 | A1 | 11/2012 | Washburn et al. |
| 2012/0301478 | A1 | 11/2012 | Ohura et al. |
| 2012/0322738 | A1 | 12/2012 | Behrens et al. |
| 2013/0004486 | A1 | 1/2013 | Chan et al. |
| 2013/0004511 | A1 | 1/2013 | Thorin et al. |
| 2013/0040889 | A1 | 2/2013 | Bolt et al. |
| 2013/0045522 | A1 | 2/2013 | Charles et al. |
| 2013/0058927 | A1 | 3/2013 | Baca et al. |
| 2013/0071394 | A1 | 3/2013 | Troyer et al. |
| 2013/0122003 | A1 | 5/2013 | Zhang |
| 2013/0129733 | A1 | 5/2013 | Ye et al. |
| 2013/0129749 | A1 | 5/2013 | Ye et al. |
| 2013/0129830 | A1 | 5/2013 | Chen et al. |
| 2013/0142796 | A1 | 6/2013 | Ray et al. |
| 2013/0195806 | A1 | 8/2013 | Gay et al. |
| 2013/0202613 | A1 | 8/2013 | Pakola et al. |
| 2013/0259881 | A1 | 10/2013 | Fandl et al. |
| 2013/0323242 | A1 | 12/2013 | Everett et al. |
| 2013/0323302 | A1 | 12/2013 | Constable et al. |
| 2013/0330341 | A1 | 12/2013 | Chiron et al. |
| 2013/0334517 | A1 | 12/2013 | Hong et al. |

(56) References Cited

U.S. PATENT DOCUMENTS

| | | | |
|---|---|---|---|
| 2013/0344129 | A1 | 12/2013 | Washburn et al. |
| 2014/0010823 | A1 | 1/2014 | Robinson et al. |
| 2014/0024776 | A1 | 1/2014 | Charles et al. |
| 2014/0051642 | A1 | 2/2014 | Castan |
| 2014/0065137 | A1 | 3/2014 | Huang et al. |
| 2014/0065142 | A1 | 3/2014 | Roschke et al. |
| 2014/0079694 | A1 | 3/2014 | Robinson et al. |
| 2014/0081003 | A1 | 3/2014 | Laird et al. |
| 2014/0086934 | A1 | 3/2014 | Shams |
| 2014/0093499 | A1 | 4/2014 | Gschwing et al. |
| 2014/0128575 | A1 | 5/2014 | Kao et al. |
| 2014/0134169 | A1 | 5/2014 | Kuhnert et al. |
| 2014/0154246 | A1 | 6/2014 | Robinson et al. |
| 2014/0154255 | A1 | 6/2014 | Akamatsu |
| 2014/0161817 | A1 | 6/2014 | Siedler et al. |
| 2014/0170140 | A1 | 6/2014 | Bennett et al. |
| 2014/0186350 | A1 | 7/2014 | Ghosh et al. |
| 2014/0193486 | A1 | 7/2014 | Liu et al. |
| 2014/0213769 | A1 | 7/2014 | Hong et al. |
| 2014/0242082 | A1 | 8/2014 | Shima et al. |
| 2014/0287025 | A1 | 9/2014 | Liu et al. |
| 2014/0294810 | A1 | 10/2014 | Lowman et al. |
| 2014/0302009 | A1 | 10/2014 | Ogura et al. |
| 2014/0339122 | A1 | 11/2014 | Weeks et al. |
| 2014/0341893 | A1 | 11/2014 | Andres et al. |
| 2014/0341977 | A1 | 11/2014 | Constable et al. |
| 2015/0004128 | A1 | 1/2015 | Charles et al. |
| 2015/0017095 | A1 | 1/2015 | Ghayur et al. |
| 2015/0017163 | A1 | 1/2015 | Patel et al. |
| 2015/0023951 | A1 | 1/2015 | Baca et al. |
| 2015/0030598 | A1 | 1/2015 | Croasdale et al. |
| 2015/0037422 | A1 | 2/2015 | Kaplan et al. |
| 2015/0037627 | A1 | 2/2015 | Armacanqui et al. |
| 2015/0044214 | A1 | 2/2015 | Imhof-Jung et al. |
| 2015/0050714 | A1 | 2/2015 | Charles |
| 2015/0056195 | A1 | 2/2015 | Bertolotto-Ballotti |
| 2015/0065781 | A1 | 3/2015 | Bais et al. |
| 2015/0071861 | A1 | 3/2015 | Kondo et al. |
| 2015/0071924 | A1 | 3/2015 | Swamy et al. |
| 2015/0071941 | A1 | 3/2015 | Sodhi et al. |
| 2015/0073381 | A1 | 3/2015 | Kauper et al. |
| 2015/0079084 | A1 | 3/2015 | Her et al. |
| 2015/0079089 | A1 | 3/2015 | Wadehra et al. |
| 2015/0093375 | A1 | 4/2015 | Junge et al. |
| 2015/0093390 | A1 | 4/2015 | Bansal |
| 2015/0098988 | A1 | 4/2015 | Bollag et al. |
| 2015/0104452 | A1 | 4/2015 | Ghayur et al. |
| 2015/0105734 | A1 | 4/2015 | Bryant et al. |
| 2015/0110788 | A1 | 4/2015 | Kim et al. |
| 2015/0125468 | A1 | 5/2015 | Schmidt et al. |
| 2015/0147317 | A1 | 5/2015 | Robblee et al. |
| 2015/0148585 | A1 | 5/2015 | Das et al. |
| 2015/0158952 | A1 | 6/2015 | Mao et al. |
| 2015/0175689 | A1 | 6/2015 | Fuh et al. |
| 2015/0182623 | A1 | 7/2015 | Everett et al. |
| 2015/0191535 | A1 | 7/2015 | Baehner et al. |
| 2015/0202289 | A1 | 7/2015 | Shima et al. |
| 2015/0203591 | A1 | 7/2015 | Liang et al. |
| 2015/0210771 | A1 | 7/2015 | Crystal et al. |
| 2015/0216795 | A1 | 8/2015 | Assadourian et al. |
| 2015/0232548 | A1 | 8/2015 | Klien et al. |
| 2015/0246124 | A1 | 9/2015 | Fyfe et al. |
| 2015/0266962 | A1 | 9/2015 | Ma et al. |
| 2015/0297675 | A1 | 10/2015 | Osborne |
| 2015/0306234 | A1 | 10/2015 | Apgar et al. |
| 2015/0307551 | A1 | 10/2015 | Doroski |
| 2015/0315283 | A1 | 11/2015 | Ghayur et al. |
| 2015/0337053 | A1 | 11/2015 | McCarthy et al. |
| 2015/0368329 | A1 | 12/2015 | Hastings et al. |
| 2015/0376272 | A1 | 12/2015 | Chung et al. |
| 2016/0008485 | A1 | 1/2016 | Marquette et al. |
| 2016/0015770 | A1 | 1/2016 | Zacks et al. |
| 2016/0024483 | A1 | 1/2016 | Kim et al. |
| 2016/0038589 | A1 | 2/2016 | Patel |
| 2016/0046730 | A1 | 2/2016 | Ghayur et al. |
| 2016/0068613 | A1 | 3/2016 | Regula et al. |
| 2016/0129080 | A1 | 5/2016 | Osborne |
| 2016/0130321 | A1 | 5/2016 | Burian |
| 2016/0130336 | A1 | 5/2016 | Lai et al. |
| 2016/0137717 | A1 | 5/2016 | Burian |
| 2016/0144025 | A1 | 5/2016 | Vitti et al. |
| 2016/0158320 | A1 | 6/2016 | Schultz et al. |
| 2016/0159893 | A1 | 6/2016 | Burian et al. |
| 2016/0159894 | A1 | 6/2016 | Hartmann et al. |
| 2016/0168240 | A1 | 6/2016 | Burian et al. |
| 2016/0194370 | A1 | 7/2016 | Quian et al. |
| 2016/0194389 | A1 | 7/2016 | Regula et al. |
| 2016/0243225 | A1 | 8/2016 | Ioffe et al. |
| 2016/0243227 | A1 | 8/2016 | Fyfe et al. |
| 2016/0257738 | A1 | 9/2016 | Baca et al. |
| 2016/0279241 | A1 | 9/2016 | Dupont et al. |
| 2016/0289317 | A1 | 10/2016 | Bollag et al. |
| 2016/0296550 | A1 | 10/2016 | Patel et al. |
| 2016/0297854 | A1 | 10/2016 | Ghosh et al. |
| 2016/0340420 | A1 | 11/2016 | Zhang et al. |
| 2016/0346400 | A1 | 12/2016 | Emrick et al. |
| 2016/0347843 | A1 | 12/2016 | Broering et al. |
| 2016/0369005 | A1 | 12/2016 | Lippincott et al. |
| 2017/0002060 | A1 | 1/2017 | Bolen et al. |
| 2017/0007581 | A1 | 1/2017 | Robinson et al. |
| 2017/0007710 | A1 | 1/2017 | Charles et al. |
| 2017/0015755 | A1 | 1/2017 | Walsh et al. |
| 2017/0029494 | A1 | 2/2017 | Ashman et al. |
| 2017/0035883 | A1 | 2/2017 | Gragoudas et al. |
| 2017/0056469 | A1 | 3/2017 | Lezzi |
| 2017/0065677 | A1 | 3/2017 | Weston-Davies |
| 2017/0079955 | A1 | 3/2017 | Boyd |
| 2017/0100478 | A1 | 4/2017 | Fyfe et al. |
| 2017/0114127 | A1 | 4/2017 | Trout et al. |
| 2017/0129962 | A1 | 5/2017 | Regula |
| 2017/0143826 | A1 | 5/2017 | Dupont et al. |
| 2017/0143841 | A1 | 5/2017 | Charles et al. |
| 2017/0143848 | A1 | 5/2017 | Calias et al. |
| 2017/0159114 | A1 | 6/2017 | Graham et al. |
| 2017/0210796 | A1 | 7/2017 | Siedler et al. |
| 2017/0224815 | A1 | 8/2017 | Tirgan |
| 2017/0232199 | A1 | 8/2017 | Fiedler |
| 2017/0233444 | A1 | 8/2017 | Stout et al. |
| 2017/0240626 | A1 | 8/2017 | Baehner et al. |
| 2017/0240629 | A1 | 8/2017 | Bedoucha et al. |
| 2017/0253651 | A1 | 9/2017 | Chen et al. |
| 2017/0275353 | A1 | 9/2017 | Sheng et al. |
| 2017/0283511 | A1 | 10/2017 | Goldenberg et al. |
| 2017/0290876 | A1 | 10/2017 | Ghosh et al. |
| 2017/0313780 | A1 | 11/2017 | Kao et al. |
| 2017/0327569 | A1 | 11/2017 | Lu et al. |
| 2017/0349669 | A1 | 12/2017 | Imhof-Jung et al. |
| 2017/0362317 | A1 | 12/2017 | Lee et al. |
| 2017/0369564 | A1 | 12/2017 | Baca et al. |
| 2017/0369566 | A1 | 12/2017 | Baehner et al. |
| 2018/0000779 | A1 | 1/2018 | Sakamoto et al. |
| 2018/0000933 | A1 | 1/2018 | Ingram et al. |
| 2018/0042765 | A1 | 2/2018 | Noronha et al. |
| 2018/0057602 | A1 | 3/2018 | Theuer et al. |
| 2018/0092897 | A1 | 4/2018 | Zarnitsyn et al. |
| 2018/0133288 | A1 | 5/2018 | Kim et al. |
| 2018/0134780 | A1 | 5/2018 | Klein et al. |
| 2018/0155431 | A1 | 6/2018 | Herting et al. |
| 2018/0161407 | A1 | 6/2018 | Borodic |
| 2018/0186866 | A1 | 7/2018 | Falkenstein et al. |
| 2018/0207292 | A1 | 7/2018 | Burian et al. |
| 2018/0208642 | A1 | 7/2018 | Lim et al. |
| 2018/0221339 | A1 | 8/2018 | Boyd et al. |
| 2018/0221483 | A1 | 8/2018 | Gaillard et al. |
| 2018/0230540 | A1 | 8/2018 | Gosh et al. |
| 2018/0236066 | A1 | 8/2018 | Maecher et al. |
| 2018/0237484 | A1 | 8/2018 | Kwon et al. |
| 2018/0251545 | A1 | 9/2018 | Cao et al. |
| 2018/0276336 | A1 | 9/2018 | Perlee et al. |
| 2018/0298092 | A1 | 10/2018 | Gekkieva et al. |
| 2018/0319893 | A1 | 11/2018 | Stephen et al. |
| 2018/0326126 | A1 | 11/2018 | Fiedler |
| 2018/0334499 | A1 | 11/2018 | Olwill et al. |
| 2018/0344847 | A1 | 12/2018 | Dupont et al. |

(56) References Cited

U.S. PATENT DOCUMENTS

| | | | |
|---|---|---|---|
| 2018/0355030 | A1 | 12/2018 | Greene et al. |
| 2018/0369380 | A1 | 12/2018 | Gragoudas et al. |
| 2018/0371072 | A1 | 12/2018 | Theuer et al. |
| 2019/0000919 | A1 | 1/2019 | Brockmeyer et al. |
| 2019/0011455 | A1 | 1/2019 | Lebert et al. |
| 2019/0016817 | A1 | 1/2019 | Taddei et al. |
| 2019/0031750 | A1 | 1/2019 | Koenig et al. |
| 2019/0031783 | A1 | 1/2019 | Gu et al. |
| 2019/0062444 | A1 | 2/2019 | Walsh et al. |
| 2019/0085056 | A1 | 3/2019 | Lebert et al. |
| 2019/0091331 | A1 | 3/2019 | Yang et al. |
| 2019/0100581 | A1 | 4/2019 | Koenig et al. |
| 2019/0100582 | A1 | 4/2019 | Blumenkran et al. |
| 2019/0127454 | A1 | 5/2019 | Yang et al. |
| 2019/0127455 | A1 | 5/2019 | Simpson et al. |
| 2019/0127457 | A1 | 5/2019 | Schlothauer |
| 2019/0142975 | A1 | 5/2019 | Keravala et al. |
| 2019/0153119 | A1 | 5/2019 | Migone et al. |
| 2019/0153471 | A1 | 5/2019 | Paul et al. |
| 2019/0161549 | A1 | 5/2019 | Choong |
| 2019/0185555 | A1 | 6/2019 | Swamy et al. |
| 2019/0194713 | A1 | 6/2019 | Mandell et al. |
| 2019/0202904 | A1 | 7/2019 | Fellouse et al. |
| 2019/0211091 | A1 | 7/2019 | Simpson et al. |
| 2019/0216945 | A1 | 7/2019 | Yang et al. |
| 2019/0218263 | A1 | 7/2019 | Trese et al. |
| 2019/0224046 | A1 | 7/2019 | Heitzmann et al. |
| 2019/0231799 | A1 | 8/2019 | Peters et al. |
| 2019/0231986 | A1 | 8/2019 | Devaraneni |
| 2019/0233517 | A1 | 8/2019 | Wu |
| 2019/0255074 | A1 | 8/2019 | Song et al. |
| 2019/0256556 | A1 | 8/2019 | Giese et al. |
| 2019/0262476 | A1 | 8/2019 | Lorenz et al. |
| 2019/0292239 | A1 | 9/2019 | Carter et al. |
| 2019/0300607 | A1 | 10/2019 | Isumi |
| 2019/0307691 | A1 | 10/2019 | Gaillard et al. |
| 2019/0321467 | A1 | 10/2019 | Santos et al. |
| 2019/0322732 | A1 | 10/2019 | Murakami et al. |
| 2019/0330335 | A1 | 10/2019 | Schwabe et al. |
| 2019/0336482 | A1 | 11/2019 | Boyd |
| 2019/0343918 | A1 | 11/2019 | Graham et al. |
| 2019/0358335 | A1 | 11/2019 | Russell et al. |
| 2019/0360027 | A1 | 11/2019 | Perlee et al. |
| 2019/0381008 | A1 | 12/2019 | Zeitz et al. |
| 2019/0381194 | A1 | 12/2019 | Tretiakova et al. |
| 2019/0382733 | A1 | 12/2019 | Brument |
| 2019/0388522 | A1 | 12/2019 | Burian et al. |
| 2020/0000930 | A1 | 1/2020 | Charles |
| 2020/0002411 | A1 | 1/2020 | Famili et al. |
| 2020/0002426 | A1 | 1/2020 | Sheng et al. |
| 2020/0048341 | A1 | 2/2020 | Ghosh et al. |
| 2020/0055923 | A1 | 2/2020 | Torella et al. |
| 2020/0055933 | A1 | 2/2020 | Hailman et al. |
| 2020/0055958 | A1 | 2/2020 | Chen et al. |
| 2020/0057058 | A1 | 2/2020 | Olsen et al. |
| 2020/0086139 | A1 | 3/2020 | Das et al. |
| 2020/0087389 | A1 | 3/2020 | Theuer et al. |
| 2020/0095309 | A1 | 3/2020 | Peters |
| 2020/0095310 | A1 | 3/2020 | Regula et al. |
| 2020/0171179 | A1 | 6/2020 | Charles et al. |
| 2020/0262905 | A1 | 8/2020 | Perlroth et al. |
| 2021/0254073 | A1 | 8/2021 | Ray et al. |
| 2021/0324063 | A1 | 10/2021 | Perlroth et al. |
| 2021/0379193 | A1 | 12/2021 | Ji et al. |
| 2021/0402015 | A1 | 12/2021 | Charles et al. |
| 2022/0096643 | A1 | 3/2022 | Charles |
| 2023/0173081 | A1 | 6/2023 | Charles et al. |
| 2023/0250133 | A1 | 8/2023 | Zurbriggen et al. |
| 2023/0382983 | A1 | 11/2023 | Perlroth et al. |
| 2024/0197810 | A1 | 6/2024 | Charles et al. |
| 2024/0209076 | A1 | 6/2024 | Perlroth et al. |
| 2024/0238427 | A1 | 7/2024 | Ehrlich et al. |
| 2024/0293585 | A1 | 9/2024 | Charles et al. |
| 2024/0368267 | A1 | 11/2024 | Jacobson et al. |

FOREIGN PATENT DOCUMENTS

| | | |
|---|---|---|
| AU | 2015207898 | 8/2015 |
| AU | 2017201930 | 4/2017 |
| BR | 11 2012 014556 | 3/2017 |
| BR | 11 2012 0261185 | 8/2017 |
| CA | 2783615 | 6/2011 |
| CA | 2795667 | 10/2011 |
| CL | 02881/2012 | 7/2013 |
| CN | 1486995 | 4/2004 |
| CN | 101053681 | 10/2007 |
| CN | 101389690 | 3/2009 |
| CN | 101575402 | 11/2009 |
| CN | 102036687 | 4/2011 |
| CN | 102250246 | 11/2011 |
| CN | 102311502 | 1/2012 |
| CN | 102811713 | 12/2012 |
| CN | 103134874 | 6/2013 |
| CN | 103193819 | 7/2013 |
| CN | 103421039 | 12/2013 |
| CN | 103492489 | 1/2014 |
| CN | 103898101 | 7/2014 |
| CN | 106075466 | 11/2016 |
| CN | 106432557 | 2/2017 |
| CN | 106905431 | 6/2017 |
| CN | 107208076 | 9/2017 |
| CN | 107428824 | 12/2017 |
| CO | 12119310 | 12/2012 |
| CO | 12203725 | 2/2013 |
| EP | 0345242 | 12/1989 |
| EP | 0306968 | 12/1993 |
| EP | 0282160 | 5/1995 |
| EP | 0524968 | 6/1995 |
| EP | 0577648 | 6/2001 |
| EP | 0968291 | 1/2004 |
| EP | 1179541 | 6/2004 |
| EP | 0929323 | 12/2004 |
| EP | 1325932 | 4/2005 |
| EP | 0971959 | 12/2005 |
| EP | 0973804 | 12/2006 |
| EP | 1465933 | 8/2007 |
| EP | 1135498 | 1/2008 |
| EP | 1592719 | 3/2008 |
| EP | 1988910 | 11/2008 |
| EP | 1605847 | 9/2009 |
| EP | 1732621 | 12/2009 |
| EP | 1968594 | 9/2010 |
| EP | 2260873 | 12/2010 |
| EP | 1802373 | 7/2011 |
| EP | 2363414 | 9/2011 |
| EP | 2301580 | 1/2012 |
| EP | 1660057 | 5/2012 |
| EP | 2029746 | 7/2012 |
| EP | 1802334 | 8/2012 |
| EP | 2329821 | 8/2012 |
| EP | 2512462 | 10/2012 |
| EP | 2203180 | 11/2012 |
| EP | 2558538 | 2/2013 |
| EP | 2199306 | 6/2013 |
| EP | 2604279 | 6/2013 |
| EP | 2155783 | 7/2013 |
| EP | 2446890 | 9/2013 |
| EP | 2344537 | 1/2014 |
| EP | 2274008 | 2/2014 |
| EP | 2042597 | 5/2014 |
| EP | 2524693 | 5/2014 |
| EP | 2540843 | 7/2014 |
| EP | 1991275 | 11/2014 |
| EP | 2443150 | 1/2015 |
| EP | 1802325 | 2/2015 |
| EP | 1989231 | 5/2015 |
| EP | 2217261 | 10/2015 |
| EP | 2596807 | 12/2015 |
| EP | 2200700 | 1/2016 |
| EP | 2307055 | 1/2016 |
| EP | 2259795 | 4/2016 |
| EP | 2516465 | 5/2016 |
| EP | 1763365 | 8/2016 |
| EP | 2411411 | 8/2016 |

(56) References Cited

FOREIGN PATENT DOCUMENTS

| | | |
|---|---|---|
| EP | 2575881 | 9/2016 |
| EP | 2473526 | 8/2017 |
| EP | 2491134 | 8/2017 |
| EP | 3222142 | 9/2017 |
| EP | 2327415 | 10/2017 |
| EP | 2785744 | 10/2017 |
| EP | 2188302 | 11/2017 |
| EP | 2467156 | 11/2017 |
| EP | 2894167 | 11/2017 |
| EP | 2925778 | 11/2017 |
| EP | 2784092 | 12/2017 |
| EP | 3254678 | 12/2017 |
| EP | 2792687 | 5/2018 |
| EP | 2319925 | 7/2018 |
| EP | 2662388 | 8/2018 |
| EP | 2872534 | 8/2018 |
| EP | 3122878 | 10/2018 |
| EP | 3401331 | 11/2018 |
| EP | 1861096 | 12/2018 |
| EP | 2726612 | 3/2019 |
| EP | 3038647 | 3/2019 |
| EP | 3020731 | 6/2019 |
| EP | 2924052 | 7/2019 |
| EP | 2846836 | 8/2019 |
| EP | 3327026 | 8/2019 |
| EP | 2951307 | 12/2019 |
| EP | 3450553 | 12/2019 |
| EP | 3600441 | 2/2020 |
| EP | 3038646 | 3/2020 |
| EP | 3104880 | 3/2020 |
| EP | 3216803 | 3/2020 |
| EP | 3041513 | 8/2020 |
| EP | 3268386 | 3/2021 |
| GB | 2200651 | 8/1988 |
| IL | 260323 | 8/2018 |
| IN | 6116/CHENP/2012 | 12/2015 |
| IN | 9473/CHENP/2012 | 12/2015 |
| JP | S58-154591 | 9/1983 |
| JP | H04-502850 | 5/1992 |
| JP | H09-504299 | 4/1997 |
| JP | H10-139832 | 5/1998 |
| JP | H11-217588 | 8/1999 |
| JP | 2000-093169 | 4/2000 |
| JP | 2002-512265 | 4/2002 |
| JP | 2003-064132 | 3/2003 |
| JP | 2003-104913 | 4/2003 |
| JP | 2005-239989 | 9/2005 |
| JP | 2005-255969 | 9/2005 |
| JP | 2006-503549 | 2/2006 |
| JP | 2007-516302 | 6/2007 |
| JP | 2007-263935 | 10/2007 |
| JP | 2007-531513 | 11/2007 |
| JP | 2007-314736 | 12/2007 |
| JP | 2008-133434 | 6/2008 |
| JP | 2008-524247 | 7/2008 |
| JP | 2008-536498 | 9/2008 |
| JP | 2008-239997 | 10/2008 |
| JP | 2008-297488 | 12/2008 |
| JP | 2009-042617 | 2/2009 |
| JP | 2009-114283 | 5/2009 |
| JP | 2009-532330 | 9/2009 |
| JP | 2009-533519 | 9/2009 |
| JP | 2009-274998 | 11/2009 |
| JP | 2009-542862 | 12/2009 |
| JP | 2009-543895 | 12/2009 |
| JP | 2010-013651 | 1/2010 |
| JP | 2010-117189 | 5/2010 |
| JP | 2010-279389 | 12/2010 |
| JP | 2011-500073 | 1/2011 |
| JP | 2015-502397 | 1/2011 |
| JP | 2011-518546 | 5/2011 |
| JP | 2012-025820 | 2/2012 |
| JP | 2012-521768 | 9/2012 |
| JP | 2013-515099 | 5/2013 |
| JP | 2013-519699 | 5/2013 |
| JP | 2013-534931 | 9/2013 |
| JP | 2014-043405 | 3/2014 |
| JP | 2014-043453 | 3/2014 |
| JP | 2014-043456 | 3/2014 |
| JP | 5528710 | 6/2014 |
| JP | 2011-501945 | 1/2015 |
| JP | 5745009 | 7/2015 |
| JP | 5760007 | 8/2015 |
| JP | 2016-14015 | 1/2016 |
| JP | 5846044 | 1/2016 |
| JP | 2016-040371 | 3/2016 |
| JP | 2016-528167 | 9/2016 |
| JP | 2016-530302 | 9/2016 |
| JP | 5990629 | 9/2016 |
| JP | 2017-031410 | 2/2017 |
| JP | 2018-087330 | 6/2018 |
| JP | 2019-081765 | 5/2019 |
| JP | 2020-183404 | 11/2021 |
| KR | 10-0808116 | 3/2008 |
| KR | 2012-0123340 | 11/2012 |
| KR | 2013-0097636 | 9/2013 |
| KR | 10-2013-0118994 A | 10/2013 |
| KR | 10-2015-0023688 A | 3/2015 |
| KR | 10-1852044 | 4/2018 |
| MX | 2012006970 | 10/2012 |
| MX | 2012011876 | 11/2012 |
| MX | 346423 | 3/2017 |
| MX | 2016017290 | 8/2017 |
| RU | 2376373 | 12/2009 |
| WO | WO 87/04462 | 7/1987 |
| WO | WO 90/07936 | 7/1990 |
| WO | WO 90/11092 | 10/1990 |
| WO | WO 91/00904 | 1/1991 |
| WO | WO 91/02805 | 3/1991 |
| WO | WO 91/10741 | 7/1991 |
| WO | WO 91/14445 | 10/1991 |
| WO | WO 91/17271 | 11/1991 |
| WO | WO 92/01047 | 1/1992 |
| WO | WO 93/01221 | 1/1993 |
| WO | WO 93/03769 | 3/1993 |
| WO | WO 93/10218 | 5/1993 |
| WO | WO 93/11230 | 6/1993 |
| WO | WO 93/12227 | 6/1993 |
| WO | WO 93/19191 | 9/1993 |
| WO | WO 93/25234 | 12/1993 |
| WO | WO 93/25673 | 12/1993 |
| WO | WO 93/25698 | 12/1993 |
| WO | WO 94/03622 | 2/1994 |
| WO | WO 94/12649 | 6/1994 |
| WO | WO 94/16748 | 8/1994 |
| WO | WO 94/16749 | 8/1994 |
| WO | WO 94/23697 | 10/1994 |
| WO | WO 94/28938 | 12/1994 |
| WO | WO 95/00655 | 1/1995 |
| WO | WO 95/07994 | 3/1995 |
| WO | WO 95/11984 | 5/1995 |
| WO | WO 95/13796 | 5/1995 |
| WO | WO 95/30763 | 11/1995 |
| WO | WO 96/17072 | 6/1996 |
| WO | WO 97/14702 | 4/1997 |
| WO | WO 97/14703 | 4/1997 |
| WO | WO 97/37029 | 10/1997 |
| WO | WO 97/42338 | 11/1997 |
| WO | WO 98/16535 | 4/1998 |
| WO | WO 98/45331 | 10/1998 |
| WO | WO 99/42133 | 8/1999 |
| WO | WO 99/64065 | 12/1999 |
| WO | WO 00/09560 | 5/2000 |
| WO | WO 00/34337 | 6/2000 |
| WO | WO 00/37502 | 6/2000 |
| WO | WO 00/37658 | 6/2000 |
| WO | WO 00/59968 | 10/2000 |
| WO | WO 00/75319 | 12/2000 |
| WO | WO 01/00854 | 1/2001 |
| WO | WO 01/18080 | 3/2001 |
| WO | WO 01/24763 | 4/2001 |
| WO | WO 01/41827 | 6/2001 |
| WO | WO 02/028929 | 4/2002 |
| WO | WO 03/020906 | 3/2003 |

(56) References Cited

FOREIGN PATENT DOCUMENTS

WO WO 03/062290 7/2003
WO WO 03/074026 9/2003
WO WO 03/074090 9/2003
WO WO 2004/003144 1/2004
WO WO 2004/010957 2/2004
WO WO 2004/020405 3/2004
WO WO 2004/063237 7/2004
WO WO 2004/065417 8/2004
WO WO 2004/091494 10/2004
WO WO 2004/113394 12/2004
WO WO 2005/028539 3/2005
WO WO 2005/058367 6/2005
WO WO 2005/117984 12/2005
WO WO 2005/120166 12/2005
WO WO 2006/063055 6/2006
WO WO 2006/113277 10/2006
WO WO 2006/118547 11/2006
WO WO 2007/005253 1/2007
WO WO 2007/011873 1/2007
WO WO 2007/075534 7/2007
WO WO 2007/100902 9/2007
WO WO 2007/100905 9/2007
WO WO 2007/148230 12/2007
WO WO 2008/003099 1/2008
WO WO 2008/020827 2/2008
WO WO 2008/025856 3/2008
WO WO 2008/055206 5/2008
WO WO 2008/098930 8/2008
WO WO 2008/112257 9/2008
WO WO 2008/112289 9/2008
WO WO 2008/119565 10/2008
WO WO 2008/119567 10/2008
WO WO 2008/144248 11/2008
WO WO 2008/155134 12/2008
WO WO 2009/012268 1/2009
WO WO 2009/052249 4/2009
WO WO 2009/053368 4/2009
WO WO 2005/047334 5/2009
WO WO 2009/066746 5/2009
WO WO 2009/052439 6/2009
WO WO 2009/092011 7/2009
WO WO 2009/097247 8/2009
WO WO 2009/099728 8/2009
WO WO 2009/105669 8/2009
WO WO 2009/117531 9/2009
WO WO 2009/120922 10/2009
WO WO 2009/134711 11/2009
WO WO 2009/134977 11/2009
WO WO 2009/138473 11/2009
WO WO 2009/149205 12/2009
WO WO 2010/040508 4/2010
WO WO 2010/068862 6/2010
WO WO 2010/068864 6/2010
WO WO 2010/085542 7/2010
WO WO 2010/111625 9/2010
WO WO 2010/126552 11/2010
WO WO 2010/136492 12/2010
WO WO 2010/147686 12/2010
WO WO 2010/148223 12/2010
WO WO 2011/057014 5/2011
WO WO 2011/075185 6/2011
WO WO 2011/075736 6/2011
WO WO 2011/101284 6/2011
WO WO 2011/116387 9/2011
WO WO 2011/119656 9/2011
WO WO 2011/130694 10/2011
WO WO 2011/153243 12/2011
WO WO 2012/145746 10/2012
WO WO 2012/146610 11/2012
WO WO 2012/163520 12/2012
WO WO 2013/059137 4/2013
WO WO 2013/063155 5/2013
WO WO 2013/071016 5/2013
WO WO 2013/082563 6/2013
WO WO 2013/093809 6/2013
WO WO 2013/173129 11/2013
WO WO 2014/006113 1/2014
WO WO 2014/007982 1/2014
WO WO 2014/033184 3/2014
WO WO 2014/060401 4/2014
WO WO 2014/068443 5/2014
WO WO 2014/072888 5/2014
WO WO 2014/101287 7/2014
WO WO 2014/160507 10/2014
WO WO 2014/177460 11/2014
WO WO 2014/196658 12/2014
WO WO 2015/004616 1/2015
WO WO 2015/035342 3/2015
WO WO 2015/058048 4/2015
WO WO 2015/058369 4/2015
WO WO 2015/059220 4/2015
WO WO 2015/101586 7/2015
WO WO 2015/109898 7/2015
WO WO 2015/110067 7/2015
WO WO 2015/135583 9/2015
WO WO 2015/157595 10/2015
WO WO 2015/168321 11/2015
WO WO 2015/168468 11/2015
WO WO 2015/198240 12/2015
WO WO 2015/198243 12/2015
WO WO 2015/200905 12/2015
WO WO 2016/008975 1/2016
WO WO 2016/044041 3/2016
WO WO 2016/045626 3/2016
WO WO 2016/061562 4/2016
WO WO 2016/073157 5/2016
WO WO 2016/073894 5/2016
WO WO 2016/085750 6/2016
WO WO 2016/145189 9/2016
WO WO 2016/160923 10/2016
WO WO 2016/170039 10/2016
WO WO 2017/046140 3/2017
WO WO 2017/075173 5/2017
WO WO 2017/100470 6/2017
WO WO 2017/117464 7/2017
WO WO 2017/120600 7/2017
WO WO 2017/120601 7/2017
WO WO 2017/129064 8/2017
WO WO 2017/204298 11/2017
WO WO 2017/205559 11/2017
WO WO 2018/114728 6/2018
WO WO 2018/122053 7/2018
WO WO 2018/139991 8/2018
WO WO 2018/175319 9/2018
WO WO 2018/175752 9/2018
WO WO 2018/182527 10/2018
WO WO 2018/185110 10/2018
WO WO 2018/191548 10/2018
WO WO 2018/217995 11/2018
WO WO 2018/218215 11/2018
WO WO 2019/020777 1/2019
WO WO 2019/038552 2/2019
WO WO 2019/040397 2/2019
WO WO 2019/043649 3/2019
WO WO 2019/057946 3/2019
WO WO 2019/067540 4/2019
WO WO 2019/091384 5/2019
WO WO 2019/099786 5/2019
WO WO 2019/104279 5/2019
WO WO 2019/113225 6/2019
WO WO 2019/134686 7/2019
WO WO 2019/147944 8/2019
WO WO 2019/154349 8/2019
WO WO 2019/154776 8/2019
WO WO 2019/164219 8/2019
WO WO 2019/169341 9/2019
WO WO 2019/173482 9/2019
WO WO 2019/175727 9/2019
WO WO 2019/178438 9/2019
WO WO 2019/184909 10/2019
WO WO 2019/195313 10/2019
WO WO 2019/200181 10/2019
WO WO 2019/201866 10/2019
WO WO 2019/204380 10/2019

(56) References Cited

FOREIGN PATENT DOCUMENTS

| | | |
|---|---|---|
| WO | WO 2019/229116 | 12/2019 |
| WO | WO 2020/006486 | 1/2020 |
| WO | WO 2020/043184 | 3/2020 |
| WO | WO 2021/226404 | 11/2021 |
| WO | WO 2022/221395 | 10/2022 |
| WO | WO 2023/154822 | 8/2023 |
| WO | WO 2024/254281 | 12/2024 |

OTHER PUBLICATIONS

Adler, A. P. et al., "Evasive resistance to VEGF blockade mediated by autocrine IL-6/STAT3 signalingin xenograft models of human cancer", Cancer Res, Aug. 2015, vol. 75, Supplement 15, p. 1378 (the reference document includes the abstract only).

Alconcel, S.N.S. et al., "FDA-approved poly(ethylene glycol)-protein conjugate drugs," www.rsc.org/polymers, Polymer Chemistry, vol. 2, Issue 7, pp. 1442, 2011.

Al-Khersan, H. et al., "Innovative therapies for neovascular age-related macular degeneration", Expert Opinion on Pharmacotherapy, Jul. 2019, vol. 20(15), in 15 pages.

Allen et al., "Combined antiangiogenic and anti-PD-L1 therapy stimulates tumor immunity through HEV formation", Science Translational Medicine, 9(385): dated Apr. 12, 2017.

Alley, S. et al., "Contribution of linker stability to the activities of anticancer immunoconjugates," Bioconjugate Chem., vol. 19, No. 3, pp. 759-765, 2008.

Altamirano, C.V. et al., "Association of tetramers of human butyrylcholinesterase is mediated byconserved aromatic residues of the carboxy terminus," Chemico-Biological Interactions, vols. 119-120, pp. 53-60, May 14, 1999.

Ambati et al., "Mechanisms of age-related macular degeneration," Neuron, vol. 75, No. 1, pp. 26-39, 2012.

Anderson, W.F., "Human gene therapy," Science, May 8, 1992, vol. 256, No. 5058, pp. 808-813.

Andrae et al., "Role of platelet-derived growth factors in physiology and medicine," Genes & Development, vol. 22, pp. 1276-1312, 2008.

Armulik, A. et al., "Endothelial/Pericyte Interactions," Circulation Research, vol. 97, Issue 6, pp. 512-523, Sep. 16, 2005.

Bakri et al., "Pharmacokinetics of Intravitreal Ranibizumab [Lucentis]," Dec. 2007, Ophthalmology vol. 114, Issue 12, pp. 2179-2182.

Baldwin, A. et al., "Reversible maleimide-thiol adducts yield glutathione-sensitive poly(ethylene glycol)-heparin hydrogels," Polymer Chemistry, vol. 4, Issue 1, pp. 133-143, Jan. 7, 2013.

Baldwin, A. et al., "Tunable degradation of maleimide-thiol adducts in reducing environments," Bioconjug Chem, vol. 22, No. 10, pp. 1946-1953, Oct. 19, 2011.

Baluk, P. et al., "Cellular abnormalities of blood vessels as targets in cancer," Current Opinion in Genetics & Development, vol. 15, Issue 1, pp. 102-111, Feb. 2005.

Bates, D.O. et al., "Vascular endothelial growth factor increases microvascular permeability via aCa(2+)-dependent pathway," American Journal of Physiology, vol. 273, No. 2, pp. H687-H694, Aug. 1, 1997.

Beranger et al., IMGT Scientific Chart created May 17, 2001, in 4 pages. URL: http://www.imgt.org/IMGTScientificChart/Numbering/Hu_IGHGnber.html.

Berthold, W. et al., "Protein Purification: Aspects of Processes for Pharmaceutical Products," Biologicals, vol. 22, Issue 2, pp. 135-150, Jun. 1994.

Binder, S. et al., "Transplantation of the RPE in AMD", Progress in Retinal and Eye Research, 2007, vol. 26, pp. 516-554.

Blong, M. Renee et al., "Tetramerization domain of human butyrylcholinesterase is at the C-terminus," Biochemical Journal, vol. 327, No. 3, pp. 747-757, Nov. 1, 1997.

Bock, F. et al. Safety Profile of Topical VEGF Neutralization at the Cornea, Investigative Ophthalmology & Visual Science, vol. 50, No. 5, pp. 2095-2012, (2009).

Boeckman, R. et al., "The Dess-Martin Periodinane: 1,1, 1-Traicetoxy-1, 1-Dihydro-1,2-Benziodoxol-3(1H)-One", Organic Syntheses, Coll., 2004, vol. 10, in 7 pages.

Bontempo, et al., "Cysteine-Reactive Polymers Synthesized by Atom Transfer Radical Polymerization for Conjugation to Proteins," J. Am. Chem. Soc. (2004), 126, pp. 15372-15373.

Bowen-Pope et al., "History of Discovery: Platelet-derived Growth Factor," Arterioscler Thromb Vasc Biol., vol. 31, No. 11, pp. 2397-2401, Nov. 2011.

Boyd et al., "The effect of the removal of sialic acid, galactose and total carbohydrate on the functional activity of Campath-1H", Molecular Immunology, Dec. 1995, vol. 32, pp. 1311-1318.

Brown, D. et al., "Ranibizumab versus Verteporfin for Neovascular Age-Related MacularDegeneration," The New England Journal of Medicine, vol. 355, No. 14, pp. 1432-1444, Oct. 5, 2006.

Brown, David, "Novel Anti-VEGF Antibody Biopolymer Conjugate KSI-301 with Potential for ExtendedDurability in Retinal Vascular Diseases," powerpoint presented at the Retina Society Annual Meeting on Sep. 15, 2019 in 19 pgs.

Cannard, K., "The acute treatment of nerve agent exposure," Journal of the Neurological Sciences, vol. 249, Issue 1, pp. 86-94 (2006).

Capel, P. J. A. et al., "Heterogeneity of human IgG Fc receptors", Immunomethods, Feb. 1994, vol. 4(1), pp. 25-34.

Capon, D. et al., "Designing CD4 immunoadhesins for AIDS therapy," Nature, 1989, vol. 337, pp. 525-531.

Carmeliet, "Mechanisms of angiogenesis and arteriogenesis," Nature Medicine, vol. 6, No. 3, pp. 389-395, 2000.

Carmeliet, P., "Angiogenesis in health and disease," Nature Medicine, vol. 9, pp. 653-660, (2003).

Carmeliet, P., "Synergism between vascular endothelial growth factor and placental growth factorcontributes to angiogenesis and plasma extravasation in pathological conditions," Nature Medicine, vol. 7, No. 5, pp. 575-583, May 2001.

Cascio, C. et al., "Use of serum cholinesterases in severe organophosphorus poisoning," Minerva Anestesiologica, vol. 54, in 6 pages, 1988. (English abstract within article on p. 5).

Casset, F. et al. A Peptide Mimetic of an Anti0CD4 Monoclonal Antibody by Rational Design, Biochemical and Biophysical Research Communications, vol. 307, pp. 198-205, (2003).

Causes and Risk Factors, Diabetic Retinopathy, United State National Library of Medicine, Sep. 15, 2009, Archived web page at http://www.nei.nih.gov/health/diabetic/retinopathy.asp, dated Sep. 23, 2009.

Chakravarthy, R. et al., "Efficacy of extrinsic stain removal by novel dentifrice containing papain and bromelain extracts", J. Young Pharm, 2012, vol. 4(4), pp. 245-249.

Chames, Patrick et al., "Therapeutic antibodies: successes, limitations and hopes for the future,"British Journal of Pharmacology, Wiley-Blackwell, UK; Biosciences Information Service, vol. 157, No. 2, May 1, 2009, pp. 220-233.

Chandler, W. et al., "Comparison of Three Methods for Measuring Factor VIII Levels in Plasma", American Journal of Clinical Pathology, Jul. 2003, vol. 120, pp. 34-39.

Chen et al., "Factors affecting endotoxin removal from recombinant therapeutic proteins by anion exchange chromatography," Protein Expression and Purification, vol. 64, pp. 76-81, 2009.

Chen, et al., "Lubrication at Physiological Pressures by Polyzwitterionic Brushes," Science, (2009), 323, pp. 1698-1701.

Chen, et al., "Polymeric Phosphorylcholine-Camptothecin Conjugates Prepared by Controlled FreeRadical Polymerization and Click Chemistry," Bioconjugate Chem., Nov. 2009, vol. 20(12), pp. 2331-2341.

Chen, Y. et al. "Selection and Analysis an Optimized Anti-VEGF Antibody: Crystal Structure of an Affinity-Matured Complex with Antigen", J. Mol. Biol,, vol. 293, pp. 865-881 (1999).

Chiou, H. et al., "In Vivo Gene Therapy via Receptor-Mediated DNA Delivery", in Gene Therapeutics: Methods and Applications of Direct Gene Transfer, J.A. Wolff, ed., 1994, in 14 pages.

Chothia, C. et al., "Canonical structures for the hypervariable regions of immunoglobulins," Journal of Molecular Biology, Aug. 20, 1987, vol. 196, Issue 4, pp. 901-917.

Chothia, C. et al., "Conformations of immunoglobulin hypervariable regions," Nature, Dec. 1989, vol. 342, pp. 877-883.

(56) References Cited

OTHER PUBLICATIONS

Christy, N.E. et al., "Antibiotic prophylaxis of postoperative endophthalmitis," Annals of Ophthalmology, vol. 11, No. 8, pp. 1261-1265, Aug. 1, 1979.
Coessens, V. et al., "Functional polymers by atom transfer radical polymerization", Progress in Polymer Science, Apr. 2001, vol. 26, pp. 337-377.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Connelly, S. et al., "In Vivo Gene Delivery and Expression of Physiological Levels of Functional Human Factor VIII in Mice", Human Gene Therapy, 1995, vol. 6, pp. 185-193.
Conti, P. "Induction of pro-inflammatory cytokines (IL-1 and IL-6) and lung inflammation byCoronavirus-19 (COVI-19 or SARS-CoV-2): anti-inflammatory strategies", Journal of Biological Regulators and Homeostatic Agents, Mar.-Apr. 2020, vol. 34(2), in 6 pages.
Correa, F. et al., "Development of Novel Bispecific Anti-Inflammatory and Anti-Angiogenic Therapyfor the Treatment of both Retinal Vascular and Inflammatory Diseases", Investigative Ophthalmology & Visual Science, Jul. 2019, vol. 60, p. 5396 (the reference document includes the abstract only).
Crowe, et al., "Recombinant human respiratory syncytial virus (RSV)effective therapeutically when introduced directly into the lungs of RSV-infected mice, " Proc. Natl. Acad. Sci. USA, (1994) 91 pp. 1386-1390.
Curiel, D. et al., "High-Efficiency Gene Transfer Mediated by Adenovirus Coupled to DNA-Polylysine Complexes", Human Gene Therapy, 1992, vol. 3(2), pp. 147-154.
Curriculum Vitae of Didier G. Benoit, filed on Feb. 4, 2013 in U.S. Appl. No. 12/281,071, in 6 pages.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Daneshian, M. et al., "In vitro pyrogen test for toxic or immunomodulatory drugs," Journal of Immunological Methods, vol. 313, Issues 1-2, pp. 169-175, Jun. 30, 2006.
Daniel et al., "Risk of Scar in the Comparison of Age-related Macular Degeneration in clinical settings," Ophthalmology, vol. 121, No. 3, pp. 656-666, 2014.
Dayhoff, M.O. (ed.) Atlas of Protein Sequence and Structure, National Biomedical Research Foundation, Washington DC vol. 5, Suppl. 3, pp. 345-358. 1978.
De Haas et al., "Fc gamma receptors of phagocytes", Journal of Laboratory and Clinical Medicine, 126(4): dated Oct. 1995, pp. 330-341.
De Pascalis, R. et al., "Grafting of 'abbreviated' complementarity-determining regions containingspecificity-determining residues essential for ligand contact to engineer a less immunogenic humanized monoclonal antibody," J. Immunol., vol. 169, No. 6, pp. 3076-3084, Sep. 15, 2002.
Declaration of Didier G. Benoit, filed in U.S. Appl. No. 12/281,071 on Feb. 5, 2013 (signed Jan. 31, 2013), in 8 pages.
Declaration of Harvey N. Masonson, M.D., under 37 C.F.R., for U.S. Appl. No. 12/465,051, filed May 13, 2009, including Exhibits A, B, and C, signed Jul. 6, 2011, in 50 pages.
Declaration of Stephen A. Charles under 37 CFR 1.132 filed in U.S. Appl. No. 13/959,563, dated Dec. 6, 2013, in 20 pages.
Dillon et al., "Structural and functional characterization of disulfide isoforms of the human IgG2 subclass," The Journal of Biological Chemistry, vol. 283, No. 23, pp. 16206-16215, 2008.
Ding, J.L. et al., "A new era of pyrogen testing," Trends in Biotechnology, vol. 19, Issue 8, pp. 277-281, Aug. 1, 2001.
Do, Diana, "Phase 1 First-In-Human Study of KSI-301: A Novel Anti-VEGF Antibody BiopolymerConjugate with Extended Durability," Powerpoint, Angiogenesis, Exudation and Degeneration 2019, Presented on Feb. 9, 2019 in 21 pgs.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Drolet et al., "Pharmacokinetics and Safety of an Anti-Vascular Endothelial Growth Factor Aptamer(NX1838) Following Injection into the Vitreous Humor of Rhesus Monkeys," 2000, Pharm Res. 17:1503-1510.
Du et al. "pH-Sensitive Vesicles based on a Biocompatible Zwitterionic Diblock Copolymer" J. Am. Chem. Soc., Dec. 1, 2005, 127, 17982-17983.
Dugel, Pravin, "Antibody Biopolymer Conjugates: a Novel Scientifc Approach and Platform forExtended-Durability Retinal Medicines," Powerpoint, presented at the American Society of Retina Specialists Annual Meeting on Jul. 27, 2019 in 19 pgs.
Dugel, Pravin, "Extended durability in exudative retinal diseases using a new class ofmolecules: novel andti-VEGF antibody biopolymer conjugate KSI-301," powerpoint , presented at the EURetina 2019 Congress on Sep. 8, 2019 in 22 pgs.
Dugel, Pravin, "Novel andti-VEGF antibody biopolymer conjugate KSI-301 with potential for extendeddurability in retinal vascular diseases," PowerPoint , presented at the EURetina 2019 Congress on Sep. 15, 2019 in 22 pgs.
Duysen, E.G. et al., "Production of ES1 Plasma Carboxylesterase Knockout Mice for ToxicityStudies", Chemical Research in Toxicology, Nov. 2011, vol. 24(11), pp. 1891-1898 (author's manuscript copy).
Dvorak, et al., "Vascular Permeability Factor/Vascular Endothelial Growth Factor and the Significance of Microvascular Hyperpermeability in Angiogenesis," 1999, Curr Top Microbiol Immunol, 237: 97-132.
Edelman et al., "The covalent structure of an entire yG immunoglobulin molecule," Proceedings of the National Academy of Sciences, vol. 63, pp. 78-85, May 1, 1969.
Edwards et al., "The Remarkable Flexibility of the Human Antibody Repertoire; Isolation of Over One Thousand Different Antibodies to a Single Protein, BLyS", J. Mol. Biol., vol. 334, pp. 103-118, 2003.
Ellman, G. et al., "A new and rapid colorimetric determination of acetylcholinesterase activity," Biochemical Pharmacology, vol. 7, Issue 2, pp. 88-95, Jul. 1961.
Engelgau, M. et al. Evolving Diabetes Burden in the United States. Ann of Int Med. 140 (11): 945-951, 2004.
Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Exhibit D filed in U.S. Appl. No. 12/281,071 on Feb. 4, 2013, in 1 page.
Exhibit E filed in U.S. Appl. No. 12/281,071 on Feb. 4, 2013, in 1 page.
Fan, Q. et al., "Preclinical evaluation of Hematide, a novel erythropoiesis stimulating agent, for the treatment of anemia", Experimental Hematology, 2006, vol. 34, pp. 1303-1311.
Fares, F.A. et al., "Design of a long-acting follitropin agonist by fusing the C-terminal sequence of thechorionic gonadotropin beta subunit to the follitropin beta subunit," Proc Natl Acad Sci USA, vol. 89, No. 10, pp. 4304-4308, May 15, 1992.
Ferrara, et al. "Development of Ranibizumab, An Anti-Vascular Endothelial Growth Factor AntigenBinding Fragment, as Therapy for Neovascular Age-Related Macular Degeneration", Retina, The Journal of Retinal and Vitreous Disease, vol. 26, Issue No. 8, pp. 859-870, (2006).
Ferrara, et al., "The Biology of VEGF and its Receptors", Nature Medicine, vol. 9 No. 6, pp. 669-676, (2003).
Ferrara, N. et al., "Discovery and development of bevacizumab, an anti-VEGF antibody for treating cancer," Nature Reviews Drug Discovery, vol. 3, pp. 391-400, May 2004.
Ferrara, N. et al., "The Biology of Vascular Endothelial Growth Factor," Endocrine Reviews, vol. 18, No. 1, pp. 4-25, (1997).

(56) References Cited

OTHER PUBLICATIONS

Findeis et al., "Targeted delivery of DNA for gene therapy via receptors" Trends Biotechnol., 1993, 11: pp. 202-205.
Finkelstein A.V. et al., *Protein Physics: a course of lectures with color and stereoscopic illustrations and training problems*, 4th ed., 2012, Moscow, p. 23.
Fiske, M. et al., "Method for reducing endotoxin in Moraxella catarrhalis UspA2 protein preparations,"Journal of Chromatography B: Biomedical Sciences and Applications, vol. 753, Issue 2, pp. 269-278, Apr. 5, 2001.
Folkman, J., "Angiogenesis: an organizing principle for drug discover?" Nature Reviews, Drug Discovery, vol. 6, pp. 273-286, Apr. 2007.
Fontaine et al., "Long-Term Stabilization of Maleimide-Thiol Conjugates," Bioconjugate Chem., vol. 26, pp. 145-152, 2015.
Foster, Graham R., "Pegylated interferons for the treatment of chronic Hepatitis C," Drugs, vol. 70, Issue 2, pp. 147-165, Jan. 2010.
Friedman, D.S. et al., "Prevalence of age-related macular degeneration in the United States," Arch. Ophthalmol., vol. 122, No. 4, pp. 564-572, Apr. 2004.
Fusion Importance of Order, Experimental Data provided by Applicant in Proceedings of European Application No. EP 16713194.5 filed Dec. 10, 2018, in 2 pages.
Gaudreault et al., "Preclinical Pharmacokinetics of Ranibizumab (rhuFabV2) after a Single Intravitreal Administration", IOVS, Feb. 2005, vol. 46, No. 2, pp. 726-733.
Gaudreault et al., "Pharmacokinetics and retinal distribution of ranibizumab, a humanized antibodyfragment directed against VEGF-A following intravitreal administration in rabbits," Nov. 2007 Retina vol. 27, Issue 9, pp. 1260-1266.
Gauthier, M. et al., "Peptide/protein-polymer conjugates: synthetic strategies and design concepts", Chemical Communications, 2008, pp. 2591-2611.
Gawlak, G. et al., "Chronic high-magnitude cyclic stretch stimulates EC inflammatory response viaVEGF receptor 2-dependent mechanism", AJP Lung Cellular and Molecular Physiology, Mar. 2016, vol. 310(11), pp. L1062-L1070.
Geng, J. et al. Site-Directed Conjugation of "Clicked" Glycopolymers To Form Glycoprotein Mimics: Binding to Mammalian Lectin and Induction of Immunological Function, J. Am. Chem. Soc., 2007, 129, pp. 15156-15163.
Gillies, E. R. et al., "Dendrimers and Dendritic Polymers in Drug Delivery," Drug Delivery today, Jan. 2005, vol. 10, No. 1, pp. 35-43.
Goel, N. et al., "Certolizumab pegol," mAbs, vol. 2, No. 2, pp. 137-147, Mar./Apr. 2010.
Goodson, R.J. et al., "Site-directed pegylation of recombinant interleukin-2 at its glycosylation site," Nature Biotechnology, vol. 8, pp. 343-346, 1990.
Gordon, M. et al., "Determination of the normality of cholinesterase solutions," Analytical Biochemistry, vol. 85, Issue 2, pp. 519-527, Apr. 1978.
Gorun, V. et al., "Modified Ellman procedure for assay of cholinesterases in crude enzymatic preparations," Analytical Biochemistry, vol. 86, Issue 1, pp. 324-326, May 1978.
Greene, T. W. et al., "Protective Groups In Organic Synthesis," 3rd Edition, John Wiley and Sons, Inc., New York, (1999). In 52 pages which includes only the Title Page and Table of Contents.
Gualberto, Antonio, "Brentuximab Vedotin (SGN-35), an antibody-drug conjugate for the treatmentof CD30-positive malignancies," Expert Opinion on Investigational Drugs, vol. 21, Issue 2, pp. 205-216, 2012.
Guyer et al., "Immunoglobulin Binding by Mouse Intestinal Epithelial Cell Receptors", The Journal of Immunology, 117(2): dated Aug. 1, 1976, pp. 587-893.
Haddleton, et al., "Phenolic Ester-Based Initiators for Transition Metal Mediated Living Polymerization," Macromolecules, (1999), 32, pp. 8732-8739.
Haishima, Y. et al. Estimation of uncertainty in kinetic-colorimetric assay of bacterial endotoxins, J Pharm Biomed Analysis, 32: 1, pp. 495-503, (2003).
Halekoh et al., "The R Package geepack for Generalized Estimating Equations," Jan. 2006, Journal of Statistical Software vol. 15, Issue 2, pp. 1-11.
Hamaguch, K., "Structure of Immunoglobulin", Biophysics and Physicobiology, 1979, vol. 19(2), pp. 29-35.
Haupt, H. et al., "Isolierung und physikalisch-chemische Charakterisierung der Cholinesterase ausHumanserum," Blut, vol. 14, Issue 2, pp. 65-75, Nov. 1966.
Hein J., 1990, Unified Approach to Alignment and Phylogenies pp. 626-645 Methods in Enzymology vol. 183, Academic Press, Inc., San Diego, CA.
Heise et al., "Starlike Polymeric Architectures by Atom Transfer Radical Polymerization: Templates forthe Production of Low Dielectric Constant Thin Films," Macromolecules, Jan. 17, 2000, 33:2346-2354.
Heise, et al., "Investigation of the Initiation Behavior of a Dendritic 12-Arm Initiator in Atom Transfer Radical Polymerization," Macromolecules, (2001), 34:11, pp. 3798-3801.
Herd, O. et al., "Palladium catalyzed P-C coupling—a powerful took for the syntheses of hydrophilic phosphines", Catalysis Today, 1998, vol. 42, pp. 413-420.
Heredia, et al., "In Situ Preparation of Protein-'Smart' Polymer Conjugates with Retention of Bioactivity," J. Am. Chem. Soc., (2005), 127, pp. 16955-16960.
Hermanson, G., *Bioconjugate Techniques*, Academic Press, 2nd ed., 2008, in 1233 pages.
Herold, T. et al., "Level of IL-6 predicts respiratory failure in hospitalized symptomatic COVID-19patients", medRxiv, Apr. 2020, in 7 pages. URL: https://www.medrxiv.org/content/10.1101/2020.04.01.20047381v2.
Higgins, D.G. and Sharp, P.M., "Fast and sensitive multiple sequence alignments on a microcomputer" CABIOS 5: dated 1989, pp. 151-153.
Hinton et al., "Engineered human OgG antibodies with longer serum half-lives in primates", Journal of Biological Chemistry, 279(8): dated Feb. 20, 2004 in 5 pages.
Hirayama, C. et al., "Chromatographic removal of endotoxin from protein solutions by polymer particles," Journal of Chromatography B, vol. 781, Issues 1-2, pp. 419-432, Dec. 5, 2002.
Hlavacek, W.S. et al., "Steric Effects on Multivalent Ligand Receptor Binding: Exclusion of Ligand Sites by Bound Cell Surface Receptors", Biophysical Journal, Jun. 1999, vol. 76(6), pp. 3031-3043.
Hoffmann, S. et al., "International validation of novel pyrogen tests based on human monocytoid cells," Journal of Immunological Methods, vol. 298, Issues 1-2, pp. 161-173, Mar. 2005.
Holash, J. et al. VEGF-Trap: A Vegf Blocker with Potent Antitumor Effects, PNAS, vol. 9, No. 17, pp. 11393-11398, (2002).
Holliger, P. et al., "Diabodies': small bivalent and bispecific antibody fragments," Proc. Natl. Acad. Sci. USA, vol. 90, No. 14, pp. 6444-6448, Jul. 15, 1993.
Hong, et al., "Preparation of Segmented Copolymers in the Presence of an Immobilized/Soluble Hybrid ATRP Catalyst System," Macromolecules, (2003), 36:1, pp. 27-35.
Hsu et al., "Differential N-Glycan Patterns of Secreted and Intracellular IgG Produced in Trichoplusia ni Cells" Journey of Biol. Chem. Vol. 272: dated 1997, pp. 9062-9070.
Huang, T. et al., "Cyclooxygenase-2 Activity Regulates Recruitment of VEGF-Secreting Ly6Chigh Monocytes in Ventilator-Induced Lung Injury", Internal Journal of Molecular Sciences, Apr. 2019, vol. 20(7), in 15 pages.
Huang, Y.J. et al., "Recombinant human butyrylcholinesterase from milk of transgenic animals toprotect against organophosphate poisoning," PNAS, vol. 104, No. 34, pp. 13603-13608, Aug. 21, 2007.
Huang, Y-S. et al., "Engineering a pharmacologically superior form of granulocyte-colony-stimulatingfactor by fusion with gelatin-like-protein polymer," European Journal of Pharmaceutics and Biopharmaceutics, vol. 74, Issue 3, pp. 435-441, Mar. 2010.
Humphreys et al., "Alternative antibody FAB' fragment PEGylation strategies: combination of strongreducing agents, disruption of the

(56) References Cited

OTHER PUBLICATIONS interchain disulphide bond and disulphide engineering," Protein Engineering, Design & Selection, vol. 20, No. 5, pp. 227-234, 2007.
Huston, James S., "Protein engineering of single-chain Fv analogs and fusion proteins," Methods of Enzymology, vol. 203, pp. 46-96, 1991.
Hwang et al., "Hepatic uptake and degradation of unilamellar sphingomyelin/cholesterol liposomes: akinetic study", Proceedings of the National Academy of Sciences of the United States of America, 77(7): dated Jul. 1980, pp. 4030-4034.
Inada, Y. et al., "Application of Polyethylene glycol-modified enzymes in biotechnological processes: organic solvent-soluble enzymes", TIBTECH, Jul. 1986, pp. 190-194.
Ishihara, K. et al., "Photoinduced graft polymerization of 2-methacryloyloxyethyl phosphorylcholine onpolyethylene membrane surface for obtaining blood cell adhesion resistance", Colloids Surf B Biointerfaces, Oct. 2000, vol. 18(3-4), pp. 325-335.
Ishikawa, K. et al., "Molecular mechanisms of subretinal fibrosis in age-related macular degeneration," Experimental Eye Research, vol. 142, pp. 19-25, Jan. 2016.
IUPAC Gold Book, "Random copolymer" [online], [retrieved on Nov. 21, 2017], in 2 pages. Retrieved from the Internet: <URL: https://goldbook.iupac.org/html/R/R05126.html>.
IUPAC Gold Book, "Random Copolymerization" [online], IUPAC Gold Book, [retrieved on Nov. 21, 2017], in 1 page. Retrieved from the Internet: <URL: https://goldbook.iupac.org/html/R/R05127.html>.
Ivens, I.A. et al., "PEGylated therapeutic proteins for hemophilia treatment; a review for haemophilia caregivers", Hemophilia, Jan. 2013, vol. 19, pp. 11-20.
Iwahashi, M. et al., "CDR substitutions of a humanized monoclonal antibody (CC49): contributions ofindividual CDRs to antigen binding and immunogenicity," Mol. Immunol. 36: Issue 15-16, 1079-1091, 1999.
Iwasaki, et al., "Platelet compatible blood filtration fabrics using a phosphorylcholine polymer having high surface mobility," Biomaterials, (2003), 24 pp. 3599-3604.
Iwasaki, Y. et al., "Preservation of platelet function on 2-methacryloyloxyethyl phosphorylcholine-graftpolymer as compared to various water-soluble graft polymers", Journal of Biomedical Materials Research, Jun. 2001, vol. 57(1), pp. 72-78.
Iwasaki, Yasuhiko et al., "Synthesis and Characterization of Amphiphilic Polyphosphates withhydrophilic graft chains and Cholesteryl Groups as Nanocarriers", Biomacromolecules, 2006, 7, 1433-1438.
Jaffe, G. et al., "Intraocular drug delivery," CRC Press, Mar. 2006 (Table of Contents only).
Jakubowski, et al., "Activators Regenerated by Electron Transfer for Atom Transfer Radical Polymerization of Styrene," Macromolecules, (2006), 39:1, pp. 39-45.
Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.
Janssen, Alzheimer Immunotherapy Research & Development, LLC, AAB-001 in Patients with Mild toModerate Alzheimer's Disease, Clinical Trials, gov, NIH, 2005, [retrieved on Jun. 19, 2012]. Retrieved from the Internet: <http://clinicaltrials.gov/ct2/show/NCT00112073?term=aab-001&rank=3>.
Jefferis et al., "Glycosylation of Antibody Molecules: Structural and Functional Significance", Antibody Engineering, vol. 65: dated 1997, pp. 111-128.
Jeon, et al., "Synthesis of High Molecular Weight 3-Arm Star PMMA by ARGET ATRP," Macromolecular, 17:4 pp. 240-244, (2009).
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.
Johnson et al., "Kabat Database and its applications: 30 years after the first variability plot", Nucleic Acids Research, 28(1): Jan. 1, 2000, pp. 214-218.
Jones, A., Analysis of Polypeptides and Proteins, Adv. Drug Delivery Rev. 10: pp. 29-90, (1993).
Joralemon et al., PEGylated Polymers For Medicine From Conjugation To Self-Assembled Systems, Chemical Communications, vol. 46, No. 9, pp. 1377, 2010.
Junghans, R.P., "Anti-Tac-H, a humanized antibody to the interleukin 2 receptor with new features forimmunotherapy in malignant and immune disorders," Cancer Research, vol. 50, pp. 1495-1502, Mar. 1, 1990.
Kabat, E.A. et al., "Sequences of proteins of immunological interest," in 10 pages, 1991 (Table of Contents only).
Kabat, E.A. et al., "Sequences of proteins of immunological interest," in 4 pages, 1987 (Table of Contents only).
Kadioglu, O. et al., "28—Targeting Angiogenesis by Therapeutic Antibodies", *Handbook ofTherapeutic Antibodies*, Stefan Dubel and Janice M. Reichert (Eds.), 2nd Edition, Aug. 2014, pp. 823-850.
Kallis, G.B. et al., "Differential reactivity of the functional sulfhydryl groups of cysteine-32 andcysteine-35 present in the reduced form of thioredoxin from *Escherichia coli*., The Journal of Biological Chemistry," vol. 255, No. 21, pp. 10261-10266, Nov. 10, 1980.
Kandori, K. et al., "Synthesis of positively charged calcium hydroxyapatite nano-crystals and theiradsorption behavior of proteins", Colloids and Surfaces B: Biointerfaces, vol. 73, Oct. 2009, pp. 140-145.
Kaner, R. J. et al., "Lung overexpression of the vascular endothelial growth factor gene inducespulmonary edema", American Journal of Respiratory Cell and Molecular Biology, Jun. 2000, vol. 22(6), pp. 657-664.
Kaplanek, R. et al., "Three-fold polyfluoroalkylated amines and isocyanates based on tris(hydroxymethyl)aminomethane (TRIS)", Journal of Fluorine Chemistry, 2007, vol. 128, pp. 179-183.
Kaplitt, "Long-term gene expression and phenotypic correction using adeno-associated virus vectors in the mammalian brain" Nature Genetics, 1994, 8:148.
Karmpaliotis, D. et al., "Angiogenic growth factors in the pathophysiology of a murine model ofacute lung injury", American Journal Of Physiology—Lung Cellular and Molecular Physiology, Sep. 2002, vol. 283(3), pp. L585-L595.
Katschke, K. et al., "Inhibiting Alternative Pathway Complement Activation by Targeting the Factor DExosite—Supplementary Material", The Journal of Biological Chemistry, Apr. 2012, vol. 287, No. 16, in 11 pages.
Katschke, K. et al., "Inhibiting Alternative Pathway Complement Activation by Targeting the Factor D Exosite", The Journal of Biological Chemistry, Apr. 2012, vol. 287, No. 16, po. 12886-12892.
Kempen, J, et al. The Prevalence of Diabetic Retinopathy Among Adults in the United States, Arch Opthalmol., vol. 122, pp. 532-563, (2004).
Kernt et al. "Improvement of Diabetic Retinopathy with Intravitreal Ranibizumab," Diabetes Research and clinical Practice, Feb. 5, 2013 (Feb. 5, 2013), vol. 100, No. 1, pp. 11-13. entire document.
Khandare, J. et al., "Polymer-drug conjugates: Progress in polymeric prodrugs", Progress in Polymer Science, Apr. 2006, vol. 31 (4), pp. 359-397.
Kim et al., "Identifying amino acid residues that influence plasma clearance of murine IgG1 fragments by site-directed mutagenesis", European Journal of Immunology, 24(3): dated Mar. 1994.
Kim, J.K. et al., "Localization of the site of the murine IgG1 molecule that is involved in binding to themurine intestinal Fc receptor", European Journal of Immunology, Oct. 1994, vol. 24(10), pp. 2429-2434.
Kimura, "Retroviral Delivery of DNA into the Livers of Transgenic Mice Bearing Premalignant and Malignant Hepatocellular Carcinomas" Human Gene Therapy, 1994, 5(7): pp. 845-852.
Kizhakkedathu, et al., "Synthesis of Well-Defined Environmentally Responsive Polymer Brushes by Aqueous ATRP," Macromolecules, (2004), 37:3, pp. 734-743.
Klein R, Klein BE, Jensen SC, Meuer SM. 1997. The five-year incidence and progression of age-related maculopathy: The Beaver Dam Eye Study. Ophthal. 104:7-21.

(56) References Cited

OTHER PUBLICATIONS

Kobayashi, M. et al., "Tribological properties of hydrophilic polymer brushes under wet conditions", The Chemical Record, vol. 10, pp. 208-216 (2010).
Kodiak KSI-301 Wet AMD Phase 2b/3 Study Top-line Results, dated Feb. 23, 2022, in 17 pages.
Kohler et al., "Continuous cultures of fused cells secreting antibody of predefined specificity", Nature, vol. 256: dated 1975, pp. 495-497.
Kong, et al., "Platelet-Derived Growth Factor-D Overexpression Contributes to Epithelial-Mesenchymal Transition of PC3 Prostate Cancer Cells," Jun. 2008, Stem Cells vol. 26, Issue 6 pp. 1425-1435.
Kostelny, S.A. et al., "Formation of a bispecific antibody by the use of leucine zippers," J. Immunol., vol. 148, No. 5, pp. 1547-1553, Mar. 1, 1992.
Krinner, E. et al., "A highly stable polyethylene glycol-conjugated human single-chain antibodyneutralizing granulocyte-macrophage colony stimulating factor at low nanomolar concentration", Protein Engineering, Design & Selection, 2006, vol. 19, No. 10, pp. 461-470.
Kuhnert, F. et al. "Soluble receptor-mediated selective inhibition of VEGFR and PDGFR_ signaling during physiologic and tumor angiogenesis", PNAS, vol. 105, No. 29, pp. 10185-10190, (2008).
Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.
Kumar, A. et al., "Platelet-derived growth factor-DD targeting arrests pathological angiogenesis bymodulating glycogen synthase kinase-3B phosphorylation," The Journal of Biological Chemistry, vol. 285, No. 20, pp. 15500-15510, May 14, 2010.
Kunik et al., "Paratome: an online tool for systematic identification of antigen-binding regions in antibodies based on sequence or structure", Nucleic Acids Research, vol. 40: Jun. 6, 2012, W521-524.
Kwiatdowski, et al., "High Molecular Weight Polymethacrylates by Aget Atrp under High Pressure," Macromolecules, (2008), 41:4, pp. 1067-1069.
Lafaut et al., "Clinicopathological correlation in exudative age related macular degeneration:histological differentiation between classic and occult choroidal neovascularisation," Br J Ophthalmol, vol. 84, pp. 239-243, 2000.
Lazar et al., "Engineered antibody Fc variants with enhanced effector function", Proc Natl Acad Sci U S A, 103(11): dated Mar. 14, 2006 in 6 pages.
Le Cras, T. et al., "VEGF causes pulmonary hemorrhage, hemosiderosis, and air space enlargementin neonatal mice", American Journal Of Physiology—Lung Cellular And Molecular Physiology, Jul. 2004, vol. 287(1), pp. L134-L142.
Lee, Ernes C., "Clinical manifestations of sarin nerve gas exposure," J. Am. Med. Assoc., vol. 290, No. 5, pp. 659-662, Aug. 6, 2003.
Lee, Vincent H.L., "Peptide and Protein Drug Delivery," CRC Press, 1991 (Table of Contents only).
Lefranc et al., "IMGT unique numbering for immunoglobulin and T cell receptor variable domains and Ig superfamily V-like domains", Developmental and Comparative Immunology, vol. 27: dated 2003, pp. 55-77.
Lena, et al., "Investigation of metal ligand affinities of atom transfer radical polymerization catalysts with a quadrupole ion trap," Dalton Transactions, (2009), 41, pp. 8884-8889.
Lenting, P. et al., "The Life Cycle of Coagulation Factor VIII in View of Its Structure and Function", Blood, Dec. 1998, vol. 92, pp. 3983-3996.
Leong, S. et al., "Adapting pharmacokinetic properties of a humanized anti-interleukin-8 antibody fortherapeutic applications using site-specific pegylation", Cytokine, Nov. 2001, vol. 16(3), pp. 106-119.
Lewis, et al., "Crosslinkable coatings from phosphorylcholine-based polymers," Biomaterials, (2001), 22, pp. 99-111.
Lewis, et al., "Poly(2-methacryloyloxyethyl phosphorylcholine) for Protein Conjugation," Bioconjugate Chem., (2008), 19:11, pp. 2144-2155.
Licciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lin, W. et al., "A novel zwitterionic copolymer with a short poly(methyl acrylic acid) block for improving both conjugation and separation efficiency of a protein without losing its bioactivity", Journal of Materials Chemistry B. May 21, 2013, vol. 1, No. 19, pp. 2482-2488. See abstract; and p. 2487.
Lindley, H., "A study of the kinetics of the reaction between thiol compounds and chloroacetamide," Biochem J., vol. 74, pp. 577-584, Mar. 1960.
Liu, et al., "Syntheses and Micellar Properties of Well-Defined Amphiphilic $AB_2$ and $A_2B$ Y-Shaped Miktoarm Star Copolymers of ϵ-Caprolactone and 2-(Dimethylamino) ethyl Methacrylate," Journal of Polymer Science: Part A: Polymer Chemistry, DOI 10.1002/pola, published online in Wiley InterSciences (www.intersience.wiley.com), Sep. 22, 2006; accepted Nov. 23, 2006.
Lloyd et al., "Food and Drug Administration approval process for ophthalmic drugs in the U.S.," May 2008, Current Opinion Ophthalmology, vol. 19 Issue 3 pp. 190-194.
Lloyd et al., "Modeling the human immune response: performance of a $10^{11}$ human antibodyrepertoire against a broad panel of therapeutically relevant antigens", Protein Engineering Design & Selection, vol. 22, No. 3, pp. 159-168, 2009.
Lockridge, O. et al., "Complete amino acid sequence of human serum cholinesterase," The Journal of Biological Chemistry, vol. 262, pp. 549-557, Jan. 15, 1987.
Lockridge, O. et al., "Large scale purification of butyrylcholinesterase from human plasma suitable for injection into monkeys; A potential new therapeutic for protection against cocaine and nerve agent toxicity, The Journal of Medical, Chemical, Biological, and Radiological Defense," 3:nimhs5095, doi: 10.1901/jaba.2005.3-nihms5095, 2005.
Lucentis ranibizumab (reb) Name of the Medicine, Active ingredient Ranibizumab, Product Information Sheet, in 30 pages, based on CDS dated Aug. 30, 2013.
Lund, L. et al., "Novel peptide ligand with high binding capacity for antibody purification", Journal of Chromatography A, Feb. 2012, vol. 1225, pp. 158-167.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.
Luxon, B. et al., "Pegylated interferons for the treatment of chronic hepatitis C infection," Clinical Therapeutics, vol. 24, Issue 9, pp. 1363-1383, Sep. 2002.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mabry, R. et al., "A dual-targeting PDGFRβ/VEGF-A molecule assembled from stable antibodyfragments demonstrates anti-angiogenic activity in vitro and in vivo", Landes Bioscience, vol. 2, Issue 2, pp. 20-34 (2010).
MacCallum, R. et al., Antibody-Antigen Interactions: Contact Analysis and Binding Site Topography, J. Mol Biol., vol. 262, pp. 732-745, (1996).
Magalhaes et al., "Methods of Endotoxin Removal from Biological Preparations: a Review," J. Pharm Pharmaceut Sci., vol. 10, No. 3, pp. 388-404, 2007.
Makabe et al., "Thermodynamic Consequences of Mutations in Vernier Zone Residues of aHumanized Anti-human Epidermal

(56) References Cited

OTHER PUBLICATIONS

Growth Factor Receptor Murine Antibody, 528", Journal of Biological Chemistry, vol. 283: dated Jan. 11, 2008, pp. 1156-1166.
Mantovani, et al., "Design and Synthesis of N-Maleimido-Functionalized Hydrophilic Polymers viaCopper-Mediated Living Radical Polymerization: A Suitable Alternative to PEGylation," J. Am. Chem. Soc., (2005), 127, pp. 2966-2973.
Marticorena, J et al., "Sterile endophthalmitis after intravitreal injections," Mediators of Inflammation, vol. 2012, 6 pages, (2012).
Martin et al., "Modeling antibody hypervariable loops: A combined algorithm", Proc. Natl. Acad. Sci. USA, vol. 86: dated Dec. 1989, pp. 9268-9272.
Masson, P. et al., "Expression and Refolding of Functional Human Butyrylcholinesterase from *E. Coli*", Multidisciplinary Approaches to Cholinesterase Functions, New York, pp. 49-52, 1992.
Matyjaszewski, et al., "Diminishing catalyst concentration in atom transfer radical polymerization with reducing agents," PNAS, (Oct. 17, 2006), 103:42, pp. 15309-15314.
Matyjaszewski, K. et al., "Controlled Radical Polymerization in the Presence of Oxygen", Marcomolecules, 1998, vol. 31(17), pp. 5967-5969.
Mayadunne, R. et al. Living Free Radical Polymerization with Reversible Addition-FragmentationChain Transfer (RAFT Polymerization): Approaches to Star Polymers, Macromolecules, vol. 36, pp. 1505-1513, (2003).
McCafferty et al., "Phage antibodies: filamentous phage displaying antibody variable domains", Nature, vol. 348: dated 1990, pp. 552-554.
McPherson, D. et al., "Production and Purification of a Recombinant Elastomeric Polypeptide, G-(VPGVG) 19-VPGV, from *Escherichia coli*," Biotechnology Process, vol. 8, Issue 4, pp. 347-352, Jul./Aug. 1992.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Medford, A. R. L. et al., "Vascular endothelial growth factor (VEGF) in acute lung injury (ALI) andacute respiratory distress syndrome (ARDS): paradox or paradigm?", Thorax, Jul. 2006, vol. 61(7), pp. 621-626.
Mei, B. et al., "Rational design of a fully active, long-acting PEGylated factor VIII for hemophilia A treatment", Thrombosis and Hemostasis, Jul. 2010, vol. 116(2), pp. 270-279.
Meng, X. et al. New Generation Recombinant hBuChe-FC Fusion with In-Vivo Performance Equivalent to Gold Standard Plasma-Derive hbuChe-A First-in-Class Broad Spectrum Bioscavenger that is Sustainable, Scalable, and Highly Cost-Effective on a Troop-Equivalent-Dose (TED) Basis, 2012, in 1 page.
Meng, X. et al., "Efficacy and safety of bevacizumab treatment for refractory brain edema: Case report", Medicine (Baltimore), Nov. 2017, vol. 96(44), in 4 pages.
Merrifield, R. B., "Solid Phase Peptide Synthesis: I. The Synthesis of a Tetrapeptide", Journal of the American Chemical Society, Jul. 1963, vol. 85, pp. 2149-2154.
Mesquida, M. et al., "Interleukin-6 blockade in ocular inflammatory diseases", Clinical and Experimental Immunology, Apr. 2014, vol. 176, No. 3, pp. 301-309.
Millard, C.B. et al., "Design and expression of organophosphorus acid anhydride hydrolase activity in human butyrylcholinesterase," Biochemistry, vol. 34, No. 49, pp. 15925-15933, 1995.
Milliporesigma, "Papain" [online], [retrieved on Aug. 10, 2021], in 4 pages. Retrieved from theInternet: <URL: https://www.sigmaaldrich.com/US/en/technical-documents/technical-article/research-and-disease-areas/metabolism-research/papain>.
Min, et al., "Use of Ascorbic Acid as Reducing Agent for Synthesis of Well-Defined Polymers by ARGET ATRP," Macromolecules, (2007), 40:6, pp. 1789-1791.
Miyamoto, D. et al., "Effect of water-soluble phospholipid polymers conjugated with papain on the enzymatic stability", Biomaterials, 2004, vol. 25, pp. 71-76.
Mones, Jordi, "Inhibiting VEGF and PDGF to Treat AMD", http://www.reviewofophthalmology.com/content/d/retinal_insider/c/29979/#stash.fJePfjQ4.dpuf, Spain, Sep. 9, 2011.
Morris, G.E., "Preface, Contents, and Contributors of Epitope Mapping Protocols" in: Methods in Molecular Biology (New Jersey, Humana Press, 1996) pp. v-xiii.
Myers, E.W. and Muller W., "Optimal alignments in linear space" CABIOS 4: dated 1988, pp. 11-17.
Neuberger, M., "Generating high-avidity human Mabs in mice," Nature Biotechnology, vol. 14, pp. 826, 1996.
Ng, et al., "Successful Cu-Mediated Atom Transfer Radical Polymerization in the Absence of Conventional Chelating Nitrogen Ligans," Macromolecules, (2010), 43:2, pp. 592-594.
NOF Corporation, "Life Science Products—Product Information—Lipidure® (MPC polymer)" [online],[retrieved on Sep. 18, 2020], in 3 pages. Retrieved from the internet: <URL: https://www.nof.co.jp/business/life/product01.html.
Nork et al., "Prevention of Experimental Choroidal Neovascularization and Resolution of Active Lesions by VEGF trap in Nonhuman Primates," 2011, Arch Opthalmol, 129(8):1042-1052.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Ong, K. et al., "A rapid highly-sensitive endotoxin detection system," Biosensors and Bioelectronics, vol. 21, Issue 12, pp. 2270-2274, Jun. 15, 2006.
Östberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variabledomains while preserving their ligand-binding properties," Molecular Immunology, vol. 28, Issues 4-5, pp. 489-498, Apr.-May 1991.
Pakula, et al., "Genetic Analysis of Protein Stability and Function," Annual Reviews of Genetics, vol. 23, pp. 289-310, Dec. 1989.
Palma, et al., "A new bisphosphonate-containing $^{99}$mTc(I) tricarbonyl complex potentially useful as bone-seeking agent: synthesis and biological evaluation," J Biol Inorg Chem, 12:667-679, (2007).
Pan, C. et al. Comparison of Long-Acting Bevacizumab Formulations in the Treatment of Choroidal Neovascularization in a Rat Model, Journal of Ocular Pharmacology and Therapeutics., vol. 27, No. 3, pp. 219-224, (2011).
Papadopoulos et al., "Binding and neutralization of vascular endothelial growth factor (VEGF) andrelated ligands by VEGF Trap, ranibizumab and bevacizumab," Angiogenesis, vol. 15, pp. 171-185, 2012.
Park, S. J. et al., "Intraocular Pharmacokinetics of Intravitreal Aflibercept (Eylea) in a Rabbit Model", Investigative Ophthalmology & Visual Science, May 2016, vol. 57(6), pp. 2612-2617.
Pasut, et al., "Protein peptide and non-peptide drug PEGylation for therapeutic application," Expert Opin. Ther. Patents, 14(6) 859-894 (2004).
Patel, S. et al. "Phase 1 first-in-human study of KSI-301: a novel anti-VEGF antibody biopolymerconjugate with extended durability", Investigative Ophthalmology & Visual Science, Jul. 2019, vol. 60(9), p. 3670 (abstract only).
Patel, S. et al., "Phase 1 First-In-Human Study of KSI-301: A Novel Anti-VEGF Antibody BiopolymerConjugate with Extended Durability Following a Single Dose Administration (3670)", Kodiak Poster, 2019, in 1 page.
Paul, "Fv Structure and Diversity in Three Dimensions," Fundamental Immunology, 1993, 3rd Edition, pp. 292-295.
Paul, W., Fundamental Immunology, 2nd ed. Raven Press, N.Y., 1989 (Table of Contents only).
Pennock, S. et al Vascular Endothelial Growth Factor A Competitively Inhibits Platelet-DerivedGrowth Factor (PDGF)-Dependent Activation of PDGF Receptor and Subsequent Signaling Events and Cellular Responses, Molecular and Cell Biology, vol. 32, No. 2, pp. 1955-1966, (2012).

(56) References Cited

OTHER PUBLICATIONS

Pepinsky et al., "Improved Pharmacokinetic Properties of a Polyethylene Glycol-Modified Form ofInterferon-b-1a with Preserved in Vitro Bioactivity", J. Pharmco. Exp. Therp., 2001, vol. 297(3), pp. 1059-1066.
Perederni, et al., "Endocrine Ophthalmopathy," Eye Diseases 5. Complete reference, Feb. 6, 2008, pp. 154-158, 162.
Perruchot, C. et al. "Synthesis of Well-Defined, Polymer-Grafted Silica Particles by Aqueous ATRP", Langmuir, 2001, vol. 17(15), pp. 4479-4481.
Petsch, D. et al., "Endotoxin removal from protein solutions," Journal of Biotechnology, vol. 76, Issues 2-3, pp. 97-119, Jan. 21, 2000.
Philip, "Efficient and sustained gene expression in primary T lymphocytes and primary and culturedtumor cells mediated by adeno-associated virus plasmid DNA complexed to cationic liposomes." Mol. Cell Biol., 1994, 14(4): pp. 2411-2418.
Piatesi, A. et al., "Immunological Optimization of a Generic Hydrophobic Pocket for High Affinity Hapten Binding and Diels-Alder Activity", ChemBio Chem, 2004, vol. 5, pp. 460-466.
Piche-Nicholas, N. M. et al., "Changes in complementarity-determining regions significantly alter IgG binding to the neonatal Fc receptor (FcRn) and pharmacokinetics", MABS, 2018, vol. 10, No. 1, pp. 81-94.
Piedmonte, D. et al., "Formulation of Neulasta® (pegfilgrastim)," Advanced Drug Delivery Reviews, vol. 60, Issue 3, pp. 50-58, Jan. 3, 2008.
Pietrasik, et al., "Synthesis of High Molecular Weight Poly(styrene-co-acrylonitrile) Copolymers with Controlled Architecture," Macromolecules, (2006), 39:19, pp. 6384-6390.
Poljak, R. "Production and structure of diabodies," Structure, vol. 2, Issue 12, pp. 1121-1123, Dec. 1994.
Pratt, et al. End-Functionalized Phosphorycholine Methacrylate and Their Use in Protein Conjugation, Biomacromolecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.
Ravetch et al., "FC Receptors," 1991, Ann. Rev. Immunol., vol. 9:457-92.
Ray et al., "Platelet-derived Growth Factor D, Tissue-specific Expression in the Eye, and a Key Role in Control of Lens Epithelial Cell Proliferation," Mar. 2005, J Biol Chem., vol. 280, No. 9 pp. 8494-8502.
RecName: Full=Complement factor D; EC=3.4.21.46; AltName: Full=Adipsin; AltName: Full=C3 convertase activator; AltName: Full=Properdin factor D; Flags: Precursor, UNIPROT, Jul. 21, 1986(Jul. 21, 1986), XP002614847, [retrieved on Jul. 21, 1986]. This appears to refer to a web page, which indicates that the page was last modified on Nov. 30, 2010. Contents of the web page may have been available at an earlier date.
*Regeneron Pharmaceuticals Inc*. vs. *Bayer Pharma AG* Approved Judgment dated Feb. 21, 2013.
Regillo, C. et al., "Randomized, double-masked, sham-controlled trial of ranibizumab for neovascularage-related macular degeneration: PIER Study Year 1," American Journal of Ophthalmology, vol. 145, Issue 2, pp. 239-248, Feb. 2008.
Regula, Jorg T. et al., "Targeting key angiogenic pathways with a bispecific CrossMab, optimized for neovascular eye diseases, " EMBO Molecular Medicine (online), vol. 8, No. 11, Oct. 14, 2016, pp. 1265-1288.
Roberts et al., "Chemistry for Peptide and Protein PEGylation," Advanced Drug Delivery Reviews 2002 54:459-476.
Roberts, W.G .et al., "Increased microvascular permeability and endothelial fenestration induced by vascular endothelial growth factor," Journal of Cell Science, vol. 108, pp. 2369-2379, (1995).
Robinson, D.F, "Comparison of Labeled Trees with Valency Three," Journal of Combinational Theory 11: pp. 105-119 (1971).
Robinson, K. et al. Controlled Polymerization of 2-Hydroxyethyl Methacrylate by ATRP at Ambient Temperature, Macromolecules, vol. 34, pp. 3155-3158, (2001).
Roitt, I. M. et al., *Immunology*, Fifth Ed., 2000, Publishing House "Mir", p. 150.
Roitt, I.M., "Immunology—Second Edition", Gower Medical Publishing, 1989, pp. 5.8, 5.9.
Rosenfeld, P. et al., "Ranibizumab for neovascular age-related macular degeneration," The New England Journal of Medicine, vol. 355, No. 14, pp. 1419-1431, Oct. 5, 2006.
Rudikoff, S. et al., Single Amino Acid Substitution Altering Antigen-Binding Specificity, Proc Natl. Acad. Sci. USA, vol. 79, pp. 1979-1983, (1982).
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Rycroft, B.W., "Penicillin and the control of deep intra-ocular infection," British J. Ophthalmol, vol. 29, No. 2, pp. 57-87, Feb. 1945.
Saidi, A. et al., "Combined targeting of interleukin-6 and vascular endothelial growth factor potently inhibits glioma growth and invasiveness", International Journal of Cancer, Sep. 2009, vol. 125, No. 5, pp. 1054-1064.
Saitou, N., Nei, M., "The neighbor-joining method: a new method for reconstructing phylogenetic trees." Mol. Biol. Evol. Vol. 4: dated 1987, pp. 406-425.
Sakaki, et al., "Stabilization of an antibody conjugated with enzyme by 2-methacryloyloxyethylphosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Samudrala et al., "Ab initio protein structure prediction using a combined hierarchical approach", Proteins, Structure, and Genetics Suppl, 37(S3): dated 1999, pp. 194-198.
Sato, A. et al., "Therapeutic peptides: technological advances driving peptides into development", Current Opinion in Biotechnology, 2006, vol. 17, pp. 638-642.
Sayers, C. et al., "The Reduced Viscosity of PolyPEG® Compared with Linear PEG" [poster],Warwick Effect Polymers Ltd, [retrieved on Feb. 11, 2009], in 1 page. Retrieved from the internet: <URL: http:www.wep-ltd.co.uk>.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Second Supplemental Declaration of Stephen A. Charles filed in U.S. Appl. No. 13/959,563, dated Jul. 22, 2014, in 3 pages.
Seo et al., "Conformational Recovery and Preservation of Protein Nature from Heat-Induced Denaturation by Water-Soluble Phospholipid Polymer Conjugation," Biomaterials, vol. 30, 2009, pp. 4859-4867.
Serruys, P. et al., "Effect of an anti-PDGF-beta-receptor-blocking antibody on restenosis in patients undergoing elective stent place-

(56) References Cited

OTHER PUBLICATIONS ment", International Journal of Cardiovascular Interventions, 2003, vol. 5, No. 4, pp. 214-222 (abstract only).
Shen, B.Q. et al., "Conjugation site modulates the in vivo stability and therapeutic activity of antibody-drug conjugates," Nature Biotechnology, vol. 30, pp. 184-189, 2012.
Shen, G. et al., "Relief Effect of Bevacizumab on Severe Edema Induced by Re-irradiation in Brain Tumor Patients", Chinese Medical Journal (Engl.), Aug. 2015, vol. 128(15), pp. 2126-2129.
Shi, C. et al., "VEGF Production by Ly6C+high Monocytes Contributes to Ventilator-Induced Lung Injury", PLoS One, Oct. 2016, vol. 11(10), in 19 pages.
Shim et al., "Structures of a platelet-derived growth factor/propeptide complex and a platelet-derived growth factor/receptor complex," PNAS, vol. 107, No. 25, pp. 11307-11312, 2010.
Simakova, A. et al., "Aqueous Arget Atrp", Macromolecules, Aug. 2012, vol. 45(16), pp. 6371-6379.
Sinapis et al., "Pharmacokinetics of intravitreal bevacizumab (Avastin®) in rabbits," 2011, Clinical Ophthalmology 5:697-704.
Sletten, E. et al., "Bioorthogonal Chemistry: Fishing for Selectivity in a Sea of Functionality", Angewandte Chemie International Edition, Dec. 2009, vol. 48, pp. 6974-6998.
Songsivilai, S. et al., "Bispecific antibody: a tool for diagnosis and treatment of disease," Clin Exp. Immunol., vol. 79, No. 3, pp. 315-321, Mar. 1990.
Stenzel, Martina H., "Bioconjugation using thiols: Old chemistry rediscovered to connect polymers with nature's building blocks," ACS Macro letters, vol. 2, No. 1, pp. 14-18, 2013.
Strandman, S. et al., "Effect of ligand on the synthesis of star polymers by resorcinarene-basedATRP initiators", Journal of Polymer Science Part A: Polymer Chemistry, Aug. 2005, vol. 43, pp. 3349-3358.
Strohl, William R, "Optimization of Fc-mediated effector functions of monoclonal antibodies," Dec. 2009, Curr Opin. In Biotech vol. 20 Issue 6, pp. 685-691.
Struble et al., "Pharmacokinetics and ocular tissue penetration of VEGF Trap after intravitreal injections in rabbits," Acta Ophthalmologica, Sep. 2008, vol. 86, Issue s243.
Stuttfeld et al., "Structure and function of VEGF receptors," Life, vol. 61, No. 9, pp. 915-922, 2009.
Supplemental Declaration of Stephen A. Charles filed in U.S. Appl. No. 13/959,563, dated May 20, 2014, in 3 pages.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.
Tao, L. et al., "Branched polymer-protein conjugates made from mid-chain-functional P (HPMA)",Biomacromolecules, 2009, vol. 10, No. 10, pp. 2487-2851. See abstract; pp. 2847 and 2850; and scheme 2.
The OpenSAFELY Collaborative et al., "OpenSAFELY: factors associated with COVID-19-related hospital death in the linked electronic health records of 17 million adult NHS patients", medRxiv, May 7, 2020, in 22 pages (pre-print article not yet peer-reviewed). URL: https://www.medrxiv.org/content/10.1101/2020.05.06.20092999v1.
Thickett, D. et al., "Vascular Endothelial Growth Factor May Contribute to Increased Vascular Permeability in Acute Respiratory Distress Syndrome", American Journal of Respiratory and Critical Care Medicine, Nov. 2001, vol. 164(9), pp. 1601-1605.
Tonkinson, J. et al., "New Drugs: Antisense Oligodeoxynucleotides as Clinical Therapeutic Agents," Cancer Investigation, vol. 14, No. 1, pp. 54-65, 1996.
Tsukamoto et al., "Combined Blockade of IL6 and PD-1/PD-L1 Signaling Abrogates MutualRegulation of Their Immunosuppressive Effects in the Tumor Microenvironment", Cancer Research, 78(17): dated Sep. 2018 in 12 pages.
Ueda, et al., "Preparation of 2-Methacryloyloxyethyl Phosphorycholine Copolymers with Alkyl Methacrylates and their Blood Compatibility," Polymer Journal, vol. 24, No. 11, pp. 1259-1269 (1992).
Umana et al., "Engineered glycoforms of an antineuroblastoma IgG1 with optimized antibody-dependent cellular cytotoxic activity." 1999, Nature Biotech. 17:176-180.
Uniprot, "UniProtKB-G3R0B5 (G3R0B5_GORGO)" [online], Dec. 9, 2015 [retrieved on Jan. 10, 2016], in 6 pages. Retrieved from the internet: <URL: http://www.uniprot.org/uniprot/G3ROB5>.
Uutela et al., "PDFG-D induces macrophage recruitment, increased interstitial pressure, and blood vessel maturation during angiogenesis," Blood, vol. 104, No. 10, pp. 3198-3204, Nov. 15, 2004.
Vafa, O. et al. An Engineered FC Variant of an IG Eliminates All Immune Effector Functions via Structural Perturbations, Methods, vol. 65, pp. 114-126, (2014).
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Venditto, et al., "Cancer Therapies Utilizing the Camptothecins: A Review of the *in Vivo* Literature," Molecular Pharmaceutics, vol. 7, No. 2, pp. 307-349 (2010).
Veronese, Francesco M., "Peptide and protein PEGylation: a review of problems and solutions," Biomaterials, vol. 22, Issue 5, pp. 405-417, Mar. 1, 2001.
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Wang, X. et al., "Disulfide scrambling in IgG2 monoclonal antibodies: Insights from molecular dynamics simulations," Pharmaceutical Research, vol. 28, Issue 12, pp. 3128-3144, Dec. 2011.
Warnecke, A. et al., "Synthesis and Biological Activity of Water-Soluble Maleimide Derivatives of the Anticancer Drug Carboplatin Designed as Albumin-Binding Prodrugs", Bioconjugate Chemistry, Oct. 2004, vol. 15, pp. 1349-1359.
Warwick Effect Polymers, PowerPoint presentation, "Polymers for the Healthcare and Specialty Materials Industries," Jan. 2009, pp. 1-29.
Watanabe, M. et al., "Genetic Delivery of Bevacizumab to Suppress Vascular Endothelial Growth Factor-Induced High-Permeability Pulmonary Edema", Human Gene Therapy, Jun. 2009, vol. 20(6), pp. 598-610.
Wiesmann, C. et al., "Crystal structure at 1.7 A resolution of VEGF in complex with domain 2 of the Flt-1 receptor", Cell, Nov. 1997, vol. 91(5), pp. 695-704.
Wilbur, W.J. and Lipman, D.J., "Rapid similarity searches of nucleic acid and protein data banks" 1983, Proc. Natl. Acad. Sci. USA 80: pp. 726-730.
Williams et al., "The Immunoglobulin Superfamily-Domains for Cell Surface Recognition," 1988, Ann. Rev. Immunol 6:381-405.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Woffendin, "Nonviral and viral delivery of a human immunodeficiency virus protective gene into primary human T cells" Proc. Natl. Acad. Sci., 1994, 91: pp. 11581-11585.
Wolfe, A. et al., "Use of cholinesterases as pretreatment drugs for the protection of rhesus monkeys against soman toxicity," Toxicology and Applied Pharmacology, vol. 117, Issue 2, pp. 189-193, Dec. 1992.
Wong, S. S., *Chemistry of Protein Conjugation and Cross-Linking*, CRC Press Inc., Aug. 1991, in 10 pages (Table of Contents only).

(56) References Cited

OTHER PUBLICATIONS

Woodworth, B. et al., "Copper Triflate as a Catalyst in Atom Transfer Radical Polymerization of Styrene and Methyl Acrylate", Macromolecules, Oct. 1998, vol. 31, No. 23, pp. 7999-8004.
Wright et al., "Effect of glycosylation on antibody function: implications for genetic engineering", Trends Biotechnol, 15(1): dated Jan. 1997, pp. 26-32.
Wu et al., "Incorporation of Adenovirus into a Ligand-based DNA Carrier System Results in Retention of Original Receptor Specificity and Enhances Targeted Gene Expression" J. Biol. Chem., 1994, 269 (15): pp. 11542-11546.
Wu et al., "Receptor-mediated Gene Delivery and Expression *in Vivo*" J. Biol. Chem., 1988, 263.
Wu et al., "Receptor-mediated Gene Delivery in Vivo" J. Biol. Chem., 1991, 266, pp. 14338-14342.
Wu, "Targeting Genes: Delivery and Persistent Expression of a Foreign Gene Driven by Mammalian Regulatory Elements in Vivo" J. Biol. Chem., 1989, 264(29):16985-19687.
Wu, G.Y. et al., "Receptor-mediated in vitro gene transformation by a soluble DNA carrier system," Journal of Biological Chemistry, vol. 262, pp. 4429-4432, Apr. 5, 1987.
Wu, H. et al., Humanization of a Murine Monoclonal Antibody by Simultaneous Optimization of Framework and CDR Residues, J. Mol. Biol., vol. 294, pp. 151-162, (1999).
Wykoff, C. C., "KSI-301 Anti-VEGF Antibody Biopolymer Conjugate for Diabetic Macular Edema: Primary Endpoint Efficacy and Safety Outcomes of the GLEAM and GLIMMER Phase 3 Pivotal Studies", 41st Annual Scientific Meeting of the American Society of Retina Specialists, Jul. 30, 2023, Seattle, WA, 23 pages.
Wyss et al., "The structural role of sugars in glycoproteins", Current Opin. Biotech. 1996, vol. 7, pp. 409-416.
Xiaoying, S. et al. Synthesis and Characterization of a Multiarm Star Polymer, Journal of Polymer Science, vol. 42, pp. 2356-2364, (2004).
Yamaguchi, J. et al., "Phospholipid polymer hydrogel formed by the photodimerization of cinnamoyl groups in the polymer side chain", Journal of Applied Polymer Science, Apr. 2007, vol. 104(1), pp. 44-50.
Yang, J. et al., "Polymeric Nanoparticles with Therapeutic Gene for Gene Therapy: I. Preparation and In Vivo Gene Transfer Study", J Biomed Eng., Jun. 2005, vol. 22(3): pp. 438-442.
Yaseen, et al., "The Structure of Zwitterionic Phosphocholine Surfactant Monolayers," Langmuir, (2006), 22:13, pp. 5825-5832.
Yeh, P. et al., "Design of yeast-secreted albumin derivatives for human therapy: biological and antiviralproperties of a serum albumin-CD4 genetic conjugate," Proc Natl Acad Sci USA, vol. 89, No. 5, pp. 1904-1908, Mar. 1, 1992.
Yeung et al., "β-Catenin Mediates the Establishment and Drug Resistance of MLL Leukemic Stem Cells", Cancer Cell, Dec. 2010, vol. 18, pp. 606-618.
Yeung, Y. et al., "A Therapeutic Anti-VEGF Antibody with Increased Potency Independent of Pharmacokinetic Half-life", Cancer Research, Apr. 2010, vol. 70(8), pp. 3269-3277.
Yong, R. et al., "Radical copolymerization of maleimide with ethyl α-ethylacrylate and a-ethylacrylic acid via RAFT", Journal of Polymer Science, Aug. 2004, vol. 42, pp. 3828-3835.
Yu, L. et al., "Interaction Between Bevacizumab and Murie VEGF-A: A Reassessment", Investigative Ophthalmology & Visual Science, 2008, vol. 49, No. 2, pp. 522-527.
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zebrowski, B. et al., "Vascular endothelial growth factor levels and induction of permeability in malignant pleural effusions," Clinical Cancer Research, vol. 5, pp. 3364-3368, Nov. 1999.
Zenke et al., "Receptor-mediated endocytosis of transferrin-polycation conjugates: an efficient way to introduce DNA into hematopoietic cells." Proc. Natl. Acad. Sci. USA, 1990, 87(10):3655-3659.
Zetter, "Angiogenesis and Tumor Metastasis," Annu. Rev. Med., vol. 49, pp. 407-424, 1998.
Zhang, X et al. Synthesis of Functional Polystyrenes by Atom Transfer Radical Polymerization Using Protected and Unprotected Carboxylic Acid Initiators, Macromolecules, vol. 32, pp. 7349-7353, (1999).
Zhang, X et al., Prevalence of Diabetic Retinopathy in the United States, 2005-2008, JAMA. Vol. 304, No. 6, pp. 649-656, (2010).
Zhang, Z. et al., "Vascular endothelial growth factor increased the permeability of respiratory barrier in acute respiratory distress syndrome model in mice", Biomedicine Pharmacotherapy, Jan. 2019, vol. 109, pp. 2434-2440.
Office Action for Australian Application No. AU in 4 pages, dated Feb. 22, 2021.
Office Action for Australian Application No. AU 2018250695 in 5 pages, dated Nov. 19, 2021.
Office Action for Australian Application No. AU 2018250695 in 5 pages, dated Feb. 9, 2022.
Office Action for Australian Application No. AU 2016381964 in 8 pages, dated Feb. 24, 2023.
Office Action for Australian Application No. AU 2016381964 in 5 pages, dated Jul. 28, 2023.
Office Action for Australian Application No. AU 2010330727 in 4 pages, dated Nov. 19, 2014.
Office Action for Australian Application No. AU 2015279560 in 3 pages, dated Mar. 18, 2020.
Notice of Acceptance for Australian Application No. AU 2015279560 in 3 pages, dated Sep. 2, 2020.
Office Action for Australian Application No. AU 2020286251 in 4 pages, dated May 22, 2023.
Office Action for Australian Application No. AU 2011239434 in 3 pages, dated Mar. 19, 2014.
Office Action for Australian Application No. AU 2015207898 in 3 pages, dated Mar. 23, 2016.
Office Action for Australian Application No. AU 2015207898 in 6 pages, dated May 27, 2016.
Office Action for Australian Application No. AU 2017201930 in 8 pages, dated Apr. 12, 2018.
Office Action for Australian Application No. AU 2017201930 in 4 pages, dated Mar. 27, 2019.
Technical Report for Brazilian Application No. BR 11 2018 013407-4 with English translation in 8 pages, dated Mar. 19, 2021.
Office Action for Brazilian Application No. BR 11 2012 014556-8 with English translation in 7 pages, dated Nov. 6, 2019.
Office Action for Brazilian Application No. BR 11 2012 014556-8 with English translation in 7 pages, dated May 12, 2020.
Office Action for Brazilian Application No. BR 11 2012 014556-8 with English translation in 6 pages, dated Aug. 5, 2021.
Office Action for Brazilian Application No. BR 11 2012 026118-5 with English translation in 6 pages, mailed Aug. 23, 2019.
Office Action for Brazilian Application No. BR 11 2012 026118-5 with English translation in 11 pages, dated Feb. 28, 2020.
Office Action for Canadian Application No. CA 3,059,938, dated Sep. 30, 2020.
Office Action for Canadian Application No. CA 3,059,938 in 4 pages, dated Sep. 27, 2021.
Office Action for Canadian Application No. CA 3,059,938 in 4 pages, dated Aug. 12, 2022.
Office Action for Canadian Application No. CA 3,059,938 in 20 pages, dated Oct. 16, 2023.
Office Action for Canadian Application No. CA 3,010,056 in 6 pages, dated Jan. 26, 2023.
Office Action for Canadian Application No. CA 2,783,615, dated Sep. 16, 2016.
Office Action for Canadian Application No. CA 2,783,615 in 4 pages, dated May 12, 2017.
Office Action for Canadian Application No. CA 2,783,615, dated Jan. 9, 2018.
Notice of Allowance for Canadian Application No. 2,783,615, dated Sep. 26, 2018.
Office Action for Canadian Application No. CA 2,795,667, dated Apr. 6, 2017.

(56) References Cited

OTHER PUBLICATIONS

Office Action for Canadian Application No. CA 2,795,667, dated Dec. 29, 2017.
Office Action for Canadian Application No. 2,953,698 in 4 pages, dated Mar. 26, 2021.
Office Action for Canadian Application No. CA 2,953,698 in 4 pages, dated Mar. 16, 2022.
Office Action for Canadian Application No. CA 2,953,698 in 3 pages, dated Feb. 21, 2023.
Office Action for Canadian Application No. CA 3,039,426 in 4 pages, dated Oct. 30, 2020.
Office Action for Canadian Application No. CA 3,039,426 in 4 pages, dated Apr. 15, 2021.
Office Action for Canadian Application No. CA 3,039,426 in 4 pages, dated Oct. 7, 2022.
Notice of Allowance for Canadian Application No. CA 3,039,426 in 1 page, dated May 5, 2023.
English translation of Office Action for Chilean Application No. CL 01621/2012 in 4 pages, dated Jun. 3, 2014.
Office Action for Chinese Application No. CN 201680082940.7 with English translation in 24 pages, dated Oct. 22, 2021.
Office Action for Chinese Application No. CN 201680082940.7 with English translation in 20 pages, dated Feb. 21, 2022.
Office Action for Chinese Application No. CN 201080062252.7 with English translation in 10 pages, dated May 17, 2013.
Office Action for Chinese Application No. CN 201080062252.7 with English translation in 9 pages, dated Apr. 9, 2014.
Office Action for Chinese Application No. CN 201080062252.7 with English translation in 7 pages, dated Oct. 27, 2014.
Office Action for Chinese Application No. CN 201080062252.7 with English translation in 11 pages, dated Apr. 23, 2015.
Office Action for Chinese Application No. CN 201080062252.7 with English translation in 8 pages, dated Oct. 9, 2016.
Office Action for Chinese Application No. CN 201080062252.7 with English summary in 4 pages, dated Apr. 20, 2017.
Office Action for Chinese Application No. CN 201180028682.1 with English translation, dated Aug. 21, 2014.
Office Action for Chinese Application No. CN 201180028682.1 with English translation, dated Jan. 26, 2015.
Office Action for Chinese Application No. CN 201180028682.1 with English translation, dated Aug. 11, 2015.
Office Action for Chinese Application No. CN 201180028682.1 with English summary in 5 pages, dated Mar. 3, 2016.
Office Action for Chinese Application No. CN 201580046779.3 with English translation in 25 pages, mailed Apr. 3, 2020.
Office Action for Chinese Application No. CN 201580046779.3 with English translation in 29 pages, dated Feb. 26, 2021.
Office Action for Chinese Application No. CN 201580046779.3 with English translation in 27 pages, dated Jun. 2, 2021.
Office Action for Chinese Application No. CN 2015800564492.2 with English translation in 10 pages, dated Apr. 22, 2020.
Office Action for Chinese Application No. CN 2015800564492 with English translation, dated Oct. 27, 2020.
Office Action for Chinese Application No. CN 201580056449.2 with English translation in 9 pages, dated Apr. 1, 2021.
Office Action for Chinese Application No. CN 201580056449.2 with English translation in 8 pages, dated Jul. 23, 2021.
Office Action for Chinese Application No. CN 201610439969.8 with English summary in 11 pages, dated Jul. 24, 2018.
Office Action for Chinese Application No. CN 201610439969.8 with English summary in 6 pages, dated Mar. 19, 2019.
Office Action for Chinese Application No. CN 201610439969.8 with English summary in 6 pages, dated Sep. 20, 2019.
Office Action for Chinese Application No. CN 201610439969.8 with English translation in 15 pages, dated Nov. 18, 2020.
Reexamination Decision for Chinese Application No. CN 201610439969.8 with English translation, dated Mar. 25, 2021.
Office Action for Chinese Application No. CN 201610446624.5 with English summary in 12 pages, dated Mar. 12, 2018.
Office Action for Chinese Application No. CN 201610446624.5 with English summary in 8 pages, dated Nov. 26, 2018.
Office Action for Chinese Application No. CN 201610446624.5 with English summary in 8 pages, dated Jun. 14, 2019.
Office Action for Chinese Application No. CN 201610446624.5 with partial English translation in 11 pages, dated Feb. 6, 2020.
Office Action for Chinese Application No. CN 201610446624.5 with English summary in 10 pages, dated Oct. 28, 2021.
Office Action for Chinese Application No. CN 201610446624.5 with English summary in 18 pages, dated Mar. 15, 2022.
English summary of Office Action for Columbian Application No. CO 12-119310 in 19 pages, dated Aug. 11, 2014.
English summary of Office Action for Columbian Application No. CO 12-203725 in 7 pages, dated Mar. 14, 2014.
Extended Search Report for European Application No. EP 18784891.6 in 15 pages, dated Jan. 21, 2021.
Office Action for European Application No. EP 18784891.6 in 6 pages, dated Jan. 2, 2023.
Partial Supplementary European Search Report for European Application No. EP 16882707.9, dated Jul. 11, 2019.
Extended European Search Report for European Application No. EP 16882707.9, mailed Nov. 19, 2019.
Office Action for European Application No. EP 16882707.9, dated Sep. 28, 2020.
Office Action for European Application No. EP 16882707.9 in 6 pages, dated Feb. 2, 2023.
Office Action with Consultation by Telephone with the Applicant/Representative for European Application No. EP 16882707.9 in 4 pages, dated Dec. 5, 2023.
Supplemental Search Report for European Application No. EP 07752096.3, dated Feb. 19, 2013.
Extended European Search Report for European Application No. EP 11769715.1, dated Jul. 18, 2016.
Office Action for European Application No. EP 11769715.1, dated Nov. 9, 2017.
Office Action for European Application No. EP 11769715.1 in 4 pages, dated Jun. 11, 2018.
Extended Search Report for European Application No. EP 14841835.3, dated Mar. 14, 2017.
Office Action for European Application No. EP 14841835.3, dated Jan. 23, 2019.
Summons to Attend Oral Proceedings for European Application No. EP 14841835.3 in 8 pages, dated Sep. 27, 2019.
Result of Consultation for European Application No. EP 14841835.3 in 3 pages, dated Feb. 6, 2020.
Supplementary Partial Search Report for European Application No. EP 15812238.2, dated Dec. 21, 2017.
Extended Search Report for European Application No. EP 15812238.2, dated Mar. 29, 2018.
Office Action for European Application No. EP 15812238.2, dated Jul. 9, 2020.
Office Action for European Application No. EP 15812238.2 dated Dec. 12, 2022, in 7 pages.
Office Action for European Application No. EP 15851363.0 in 8 pages, dated Jan. 30, 2018.
Office Action for European Application No. EP 15851363.0 in 4 pages, dated Feb. 21, 2019.
Office Action for European Application No. EP 15851363.0, dated Oct. 18, 2019.
Office Action forEuropean Application No. EP 15851363.0, dated May 27, 2020.
Supplemental Search Report for European Application No. EP 10838353.0, dated Feb. 3, 2015.
Office Action for European Application No. EP 10838353.0 in 8 pages, dated Jun. 10, 2015.
Office Action for European Application No. EP 10838353.0, dated Oct. 4, 2016.
Extended Search Report for European Application No. EP 17181272.0, dated Feb. 23, 2018.
Office Action for European Application No. EP 17181272.0, dated Oct. 31, 2018.
Office Action for European Application No. EP 20151266.2 in 6 pages, dated Feb. 28, 2020.

(56) References Cited

OTHER PUBLICATIONS

Office Action for European Application No. EP 20151266.2 in 3 pages, dated Jan. 12, 2023.
Extended Search Report for European Application No. EP 17165316.5, dated Aug. 2, 2017.
Office Action for European Application No. EP 17181272.0 in 3 pages, dated Mar. 22, 2019.
Partial Search Report for European Application No. EP 19175761.6, in 20 pages, dated Aug. 21, 2019.
Extended European Search Report for European Application No. EP 19175761.6, dated Nov. 27, 2019.
Office Action for European Application No. EP 19175761.6 in 9 pages, dated Nov. 2, 2020.
Office Action for European Application No. EP 21215256.5 in 17 pages, dated Jun. 10, 2022.
Office Action for European Application No. EP 21215256.5 in 5 pages, dated Jul. 25, 2023.
Extended Search Report for European Application No. EP 20188750.2-1109 in 13 pages, dated Nov. 5, 2020.
Office Action for European Application No. EP 20188750.2 in 6 pages, dated Feb. 15, 2023.
Office Action for European Application No. EP 19761694.9 in 18 pages, dated Sep. 9, 2022.
Office Action for European Application No. EP 20874351.8 in 12 pages, dated Nov. 16, 2023.
Office Action for Israeli Application No. IL 260323 with English translation in 8 pages, dated Oct. 21, 2021.
Office Action for Israeli Application No. IL 260323 with English translation in 8 pages, dated Aug. 16, 2022.
Office Action for Israeli Application No. IL 260323 with English translation in 8 pages, dated Mar. 27, 2023.
Office Action for Israeli Application No. IL 260323 with English translation in 9 pages, dated Oct. 19, 2023.
Office Action for Israeli Application No. IL 290457 in 4 pages, dated Aug. 16, 2022.
Office Action for Clarification for Israeli Application No. IL 290457 in 4 pages, dated Aug. 16, 2022.
Office Action for Israeli Application No. IL 290457 in 4 pages, dated Mar. 26, 2023.
Office Action for Israeli Application No. IL 290457 in 4 pages, dated Oct. 18, 2023.
Office Action for Indian Application No. IN 201817026516 in 10 pages, dated Feb. 2, 2023.
Office Action for Indian Application No. IN 6116/CHENP/2012, dated Feb. 8, 2018.
Notice of Hearing for Indian Application No. IN 6116/CHENP/2012 with English translation in 3 pages, dated Jun. 24, 2019.
Office Action for Indian Application No. IN 9473/CHENP/2012 in 5 pages, dated Jun. 27, 2018.
Notice of Hearing for Indian Application No. IN 9473/CHENP/2012 with English translation in 2 pages, dated Aug. 19, 2019.
Office Action for Japanese Application No. JP 2018-534732 with English translation in 9 pages, dated Jan. 26, 2021.
Office Action for Japanese Application No. JP 2018-534732 with English translation in 9 pages, dated Aug. 10, 2021.
Office Action for Japanese Application No. JP 2018-534732 with English translation in 3 pages, dated Mar. 29, 2022.
Office Action for Japanese Application No. JP 2021-199881 with English translation in 14 pages, dated Jan. 24, 2023.
Office Action for Japanese Application No. JP 2021-199881 with English translation in 5 pages, dated Jul. 25, 2023.
Office Action for Japanese Application No. JP 2008-557399 with English translation in 9 pages, dated Sep. 18, 2012.
Office Action for Japanese Application No. JP 2008-557399 with English translation, dated May 25, 2013.
Office Action for Japanese Application No. JP 2016-540916 with English translation, dated Jul. 13, 2018.
Office Action for Japanese Application No. JP 2016-575823 with English translation in 12 pages, dated Jun. 4, 2019.
Office Action for Japanese Application No. JP 2016-575823 with English translation in 15 pages, dated Jan. 20, 2020.
Decision of Refusal for Japanese Application No. 2016-575823 with English translation in 11 pages, dated Oct. 27, 2020.
Pre-Appeal Report for Japanese Application No. JP 2016-575823 with English translation, dated May 11, 2021.
Office Action for Japanese Application No. JP 2016-575823 with English translation in 4 pages, dated Jan. 18, 2022.
Trial Decision to Grant for Japanese Application No. JP 2016-575823 with English translation in 3 pages, dated Jun. 14, 2022.
Office Action for Japanese Application No. JP 2021-029145 with English translation in 22 pages, dated Mar. 1, 2022.
Office Action for Japanese Application No. JP 2021-029145 with English translation in 8 pages, dated Sep. 20, 2022.
Office Action for Japanese Application No. JP 2021-029145 with English translation in 10 pages, dated Mar. 22, 2023.
Decision to Grant for Japanese Application No. JP 2021-029145 with English translation in 6 pages, dated Oct. 10, 2023.
Office Action for Japanese Application No. JP 2017-520515 with English translation in 17 pages, dated May 8, 2018.
Office Action for Japanese Application No. JP 2017-520515 with English summary in 7 pages, dated Dec. 18, 2018.
Office Action for Japanese Application No. JP 2017-520515 with English translation in 19 pages, dated Feb. 17, 2020.
Office Action for Japanese Application No. JP 2017-520515 with English Translation, dated Sep. 2, 2020.
Office Action for Japanese Application No. JP 2012-544945 with English translation, dated Jul. 9, 2014.
Office Action for Japanese Application No. JP 2013-505199 with English translation, dated Feb. 19, 2015.
Office Action for Japanese Application No. JP 2015-165282 with English translation, dated Aug. 15, 2016.
Office Action for Japanese Application No. JP 2015-165282 with English translation, dated Aug. 1, 2017.
Office Action for Japanese Application No. JP 2015-165282 with English translation, dated Sep. 27, 2018.
Office Action for Japanese Application No. JP 2019-000261 with English translation, mailed Feb. 12, 2020.
Office Action for Japanese Application No. JP 2016-159104 with English translation, dated Jun. 27, 2017.
Office Action for Japanese Application No. JP 2016-159104 with English translation in 4 pages, dated Mar. 6, 2018.
Office Action for Japanese Application No. JP 2017-231724 with English translation in 8 pages, dated Nov. 27, 2018.
Office Action for Japanese Application No. JP 2017-231724 with English translation in 9 pages, dated Jun. 4, 2019.
Office Action for Japanese Application No. JP 2017-231724 with English translation in 6 pages, dated Dec. 24, 2019.
Office Action for Japanese Application No. JP 2018-189049 with English translation in 11 pages, dated Dec. 3, 2019.
Office Action for Japanese Application No. JP 2018-189049 with English translation in 8 pages, dated May 19, 2020.
Office Action for Japanese Application No. JP 2020-170314 with English translation in 11 pages, dated Dec. 7, 2021.
Office Action for Japanese Application No. JP 2020-170314 with English translation in 12 pages, dated Oct. 18, 2022.
Reconsideration Report by Examiner before Appeal for Japanese Application No. JP 2020-170314 with English translation in 7 pages, dated May 17, 2023.
Office Action for Japanese Application No. JP 2020-077026 with English translation in 12 pages, dated May 11, 2021.
Office Action for Japanese Application No. JP 2020-077026 with English translation in 7 pages, dated Mar. 22, 2022.
Office Action for Japanese Application No. JP 2020-077026 with English translation in 2 pages, dated Aug. 2, 2022.
Office Action for Japanese Application No. JP 2020-077026 with English translation in 4 pages, dated Oct. 4, 2022.
Office Action for Japanese Application No. JP 2020-077026 with English translation in 5 pages, dated Jan. 10, 2023.
Office Action for Japanese Application No. JP 2022-117091 with English translation in 8 pages, dated Aug. 22, 2023.
Office Action for Japanese Application No. JP 2020-117047 with English translation in 10 pages, dated Aug. 31, 2021.

(56) References Cited

OTHER PUBLICATIONS

Office Action for Japanese Application No. JP 2020-117047 with English translation in 6 pages, dated Jul. 19, 2022.
Office Action for Japanese Application No. JP 2020-117047 with English translation in 5 pages, dated Jan. 17, 2023.
Decision to Grant for Japanese Application No. JP 2020-117047 with English translation in 5 pages, dated Feb. 14, 2023.
Office Action for Japanese Application No. JP 2020-545729 with English translation in 9 pages, dated Jan. 31, 2023.
Office Action for Japanese Application No. JP 2020-545729 with English translation in 13 pages, dated Jul. 25, 2023.
Office Action for Korean Application No. KR 10-2012-7018788 with English translation, dated Mar. 10, 2017.
Notice to File a Response for Korean Application No. KR 10-2012-7018788 with English translation, dated Sep. 13, 2017.
Office Action for Korean Application No. KR 10-2012-7018788 with English translation in 3 pages, dated Jan. 19, 2018.
Office Action for Korean Application No. KR 10-2012-7029878 with English translation, dated Mar. 8, 2017.
Notice of Final Rejection for Korean Application No. KR 10-2012-7029878 with English translation, dated Aug. 28, 2017.
Notice of Final Rejection for Korean Application No. KR 10-2012-7029878 with English translation, dated Oct. 27, 2017.
Trial Decision for Korean Application No. KR 10-2012-7029878 with English translation in 24 pages, dated Jul. 23, 2019.
Office Action for Korean Application No. KR 10-2017-7013268 with English translation in 12 pages, dated Apr. 23, 2019.
Office Action for Korean Application No. KR 10-2017-7013268 with English translation, dated Nov. 14, 2019.
Office Action for Korean Application No. KR 10-2017-7013268 with English translation in 7 pages, dated Feb. 17, 2020.
Notice of Allowance for Korean Application No. 10-2017-7013268 with English translation, dated Oct. 26, 2020.
Office Action for Korean Application No. KR 10-2017-7034546 with English translation, dated Mar. 9, 2018.
Office Action for Korean Application No. KR 10-2017-7034546 with English translation in 8 pages, dated Aug. 28, 2018.
Office Action for Korean Application No. KR 10-2017-7034546 with English translation in 8 pages, dated Oct. 26, 2018.
Office Action for Korean Application No. KR 10-2021-7002410 with English translation in 10 pages, dated May 11, 2021.
Office Action for Korean Application No. KR 10-2021-7002410 with English translation in 6 pages, dated Nov. 26, 2021.
Office Action for Korean Application No. KR 10-2021-7002410 with English translation in 6 pages, dated Jan. 27, 2022.
Office Action for Korean Application No. KR 10-2018-7034569 with English translation in 11 pages, dated May 21, 2019.
Office Action for Korean Application No. KR 10-2018-7034569 with English translation, dated Jan. 22, 2020.
Office Action for Korean Application No. KR 10-2018-7034569 with English translation in 8 pages, dated Apr. 8, 2020.
Notice of Trial Decision for Korean Application No. KR 10-2018-7034569 with Partial English Translation, dated Apr. 22, 2021.
Final Office Action for Korean Application No. KR 10-2020-7016413 with English translation, dated Sep. 24, 2020.
Final Office Action for Korean Application No. KR 10-2020-7016413 with English translation, dated Mar. 30, 2021.
Decision to Dismiss an Amendment for Korean Application No. KR 10-2020-7016413 with English translation, dated Jul. 16, 2021.
Notice of Final Rejection for Korean Application No. KR 10-2020-7016413 with English translation, dated Jul. 16, 2021.
Office Action for Korean Application No. KR 10-2021-7020330 with English translation in 11 pages, dated Oct. 27, 2021.
Notice of Allowance for Korean Application No. KR 10-2021-7020330 with English translation in 3 pages, dated Apr. 27, 2022.
Office Action for Korean Application No. KR 10-2022-7009924 with English translation in 10 pages, dated Jun. 30, 2022.
Notice of Allowance for Korean Application No. KR 10-2022-7009924 with English translation in 10 pages, dated Apr. 27, 2023.
Office Action for Mexican Application No. MX/a/2018/008068 with English summary, dated Aug. 20, 2021.
Office Action for Mexican Application No. MX/a/2018/008068 with English summary in 8 pages, dated Feb. 4, 2022.
Office Action for Mexican Application No. MX/a/2018/008068 with English translation in 10 pages, dated Aug. 19, 2022.
Office Action for Mexican Application No. MX/a/2018/008068 with English translation in 8 pages, dated Mar. 6, 2023.
Notice of Allowance for Mexican Application No. MX/a/2018/008068 with English translation in 4 pages, dated Aug. 14, 2023.
Office Action for Mexican Application No. MX/a/2012/006970 with English translation in 2 pages, dated Sep. 22, 2014.
Office Action for Mexican Application No. MX/a/2012/006970 with English translation, dated Dec. 15, 2015.
Office Action for Mexican Application No. MX/a/2012/011876 with English summary, dated Jul. 13, 2017.
Office Action for Mexican Application No. MX/a/2012/011876 with English summary, dated Jan. 16, 2018.
Office Action for Mexican Application No. MX/a/2012/011876 with English summary in 8 pages, dated Jun. 6, 2018.
Office Action for Mexican Application No. MX/a/2012/011876 with English summary in 4 pages, dated Dec. 17, 2018.
Office Action for Mexican Application No. MX/a/2016/017290 with English translation in 9 pages, dated Jul. 15, 2020.
Office Action for Mexican Application No. MX/a/2016/010818 with English summary, dated Apr. 5, 2019.
Office Action for Mexican Application No. MX/a/2016/010818 with English translation, dated Oct. 1, 2019.
Office Action for New Zealand Application No. NZ 600949 in 2 pages, dated Mar. 14, 2013.
Office Action for New Zealand Application No. NZ 603048 in 2 pages, dated Jun. 13, 2013.
Office Action for Russian Application No. RU 2018126519 with English translation in 12 pages, dated Apr. 28, 2020.
Search Report for Russian Application No. RU 2018126519 with English translation, dated Sep. 8, 2020.
Decision to Grant for Russian Application No. RU 2018126519/10 with English translation, dated Jan. 21, 2021.
Office Action for Russian Application No. RU 2020128737 with English translation in 11 pages, dated Aug. 17, 2022.
Office Action for Russian Application No. RU 2020128737 with English translation in 18 pages, dated Jan. 13, 2023.
Office Action for Russian Application No. RU 2020128737 with English translation in 13 pages, dated Apr. 13, 2023.
Written Opinion for Singapore Application No. SG 11201805420S in 6 pages, mailed Dec. 22, 2019.
Search Report for Singapore Application No. SG 11201805420S in 6 pages, mailed Dec. 22, 2019.
Examination Report for Singapore Application No. SG 11201805420S, dated Jan. 22, 2021.
Examiners Comments Letter for Singaporean Application No. SG 11201805420S in 3 pages, received Feb. 10, 2021.
Office Action for Singapore Application No. SG 11201805420S in 7 pages, dated Nov. 16, 2022.
Office Action for Singapore Application No. SH 11202008242X in 16 pages, dated Apr. 5, 2022.
Invitation to Pay Additional Fees for International Application No. PCT/US2018/027378, dated Aug. 1, 2018.
International Search Report and Written Opinion for International Application No. PCT/US2018/027378, dated Sep. 27, 2018.
International Preliminary Report on Patentability for International Application No. PCT/US2018/027378, dated Oct. 24, 2019.
International Search Report and Written Opinion for International Application No. PCT/US2016/069336, dated Mar. 30, 2017.
International Preliminary Report on Patentability for International Application No. PCT/US2016/069336, dated Jul. 3, 2018.
International Search Report and Written Opinion for International Application No. PCT/US2007/005372, dated Aug. 8, 2008.
International Preliminary Report on Patentability for International Application No. PCT/US2007/005372, dated Oct. 21, 2008.
International Search Report and Written Opinion for International Application No. PCT/US2011/032768, dated Dec. 16, 2011.

(56) References Cited

OTHER PUBLICATIONS

International Preliminary Report on Patentability for International Application No. PCT/US2011/032768, dated Feb. 11, 2014.
International Search Report and Written Opinion for International Application No. PCT/US2014/054622 in 19 pages, dated Feb. 27, 2015.
International Preliminary Report on Patentability for International Application No. PCT/US2014/054622, dated Mar. 17, 2016.
International Search Report and Written Opinion for International Application No. PCT/US2015/038203, dated Dec. 8, 2015.
International Preliminary Report on Patentability for International Application No. PCT/US2015/038203, dated Jul. 5, 2016.
Invitation to Pay Additional Fees for International Application No. PCT/US2015/056112, dated Feb. 3, 2016.
International Search Report and Written Opinion for International Application No. PCT/US2015/056112, dated Apr. 1, 2016.
International Preliminary Report on Patentability for International Application No. PCT/US2015/056112, dated Apr. 18, 2017.
International Search Report and Written Opinion for International Application No. PCT/US2012/060301, dated Feb. 27, 2013.
International Search Report and Written Opinion for International Application No. PCT/US2019/020418, dated Jun. 20, 2019.
International Preliminary Report on Patentability for International Application No. PCT/US2019/020418, dated Sep. 17, 2020.
International Search Report and Written Opinion for International Application No. PCT/US2020/055074, mailed Feb. 8, 2021.
International Preliminary Report on Patentability for International Application No. PCT/US2020/055074 in 14 pages, dated Apr. 21, 2022.
International Search Report and Written Opinion for International Application No. PCT/US2021/031194 in 18 pages, mailed Sep. 16, 2021.
International Preliminary Report on Patentability for International Application No. PCT/US2021/031194 in 10 pages, mailed Nov. 17, 2022.
Invitation to Pay Additional Fees for International Application No. PCT/US2022/024598 in 3 pages, dated Jul. 5, 2022.
International Search Report and Written Opinion for International Application No. PCT/US2022/024598 in 19 pages, dated Sep. 13, 2022.
International Search Report for International Application No. PCT/IB2012/057491, dated Jun. 4, 2013.
International Preliminary Report on Patentability for International Application No. PCT/IB2012/057491 in 10 pages, dated Jun. 24, 2014.
International Search Report and Written Opinion for International Application No. PCT/US2010/034252, dated Sep. 9, 2010.
International Preliminary Report on Patentability for International Application No. PCT/US2010/034252, dated Jun. 28, 2012.
International Search Report and Written Opinion for International Application No. PCT/US2010/061358, dated May 9, 2011.
International Preliminary Report on Patentability for International Application No. PCT/US2010/061358, dated Jun. 28, 2012.
Restriction Requirement for U.S. Appl. No. 15/952,092, dated Mar. 3, 2020.
Office Action for U.S. Appl. No. 15/952,092, dated Jun. 30, 2020.
Final Office Action for U.S. Appl. No. 15/952,092, dated Nov. 27, 2020.
Office Action for U.S. Appl. No. 15/952,092 in 29 pages, dated May 21, 2021.
Office Action for U.S. Appl. No. 15/952,092 in 17 pages, dated Sep. 13, 2021.
Notice of Allowance for U.S. Appl. No. 15/952,092 in 10 pages, dated Feb. 8, 2022.
Notice of Allowance for U.S. Appl. No. 15/952,092 in 9 pages, dated May 27, 2022.
Notice of Allowance for U.S. Appl. No. 15/952,092 in 9 pages, dated Oct. 17, 2022.
Notice of Allowance for U.S. Appl. No. 15/952,092 in 3 pages, dated Jan. 19, 2023.
Restriction Requirement for U.S. Appl. No. 15/394,500, dated Mar. 7, 2018.
Office Action for U.S. Appl. No. 15/394,500, dated Jun. 21, 2018.
Office Action for U.S. Appl. No. 15/394,500, dated Jan. 7, 2019.
Advisory Action for U.S. Appl. No. 15/394,500, dated Apr. 18, 2019.
Office Action for U.S. Appl. No. 15/394,500, dated Aug. 7, 2019.
Final Office Action for U.S. Appl. No. 15/394,500, dated Dec. 30, 2019.
Office Action for U.S. Appl. No. 15/394,500, dated Jun. 23, 2020.
Office Action for U.S. Appl. No. 15/394,500, dated Nov. 30, 2020.
Notice of Allowance for U.S. Appl. No. 15/394,500, dated Mar. 11, 2021.
Notice of Allowability for U.S. Appl. No. 15/394,500, dated Mar. 25, 2021.
Notice of Allowability for U.S. Appl. No. 15/394,500, dated Apr. 8, 2021.
Notice of Allowability for U.S. Appl. No. 15/394,500, dated Jun. 9, 2021.
Notice of Allowability for U.S. Appl. No. 15/394,500, dated Jun. 17, 2021.
Office Action for U.S. Appl. No. 17/301,599 in 128 pages, dated May 15, 2023.
Office Action for U.S. Appl. No. 17/301,599 in 19 pages, dated Oct. 23, 2023.
Office Action for U.S. Appl. No. 13/959,563, dated Oct. 10, 2013.
Office Action for U.S. Appl. No. 13/959,563, dated Feb. 20, 2014.
Advisory Action for U.S. Appl. No. 13/959,563, dated Jun. 12, 2014.
Notice of Allowance for U.S. Appl. No. 13/959,563, dated Jul. 31, 2014.
Notice of Allowance for U.S. Appl. No. 13/959,563, dated Aug. 18, 2014.
Office Action for U.S. Appl. No. 14/456,875, dated Jun. 9, 2015.
Office Action for U.S. Appl. No. 14/456,875 in 20 pages, dated Nov. 9, 2015.
Office Action for U.S. Appl. No. 14/456,875 in 10 pages, dated Oct. 5, 2016.
Office Action for U.S. Appl. No. 14/456,875, dated Apr. 20, 2017.
Office Action for U.S. Appl. No. 14/456,875, dated Dec. 14, 2017.
Office Action for U.S. Appl. No. 14/456,875, dated Aug. 28, 2018.
Office Action for U.S. Appl. No. 14/456,875, dated Mar. 8, 2019.
Restriction Requirement for U.S. Appl. No. 16/424,265, dated Apr. 21, 2020.
Office Action for U.S. Appl. No. 16/424,265, dated Oct. 21, 2020.
Office Action for U.S. Appl. No. 16/424,265, dated Jun. 17, 2021.
Restriction Requirement for U.S. Appl. No. 17/553,605 in 6 pages, dated Mar. 16, 2023.
Office Action for U.S. Appl. No. 17/553,605 in 31 pages, dated Aug. 29, 2023.
Restriction Requirement for U.S. Appl. No. 12/281,071, dated Jun. 20, 2011.
Office Action for U.S. Appl. No. 12/281,071, dated Feb. 7, 2012.
Office Action for U.S. Appl. No. 12/281,071, dated Aug. 2, 2012.
Restriction Requirement for U.S. Appl. No. 14/265,174, dated Jul. 15, 2015.
Office Action for U.S. Appl. No. 14/265,174, dated Dec. 14, 2015.
Restriction Requirement for U.S. Appl. No. 15/182,278, dated Feb. 17, 2017.
Restriction Requirement for U.S. Appl. No. 13/515,913, dated Aug. 14, 2013.
Notice of Allowance for U.S. Appl. No. 13/515,913, dated Jan. 28, 2014.
Restriction Requirement for U.S. Appl. No. 13/516,173, dated Sep. 3, 2023.
Office Action for U.S. Appl. No. 13/516,173, dated Dec. 31, 2013.
Office Action for U.S. Appl. No. 13/516,173, dated Jul. 2, 2014.
Office Action for U.S. Appl. No. 13/516,173, dated Dec. 16, 2014.
Office Action for U.S. Appl. No. 13/516,173, dated Oct. 14, 2015.
Restriction Requirement for U.S. Appl. No. 15/099,234, dated Feb. 9, 2017.
Office Action for U.S. Appl. No. 15/099,234, dated May 30, 2017.

(56) References Cited

OTHER PUBLICATIONS

Final Office Action for U.S. Appl. No. 15/099,234, dated Nov. 27, 2017.
Office Action for U.S. Appl. No. 15/099,234, dated Oct. 19, 2018.
Office Action for U.S. Appl. No. 15/099,234, dated May 14, 2019.
Final Office Action for U.S. Appl. No. 15/099,234, dated Nov. 26, 2019.
Advisory Action for U.S. Appl. No. 15/099,234, dated Apr. 1, 2020.
Restriction Requirement for U.S. Appl. No. 15/099,234, dated Sep. 18, 2020.
Office Action for U.S. Appl. No. 15/099,234, dated Feb. 26, 2021.
Office Action for U.S. Appl. No. 15/099,234 in 14 pages, dated Oct. 8, 2021.
Notice of Allowance for U.S. Appl. No. 15/099,234 in 22 pages, dated Aug. 17, 2022.
Supplemental Notice of Allowability for U.S. Appl. No. 15/099,234 in 3 pages, dated Sep. 14, 2022.
Office Action for U.S. Appl. No. 15/099,234 in 9 pages, dated Mar. 10, 2023.
Notice of Allowance for U.S. Appl. No. 15/099,234 in 7 pages, dated Jul. 19, 2023.
Restriction Requirement for U.S. Appl. No. 13/901,483, dated Nov. 3, 2015.
Office Action for U.S. Appl. No. 13/901,483, dated Jun. 2, 2016.
Restriction Requirement for U.S. Appl. No. 15/368,376, dated Aug. 21, 2017.
Office Action for U.S. Appl. No. 15/368,376, dated Feb. 9, 2018.
Office Action for U.S. Appl. No. 15/368,376, dated Sep. 10, 2018.
Office Action for U.S. Appl. No. 15/368,376, dated Mar. 11, 2019.
Office Action for U.S. Appl. No. 15/368,376, dated Aug. 2, 2019.
Restriction Requirement for U.S. Appl. No. 16/779,102, dated Nov. 10, 2020.
Office Action for U.S. Appl. No. 16/779,102, dated Feb. 22, 2021.
Non-Final Office Action for U.S. Appl. No. 17/409,578 in 25 pages, dated Apr. 12, 2023.
Restriction Requirement for U.S. Appl. No. 17/409,578 in 4 pages, dated Sep. 9, 2022.
Office Action for U.S. Appl. No. 16/781,869 in 10 pages, dated Nov. 13, 2020.
Final Office Action for U.S. Appl. No. 16/781,869 in 10 pages, dated Mar. 17, 2021.
Non-Final Office Action for U.S. Appl. No. 16/781,869 in 12 pages, dated Sep. 28, 2021.
Notice of Allowance for U.S. Appl. No. 16/781,869 in 6 pages, dated Jul. 14, 2022.
Notice of Allowance for U.S. Appl. No. 16/781,869 in 8 pages, dated Oct. 26, 2022.
Restriction Requirement for U.S. Appl. No. 14/916,180, dated Jan. 30, 2017.
Restriction Requirement for U.S. Appl. No. 14/916,180, dated Aug. 16, 2017.
Office Action for U.S. Appl. No. 14/916,180, dated Jan. 24, 2018.
Office Action for U.S. Appl. No. 14/916,180, dated Aug. 10, 2018.
Advisory Action for U.S. Appl. No. 14/916,180, dated Nov. 29, 2018.
Advisory Action for U.S. Appl. No. 14/916,180, dated Dec. 11, 2018.
Office Action for U.S. Appl. No. 14/916,180, dated Mar. 8, 2019.
Office Action for U.S. Appl. No. 14/916,180, dated Jun. 26, 2019.
Advisory Action for U.S. Appl. No. 14/916,180, dated Sep. 9, 2019.
Notice of Allowance for U.S. Appl. No. 14/916,180, dated Nov. 5, 2019.
Restriction Requirement for U.S. Appl. No. 14/753,824, dated Jul. 20, 2016.
Office Action for U.S. Appl. No. 14/753,824, dated Feb. 27, 2017.
Notice of Allowance for U.S. Appl. No. 14/753,824, dated Aug. 9, 2017.
Corrected Notice of Allowability for U.S. Appl. No. 14/753,824, dated Sep. 29, 2017.
Restriction Requirement for U.S. Appl. No. 16/795,450 in 5 pages, dated Mar. 24, 2021.
Office Action for U.S. Appl. No. 16/795,450 in 117 pages, dated Jun. 25, 2021.
Final Office Action for U.S. Appl. No. 16/795,450 in 14 pages, dated Jan. 6, 2022.
Office Action for U.S. Appl. No. 16/795,450 in 15 pages, dated Apr. 28, 2022.
Office Action for U.S. Appl. No. 16/795,450 in 16 pages, dated Nov. 10, 2022.
Office Action for U.S. Appl. No. 16/795,450 in 18 pages, dated May 23, 2023.
Office Action for U.S. Appl. No. 15/820,325, dated Jan. 9, 2019.
Office Action for U.S. Appl. No. 15/820,325 dated Jul. 29, 2019.
Notice of Allowance for U.S. Appl. No. 15/820,325, dated Nov. 15, 2019.
Corrected Notice of Allowability for U.S. Appl. No. 15/820,325, dated Feb. 27, 2020.
Notice of Allowance for U.S. Appl. No. 15/820,325, dated Apr. 2, 2020.
Corrected Notice of Allowability for U.S. Appl. No. 15/820,325, dated Apr. 29, 2020.
Notice of Allowance for U.S. Appl. No. 15/820,325, dated Jun. 10, 2020.
Notice of Allowance for U.S. Appl. No. 15/820,325, dated Sep. 4, 2020.
Corrected Notice of Allowability for U.S. Appl. No. 15/820,325, dated Oct. 16, 2020.
Notice of Allowance U.S. Appl. No. 15/820,325, dated Dec. 22, 2020.
Notice of Allowance for U.S. Appl. No. 15/820,325, dated Apr. 15, 2021.
Corrected Notice of Allowability for U.S. Appl. No. 15/820,325 in 6 pages, dated Jun. 23, 2021.
Corrected Notice of Allowability for U.S. Appl. No. 15/820,325 in 5 pages, dated Jul. 21, 2021.
Corrected Notice of Allowability for U.S. Appl. No. 15/820,325 in 5 pages, dated Sep. 22, 2021.
Restriction Requirement for U.S. Appl. No. 14/932,913, dated Jan. 13, 2017.
Office Action for U.S. Appl. No. 14/932,913, dated May 8, 2017.
Office Action for U.S. Appl. No. 14/932,913, dated Aug. 16, 2017.
Office Action for U.S. Appl. No. 14/932,913, dated Dec. 15, 2017.
Office Action for U.S. Appl. No. 14/932,913, dated May 4, 2018.
Notice of Allowance for U.S. Appl. No. 14/932,913, dated Sep. 11, 2018.
Notice of Allowability for U.S. Appl. No. 14/932,913, dated Sep. 21, 2018.
Notice of Allowance for U.S. Appl. No. 14/932,913, dated Jan. 30, 2019.
Notice of Allowability for U.S. Appl. No. 14/932,913, dated Jun. 12, 2019.
Office Action for U.S. Appl. No. 16/402,602, dated Apr. 13, 2020.
Office Action for U.S. Appl. No. 16/402,602, dated Aug. 3, 2020.
Office Action for U.S. Appl. No. 16/402,602, dated Nov. 20, 2020.
Notice of Allowance for U.S. Appl. No. 16/402,602 in 13 pages, dated Mar. 10, 2021.
Restriction Requirement for U.S. Appl. No. 16/290,128, dated Feb. 12, 2020.
Office Action for U.S. Appl. No. 16/290,128, dated May 22, 2020.
Office Communication for U.S. Appl. No. 16/290,128, dated Nov. 12, 2020.
Final Office Action for U.S. Appl. No. 16/290,128 in 78 pages, dated Mar. 22, 2021.
Office Action for U.S. Appl. No. 16/290,128 in 25 pages, dated Sep. 14, 2021.
Office Action for U.S. Appl. No. 16/290,128 in 20 pages, dated Feb. 14, 2022.
Office Action for U.S. Appl. No. 16/290,128 in 19 pages, dated Sep. 1, 2022.
Office Action for U.S. Appl. No. 16/290,128 in 12 pages, dated Apr. 18, 2023.

(56) References Cited

OTHER PUBLICATIONS

Office Action for U.S. Appl. No. 16/290,128 in 14 pages, dated Oct. 6, 2023.
File History of U.S. Appl. No. 15/952,092, filed Apr. 12, 2018.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 16/424,265, filed Aug. 11, 2014.
File History of U.S. Appl. No. 12/281,071, filed Aug. 28, 2008.
File History of U.S. Appl. No. 14/265,174 filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173 filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 15/368,376, filed Dec. 2, 2016.
File History of U.S. Appl. No. 13/641,342, filed Dec. 2, 2016.
File History of U.S. Appl. No. 16/781,869, filed Mar. 2, 2016.
File History of U.S. Appl. No. 14/916,180 filed Mar. 2, 2016.
File History of U.S. Appl. No. 16/779,102 filed Jan. 31, 2020.
File History of U.S. Appl. No. 14/753,824, filed Jun. 29, 2015.
File History of U.S. Appl. No. 16/795,450, filed Jun. 29, 2015.
File History of U.S. Appl. No. 15/820,325, filed Nov. 21, 2017.
File History of U.S. Appl. No. 14/932,913, filed Nov. 4, 2015.
File History of U.S. Appl. No. 16/402,602, filed Nov. 4, 2015.
File History of U.S. Appl. No. 16/290,128 filed Mar. 1, 2019.
Notice of Acceptance for Australian Application No. AU 2016381964 in 3 pages, dated Feb. 5, 2024.
Office Action for Canadian Application No. CA 3,010,056 in 8 pages, dated Mar. 28, 2024.
Office Action for Israeli Application No. IL 260323 with English translation in 9 pages, dated May 2, 2024.
Notice of Acceptance for Israeli Application No. IL 260323 with English translation in 2 pages, dated Jul. 28, 2024.
Notice before Acceptance for Israeli Application No. IL 290457 in 3 pages, dated Jul. 1, 2024.
Decision to Grant for Japanese Application No. JP 2021-199881 with English translation in 6 pages, dated Nov. 28, 2023.
Office Action for Japanese Application No. JP 2022-521198 with English translation in 9 pages, dated Aug. 6, 2024.
Office Action for Korean Application No. KR 10-2018-7021875 with partial English translation in 12 pages, dated Jan. 10, 2024.
Office Action for Russian Application No. RU 2021103004 with English translation in 14 pages, dated Apr. 27, 2024.
International Preliminary Report on Patentability for PCT Application No. PCT/US2022/024598 in 10 pages, dated Oct. 26, 2023.
Invitation to Pay Additional Fees for PCT Application No. PCT/US2024/032770 in 4 pages, dated Aug. 21, 2024.
Office Action for U.S. Appl. No. 17/301,599 in 21 pages, dated Apr. 11, 2024.
Notice of Allowance for U.S. Appl. No. 17/301,599 in 12 pages, dated Sep. 3, 2024.
Restriction Requirement for U.S. Appl. No. 17/066,856 in 6 pages, dated Feb. 2, 2021.
Office Action for U.S. Appl. No. 17/066,856 in 87 pages, dated May 24, 2021.
Notice of Allowance for U.S. Appl. No. 17/066,856, dated Sep. 9, 2021.
Corrected Notice of Allowance in U.S. Appl. No. 17/066,856 dated Oct. 8, 2021.
Notice of Allowance for U.S. Appl. No. 17/066,856 in 20 pages, dated Dec. 27, 2021.
Notice of Allowance for U.S. Appl. No. 17/066,856 in 14 pages, dated Apr. 14, 2022.
Notice of Allowance for U.S. Appl. No. 17/066,856 in 6 pages, dated Jun. 14, 2022.
Notice of Allowance for U.S. Appl. No. 17/066,856 in 11 pages, dated Jul. 25, 2022.
Notice of Allowance for U.S. Appl. No. 17/066,856 in 12 pages, dated Oct. 26, 2022.
Notice of Allowability for U.S. Appl. No. 17/066,856 in 14 pages, dated Mar. 1, 2023.
Notice of Allowability for U.S. Appl. No. 17/066,856 in 13 pages, dated Jun. 22, 2023.
Notice of Allowability for U.S. Appl. No. 17/066,856 in 12 pages, dated Oct. 3, 2023.
Notice of Allowability for U.S. Appl. No. 17/066,856 in 6 pages, dated Nov. 22, 2023.
Notice of Allowability for U.S. Appl. No. 17/066,856 in 6 pages, dated Dec. 20, 2023.
File History of U.S. Appl. No. 17/066,856, filed Oct. 9, 2020.
Derksen, P. W. B. et al., "Illegitimate WNT signaling promotes proliferation of multiple myeloma cells", Proceedings of the National Academy of Sciences, 2004, vol. 101(16), p. 6122-6127.
Dirks, P. B., "Brain Tumor Stem Cells: Bringing Order to the Chaos of Brain Cancer", Journal of Clinical Oncology, 2008, vol. 26, No. 17, pp. 2916-2924.
Lopez-Lazaro, M., "The migration ability of stem cells can explain the existence of cancer of unknown primary site. Rethinking metastasis", Oncoscience, May 2015, vol. 2(5), pp. 467-475.
Tarantul, V. Z., Definition of "Antibodies", Explanatory Biotechnological Dictionary of Russian-English, Languages of Slavic Cultures, Moscow, 2009, p. 72.
Tran, B. et al., "Survival comparison between glioblastoma multiforme and other incurable cancers", Journal of Clinical Neuroscience, 2010, vol. 17, No. 4, pp. 417-421.
Office Action for Korean Application No. KR 10-2018-7021875 with English translation in 7 pages, dated Sep. 20, 2024, 2024.
Office Action for New Zealand Application No. NZ 744185 in 7 pages, dated Sep. 4, 2024.
Office Action for New Zealand Application No. NZ 783685 in 6 pages, dated Sep. 4, 2024.
Office Action for Russian Application No. RU 2021103004 with English translation in 19 pages, dated Sep. 24, 2024.
International Search Report and Written Opinion for PCT Application No. PCT/US2024/032770 in 28 pages, dated Nov. 15, 2024.
"Kodiak Sciences Announces Presentation of KSI-301 Phase 1b Clinical Study Data Focused on DME at AAO 2020 Virtual Meeting", Eyewire+, Kodiak Sciences, Dec. 2020, in 6 pages. URL: https://eyewire.news/articles/kodiak-sciences-announces-presentation-of-ksi-301-phase-ib-clinical-study-data-focused-on-dme-at-aao-2020-virtual-meeting/?c4src=article:infinite-scroll.
Khanani, A. M., "One Year and Beyond: Long-Term Multiple-Dose Study of KSI-301, an Anti-VEGF Antibody Biopolymer Conjugate with Extended Durability, in wAMD, DME and RVO" [presentation], AAO—Retina Subspecialty Day 2020, Nov. 2020, in 30 pages. URL: https://ir.kodiak.com/static-files/53d37c56-cf00-4b79-b4c0-a5989f5884a2.
Regillo, C., "Efficacy, durability and safety of KSI-301 antibody biopolymer conjugate in wet AMD—Primary results of the Phase 2b/3 DAZZLE study" [presentation], The Association for Research in Vision and Ophthalmology (ARVO) Annual Meeting, May 2022, in 25 pages. URL: https://ir.kodiak.com/static-files/a1c2fb74-a7e1-48fd-8b4d-368e56edf3a7.
Stern, H. et al., "KSI-301: an investigational anti-VEGF biopolymer conjugate for retinal diseases", Expert Opinion on Investigational Drugs, 2022, vol. 31, No. 5, pp. 443-449.
Partial Supplementary Search Report for European Application No. 22788845.0 in 12 pages, dated Dec. 17, 2024.
Office Action for Japanese Application No. JP 2023-220012 with English translation in 9 pages, dated Jan. 7, 2025.
Extended European Search Report for European Application No. 22788845.0 in 11 pages, dated Mar. 10, 2025.
Notice of Allowance for U.S. Appl. No. 17/301,599 in 11 pages, dated Apr. 15, 2025.
Office Action for Japanese Patent Application No. 2022-521198 with English translation in 7 pages, dated Apr. 1, 2025.
Kuzmin A.G. et al., "Anti-VEGF drugs for the treatment of diabetic retinopathy", Ophthalmous Surgery, 2009, No. 3, pp. 53-57.
Technical Report for Brazilian Application No. BR 11 2018 013407-4 with English translation in 16 pages, dated May 30, 2025.
Notice of Allowance for Korean Application No. KR 10-2018-7021875 with English translation in 4 pages, dated Jan. 20, 2025.

(56) References Cited

OTHER PUBLICATIONS

Office Action for New Zealand Application No. NZ 744185 in 5 pages, dated Mar. 27, 2025.
Office Action for New Zealand Application No. NZ 783685 in 5 pages, dated Mar. 27, 2025.
Office Action for Singapore Application No. SG 11202203583W in 9 pages, dated Jun. 2, 2025.
Poosarla, V. G. et al., "Computational De Novo Design of Antibodies Binding to a Peptide with High Affinity", Biotechnology and Bioengineering, Jun. 2017, vol. 114, No. 6, pp. 1331-1342.
Office Action for Canadian Application No. CA 3,010,056 in 6 pages, dated Sep. 29, 2025.
Office Action for Japanese Application No. JP 2023-220012 with English translation in 9 pages, dated Jul. 8, 2025.
Office Action for Mexican Application No. MX/a/2022/014125 with English translation in 16 pages, dated Sep. 30, 2025.
Office Action for New Zealand Application No. NZ 744185 in 2 pages, dated Jul. 16, 2025.
Office Action for New Zealand Application No. NZ 744185 in 2 pages, dated Sep. 2, 2025.
Office Action for New Zealand Application No. NZ 783685 in 2 pages, dated Jul. 16, 2025.
Office Action for New Zealand Application No. NZ 783685 in 2 pages, dated Sep. 2, 2025.
Office Action for U.S. Appl. No. 17/301,599 in 39 pages, dated Sep. 18, 2025.
Reconsideration Report by Examiner before Appeal for Japanese Application No. JP 2022-521198 with English translation in 7 pages, dated Nov. 26, 2025.

* cited by examiner

FIG. 14

Heavy chain amino acid sequence of the anti-VEGF-A antibody component of KSI-301

EVQLVESGGG LVQPGGSLRL SCAASGYDFT HYGMNWVRQA PGKGLEWVGW
CDRH1 (SEQ ID NO: 9)
INTYTGEPTY AADFKRRFTF SLDTSKSTAY LQMNSLRAED TAVYYCAKYP
CDRH2 (SEQ ID NO: 10)
YYYGTSHWYF DVWGQGTLVT VSSASTKGPS VFPLAPSSKS TSGGTAALGC
CDRH3 (SEQ ID NO: 11)
LVKDYFPEPV TVSWNSGALT SGVHTFPAVL QSSGLYSLSS VVTVPSSSLG

TQTYICNVNH KPSNTKVDKK VEPKSCDKTH TCPPCPAPEA AGAPSVFLFP

PKPKDTLMIS RTPEVTCVVV DVSHEDPEVK FNWYVDGVEV HNAKTKPREE

QYNSTYRVVS VLTVLHQDWL NGKEYKCKVS NKALPAPIEK TISKAKGQPR

EPQVYTLPPS REEMTKNQVS LTCLVKGFYP SDIAVEWESN GQPENNYKTT

PPVLDSDGSF FLYSKLTVDK SRWQQGNVFS CSVMHEALHN HYTQKSLSCS

PGK (SEQ ID NO: 1)

Light chain amino acid sequence of the anti-VEGF-A antibody component of KSI-301

DIQLTQSPSS LSASVGDRVT ITCSASQDIS NYLNWYQQKP GKAPKVLIYF
CDRL1 (SEQ ID NO: 12)
TSSLHSGVPS RFSGSGSGTD FTLTISSLQP EDFATYYCQQ YSTVPWTFGQ
CDRL2 (SEQ ID NO: 13) CDRL3 (SEQ ID NO: 14)
GTKVEIKRTV AAPSVFIFPP SDEQLKSGTA SVVCLLNNFY PREAKVQWKV

DNALQSGNSQ ESVTEQDSKD STYSLSSTLT LSKADYEKHK VYACEVTHQG

LSSPVTKSFN RGEC (SEQ ID NO: 2)

FIG. 15

Heavy chain amino acid sequence of bevacizumab

EVQLVESGGG LVQPGGSLRL SCAASGYTFT NYGMNWVRQA PGKGLEWVGW
INTYTGEPTY AADFKRRFTF SLDTSKSTAY LQMNSLRAED TAVYYCAKYP
HYYGSSHWYF DVWGQGTLVT VSSASTKGPS VFPLAPSSKS TSGGTAALGC
LVKDYFPEPV TVSWNSGALT SGVHTFPAVL QSSGLYSLSS VVTVPSSSLG
TQTYICNVNH KPSNTKVDKK VEPKSCDKTH TCPPCPAPEL LGGPSVFLFP
PKPKDTLMIS RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS REEMTKNQVS LTCLVKGFYP SDIAVEWESN GQPENNYKTT
PPVLDSDGSF FLYSKLTVDK SRWQQGNVFS CSVMHEALHN HYTQKSLSLS
PGK (SEQ ID NO: 3)

Light chain amino acid sequence of bevacizumab

DIQMTQSPSS LSASVGDRVT ITCSASQDIS NYLNWYQQKP GKAPKVLIYF
TSSLHSGVPS RFSGSGSGTD FTLTISSLQP EDFATYYCQQ YSTVPWTFGQ
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC (SEQ ID NO: 4)

Heavy chain amino acid sequence of ranibizumab

EVQLVESGGG LVQPGGSLRL SCAASGYDFT HYGMNWVRQA PGKGLEWVGW
INTYTGEPTY AADFKRRFTF SLDTSKSTAY LQMNSLRAED TAVYYCAKYP
YYYGTSHWYF DVWGQGTLVT VSSASTKGPS VFPLAPSSKS TSGGTAALGC
LVKDYFPEPV TVSWNSGALT SGVHTFPAVL QSSGLYSLSS VVTVPSSSLG
TQTYICNVNH KPSNTKVDKK VEPKSCDKTH L (SEQ ID NO: 5)

Light chain amino acid sequence of ranibizumab

DIQLTQSPSS LSASVGDRVT ITCSASQDIS NYLNWYQQKP GKAPKVLIYF
TSSLHSGVPS RFSGSGSGTD FTLTISSLQP EDFATYYCQQ YSTVPWTFGQ
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC (SEQ ID NO: 6)

In addition to the conversion from PDR to NPDR, this patient exhibited signs of peripheral vascular reperfusion

DAY 1
Proliferative DR (DRSS 65)

WEEK 22
Non-Proliferative DR (DRSS 53)

PDR = Proliferative DR; NPDR = Non-Proliferative DR; DRSS = DR Severity Scale; DRSS 53 = Severe NPDR; DRSS 65 = Moderate PDR

**It possible to get a fast *AND* lasting effect of up to 5 months without retreatment after only 3 loading injections in RVO**

| | Date | Treatment | VA Snellen |
|---|---|---|---|
| | 1/2018 | Bevacizumab | 20/64 |
| | 3/2018 | Bevacizumab | 20/100 |
| | 4/2018 | Bevacizumab | 20/150 |
| | 5/2018 | | 20/160 |
| | 7/2018 | KSI-301 | 20/80 |

FIG. 26

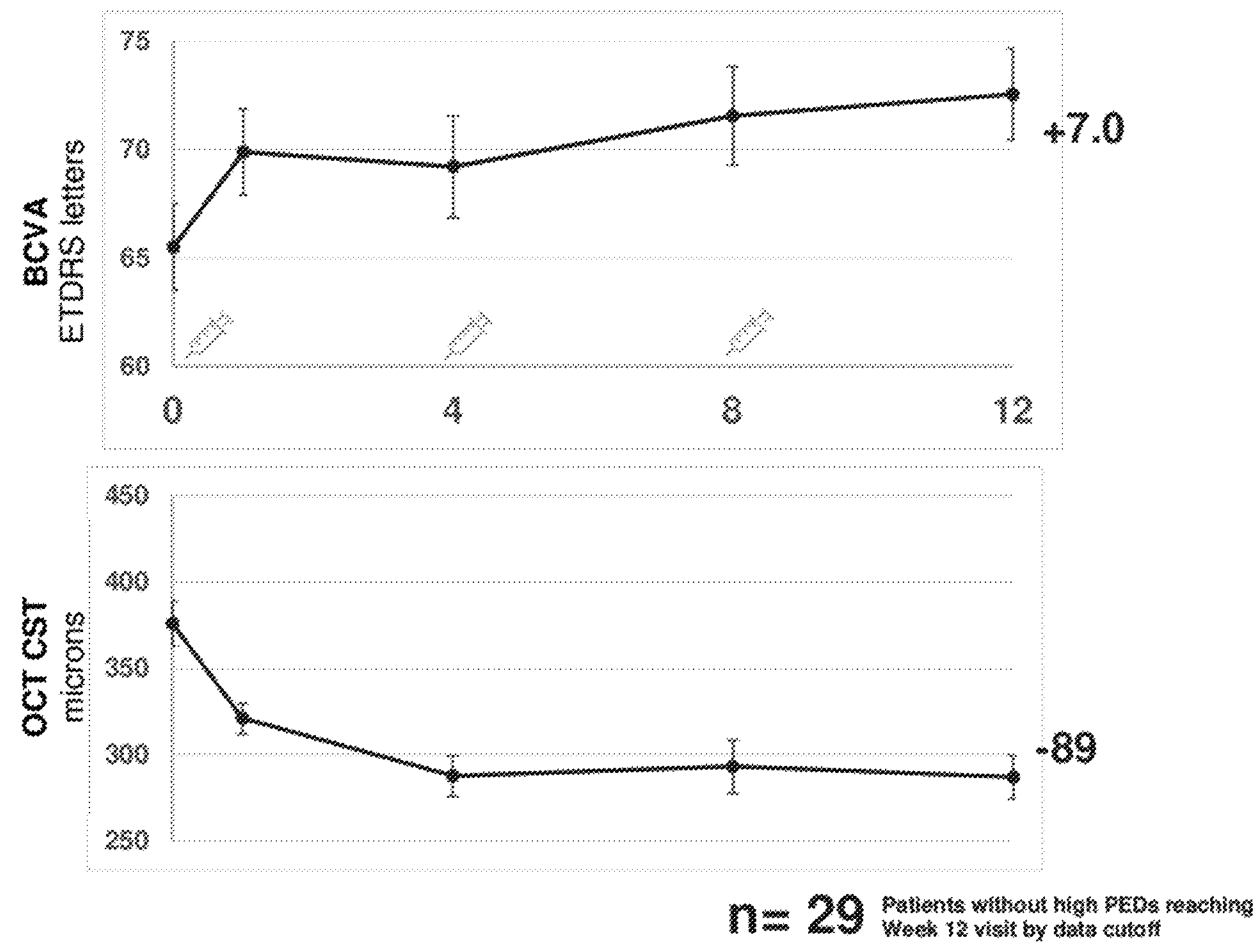

Interim data. Includes only randomized patients that reached Week 12 visit by the data cutoff date; 2.5 & 5 mg doses pooled. Error bars represent standard error of the mean. OCT CST values are site reported. BCVA= best corrected visual acuity; OCT= optical coherence tomography; CST= central subfield thickness.
High PED defined as presence of a PED with baseline CST ≥500 microns.

Interim data. Includes only randomized patients that reached Week 20 visit by the data cutoff date; 2.5 & 5 mg doses pooled. Error bars represent standard error of the mean. OCT CST values are site reported. BCVA= best corrected visual acuity; OCT= optical coherence tomography; CST= central subfield thickness Interim data. Includes only randomized patients that reached Week 12 visit by the data cutoff date; 2.5 & 5 mg doses pooled. Error bars represent standard error of the mean. OCT CST values are site reported. BCVA= best corrected visual acuity; OCT= optical coherence tomography; CST= central subfield thickness

| First Retreatment | Percentage |
|---|---|
| At or before 3 months | 14% (5/35) |
| Longer than 3 months | 86% (30/35) |
| 4 months or longer | 84% (27/32) |
| 5 months or longer | 72% (21/29) |
| 6 months | 55% (16/29) |

FIG. 36

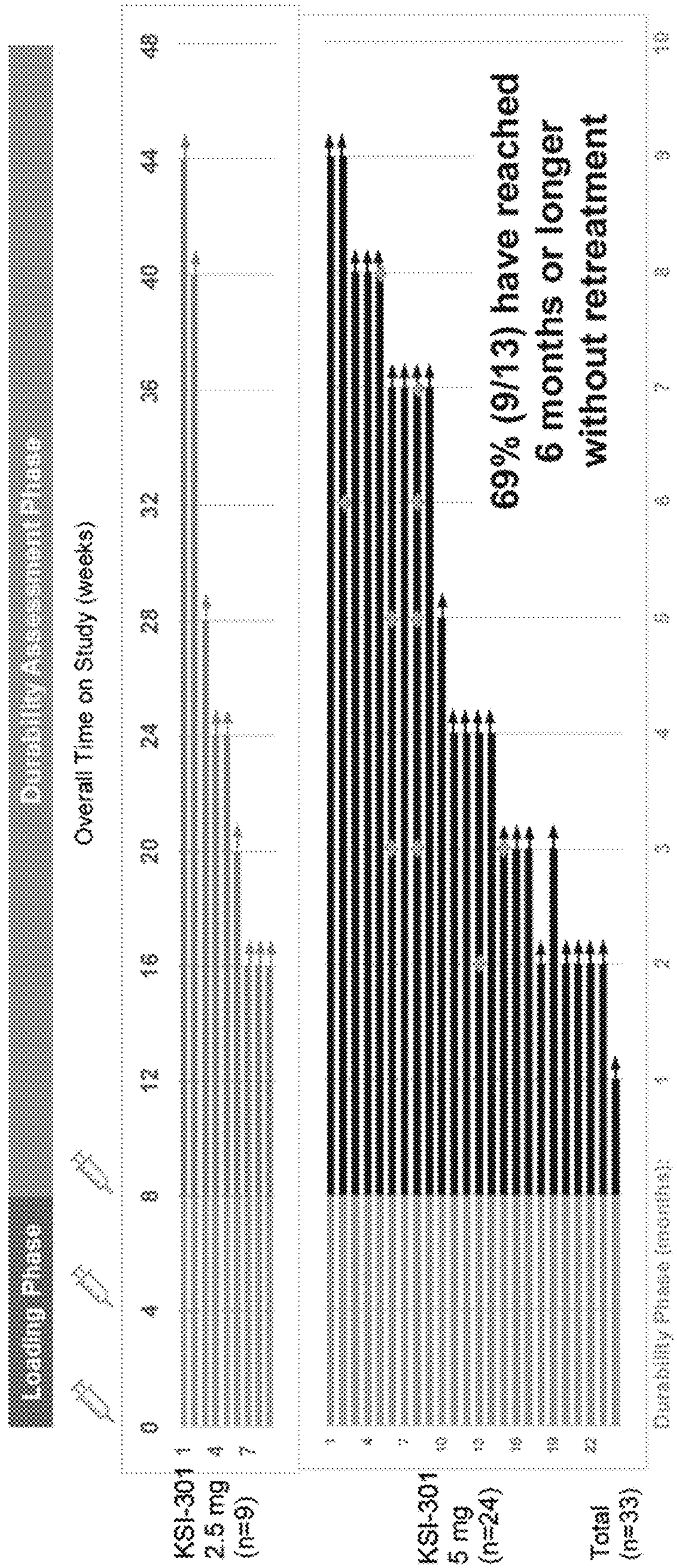

◆ Retreatment with KSI-301
➔ Continuing follow-up

| First Retreatment | Percentage |
|---|---|
| At or before 3 months | 17% (4/24) |
| Longer than 3 months | 83% (20/24) |
| 4 months or longer | 80% (16/20) |
| 5 months or longer | 73% (11/15) |
| 6 months or longer | 69% (9/13) |

Interim data, includes only randomized patients that reached the first retreatment opportunity (Week 12 visit) by the data cutoff date. Each bar represents an individual patient. All depicted patients continue to be followed (no discontinuations)

FIG. 37

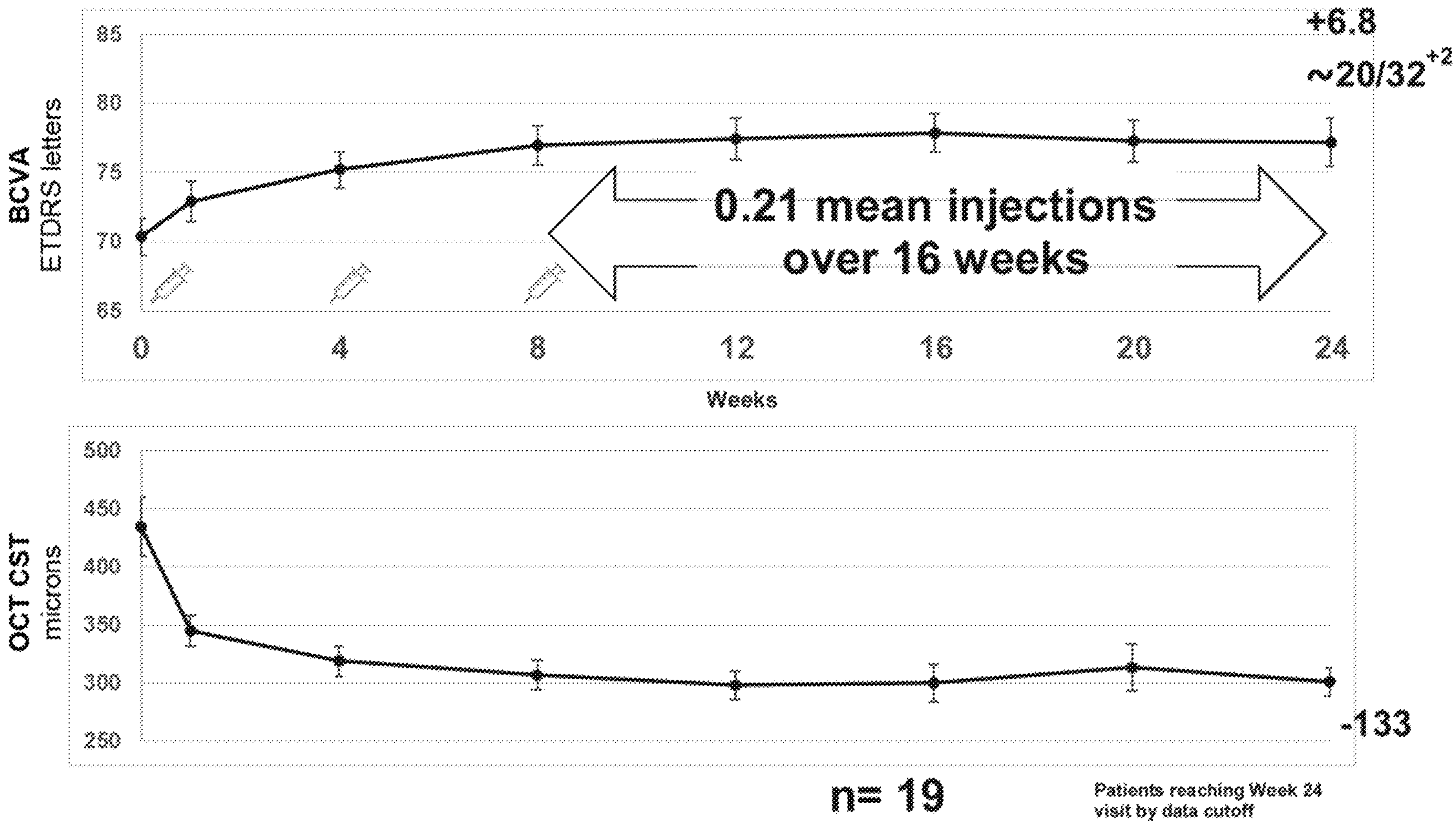

Interim data. Includes only randomized patients that reached Week 24 visit by the data cutoff date; 2.5 & 5 mg doses pooled. Error bars represent standard error of the mean. OCT CST values are site reported. BCVA= best corrected visual acuity; OCT= optical coherence tomography; CST= central subfield thickness. Mean injections reflect the average number of injections received per patient between Week 8 and 24 (compare to aflibercept per label and brolucizumab per pivotal study design has mean number of injections 2.0).

FIG. 39

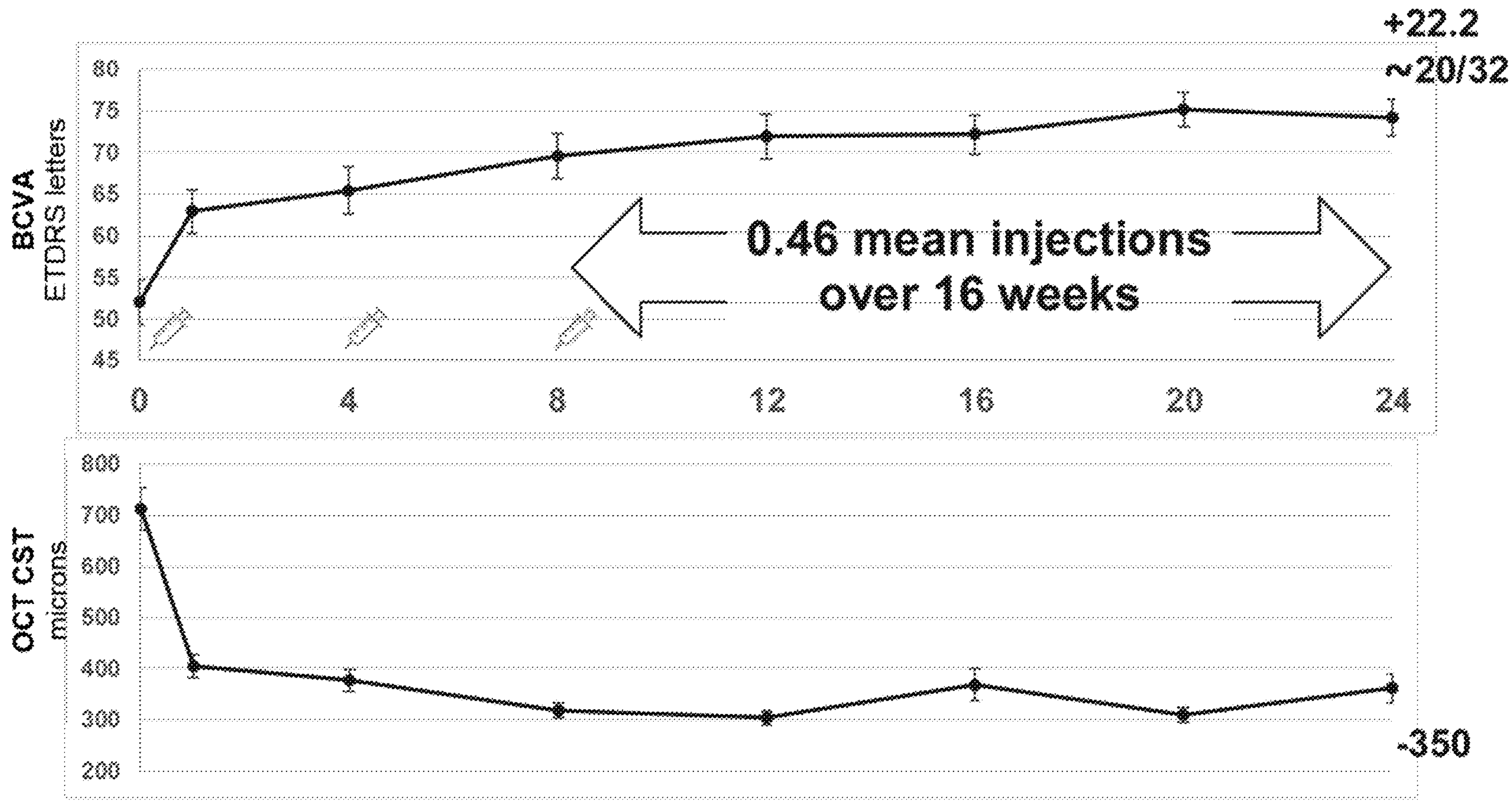

n= 30 Patients reaching Week 24 visit by data cutoff

BRVO n= 17
CRVO n= 13

Interim data. Includes only randomized patients that reached Week 24 visit by the data cutoff date; 2.5 & 5 mg doses pooled. Datapoints include two subjects that discontinued after Week 12 ~ Observed data. Error bars represent standard error of the mean. OCT CST values are site reported. BCVA= best corrected visual acuity; OCT= optical coherence tomography; CST= central subfield thickness. Mean injections reflect the average number of injections received per patient between Week 8 and 24 (compare to aflibercept per label and brolucizumab per pivotal study design have mean number of injections 3.0).

Interim data. Includes only randomized patients that would have met retreatment criteria before or at Week 28 by the data cutoff date. Each bar represents an individual patient.

Interim data. Includes only randomized patients that would have met retreatment criteria before or at Week 28 by the data cutoff date. Each bar represents an individual patient.

Interim data. Includes only randomized patients that reached the first retreatment opportunity (Week 12 visit) by the data cutoff date. Each bar represents an individual patient.

FIG. 45B

| First Retreatment | Percentage |
| --- | --- |
| At or before 2 months | 8% (4/49) |
| 3 months or longer | 92% (45/49) |
| 4 months or longer | 82% (40/49) |
| 5 months or longer | 66% (27/41) |
| 6 months | 49% (20/41) |

72% have achieved a 6-month treatment interval at least once during follow-up

1. Gillies MC, et al. Effect of Ranibizumab and Aflibercept on Best-Corrected Visual Acuity in Treat-and-Extend for Neovascular Age-Related Macular Degeneration: A Randomized Clinical Trial. JAMA Ophthalmol. 2019;137(4):372–379. doi:10.1001/jamaophthalmol.2018.6776
2. For KSI-301: Includes randomized patients that reached the first retreatment opportunity (Week 12 visit) by the data cutoff date.

FIG. 48

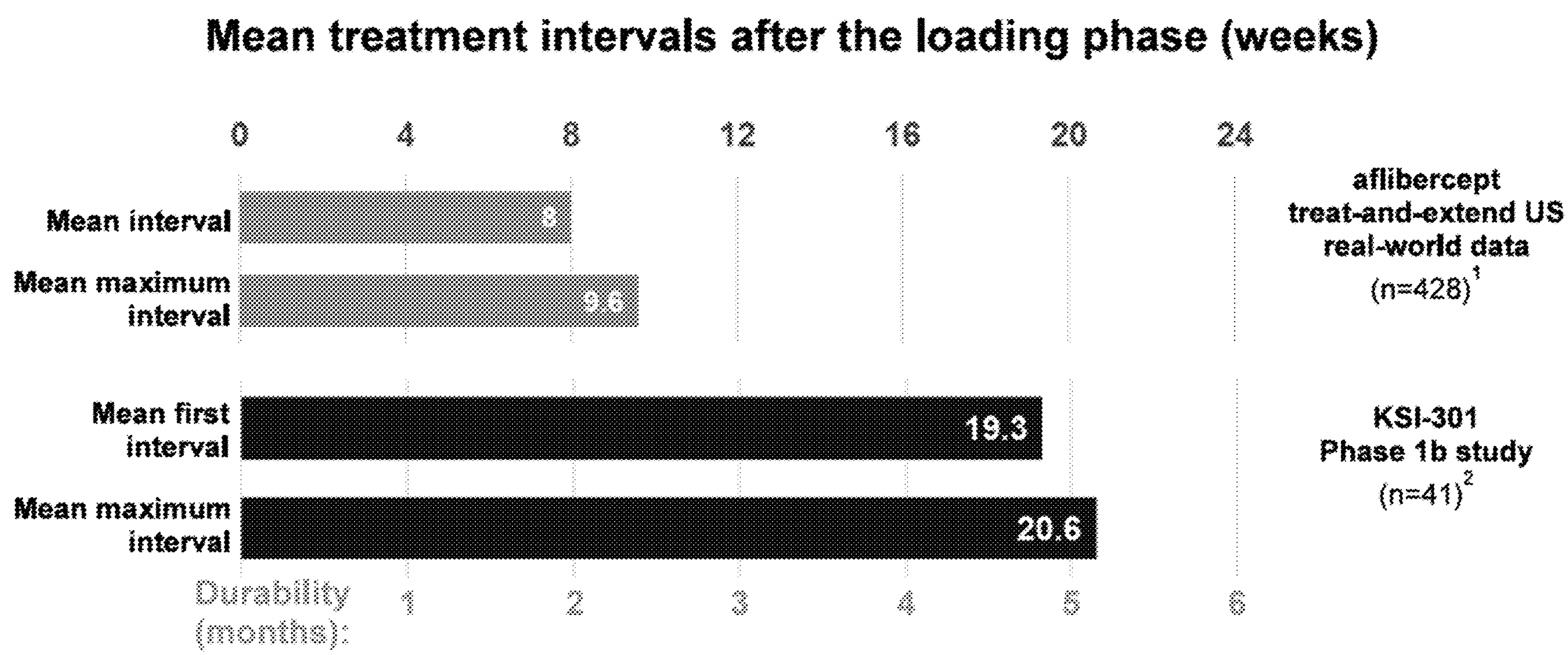

1. Singer MA, et al. Two-Year Real-World Treat and Extend Patterns and Fluid Outcomes Among Neovascular Age-Related Macular Degeneration Patients Treated With Anti-VEGFs. ASRS 2020 virtual meeting. Available at asrs.org. 2. Includes all randomized patients that received all three loading doses and a first retreatment by the data cutoff date. For Eylea data set, mean interval is the average interval per patient over two years, and mean maximum interval is the average of the longest interval achieved per patient at any point during follow-up. For KSI-301 data set, first interval refers to the first retreatment, and mean maximum interval is the average of the longest interval per patient at any point during follow-up.

Interim data. Includes only randomized patients that reached the first retreatment opportunity (Week 12 visit) by the data cutoff date. Each bar represents an individual patient. All depicted patients continue to be followed (no discontinuations)

FIG. 50B

| First Retreatment | Percentage |
|---|---|
| Before 2 months | 0% (0/33) |
| At 2 months | 3% (1/33) |
| 3 months or longer | 97% (32/33) |
| 4 months or longer | 76% (25/33) |
| 5 months or longer | 70% (23/33) |
| 6 months or longer | 67% (22/33) |

45% (15/33) have not yet required a single retreatment; 79% have achieved a 6-month treatment interval at least once during follow-up

1. Wells JA. Aflibercept, bevacizumab, or ranibizumab for diabetic macular edema (DRCR Protocol T). N Engl J Med. 2015 Mar 26;372(13):1193-203 (supplemental data).
2. Interim data. Annualized injections based on the current monthly injection rate of all DME patients as of the data cutoff.

FIG. 53

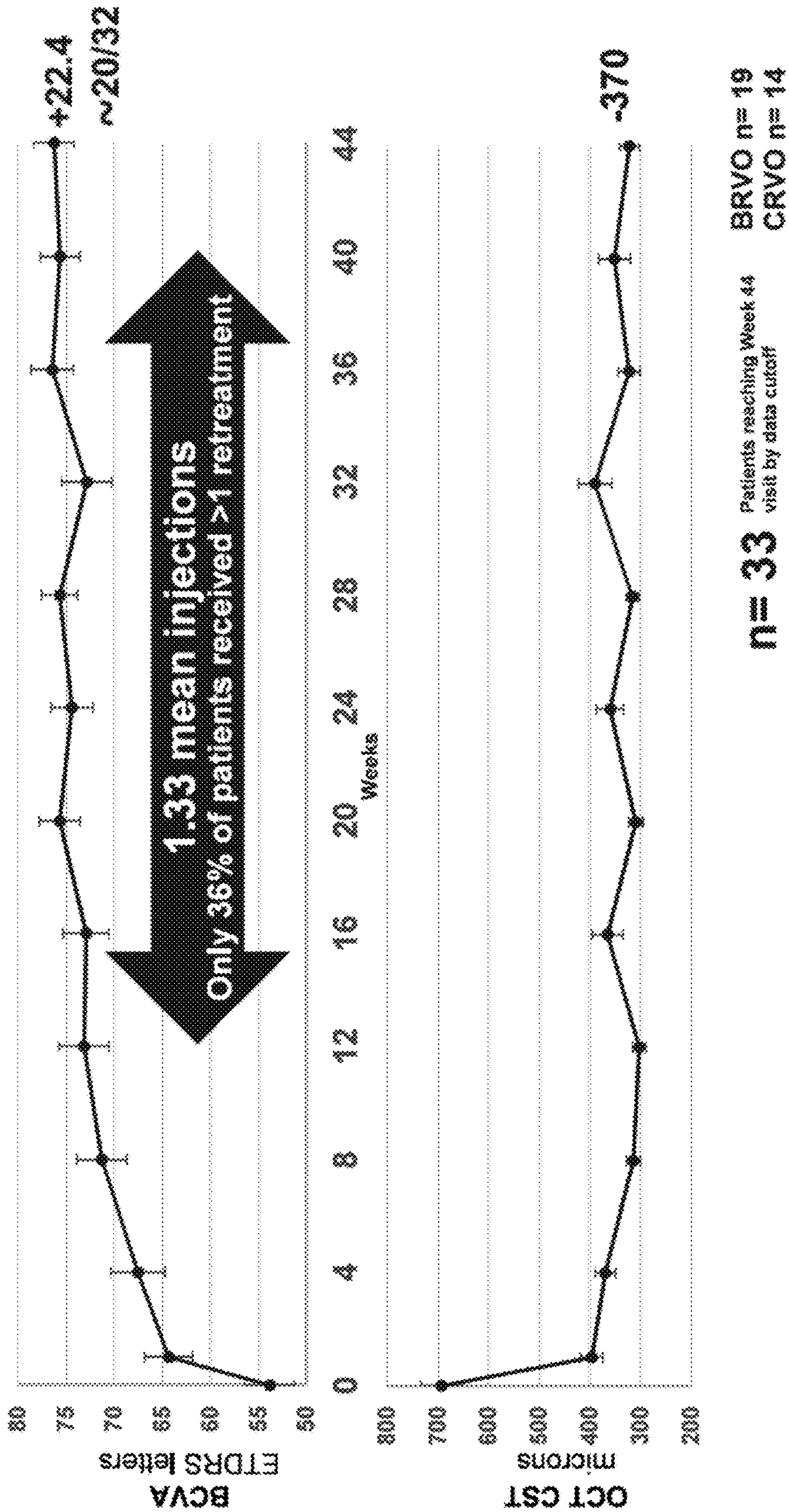

Interim data. Includes only randomized patients that reached Week 44 visit by the data cutoff date; 2, 5 & 5 mg doses pooled. Observed data. Error bars represent standard error of the mean. OCT CST values are site reported. BCVA= best corrected visual acuity; OCT= optical coherence tomography; CST= central subfield thickness. Mean injections reflect the average number of injections received per patient between Week 12 and 40 (aflibercept per label mean number of injections 8.0).

Interim data. Includes only randomized patients that reached the first retreatment opportunity (Week 12 visit) by the data cutoff date. Each bar represents an individual patient.

FIG. 54B

| First Retreatment | Percentage |
|---|---|
| At 1 month | 6% (2/34) |
| 2 months or longer | 94% (31/33) |
| 3 months or longer | 66% (21/32) |
| 4 months or longer | 56% (18/32) |

81% have achieved a 4-month or longer treatment interval at least once during follow-up

FIG. 55

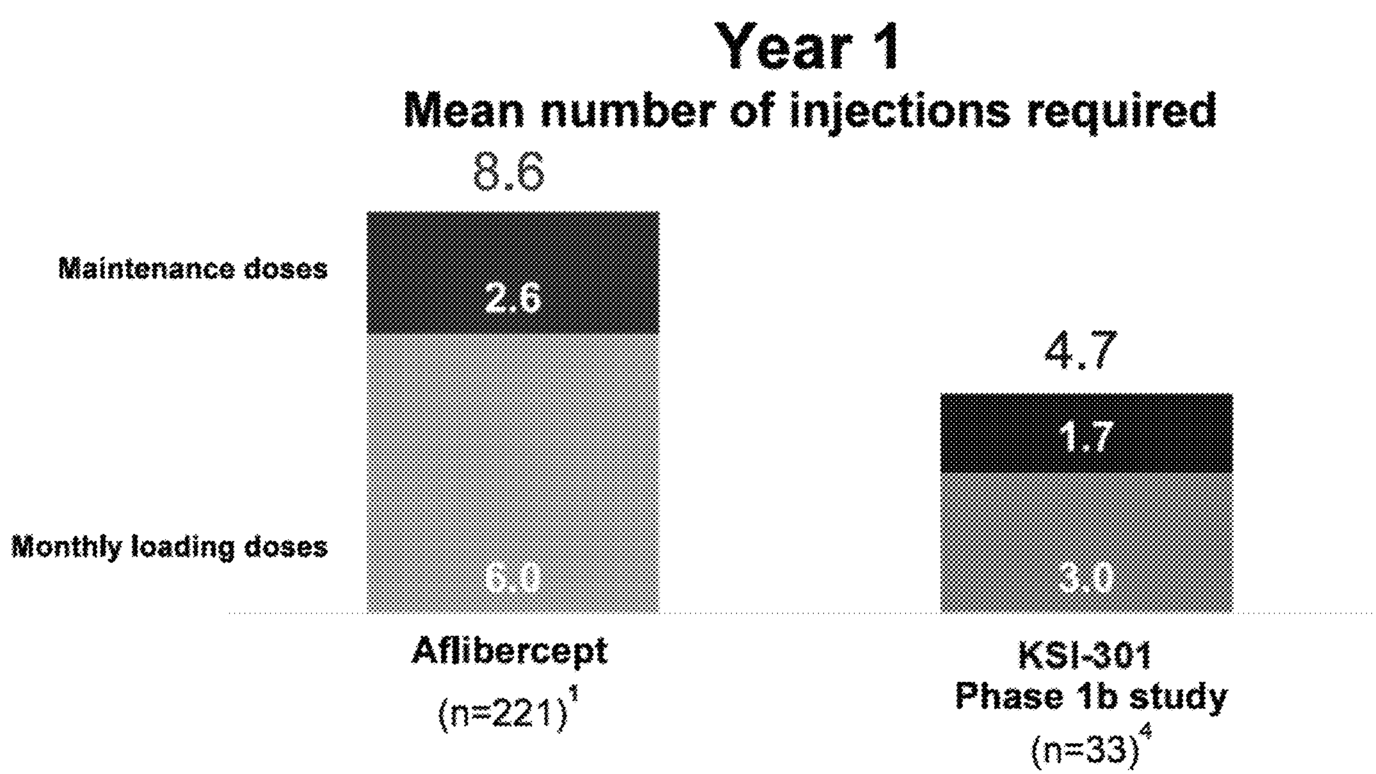

1. Injections averaged between the two pivotal aflibercept trials; n represents the total randomized in the aflibercept groups in both studies. Brown DM. Intravitreal Aflibercept Injection for Macular Edema Secondary to Central Retinal Vein Occlusion: 1-Year Results From the Phase 3 COPERNICUS Study. Am J Ophthalmol 2013;155:429–437,Korobelnik JF, et al. Intravitreal Aflibercept Injection for Macular Edema Resulting from Central Retinal Vein Occlusion. Ophthalmology 2014;121:202-208
2. Interim data. Annualized injections based on the current monthly injection rate of all RVO patients.

METHODS OF TREATING AN EYE DISORDER

CROSS-REFERENCE TO RELATED APPLICATION

This application is a divisional application of U.S. application Ser. No. 17/066,856, filed Oct. 9, 2020, which claims priority to U.S. Provisional Application Nos. 62/913,567, filed Oct. 10, 2019; 62/935,434, filed Nov. 14, 2019; and 62/971,738, filed Feb. 7, 2020. Each of these related applications is incorporated herein by reference in its entirety.

SEQUENCE LISTING

The present application is being filed along with a Sequence Listing in electronic format. The Sequence Listing is provided as a file entitled SEQLIST_KDIAK102D1.xml, created Nov. 2, 2023, which is 22,236 bytes in size. The information in the electronic format of the Sequence Listing is incorporated herein by reference in its entirety.

FIELD

The present disclosure relates to antibodies and conjugates thereof and methods of using and manufacturing said antibodies, conjugates thereof, and other protein conjugates.

BACKGROUND

Vascular endothelial growth factor (VEGF) stimulates vascular endothelial cell growth and induces vascular permeability. These biologic activities give it a central role in angiogenesis, both in normal and pathologic conditions. Inappropriate over-expression of VEGF has played a key role in retinal vascular diseases such as diabetic retinopathy (DR), diabetic macular edema (DME), wet age-related macular degeneration (wAMD), and retinal vein occlusion (RVO). In addition, increased retinal VEGF expression has been demonstrated in patients with retinal ischemic diseases. Inhibition of inappropriate VEGF activity is an "antiangiogenic" approach to treatment of these diseases and has been an effective method of preserving and improving visual acuity in patients with these retinal vascular diseases.

Intravitreal antiangiogenic therapy is currently the primary treatment for DME, wAMD, and macular edema due to RVO. However, standard treatment of these eye disorders with therapeutic VEGF-A inhibitors such as intravitreal aflibercept and intravitreal ranibizumab involve dosing every month or every 8 weeks (after initial monthly loading doses), depending on the eye disorder. Thus, real world outcomes have fallen short of expectation because of the burden involved in monthly visits to the retina specialist for evaluation and treatment. There is a medical need to achieve therapeutic results with fewer and/or less frequent intravitreal injections.

SUMMARY

Provided herein are methods of treating an eye disorder by administering an anti-VEGF antibody or anti-VEGF protein to a subject having an eye disorder. The anti-VEGF antibody of the present disclosure may be an anti-VEGF antibody conjugate (e.g., KSI-301), or anti-VEGF protein conjugate, that includes a polymeric moiety that extends the half-life (e.g., ocular half-life, etc.) of the antibody or protein when administered to a subject. Methods of the present disclosure may provide for a course of treatment for an eye disorder that includes fewer doses (e.g., less frequent administration) of the anti-VEGF antibody conjugates or anti-VEGF protein conjugates than conventional anti-VEGF therapies, to achieve a therapeutic effect of the anti-VEGF therapy on the subject.

Provided herein is a method of treating an eye disorder, wherein the method comprises: administering an anti-VEGF antibody conjugate (e.g., KSI-301), or anti-VEGF protein conjugate (e.g., an aflibercept biopolymer conjugate), to a subject in need of treating an eye disorder at a first loading dose; and repeating the loading dose at least once, but not more than twice, whereby the subject retains a therapeutic result of the anti-VEGF antibody conjugate, e.g., KSI-301, therapy for at least 12 weeks after a final loading dose. Optionally, the eye disorder is at least one of diabetic macular edema (DME), retinal vein occlusion (RVO), wet age-related macular degeneration (AMD), and diabetic retinopathy (DR). In some embodiments, the eye disorder is either DME or RVO.

Also provided herein is a method of treating retinal vein occlusion (RVO), wherein the method comprises: administering anti-VEGF antibody conjugate (e.g., KSI-301), or anti-VEGF protein conjugate (e.g., an aflibercept biopolymer conjugate), to a subject with RVO at a first loading dose; and repeating the loading dose once; whereby the subject retains a therapeutic result of the anti-VEGF antibody conjugate, e.g., KSI-301, therapy for at least 8 weeks after a final loading dose.

In some embodiments, the therapeutic result of the anti-VEGF antibody conjugate, e.g., KSI-301, therapy lasts for at least 12, at least 14, including at least 16 weeks past a final loading dose. In some embodiments, the therapeutic result of the anti-VEGF antibody conjugate therapy lasts for at least 20 weeks past a final loading dose.

Optionally, no further administration of the anti-VEGF antibody conjugate (e.g., KSI-301) is provided to the subject within four weeks of a final loading dose. In some embodiments, no further administration of the anti-VEGF antibody conjugate, e.g., KSI-301, is provided to the subject within ten, within 12, or within 16 weeks of a final loading dose. In some embodiments, no further administration of the anti-VEGF antibody conjugate, e.g., KSI-301 is provided to the subject within 14 weeks of a final loading dose. In some embodiments, no further administration of the anti-VEGF antibody conjugate, e.g., KSI-301, is provided to the subject within twenty weeks of a final loading dose.

Optionally, the loading doses are administered with one month between each loading dose. In some embodiments, the loading doses are administered with about one to two months between each loading dose. In some embodiments, the loading doses are administered with about two months between each loading dose.

Optionally, a method of the present disclosure includes administering one or more subsequent doses of the anti-VEGF antibody conjugate (e.g., KSI-301) to the subject after the final loading dose. In some embodiments, any subsequent dose of the anti-VEGF antibody conjugate, e.g., KSI-301 is administered no more frequently than once every 12 weeks. In some embodiments, any subsequent dose of the anti-VEGF antibody conjugate, e.g., KSI-301, is administered no more frequently than once every 20 weeks. In some embodiments, the one or more subsequent doses of the anti-VEGF antibody conjugate is administered on average no more frequently than once every 24 weeks. Optionally, the method includes administering a first subsequent dose of the anti-VEGF antibody conjugate, e.g., KSI-301, at a first time period after the final loading dose; and administering a second subsequent dose at a second time period after the first subsequent dose, wherein anti-VEGF antibody conjugate, e.g., KSI-301, is not administered between the first subsequent dose and the second subsequent dose, wherein the first time period is shorter than the second time period. In some embodiments, the first time period is 8 weeks or more. In some embodiments, the second time interval is longer than the first time period by at least 4 weeks.

Optionally, about 1.25 mg of antibody per loading dose is administered to the subject in the form of the anti-VEGF antibody conjugate, e.g., KSI-301. In some embodiments, about 5 mg of antibody per loading dose is administered to the subject in the form of the anti-VEGF antibody conjugate, e.g., KSI-301.

In some embodiments, no dose following the loading dose is administered until at least 20 weeks following the last loading dose.

Optionally, the therapeutic result comprises one or more of improved visual acuity, reduced retinal thickness, improved perfusion in at least one eye (e.g., at least one eye to which anti-VEGF antibody conjugate, e.g., KSI-301, has been administered), improved diabetic retinopathy severity score (DRSS), or reduced disease activity of the eye disorder, compared to a pre-treatment level.

Also provided herein is a method of improving perfusion of an eye, the method comprising: identifying a subject with DME, DR or RVO; and administering at least 2 loading doses of the anti-VEGF antibody conjugate (e.g., KSI-301), or anti-VEGF protein conjugate (e.g., an aflibercept biopolymer conjugate), to the subject; providing one or more further doses of the anti-VEGF antibody conjugate, e.g., KSI-301, or anti-VEGF protein conjugate (e.g., aflibercept biopolymer conjugate), to the subject, until the subject displays improved perfusion in at least one eye. Optionally, each of the loading dose of the anti-VEGF antibody conjugate, e.g., KSI-301, comprises at least 1.25 mg of antibody protein. Optionally, no dose following the loading doses is administered until at least 20 weeks following a last loading dose. In some embodiments, no dose following the loading dose is administered until at least 24 weeks following the last loading dose.

The present disclosure also provides a method of improving perfusion of an eye, the method comprising: identifying a subject with non-proliferative DR; and administering an initial dose of the anti-VEGF antibody conjugate (e.g., KSI-301), or anti-VEGF protein conjugate (e.g., an aflibercept biopolymer conjugate), to the subject, to provide improved perfusion in at least one eye. Optionally, the method comprises providing one or more further doses of the anti-VEGF antibody conjugate, e.g., KSI-301, to the subject after the initial dose. In some embodiments, no dose is administered until at least 20 weeks following the initial dose. In some embodiments, no loading dose of the anti-VEGF antibody conjugate, e.g., KSI-301, is administered to the subject. Optionally, each dose of the anti-VEGF antibody conjugate, e.g., KSI-301, comprises at least 1.25 mg of antibody protein. Optionally, the improved perfusion comprises at least a reduction in the rate of progressive non-perfusion in the at least one eye. In some embodiments, the improved perfusion comprises a reduction in the area of non-perfusion of at least 10% over pre-treatment.

Also provided herein is a method of treating a subject with DME, DR or RVO, the method comprising: administering 1-3 loading doses of the anti-VEGF antibody conjugate (e.g., KSI-301), or anti-VEGF protein conjugate (e.g., an aflibercept biopolymer conjugate), to a subject with DME, DR or RVO; not administering more than 3 loading doses to the subject; providing a follow-on application of the anti-VEGF antibody conjugate, e.g., KSI-301, or anti-VEGF protein conjugate (e.g., aflibercept biopolymer conjugate), at a point in time no sooner than 12 weeks after a last loading dose or a last follow-on application of the anti-VEGF antibody conjugate, e.g., KSI-301, or anti-VEGF protein conjugate (e.g., aflibercept biopolymer conjugate), wherein the loading doses are administered to the subject on a monthly basis. Optionally, the subject has proliferative DR, and wherein the method comprises administering 3 loading doses of the anti-VEGF antibody conjugate, e.g., KSI-301, to the subject.

Also provided is a method of treating a subject with non-proliferative DR, the method comprising: administering 1 or 2 loading doses of the anti-VEGF antibody conjugate (e.g., KSI-301), or anti-VEGF protein conjugate (e.g., an aflibercept biopolymer conjugate), to a subject with non-proliferative DR; not administering more than 2 loading doses to the subject; and providing a follow-on administration of the anti-VEGF antibody conjugate, e.g., KSI-301, or anti-VEGF protein conjugate (e.g., aflibercept biopolymer conjugate), at a point in time no sooner than 12 weeks after a last loading dose, wherein the loading doses are administered to the subject on a monthly basis.

The present disclosure also provides a method of treating a subject with RVO, the method comprising: administering 1 or 2 loading doses of the anti-VEGF antibody conjugate (e.g., KSI-301), or anti-VEGF protein conjugate (e.g., an aflibercept biopolymer conjugate), to a subject with RVO; not administering more than 2 loading doses to the subject; providing a follow-on administration of the anti-VEGF antibody conjugate, e.g., KSI-301, or anti-VEGF protein conjugate (e.g., aflibercept biopolymer conjugate), at a point in time no sooner than 8 weeks after a last loading dose, wherein the loading doses are administered to the subject on a monthly basis.

Optionally, each of the loading dose of the anti-VEGF antibody conjugate, e.g., KSI-301, comprises at least 1.25 mg of antibody protein.

Optionally, the anti-VEGF antibody conjugate, e.g., KSI-301, is administered via intravitreal injection. Optionally, the anti-VEGF antibody conjugate, e.g., KSI-301, is administered at an amount of 5 mg.

Optionally, the anti-VEGF antibody conjugate, e.g., KSI-301, comprises: an antibody conjugate comprising an anti-VEGF-A immunoglobulin G (IgG) bonded to a polymer, which polymer comprises MPC monomers, wherein the sequence of the anti-VEGF-A antibody heavy chain is SEQ ID NO: 1, and the sequence of the anti-VEGF-A antibody light chain is SEQ ID NO. 2, and wherein the antibody is bonded at C449 in SEQ ID NO. 1 to the polymer. In some embodiments, the anti-VEGF antibody conjugate, e.g., KSI-301, comprises an antibody conjugate comprising a light chain and a heavy chain, wherein the anti-VEGF-A antibody heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and the anti-VEGF-A antibody light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14). In some embodiments, the antibody conjugate has the following structure:

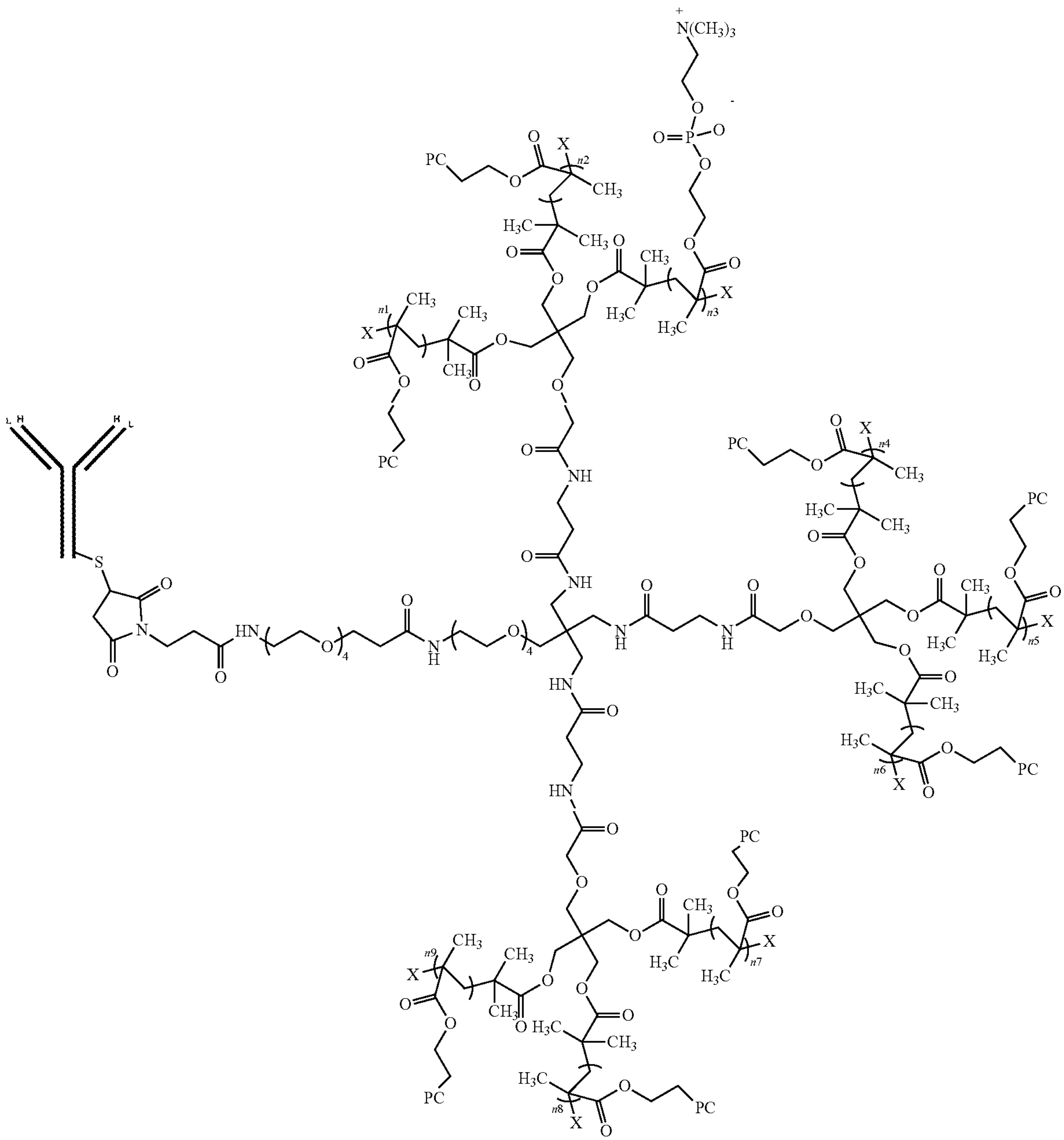

where each heavy chain of the anti-VEGF-A antibody is denoted by the letter H, and each light chain of the anti-VEGF-A antibody is denoted by the letter L; the polymer is bonded to the anti-VEGF-A antibody through the sulfhydryl of C443 (EU numbering), which bond is depicted on one of the heavy chains; PC is

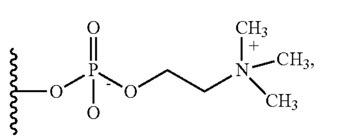

where the curvy line indicates the point of attachment to the rest of the polymer, where X is a) —OR where R is H, methyl, ethyl, propyl, or isopropyl, b) —H, c) any halogen, including —Br, —Cl, or —I, d) —SCN, or e) —NCS; and n1, n2, n3, n4, n5, n6, n7, n8 and n9 are the same or different such that the sum of n1, n2, n3, n4, n5, n6, n6, n7, n8 and n9 is 2500 plus or minus 15%.

Also provided herein is a method of treating RVO, wherein the method comprises: administering an anti-VEGF antibody conjugate (e.g., KSI-301), or anti-VEGF protein conjugate (e.g., an aflibercept biopolymer conjugate), to a subject in need of treating RVO at 1-3 loading doses; and whereby the subject retains a therapeutic result of the anti-VEGF antibody conjugate, e.g., KSI-301, therapy, or anti-VEGF protein conjugate (e.g., aflibercept biopolymer conjugate) therapy, for RVO for at least 8 weeks after a final loading dose and/or for one or more subsequent dosing intervals of at least 8 weeks. Optionally, the subject is not retreated with the anti-VEGF antibody conjugate, e.g., KSI-301, more frequently than once every 10 weeks. Optionally, the subject is not retreated with the anti-VEGF antibody conjugate, e.g., KSI-301, more frequently than once every 12 weeks.

The present disclosure also provides a method of disease modification of an eye disorder, wherein the method comprises: administering anti-VEGF antibody conjugate (e.g., KSI-301), or anti-VEGF protein conjugate (e.g., an aflibercept biopolymer conjugate), to a subject having an eye disorder at a first loading dose, whereby the eye disorder is thereby modified in a beneficial manner to the subject.

Also provided herein is a method of treating an eye disorder, the method comprising: identifying a subject with DME, DR or RVO; and administering 1-6 loading doses of the anti-VEGF antibody conjugate (e.g., KSI-301), or anti-VEGF protein conjugate (e.g., an aflibercept biopolymer conjugate), to the subject; providing a first retreatment dose of the anti-VEGF antibody conjugate or anti-VEGF protein conjugate to the subject following a first amount of time from the last loading dose; and providing a second retreatment dose of the anti-VEGF antibody conjugate, e.g., KSI-301, or anti-VEGF protein conjugate (e.g., an aflibercept biopolymer conjugate), to the subject, following a second amount of time from the first retreatment dose of the anti-VEGF antibody conjugate, e.g., KSI-301, or anti-VEGF protein conjugate (e.g., an aflibercept biopolymer conjugate), wherein the second amount of time is equal to or greater than the first amount of time. Optionally, the method includes administering 1-3 loading doses of the anti-VEGF antibody conjugate to the subject. Optionally, the second amount of time is at least 1 week more than the first amount of time. In some embodiments, the second amount of time is at least 2 weeks more than the first amount of time. In some embodiments, the second amount of time is at least 4 weeks more than the first amount of time.

Also provided herein is a method of treating an eye disorder, comprising: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is diabetic macular edema (DME); and repeating the loading dose at least once, but not more than twice, whereby the subject retains a therapeutic result of the anti-VEGF antibody conjugate therapy, or anti-VEGF protein conjugate therapy for at least 8 weeks after a final loading dose. Optionally, the method further includes administering one or more subsequent doses of the anti-VEGF antibody conjugate to the subject after the final loading dose. In some embodiments, the method includes administering the one or more subsequent doses of the anti-VEGF antibody conjugate at a dosing schedule of Q8W or longer. In some embodiments, the dosing schedule is between Q8W and Q24W. In some embodiments, no subsequent dose of the anti-VEGF antibody conjugate is administered to the subject within at least about one year after the first loading dose.

Also provided herein is method of treating an eye disorder, comprising: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is wet age-related macular degeneration (wAMD); and repeating the loading dose at least once, but not more than twice, whereby the subject retains a therapeutic result of the anti-VEGF antibody conjugate therapy, or anti-VEGF protein conjugate therapy, for at least 12 weeks after a final loading dose. Optionally, the method further includes administering one or more subsequent doses of the anti-VEGF antibody conjugate to the subject after the final loading dose at a dosing schedule of Q12W or longer. Optionally, the dosing schedule is between Q12W and Q20W. In some embodiments, no more than one subsequent dose of the anti-VEGF antibody conjugate is administered to the subject within about one year of the first loading dose.

Also provided herein is a method of treating an eye disorder, comprising: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is retinal vein occlusion (RVO); and repeating the loading dose at least once, but not more than twice, whereby the subject retains a therapeutic result of the anti-VEGF antibody conjugate therapy, or anti-VEGF protein conjugate therapy, for at least 8 weeks after a final loading dose. In some embodiments, the method further includes administering one or more subsequent doses of the anti-VEGF antibody conjugate to the subject after the final loading dose. Optionally, the method includes administering the one or more subsequent doses of the anti-VEGF antibody conjugate at a dosing schedule of Q8W or longer.

Provided herein is a method of treating an eye disorder, comprising administering to a subject in need of treating an eye disorder a therapeutically effective amount of an anti-VEGF antibody conjugate, e.g., KSI-301, or anti-VEGF protein conjugate (e.g., an aflibercept biopolymer conjugate), at dosing schedule of Q12W or longer, wherein the eye disorder is diabetic retinopathy (DR), thereby treating the eye disorder. In some embodiments, the dosing schedule is between Q12W and Q24W. In some embodiments, the method further comprises administering to the subject no more than two loading doses of the anti-VEGF antibody conjugate. Optionally, the time between any two consecutive loading doses is about 8 weeks.

Also provided is a method of treating an eye disorder, comprising administering to a subject in need of treating an eye disorder a first dose of a plurality of doses of an anti-VEGF antibody conjugate, e.g., KSI-301, or anti-VEGF protein conjugate (e.g., an aflibercept biopolymer conjugate), in a dosing schedule comprising: a loading dosing schedule comprising 1-3 loading doses of the anti-VEGF antibody conjugate or anti-VEGF protein conjugate, wherein the first dose is a loading dose; followed by a maintenance dosing schedule comprising one or more subsequent doses of the anti-VEGF antibody conjugate or anti-VEGF protein conjugate after a final loading dose, wherein the maintenance dosing schedule comprises a predetermined dosing schedule of Q8W or longer. Optionally, the method further comprises: evaluating a therapeutic result of the anti-VEGF antibody conjugate therapy in the subject at one or more time points after the first dose; and administering a subsequent dose of the anti-VEGF antibody conjugate to the subject at a subsequent time point specified by the predetermined dosing schedule, unless the therapeutic result is retained by the subject, in which case extending the time interval until administering the subsequent dose. In some embodiments, the eye disorder is wAMD, and the predetermined dosing schedule is Q12W or longer. In some embodiments, the eye disorder is DME, DR, or RVO.

Also provided herein is a method of treating an eye disorder, comprising: identifying a subject in need of treating an eye disorder, wherein the eye disorder is presumed ocular histoplasmosis syndrome; and intravitreally administering to the subject a therapeutically effective amount of the anti-VEGF antibody conjugate, e.g., KSI-301, or anti-VEGF protein conjugate (e.g., an aflibercept biopolymer conjugate), thereby treating the eye disorder. Optionally, the therapeutically effective amount comprises about 1 mg to about 5 mg of the anti-VEGF antibody conjugate.

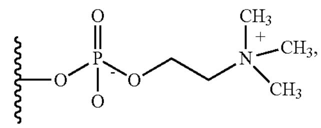

where the curvy line indicates the point of attachment to the rest of the polymer; and n1, n2, n3, n4, n5, n6, n7, n8 and n9 are the same or different such that the sum of n1, n2, n3, n4, n5, n6, n6, n7, n8 and n9 is 2500 plus or minus 15%.

FIG. 14 depicts an amino acid sequence of the heavy and light chains of KSI-301, according to some embodiments of the present disclosures.

FIG. 15 is a set of amino acid sequences for various antibodies.

Figure 16:
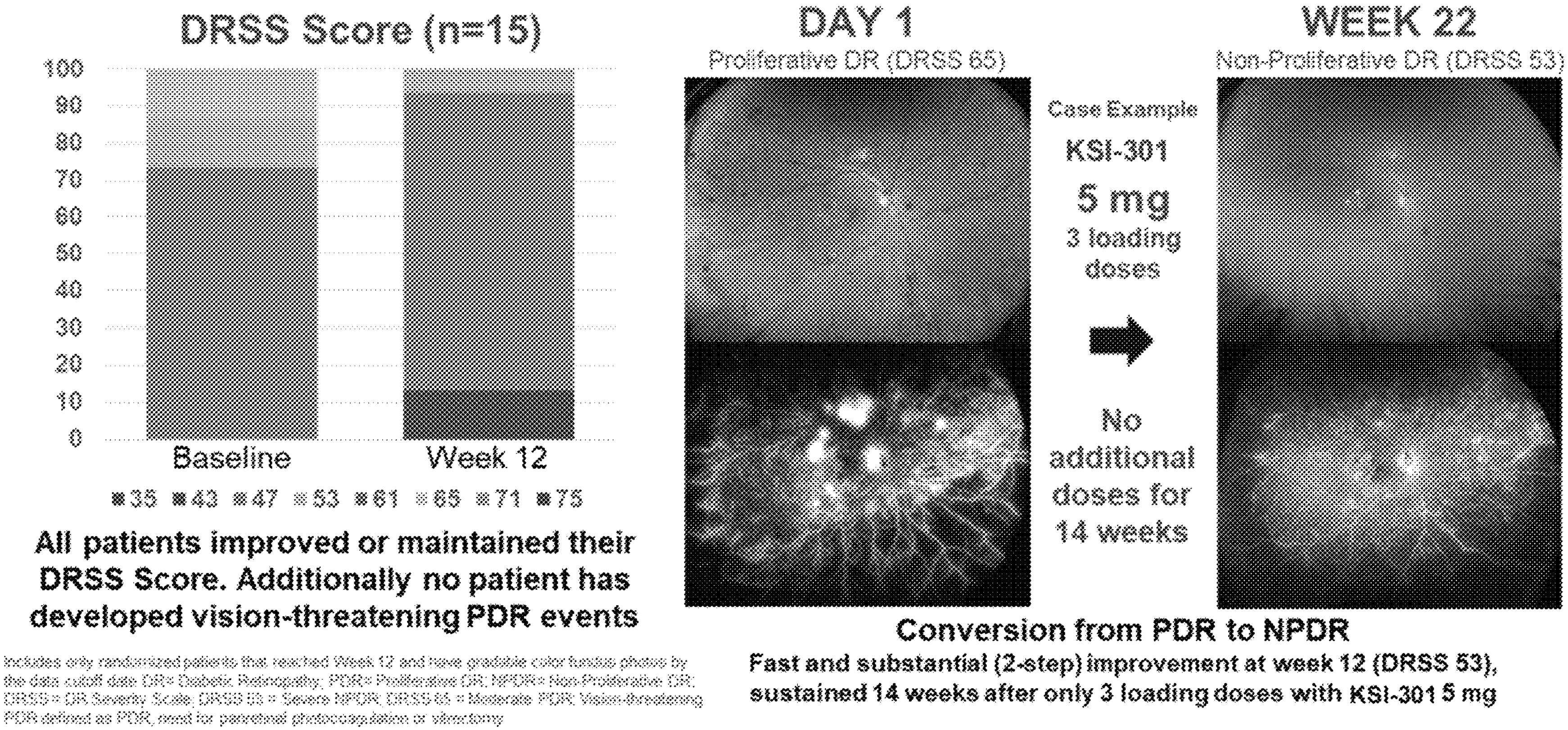

FIG. 16 is a graph showing the proportion of patients with differing levels of diabetic retinopathy severity, measured on a standardized photographic reading scale.

Figure 17A:
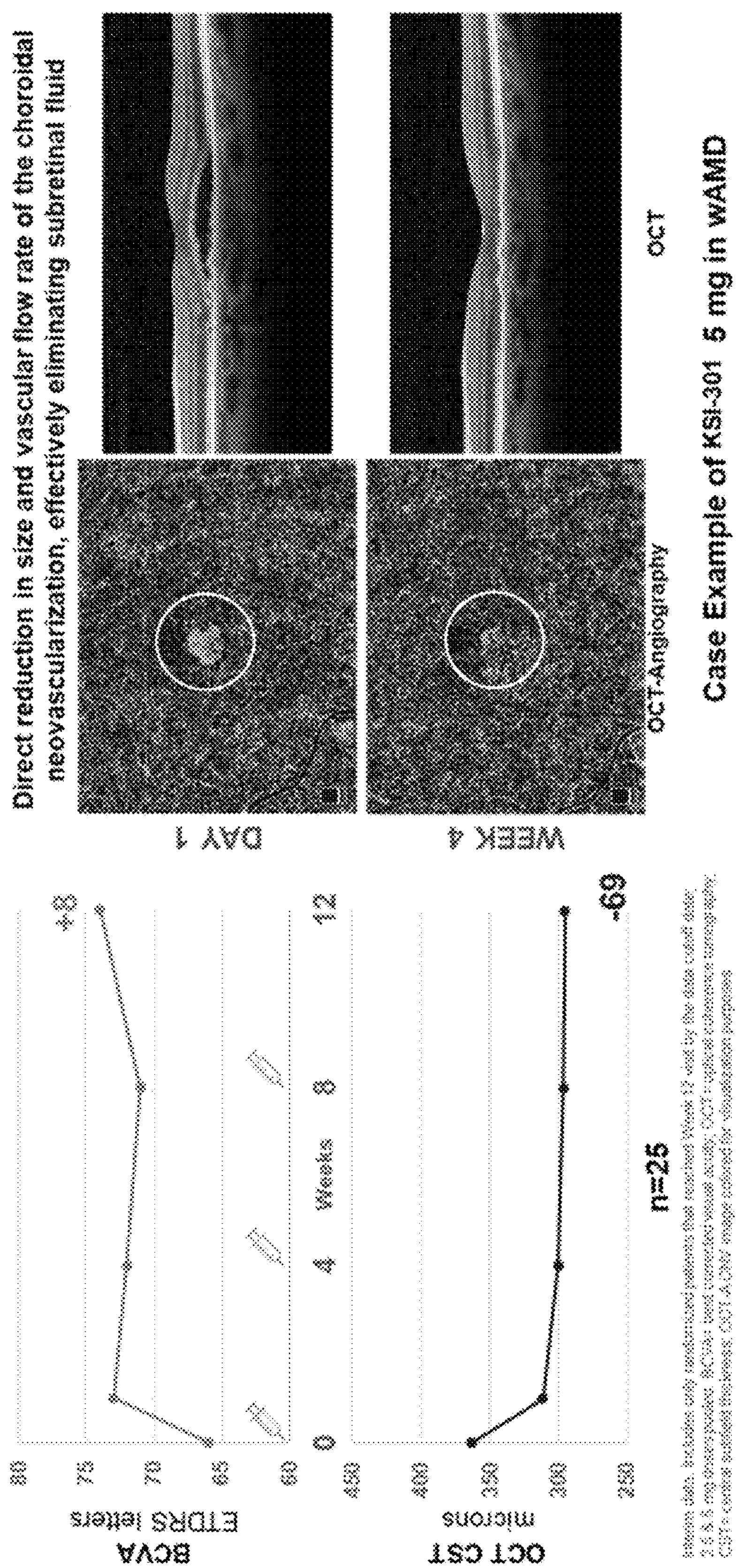
Figure 17B:
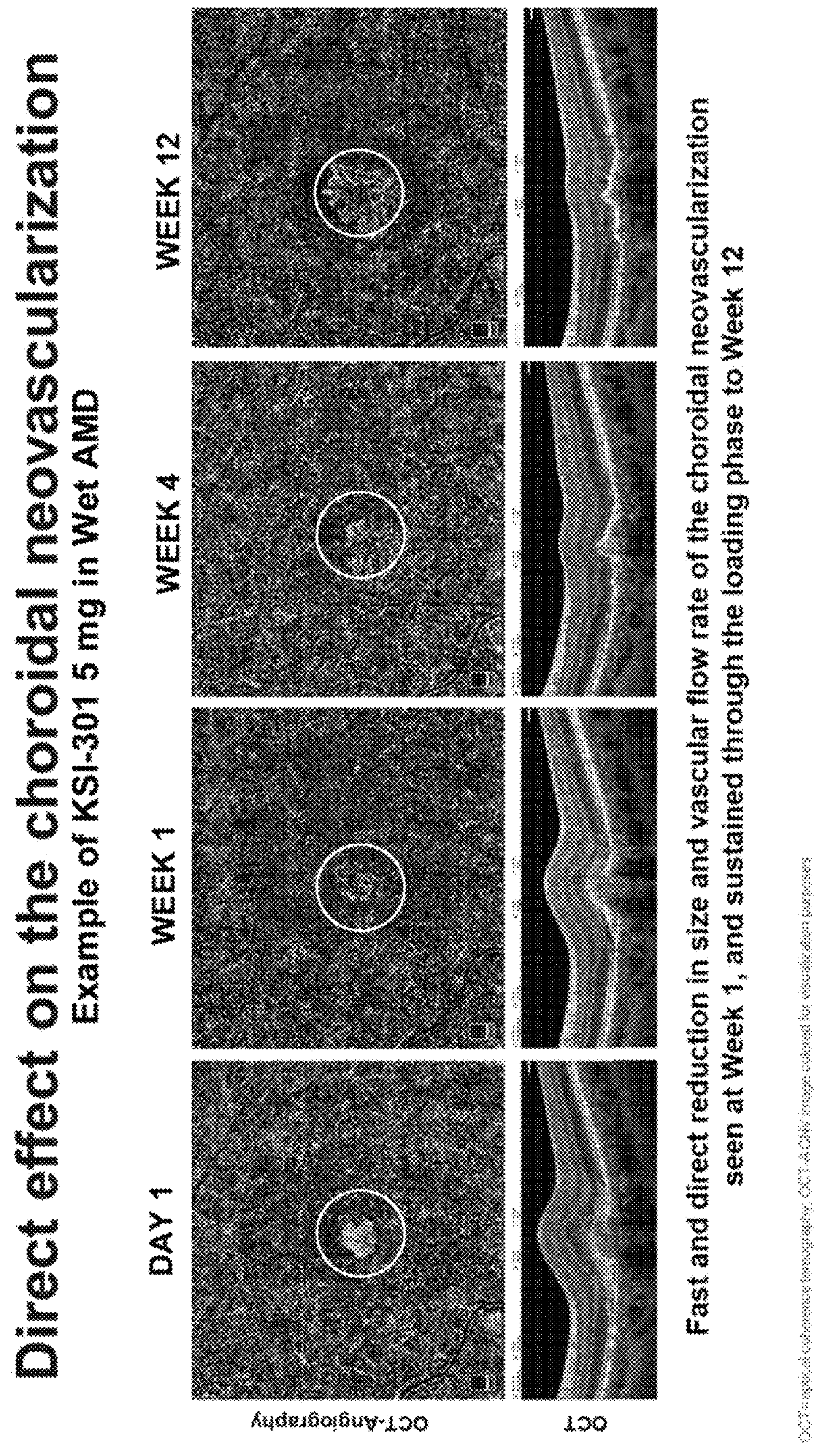

FIGS. 17A and 17B display the efficacy of KSI-301 in Wet AMD and the direct effect on the choroidal neovascularization. FIG. 17A displays the efficacy of KSI-301 in Wet AMD, and the change from baseline to week in median BCVA and OCT CST.

FIGS. 18A-18D show the results in a DME patient with disease modification post 3 loading doses, with significant DRSS improvement and reperfusion representing disease modification.

Figure 19:
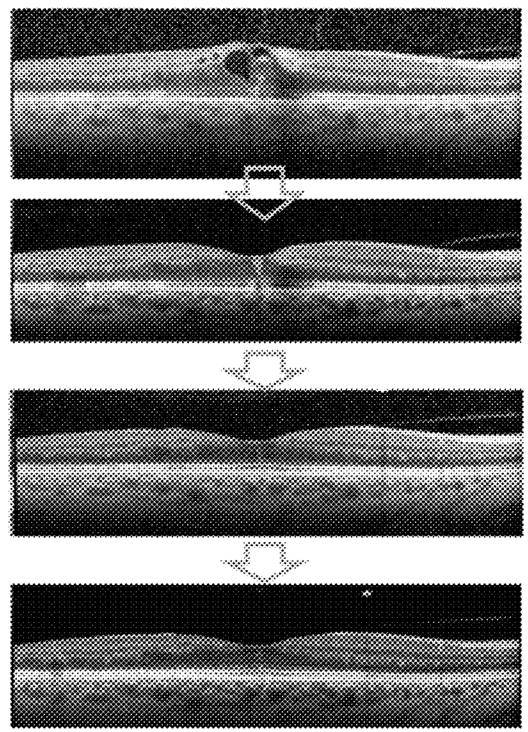

FIG. 19 shows the results of an RVO patient that after 3 loading doses with no additional doses required for at least 5 months, representing possible disease modification.

Figure 20:
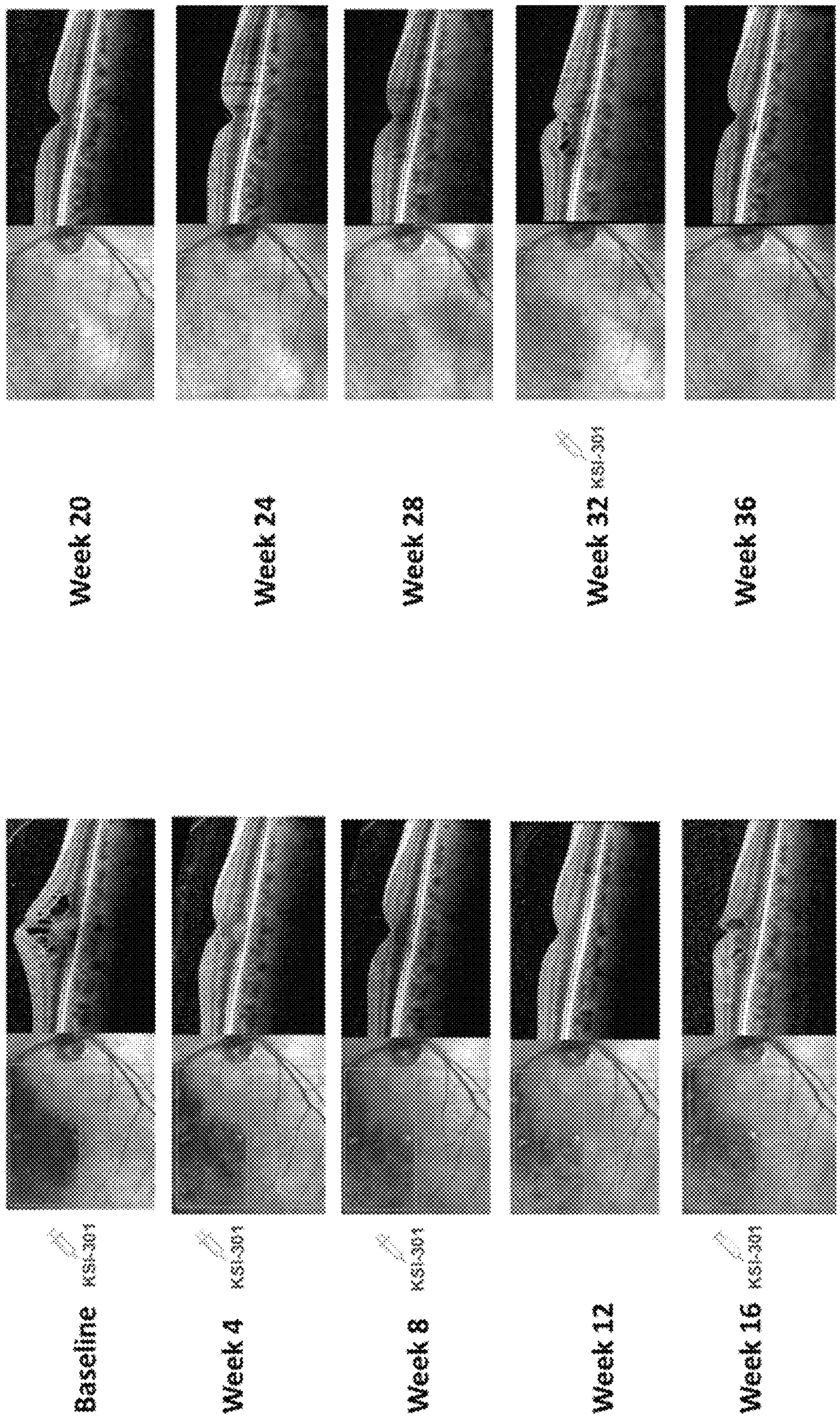

FIG. 20 displays a set of OCT images of a patient showing the effect of 3 loading doses lasting 8 weeks until diseases recurs and the patient receives retreatment.

Figure 21A:
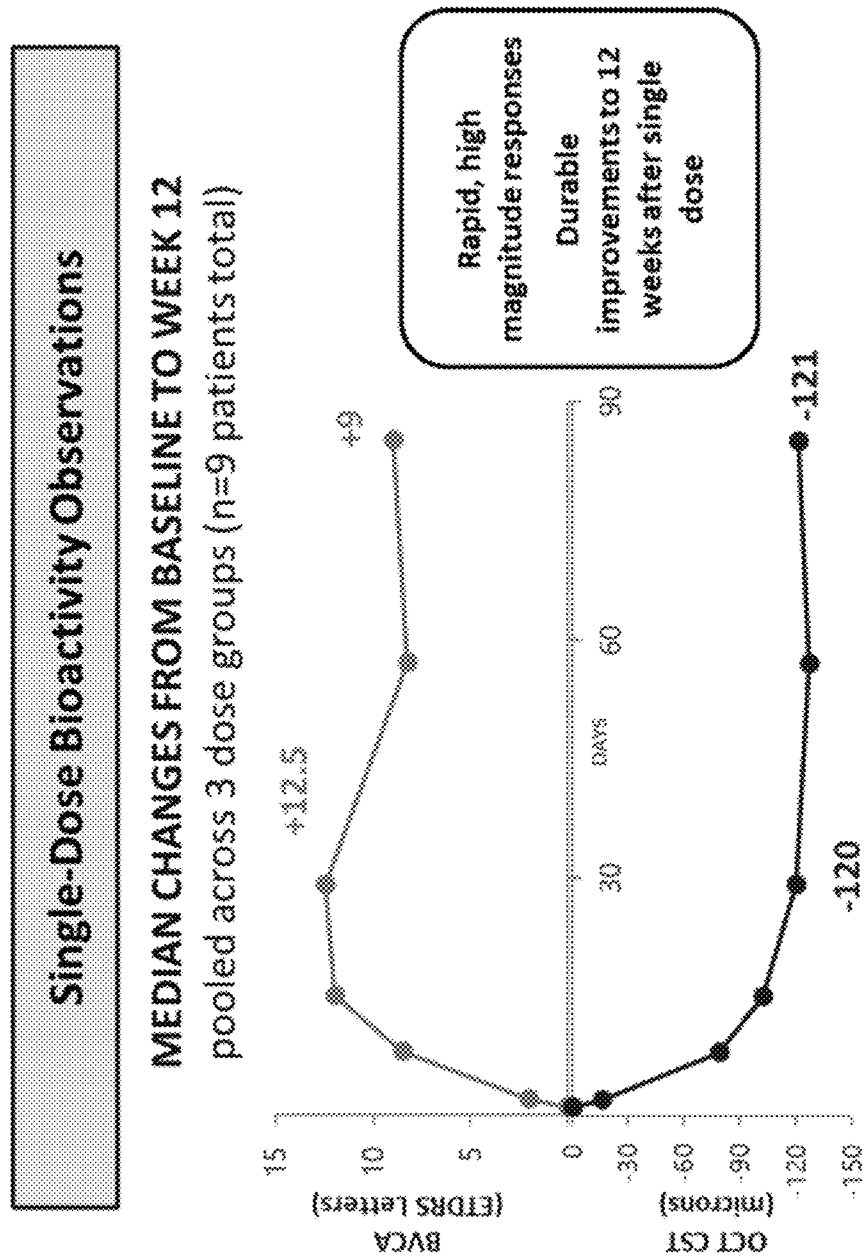
Figure 21B:
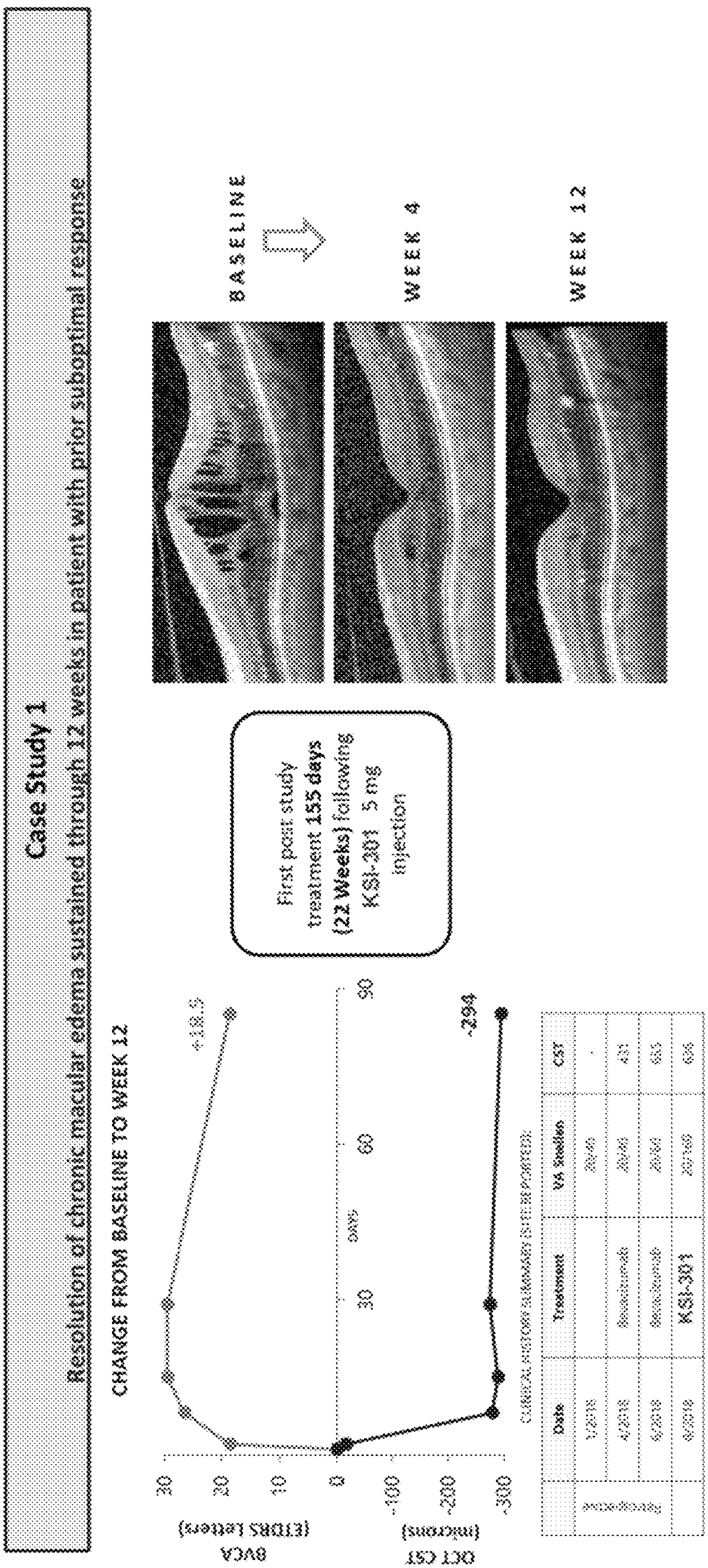
Figure 21C:
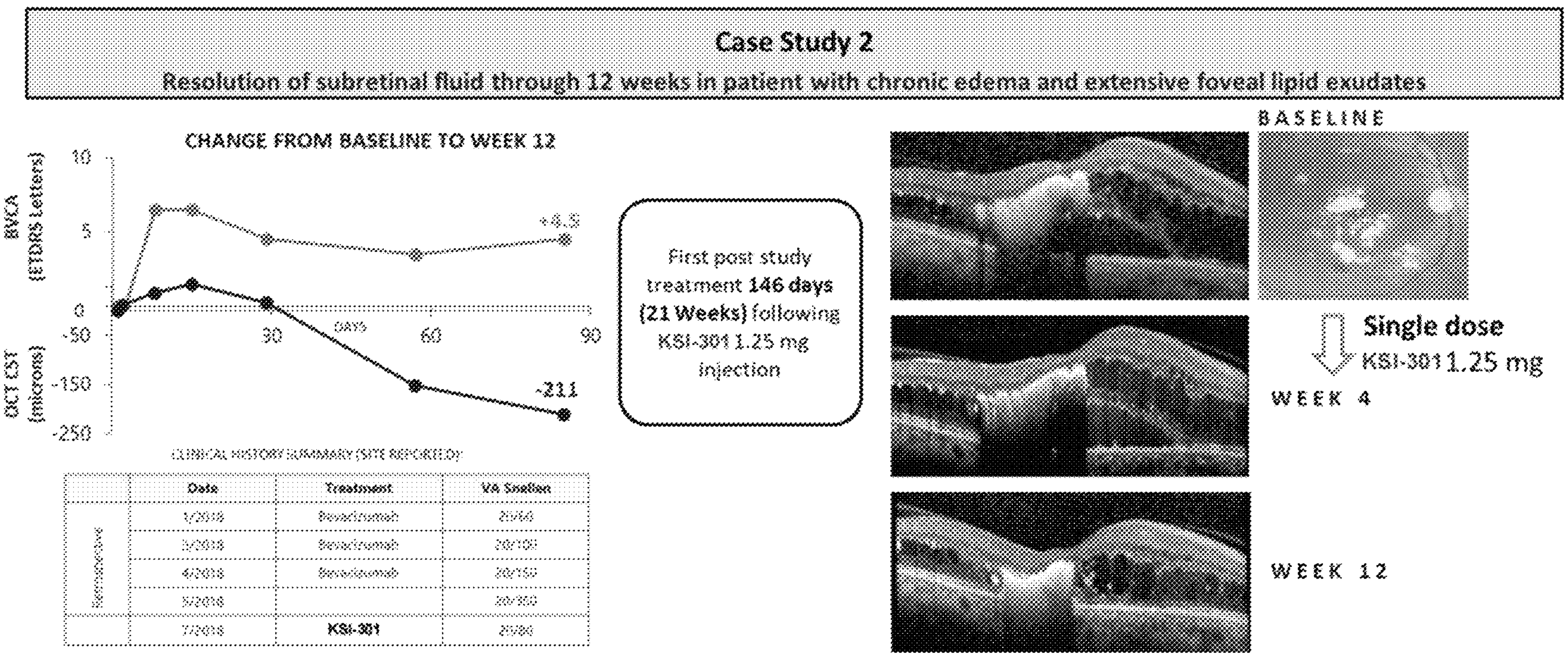

FIGS. 21A-21C depict the results from a single-dose bioactivity study.

Figure 22:
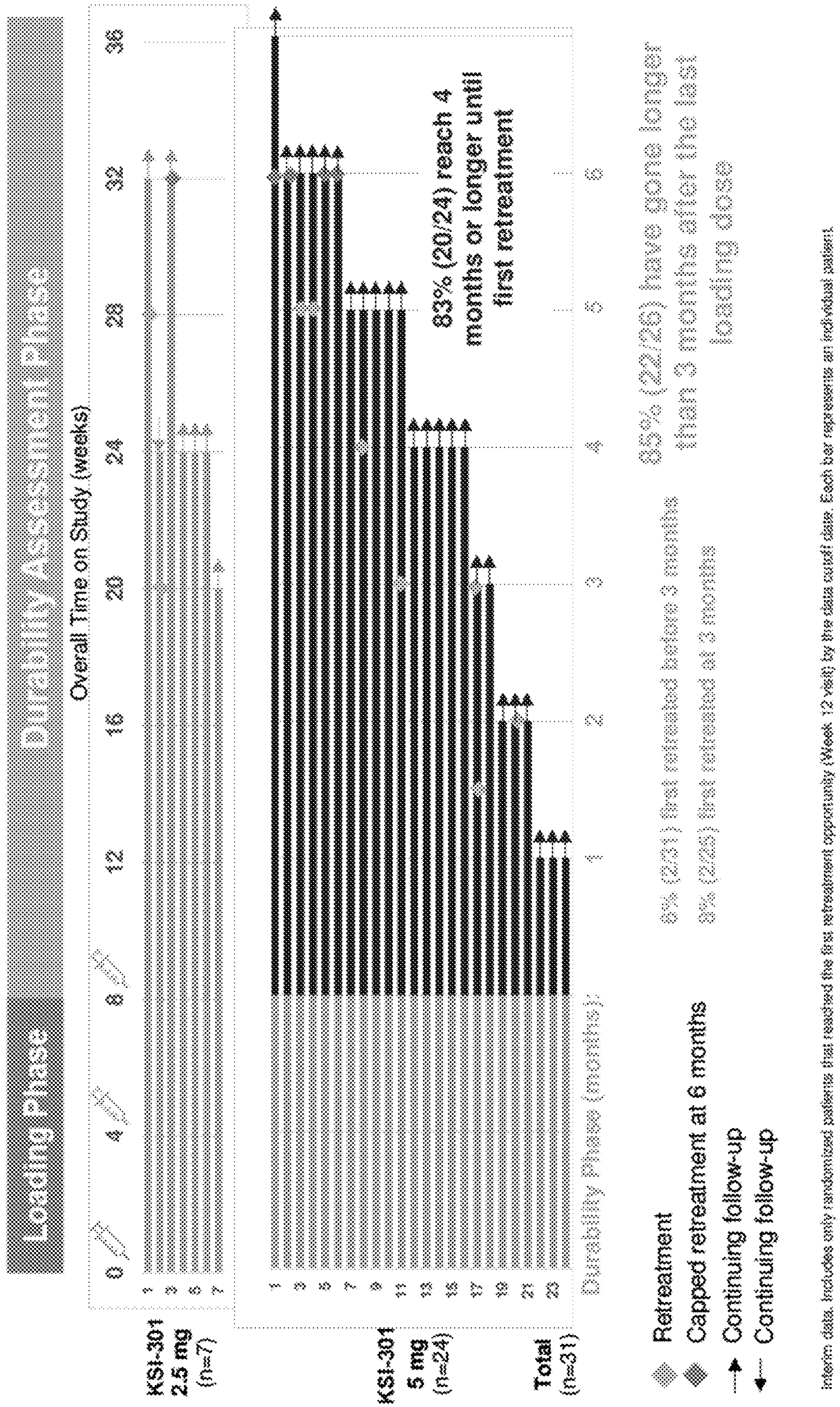

FIG. 22 is a set of graphs showing the schedule of intravitreal administration of KSI-301 received by individual patients treated for wAMD, according to some embodiments of the present disclosure.

Figure 23:
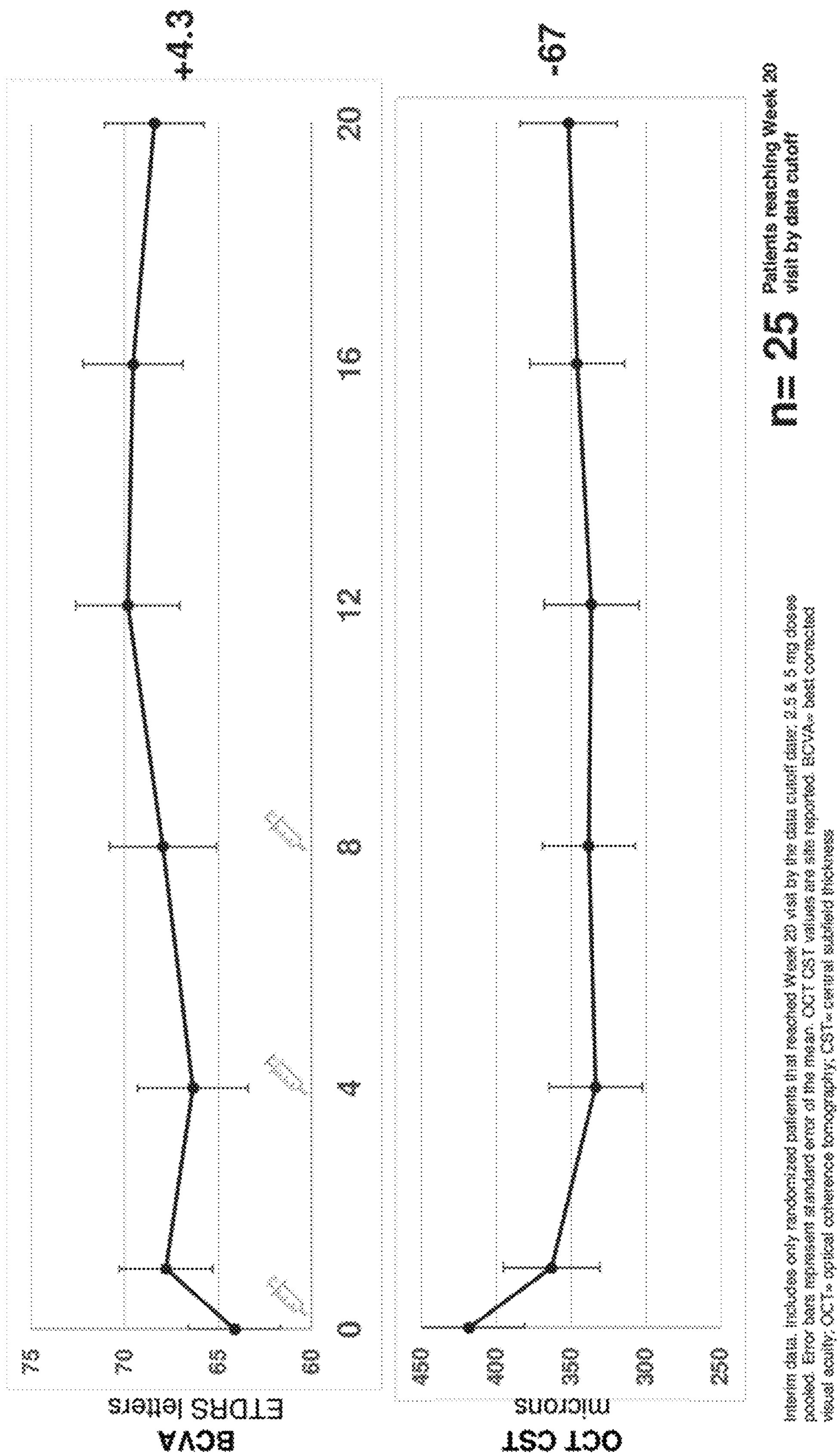

FIG. 23 is a set of graphs showing sustained therapeutic effects of KSI-301 after intravitreal administration of loading doses of KSI-301 to patients with wet age-related macular degeneration (wAMD), according to some embodiments of the present disclosure.

Figure 24:
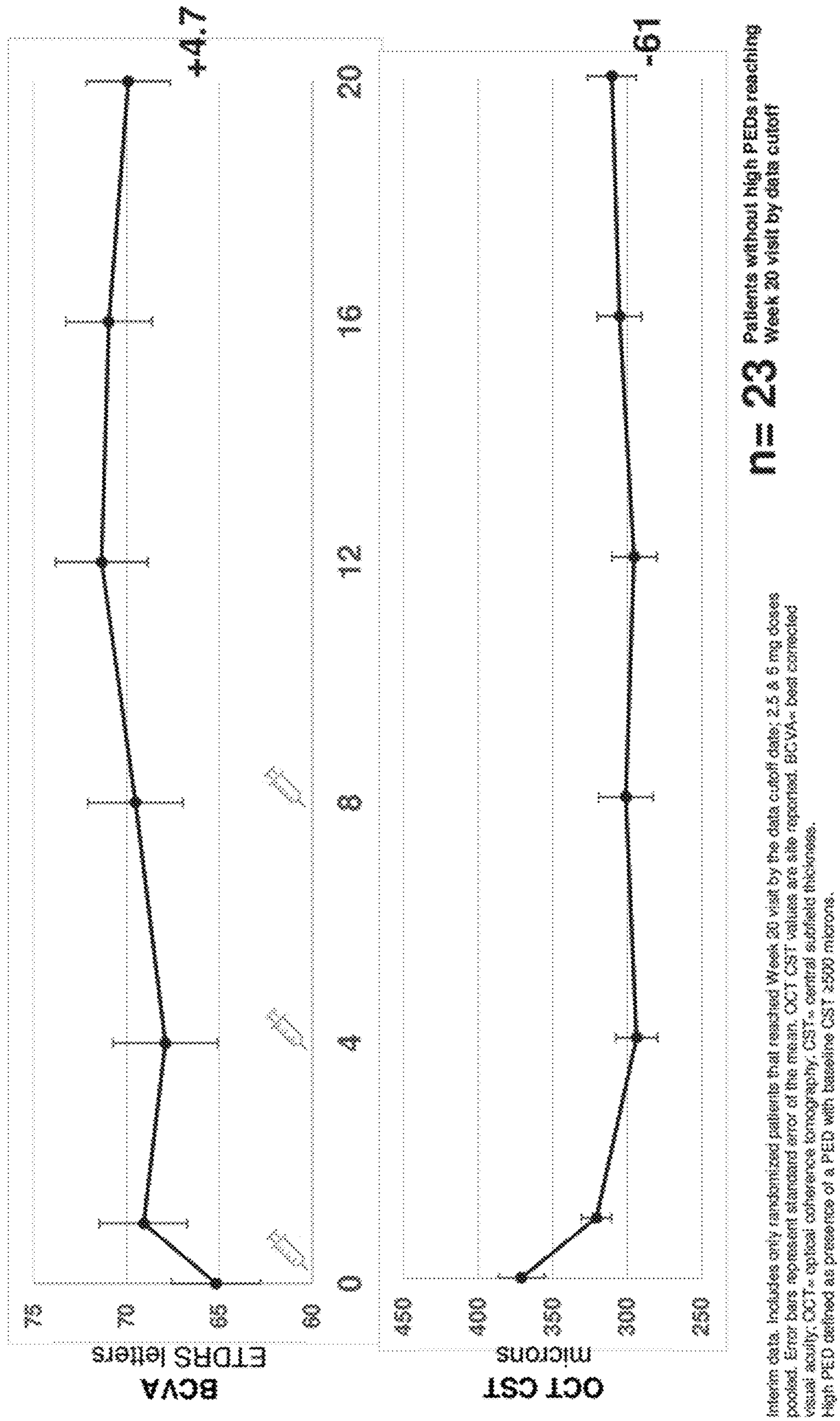

FIG. 24 is a set of graphs showing sustained therapeutic effects of KSI-301 after intravitreal administration of loading doses of KSI-301 to patients with wet age-related macular degeneration (wAMD), but without high pigment epithelial detachment, according to some embodiments of the present disclosure.

Figure 25:
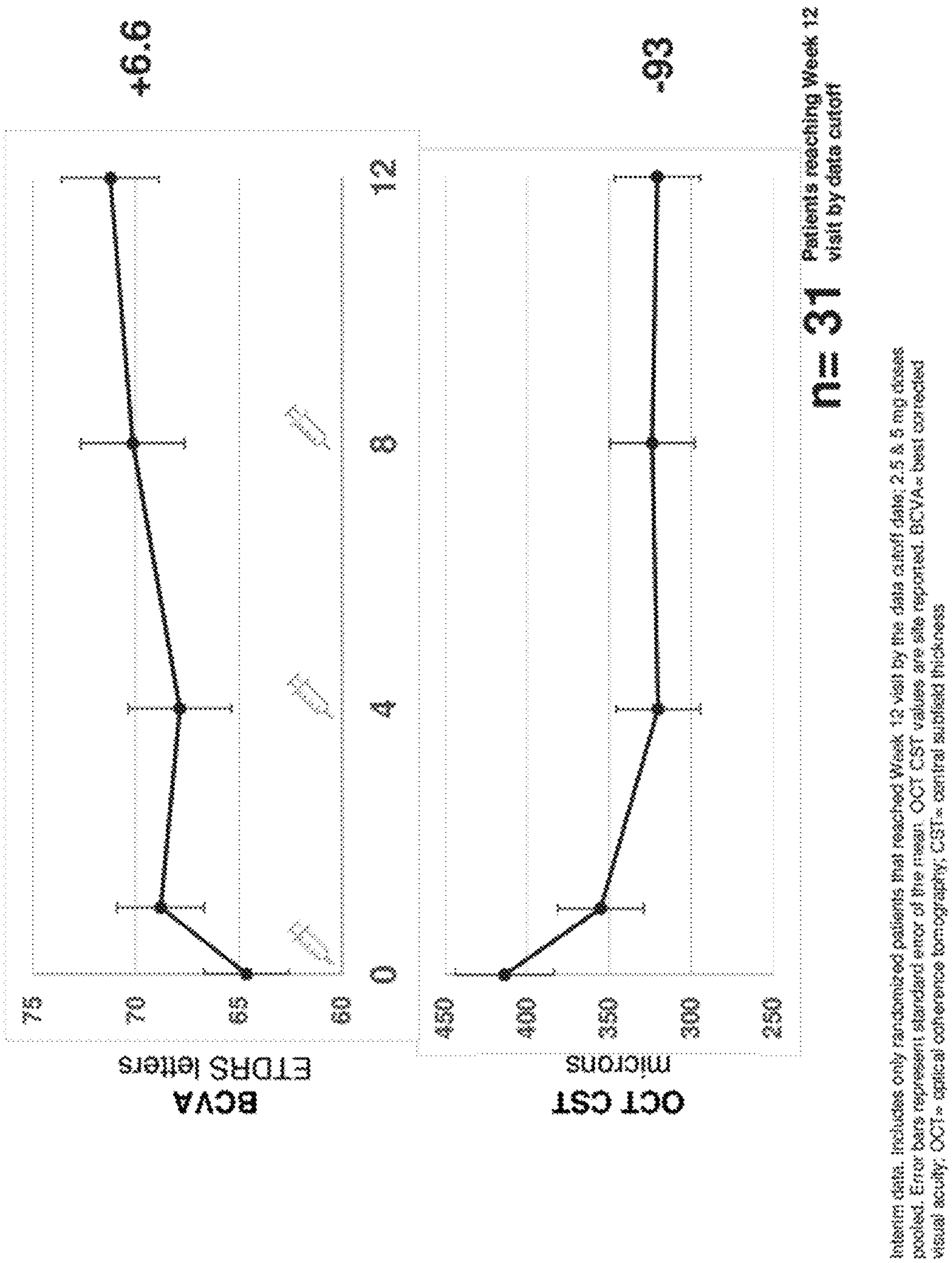

FIG. 25 is a set of graphs showing sustained therapeutic effects of KSI-301 after intravitreal administration of loading doses of KSI-301 to patients with wet age-related macular degeneration (wAMD), according to some embodiments of the present disclosure.

FIG. 26 is a set of graphs showing sustained therapeutic effects of KSI-301 after intravitreal administration of loading doses of KSI-301 to patients with wet age-related macular degeneration (wAMD), but without high pigment epithelial detachment, according to some embodiments of the present disclosure.

Figure 27:
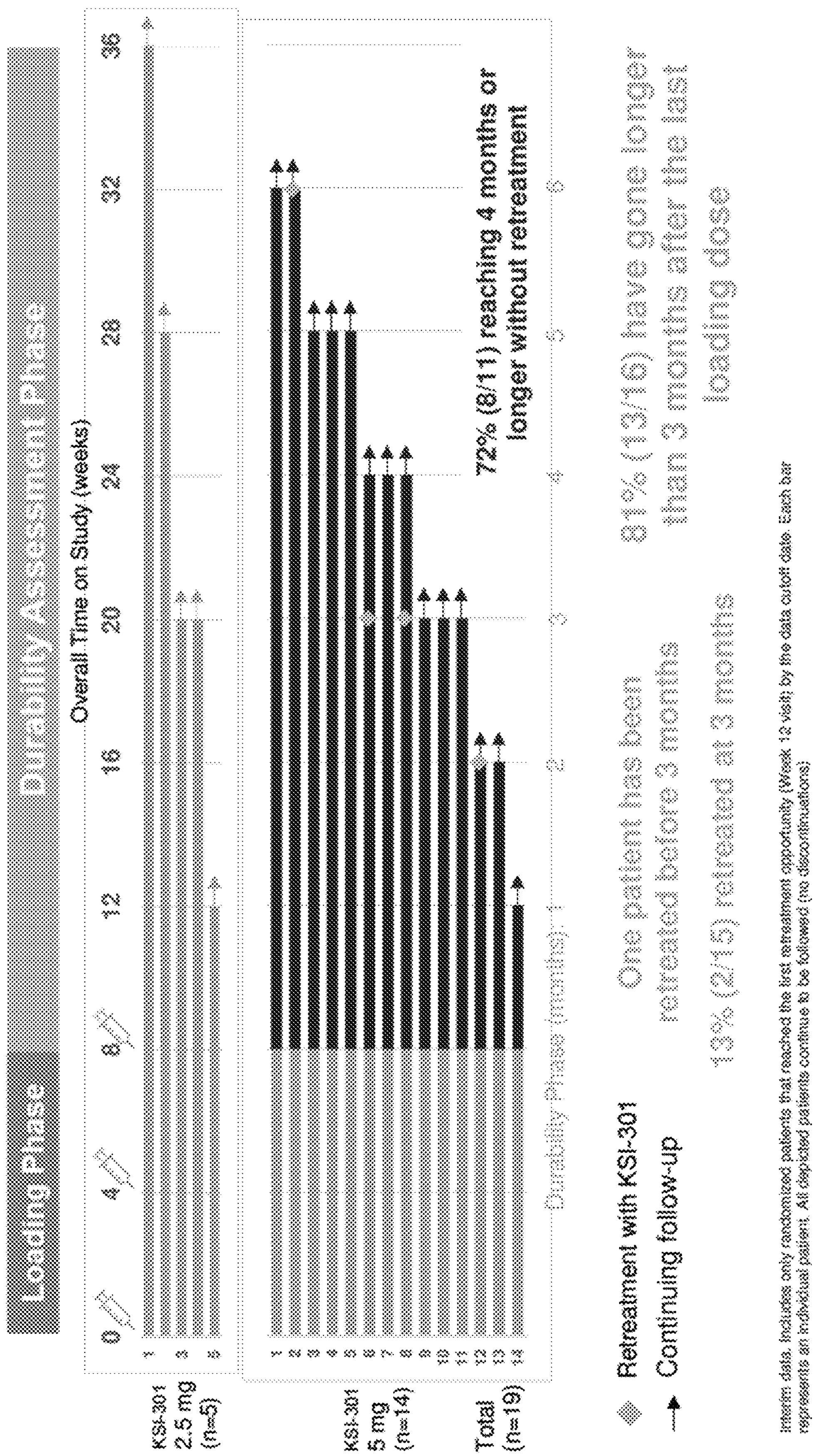

FIG. 27 is a set of graphs showing the schedule of intravitreal administration of KSI-301 received by individual patients treated for DME, according to some embodiments of the present disclosure.

Figure 28:
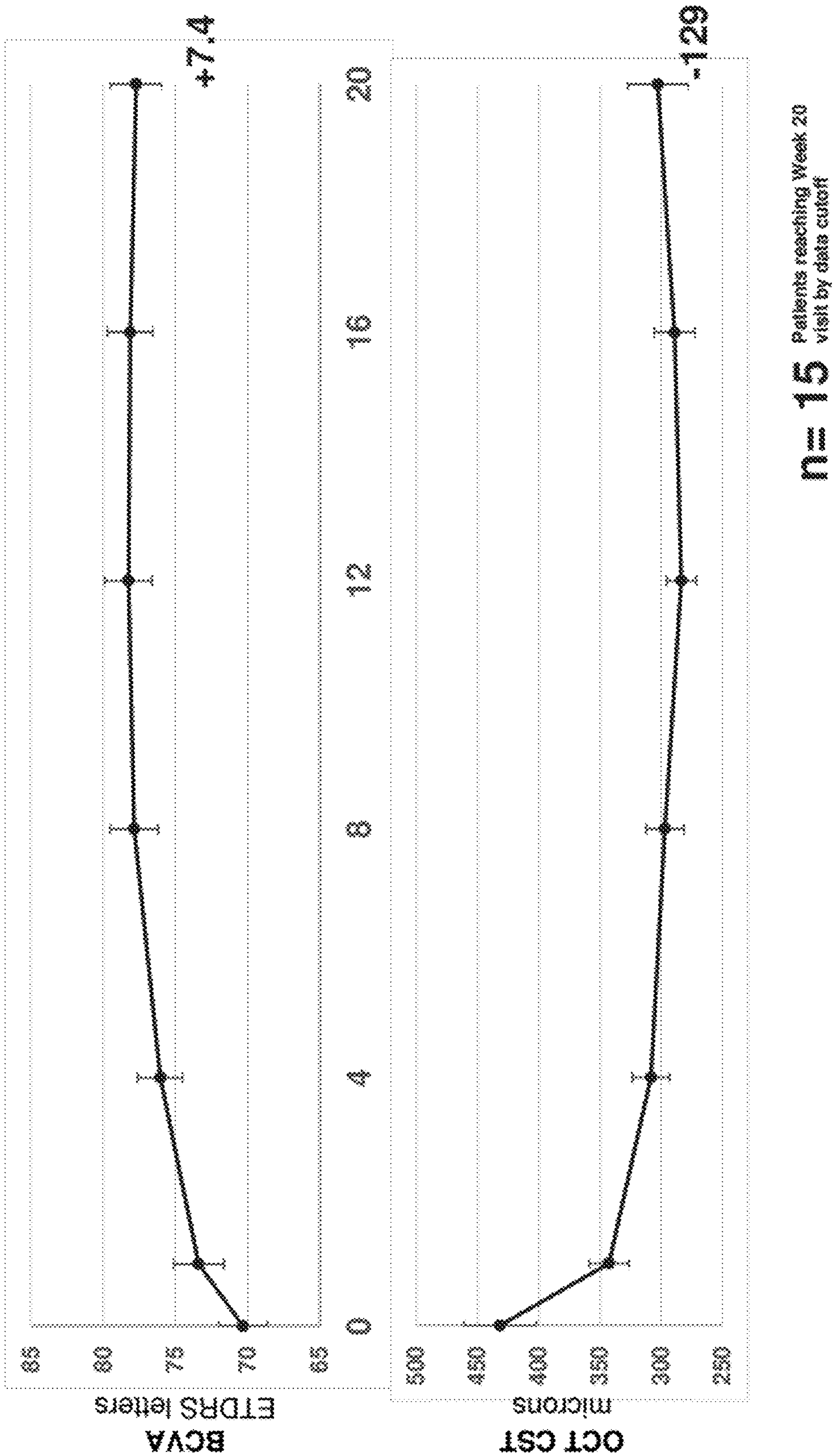

FIG. 28 is a set of graphs showing sustained therapeutic effects of KSI-301 after intravitreal administration of loading doses of KSI-301 to patients with diabetic macular edema (DME), according to some embodiments of the present disclosure.

Figure 29:
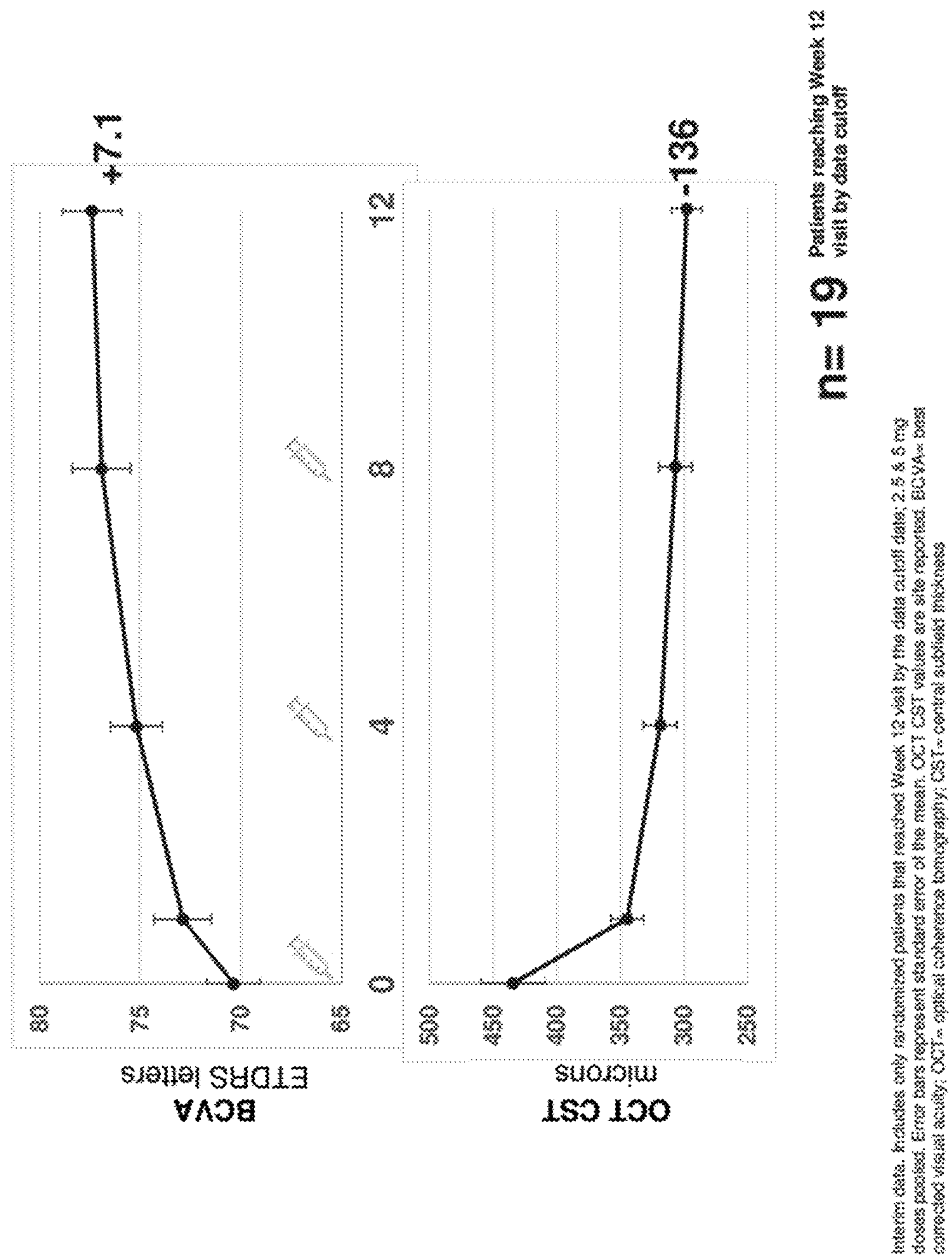

FIG. 29 is a set of graphs showing sustained therapeutic effects of KSI-301 after intravitreal administration of loading doses of KSI-301 to patients with diabetic macular edema (DME), according to some embodiments of the present disclosure.

Figure 30:
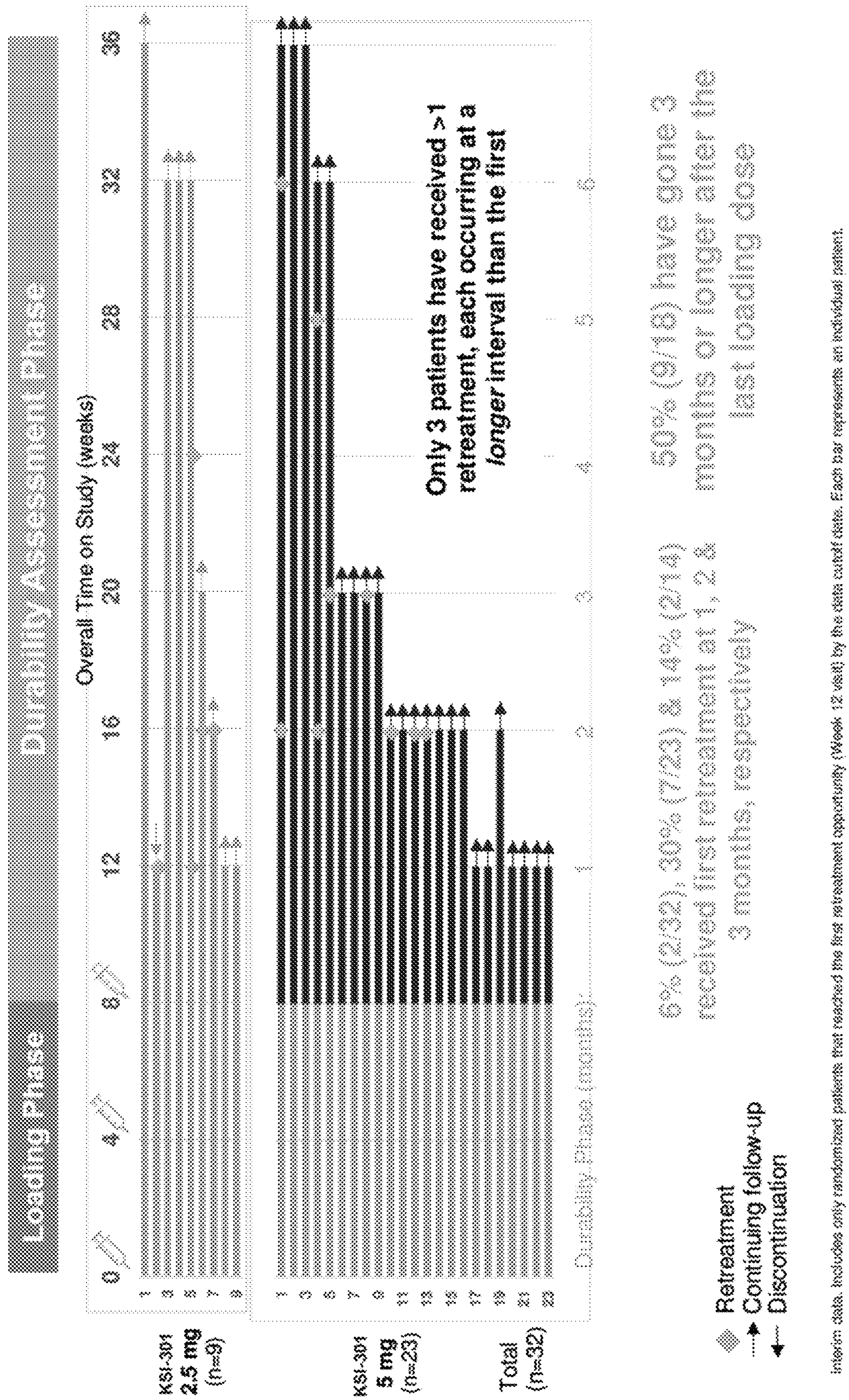

FIG. 30 is a graph showing the schedule of intravitreal administration of KSI-301 received by individual patients treated for RVO, according to some embodiments of the present disclosure.

Figure 31:
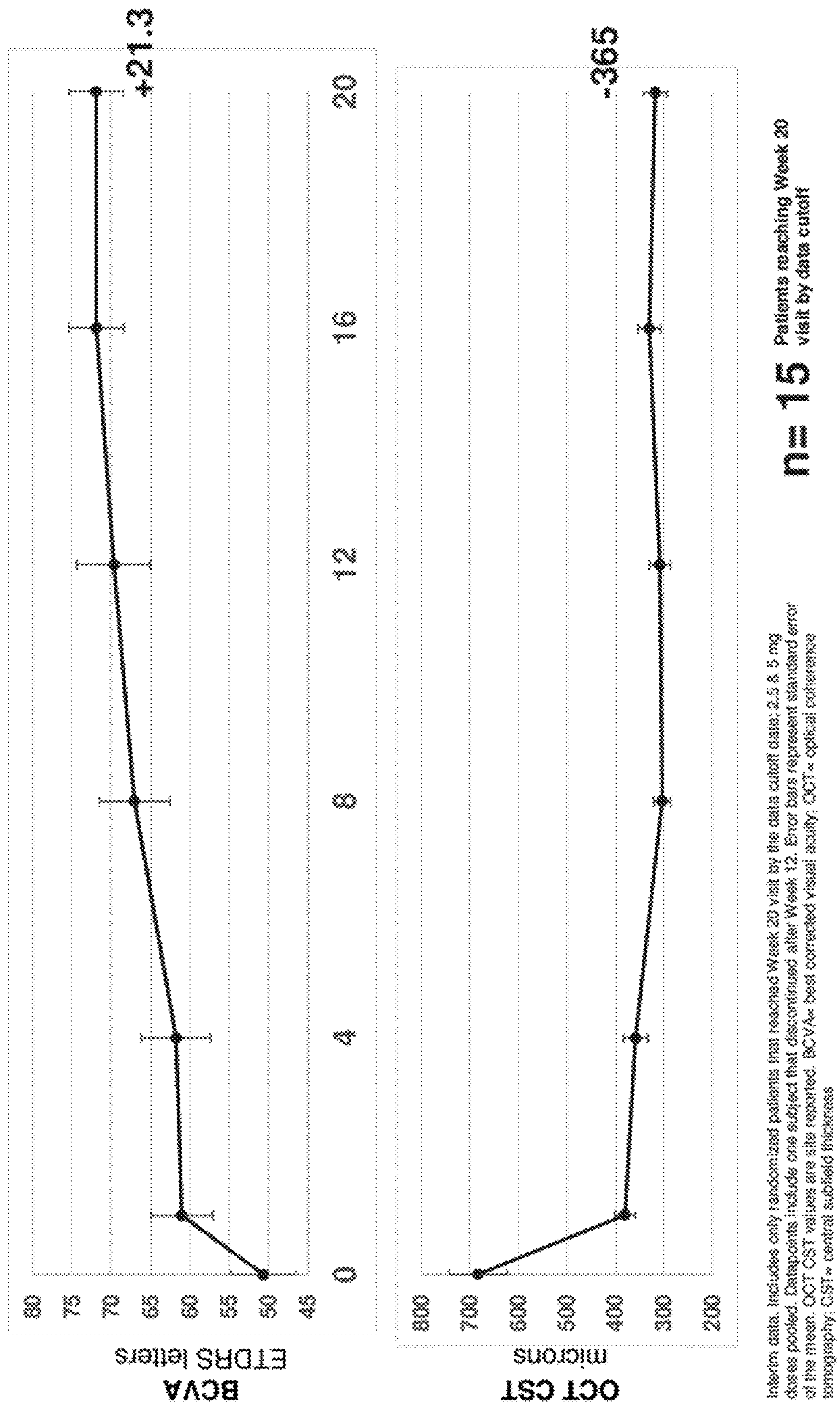

FIG. 31 is a set of graphs showing sustained therapeutic effects of KSI-301 after intravitreal administration of loading doses of KSI-301 to patients with retinal vein occlusion (RVO), according to some embodiments of the present disclosure.

Figure 32:
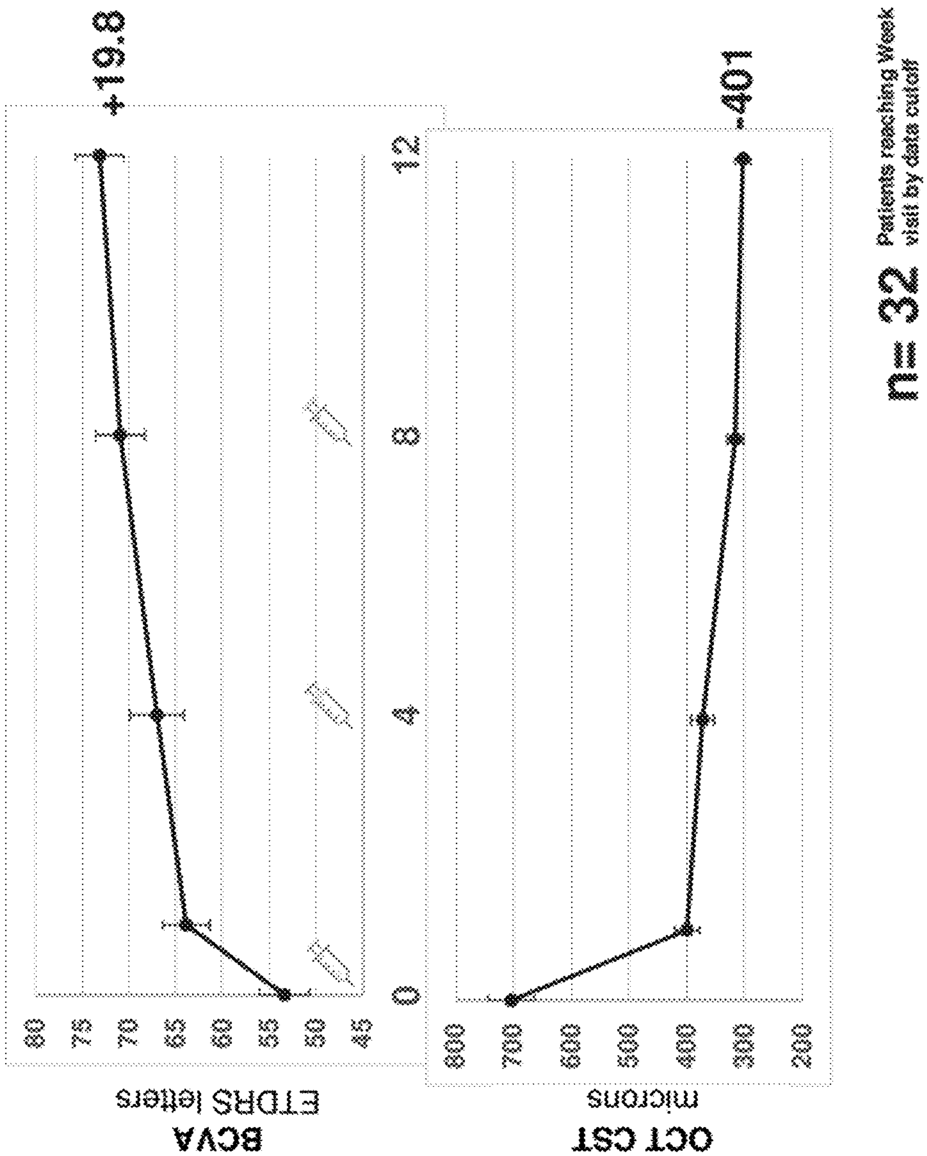

FIG. 32 is a set of graphs showing sustained therapeutic effects of KSI-301 after intravitreal administration of loading doses of KSI-301 to patients with retinal vein occlusion (RVO), according to some embodiments of the present disclosure.

Figure 33:
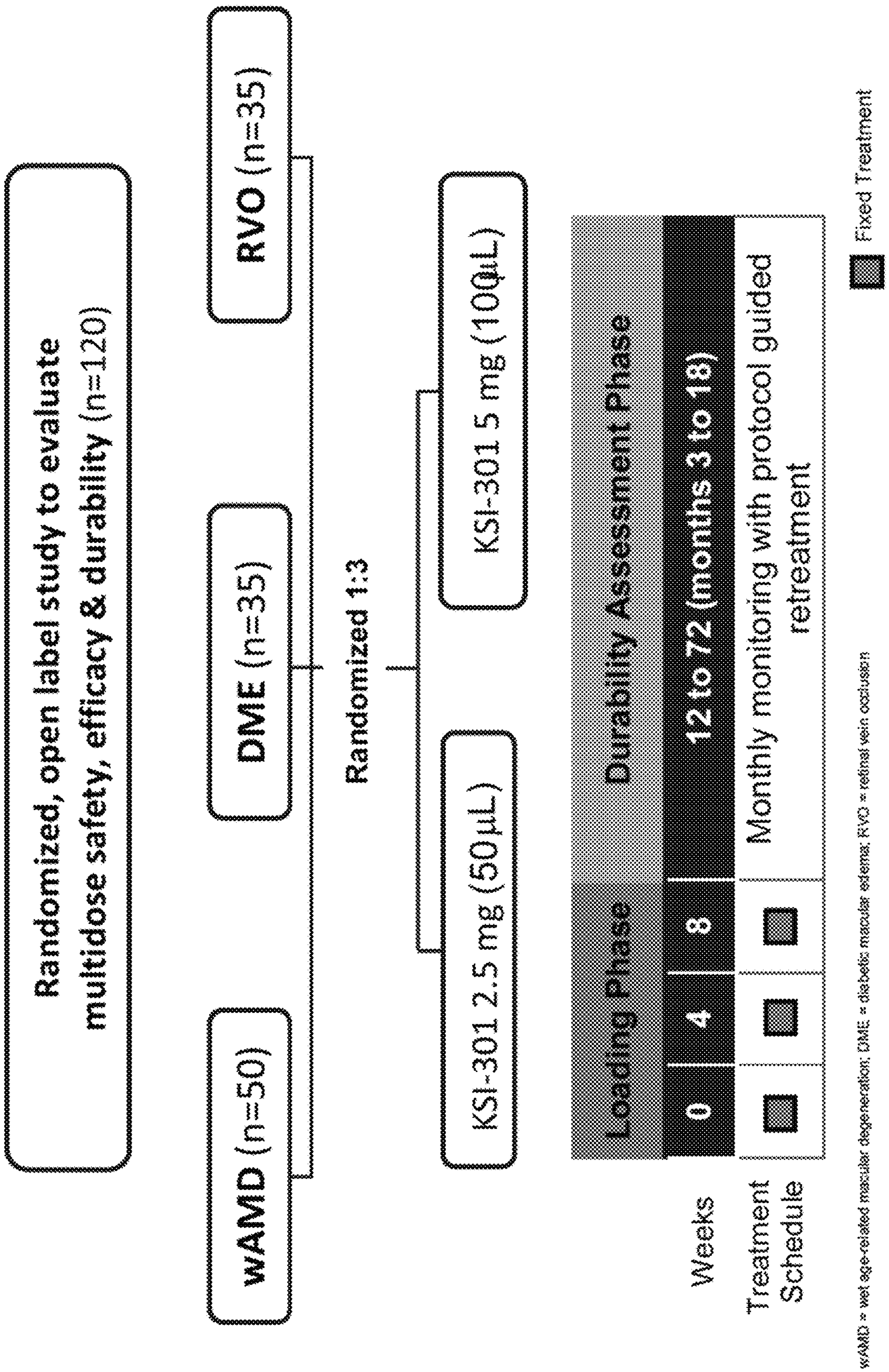

FIG. 33 is a schematic diagram representing an antibody binding construct A intravitreal administration schedule in age-related macular degeneration (wAMD), diabetic macular edema (DME), and retinal vein occlusion (RVO), according to some embodiments of the present disclosure.

Figure 34:
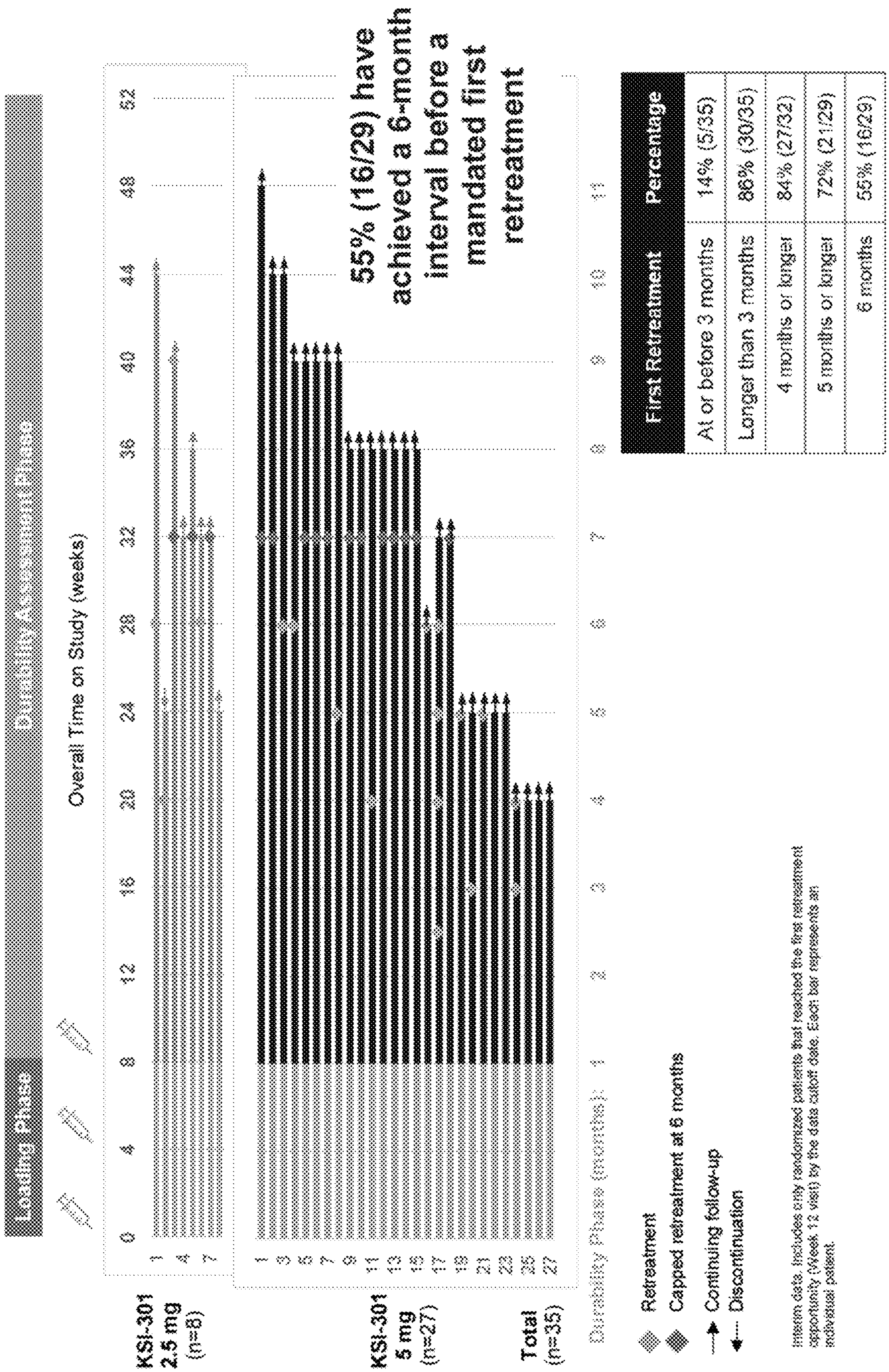

FIG. 34 is a set of graphs showing the schedule of intravitreal administration of KSI-301 received by individual patients treated for wAMD, according to some embodiments of the present disclosure.

Figure 35:
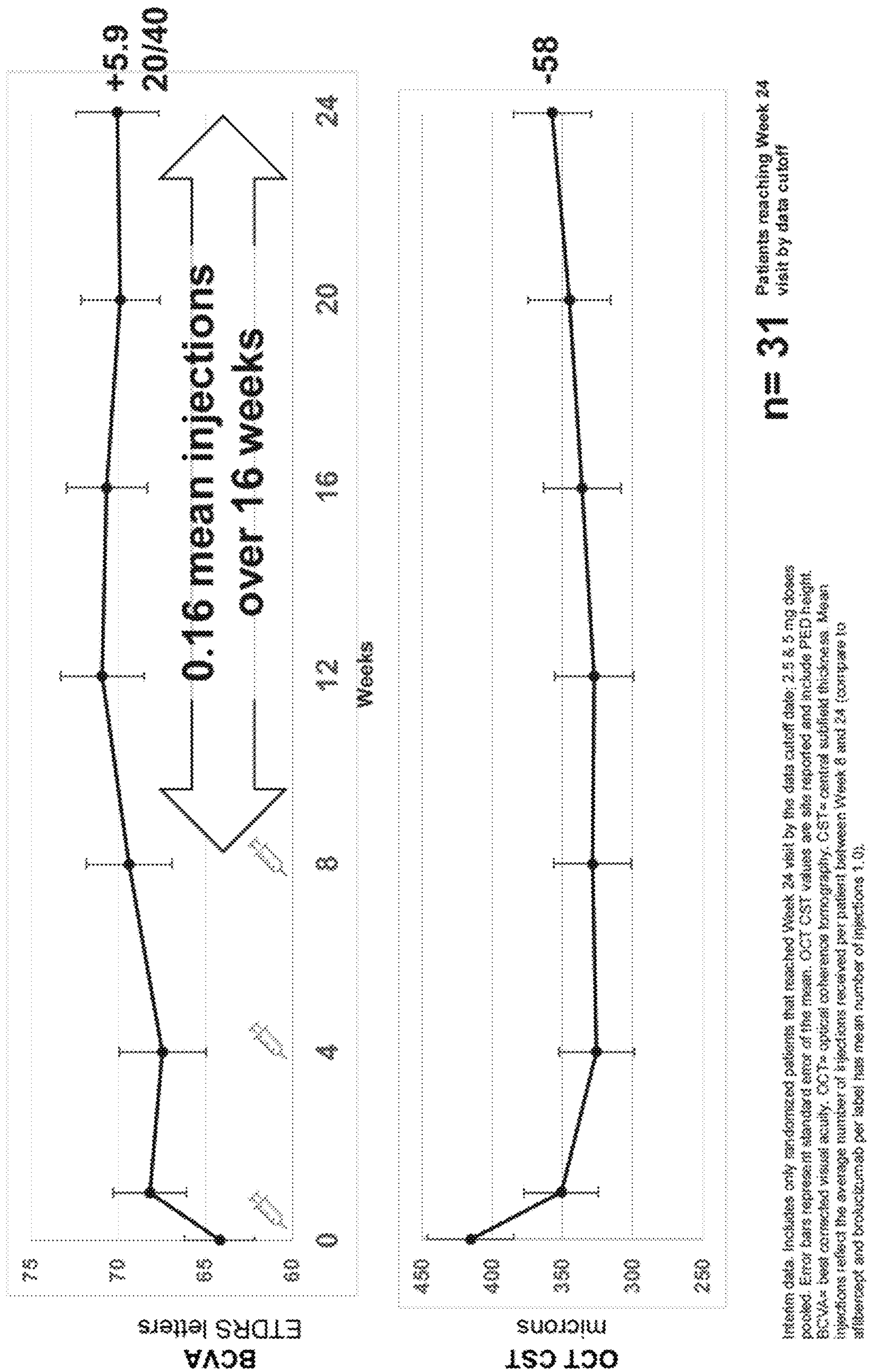

FIG. 35 is a set of graphs showing sustained therapeutic effects of KSI-301 after intravitreal administration of loading doses of KSI-301 to patients with wAMD, according to some embodiments of the present disclosure.

FIG. 36 is a set of graphs showing the schedule of intravitreal administration of KSI-301 received by individual patients treated for DME, according to some embodiments of the present disclosure.

FIG. 37 is a set of graphs showing sustained therapeutic effects of KSI-301 after intravitreal administration of loading doses of KSI-301 to patients with DME, according to some embodiments of the present disclosure.

Figure 38:
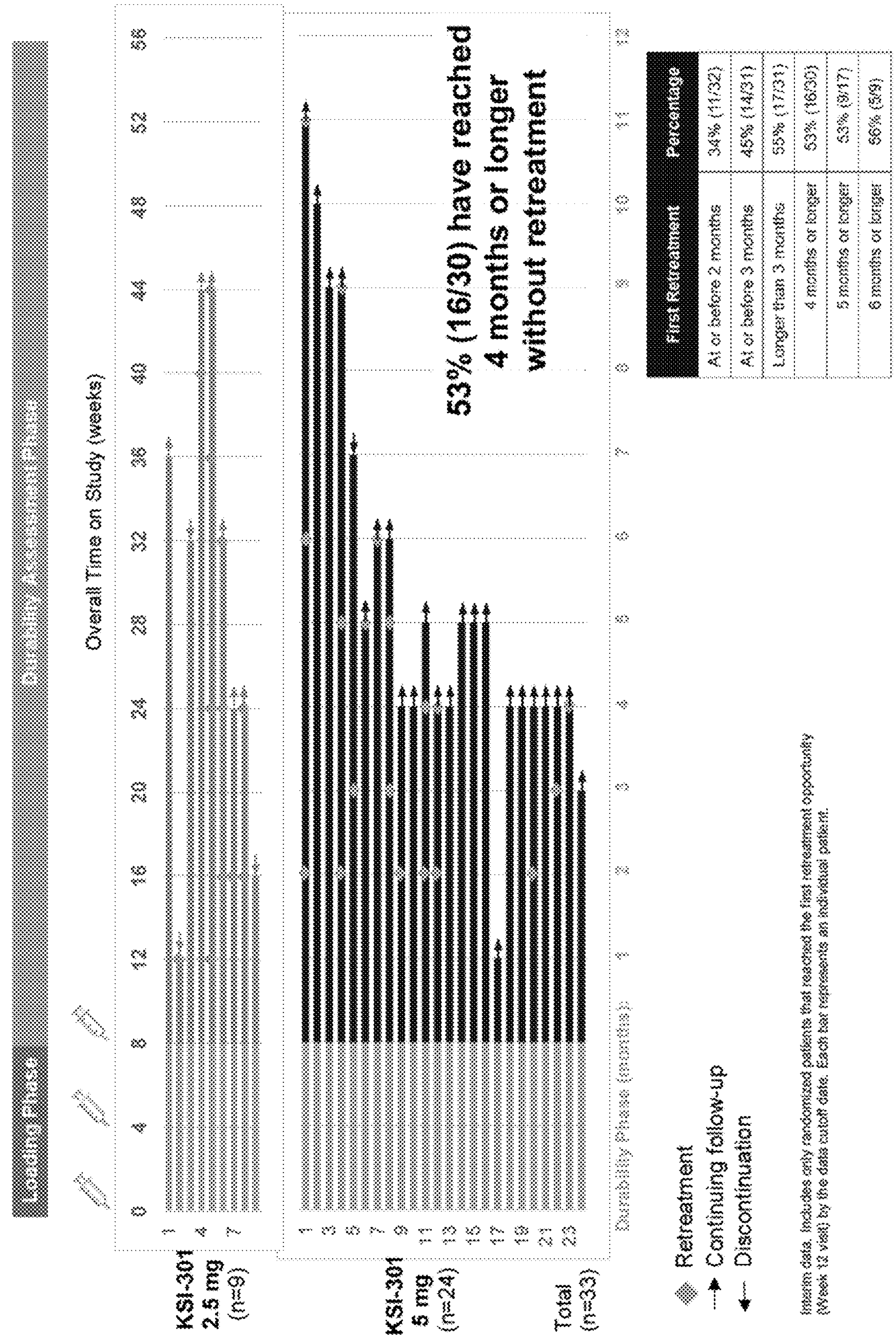

FIG. 38 is a set of graphs showing the schedule of intravitreal administration of KSI-301 received by individual patients treated for RVO, according to some embodiments of the present disclosure.

FIG. 39 is a set of graphs showing sustained therapeutic effects of KSI-301 after intravitreal administration of loading doses of KSI-301 to patients with retinal vein occlusion (RVO), according to some embodiments of the present disclosure.

Figure 40:
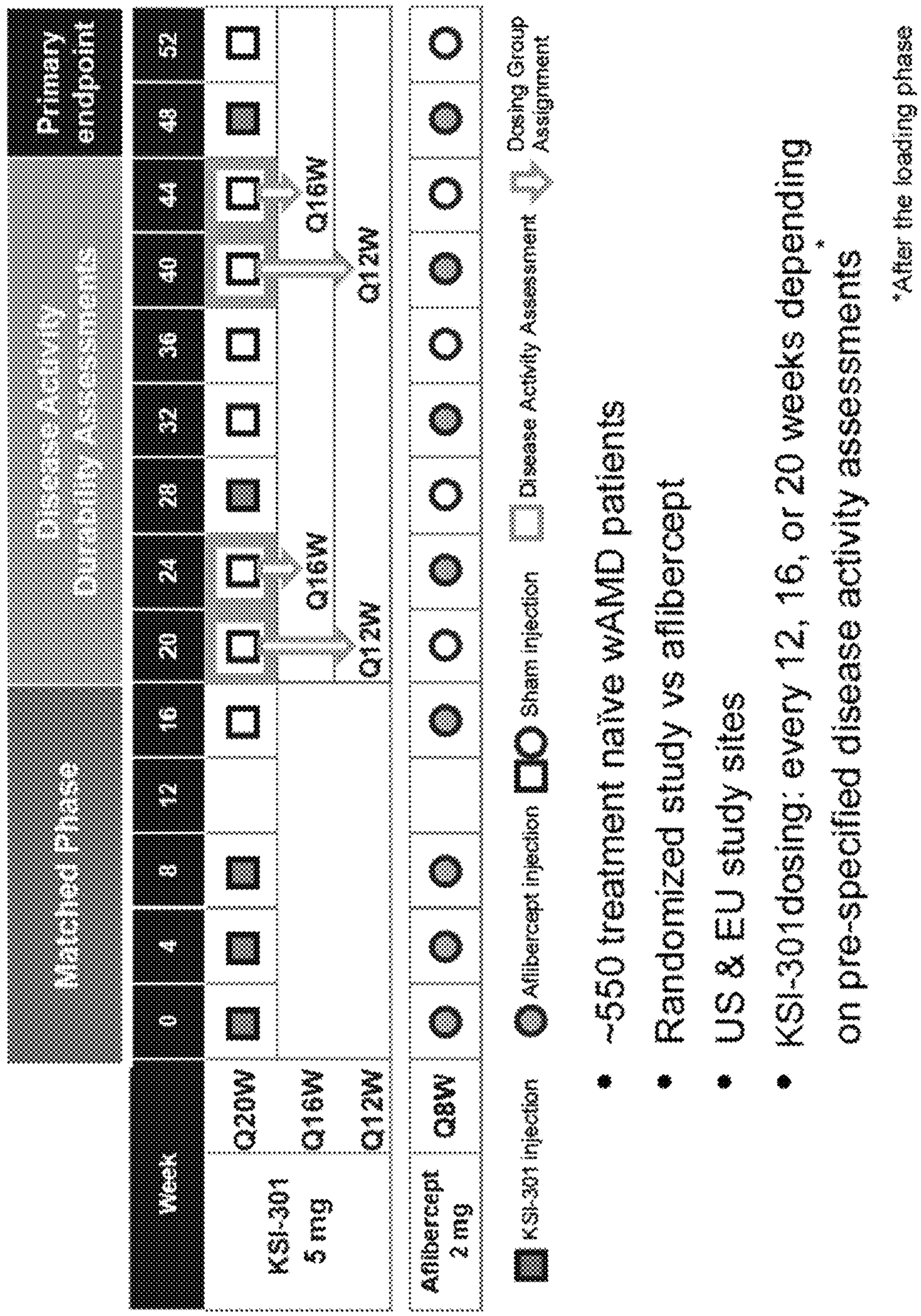

FIG. 40 is a schematic diagram representing a Phase 2 study design for KSI-301 treatment in treatment-naïve wAMD patients and comparison with a standard of care treatment, according to some embodiments of the present disclosure.

Figure 41A:
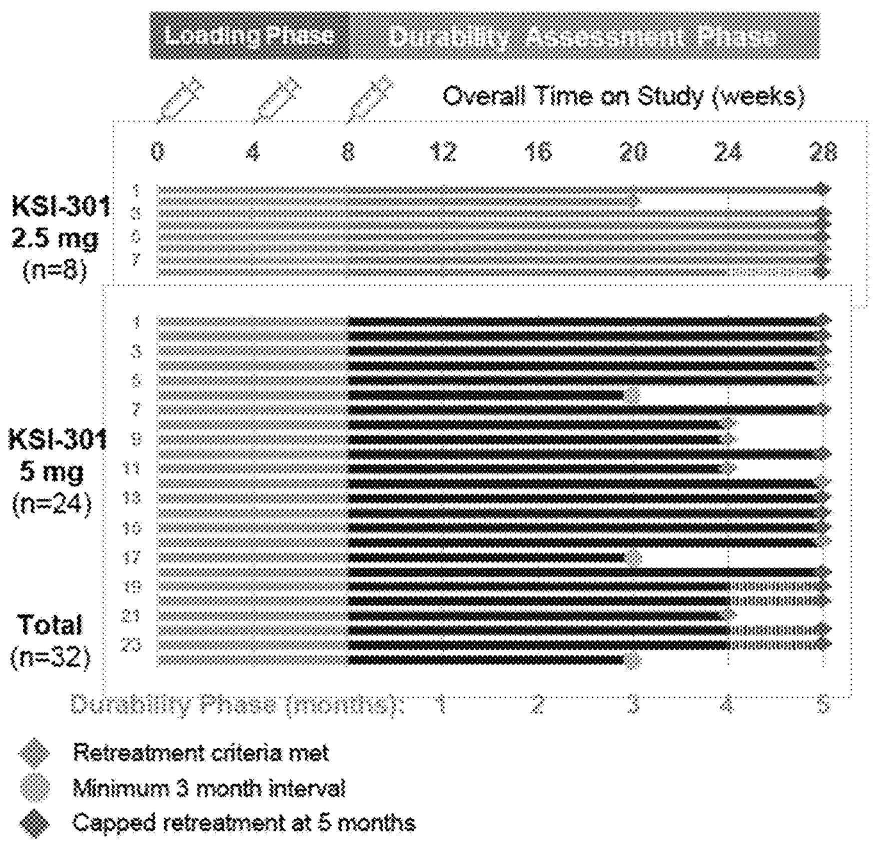
Figure 41B:
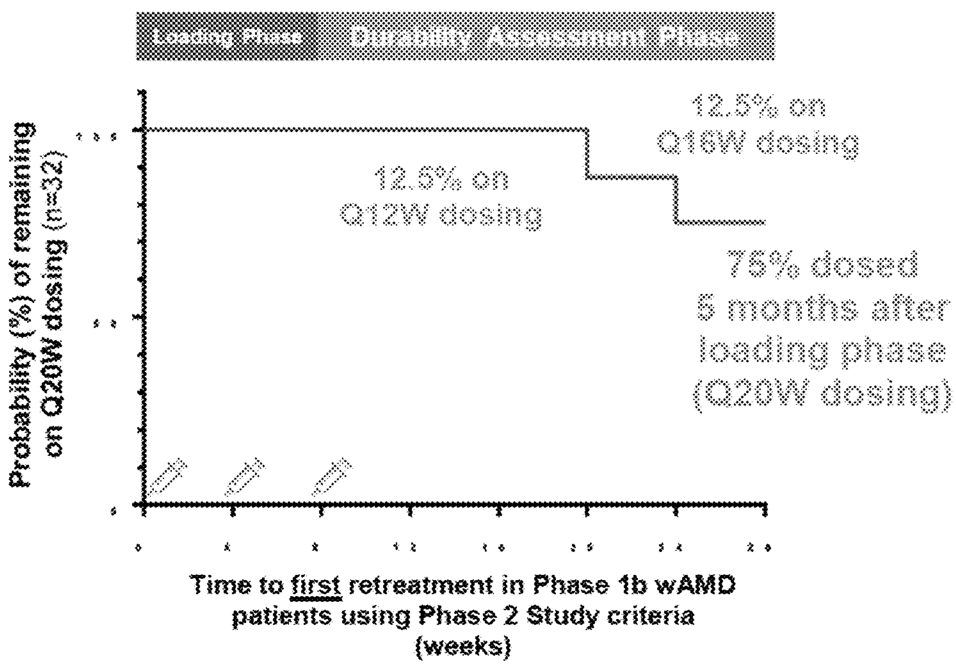

FIGS. 41A and 41B are a collection of graphs showing hypothetical schedule of treatment and probability of remaining on Q20W dosing, based on data from patients from the Phase 1b study but applying the Phase 2 retreatment criteria, according to some embodiments of the present disclosure.

Figure 42:
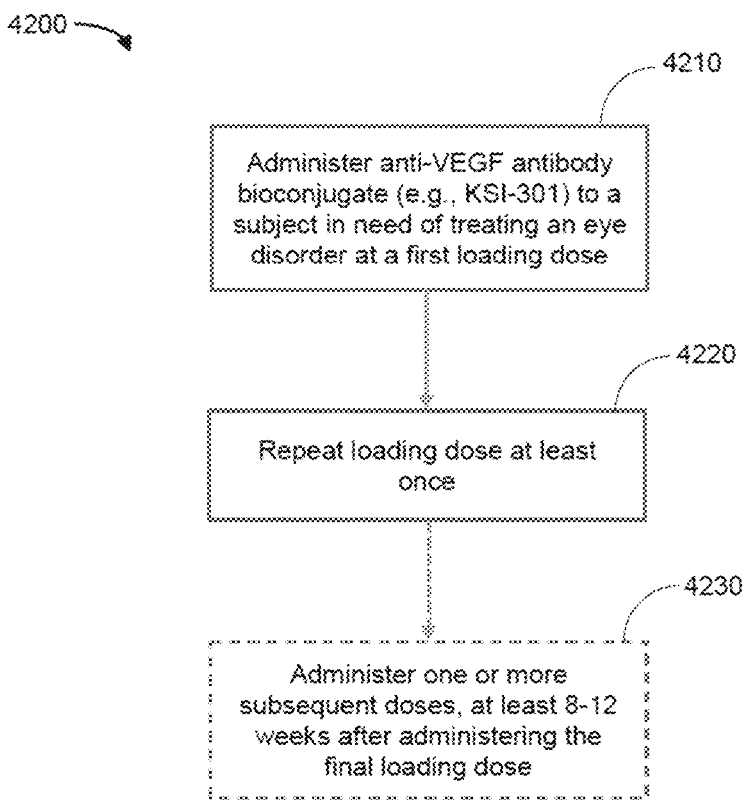

FIG. 42 is a flow chart depicting an embodiment of a method of the present disclosure.

Figure 43:
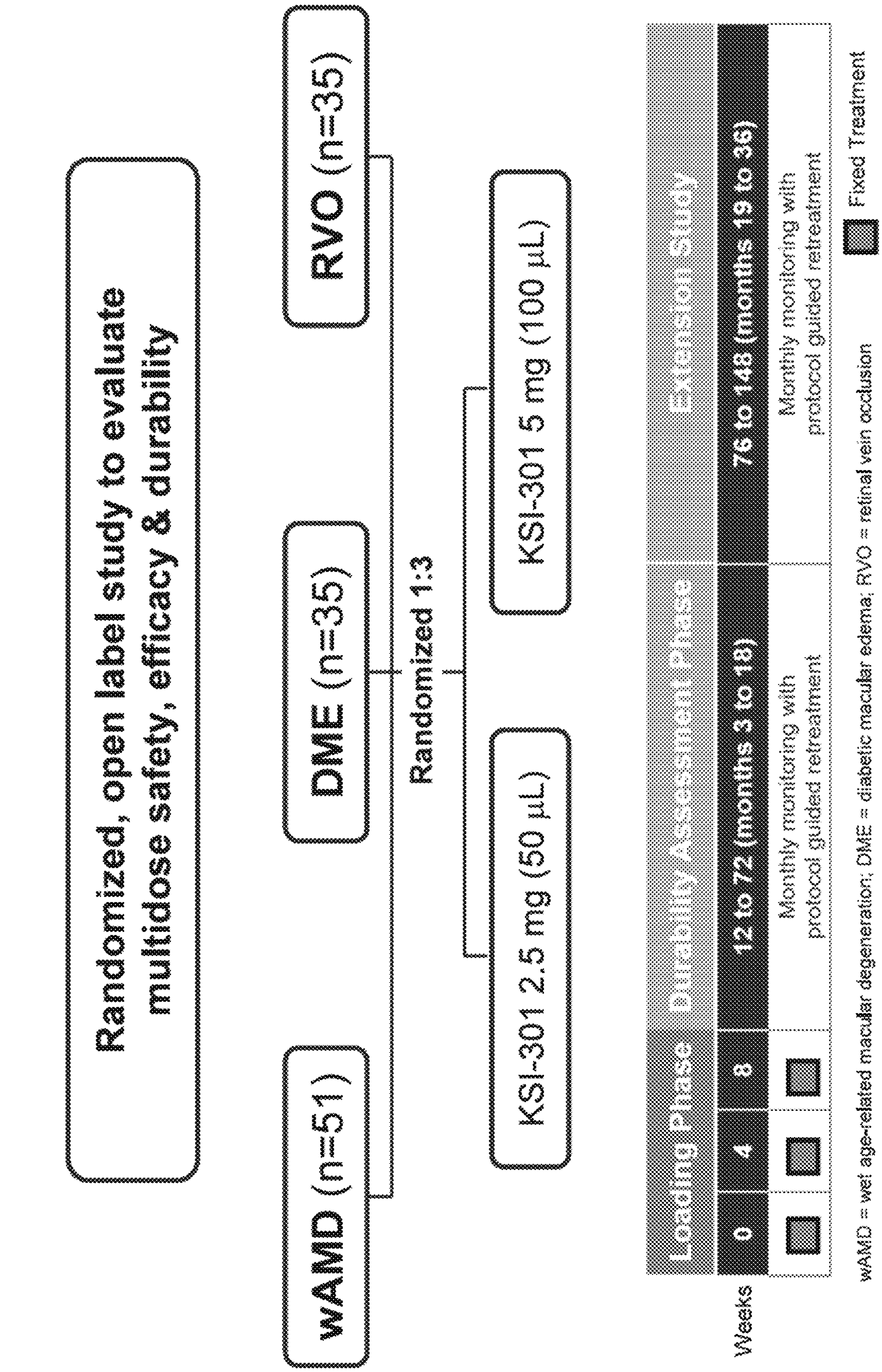

FIG. 43 is a schematic diagram representing KSI-301 intravitreal administration schedule in age-related macular degeneration (wAMD), diabetic macular edema (DME), and retinal vein occlusion (RVO), according to some embodiments of the present disclosure.

Figure 44:
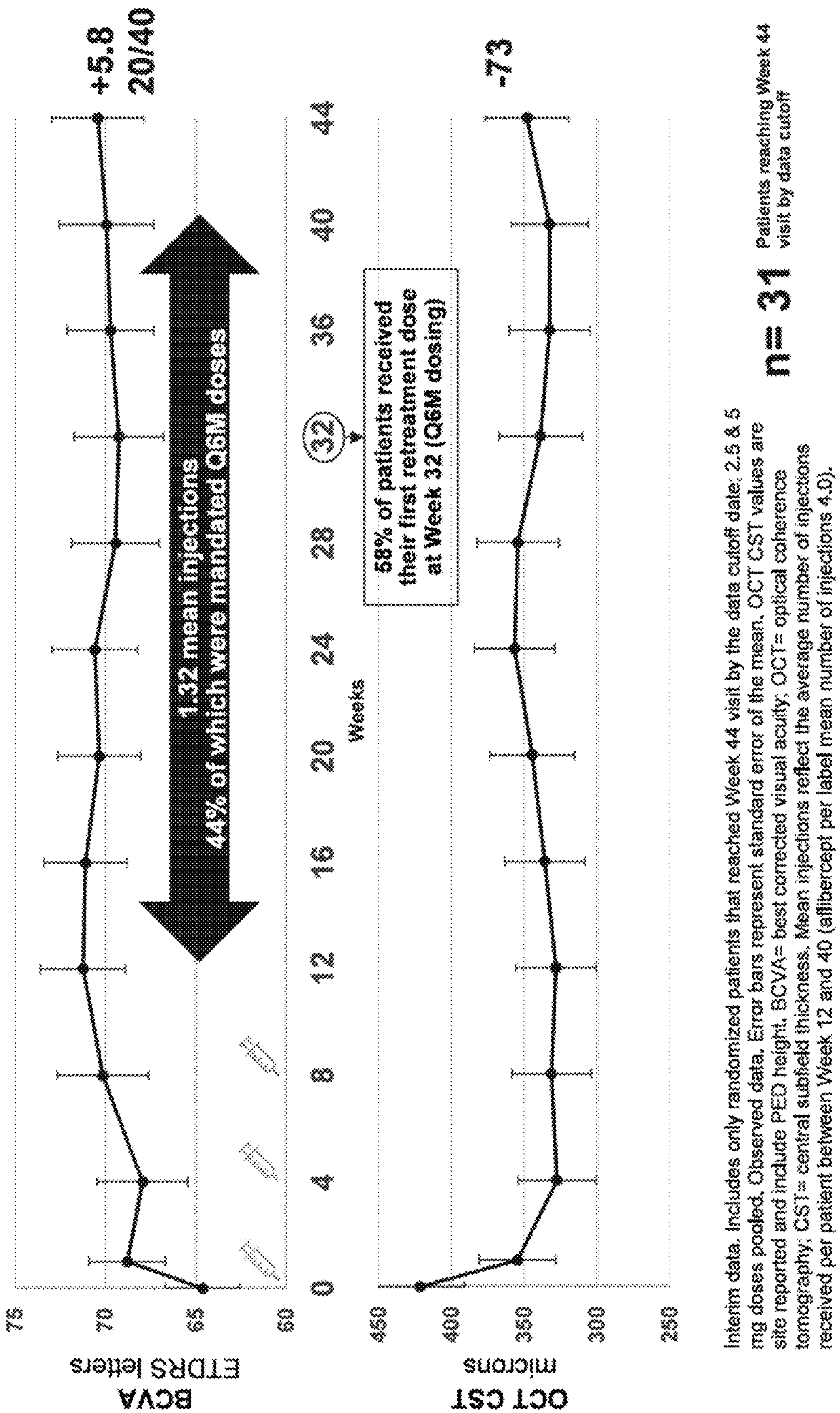

FIG. 44 is a set of graphs showing sustained therapeutic effects of KSI-301 administered to patients with wet age-related macular degeneration (wAMD), according to some embodiments of the present disclosure.

Figure 45A:
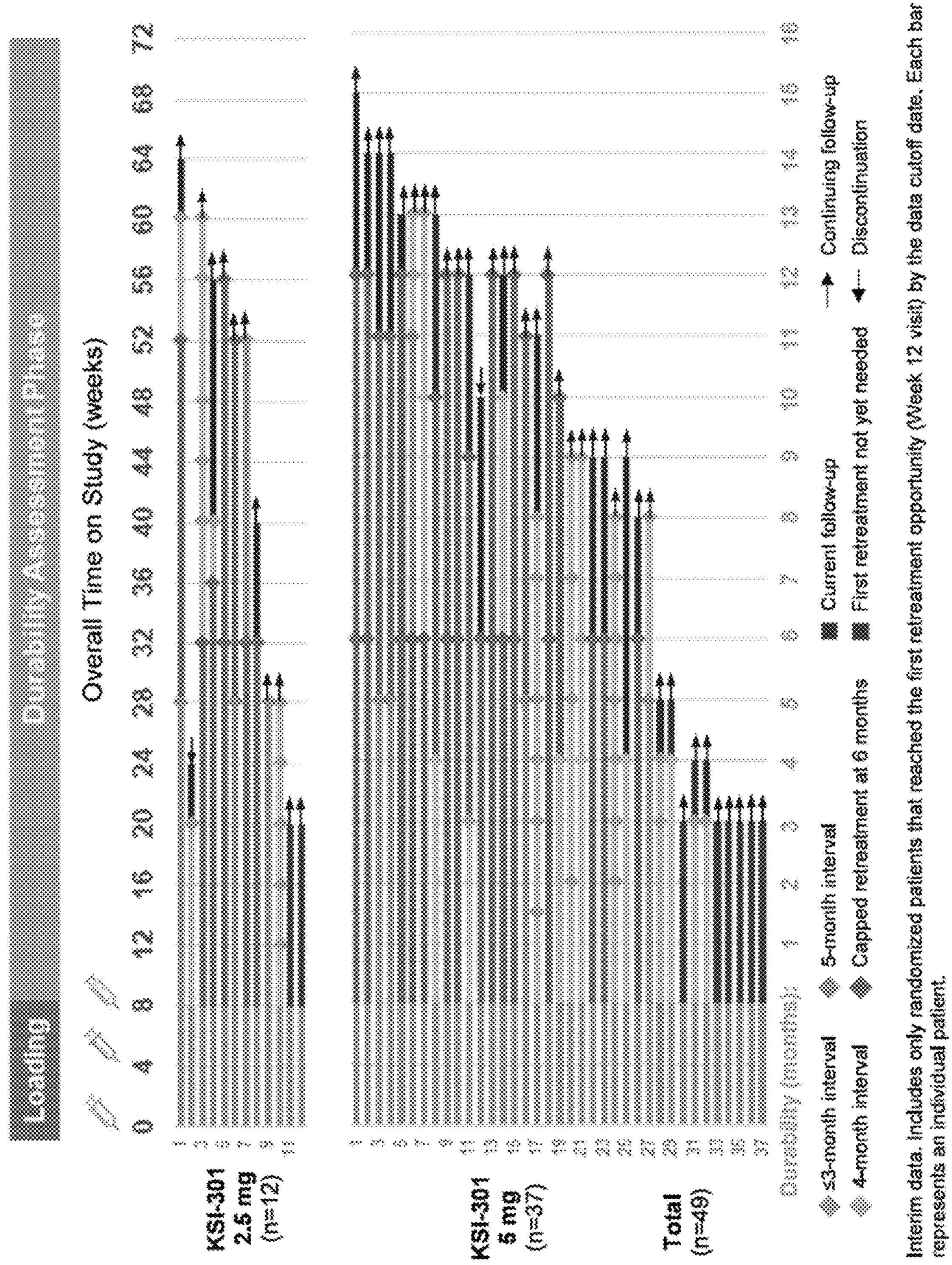

FIG. 45A is a set of graphs showing the schedule of intravitreal administration of KSI-301 received by individual patients treated for wAMD, according to some embodiments of the present disclosure.

FIG. 45B is a table summarizing the administration interval of KSI-301 in wAMD patients shown in FIG. 45A.

Figure 46:
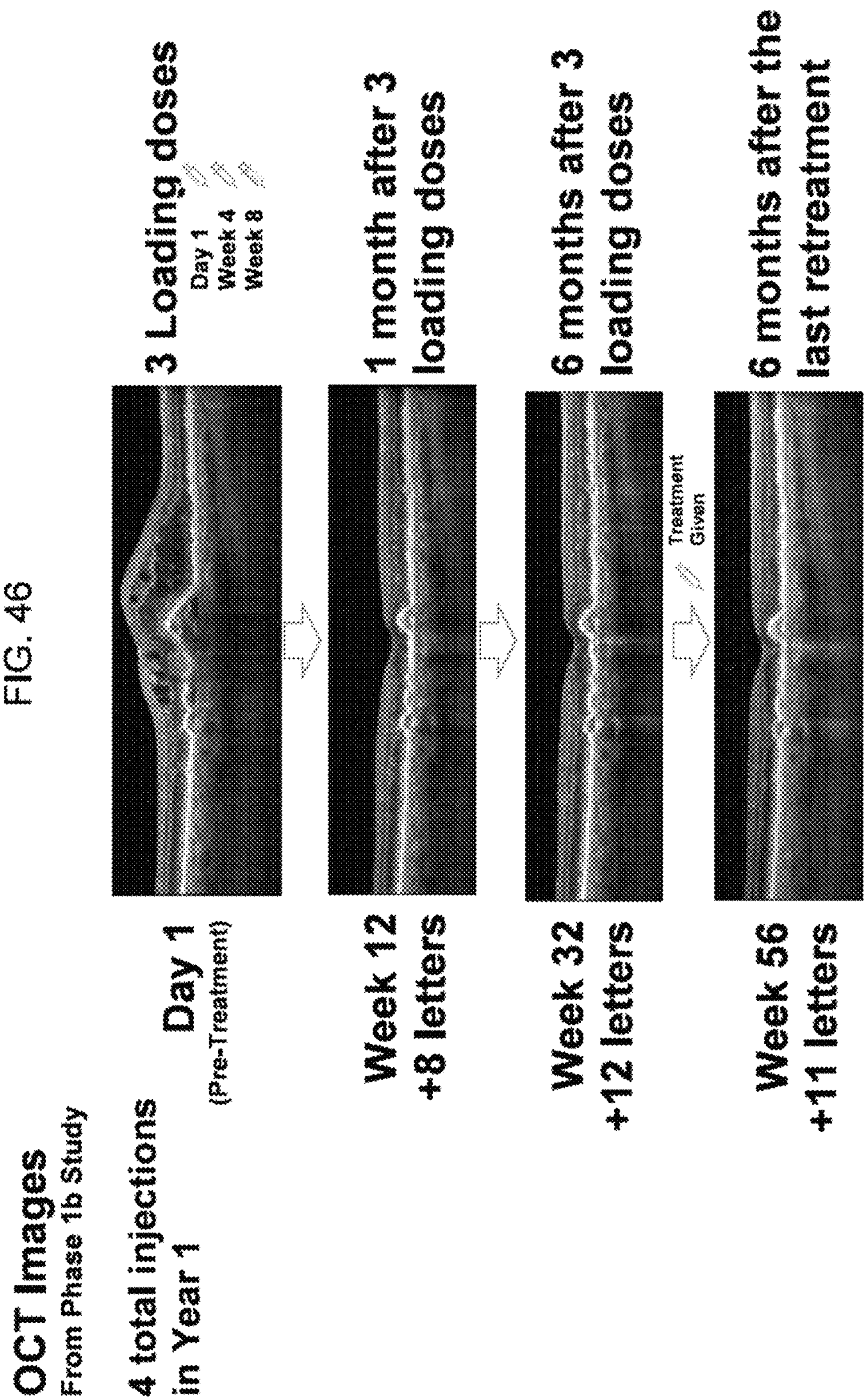

FIG. 46 is a collection of OCT images of a wAMD patient treated with KSI-301, according to some embodiments of the present disclosure.

Figure 47:
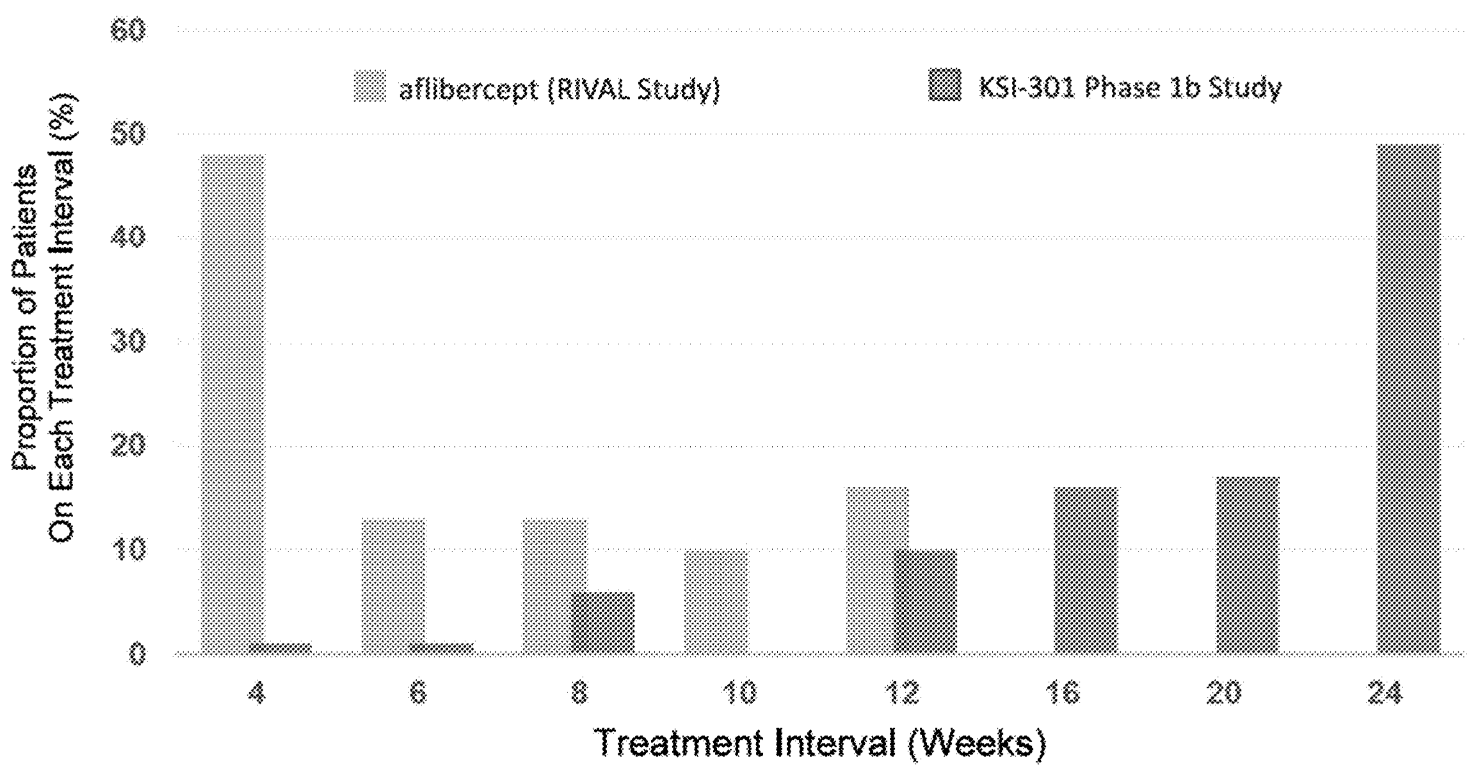

FIG. 47 is a graph showing benchmarking of KSI-301 in wAMD against a standard-of-care treatment, according to some embodiments of the present disclosure.

FIG. 48 is a graph showing benchmarking of KSI-301 in wAMD against a standard-of-care treatment, according to some embodiments of the present disclosure.

Figure 49:
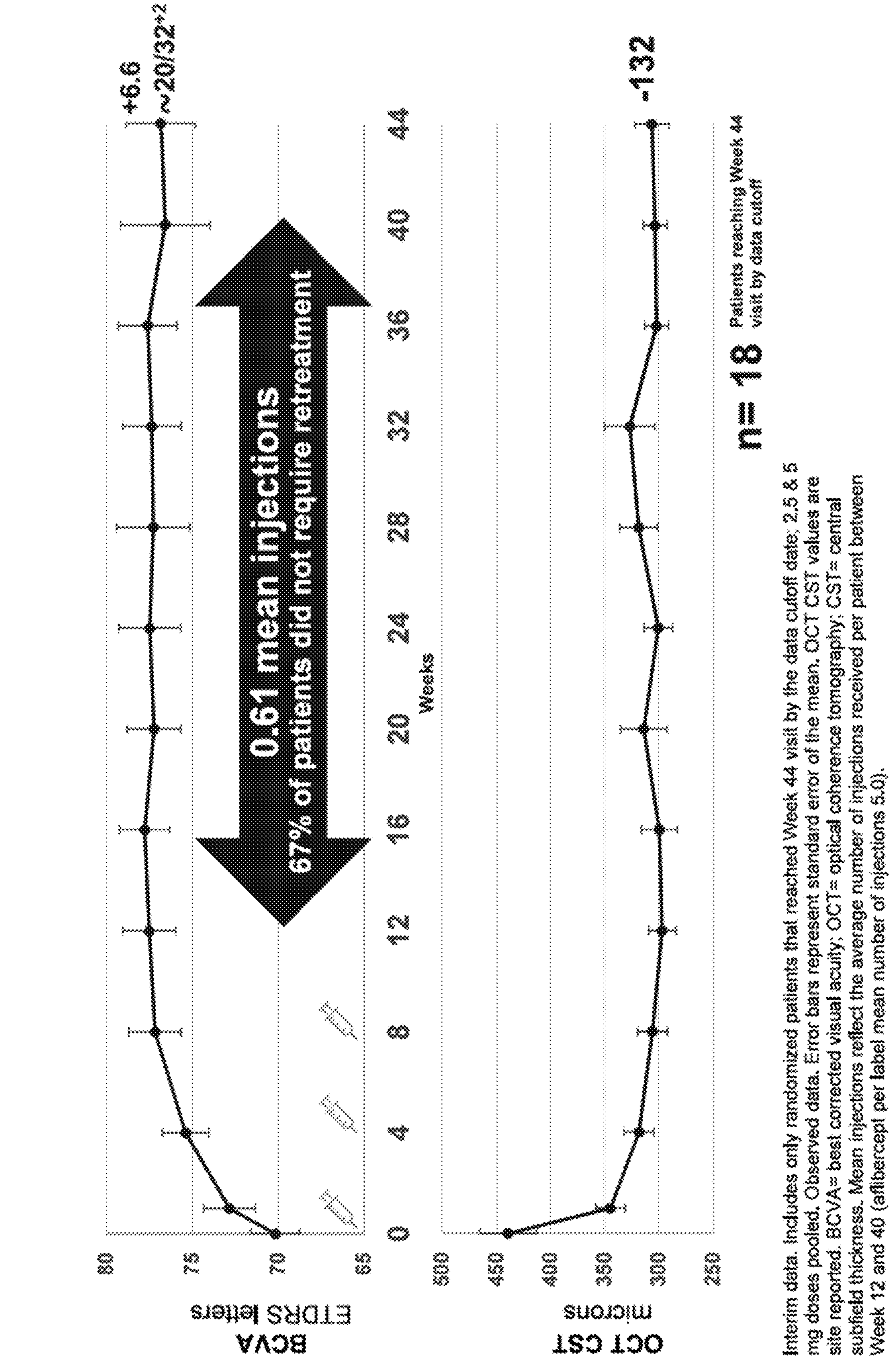

FIG. 49 is a set of graphs showing sustained therapeutic effects of KSI-301 administered to patients with diabetic macular edema (DME), according to some embodiments of the present disclosure.

Figure 50A:
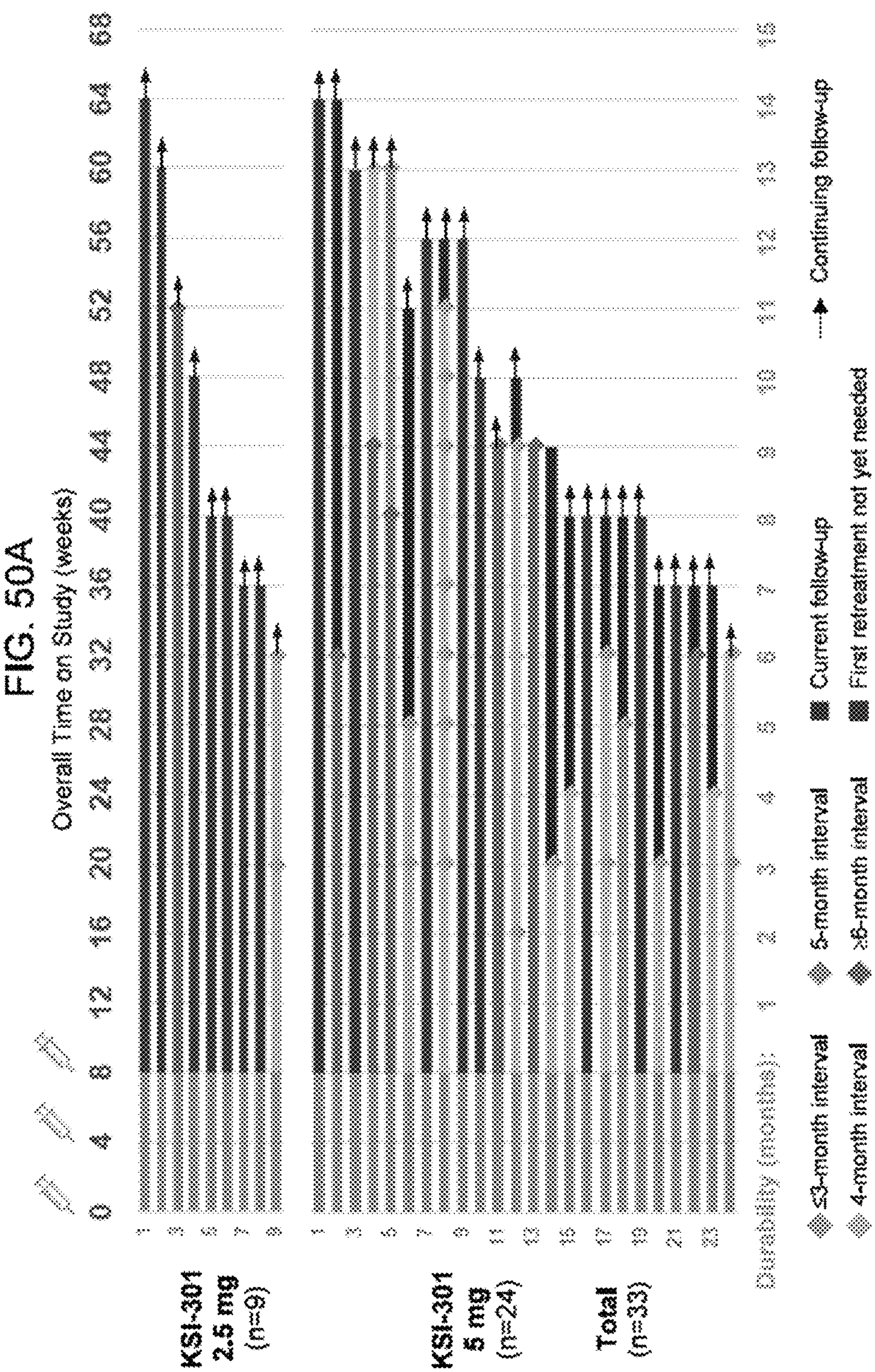

FIG. 50A is a set of graphs showing the schedule of intravitreal administration of KSI-301 received by individual patients treated for DME, according to some embodiments of the present disclosure.

FIG. 50B is a table summarizing the administration interval of KSI-301 in DME patients shown in FIG. 50A.

Figure 51:
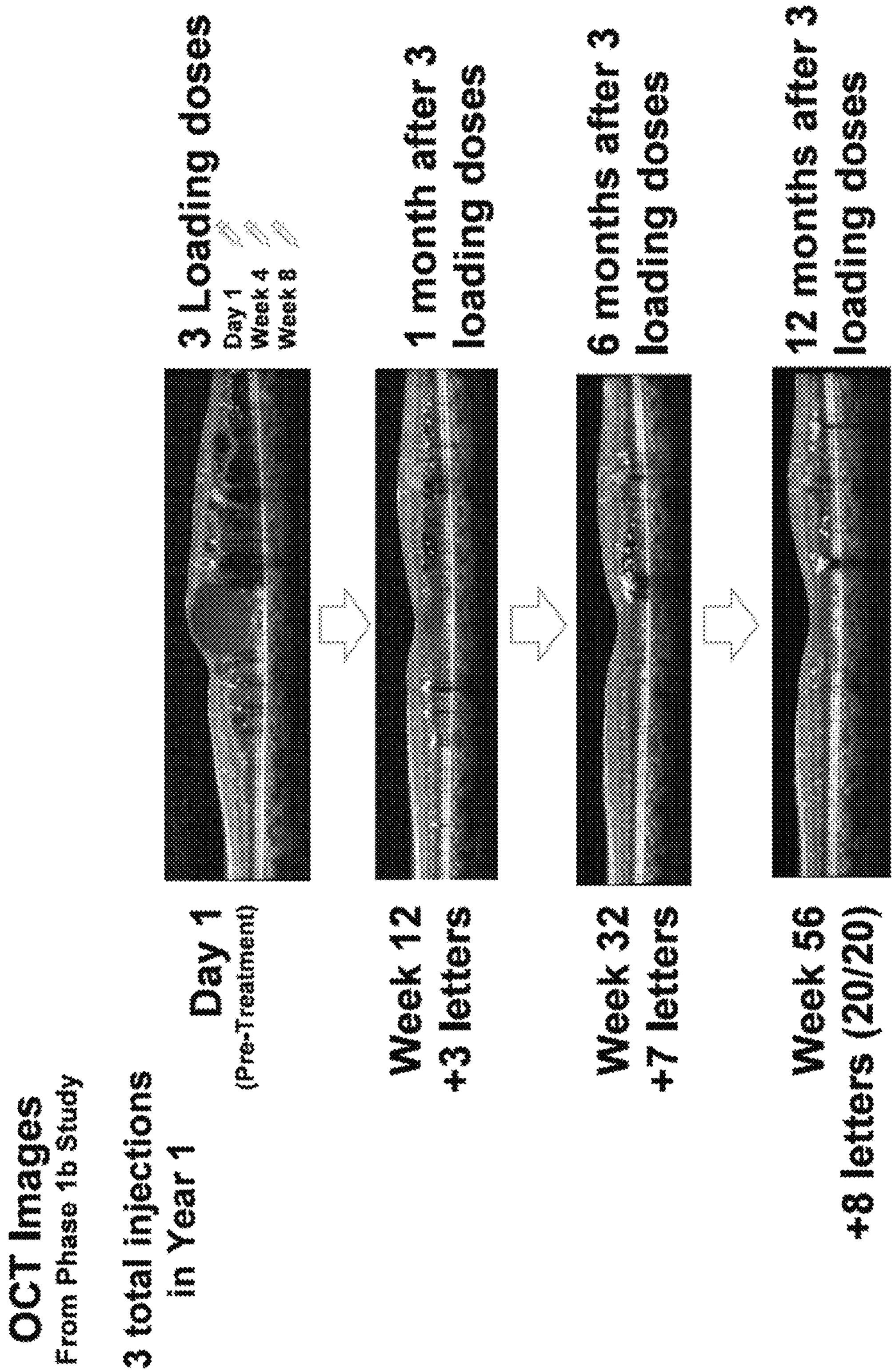

FIG. 51 is a collection of OCT images of a DME patient treated with KSI-301, according to embodiments of the present disclosure.

Figure 52:
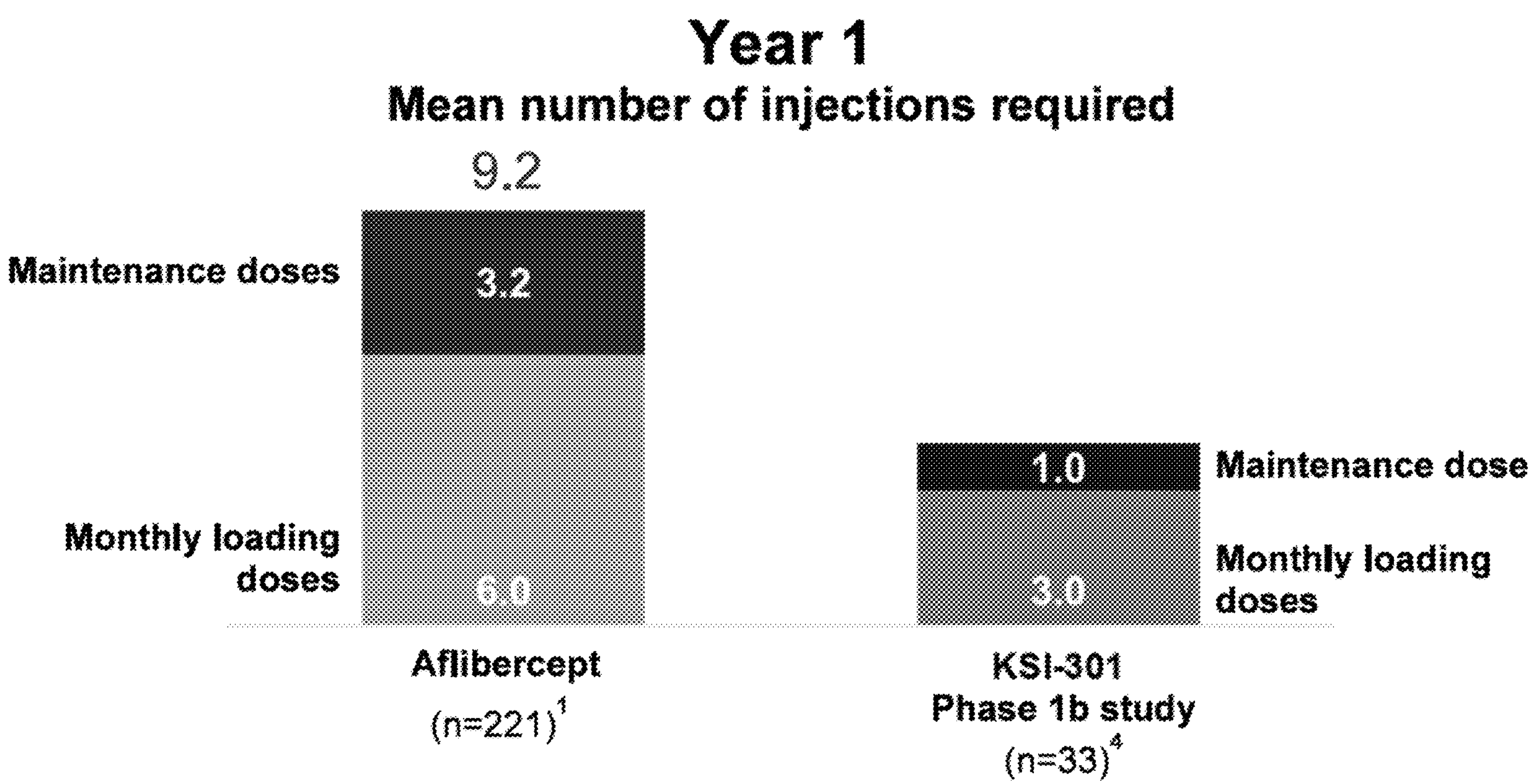

FIG. 52 is a collection of OCT images of a DME patient treated with KSI-301, according to some embodiments of the present disclosure.

FIG. 53 is a set of graphs showing sustained therapeutic effects of KSI-301 administered to patients with retinal vein occlusion (RVO), according to some embodiments of the present disclosure.

Figure 54A:
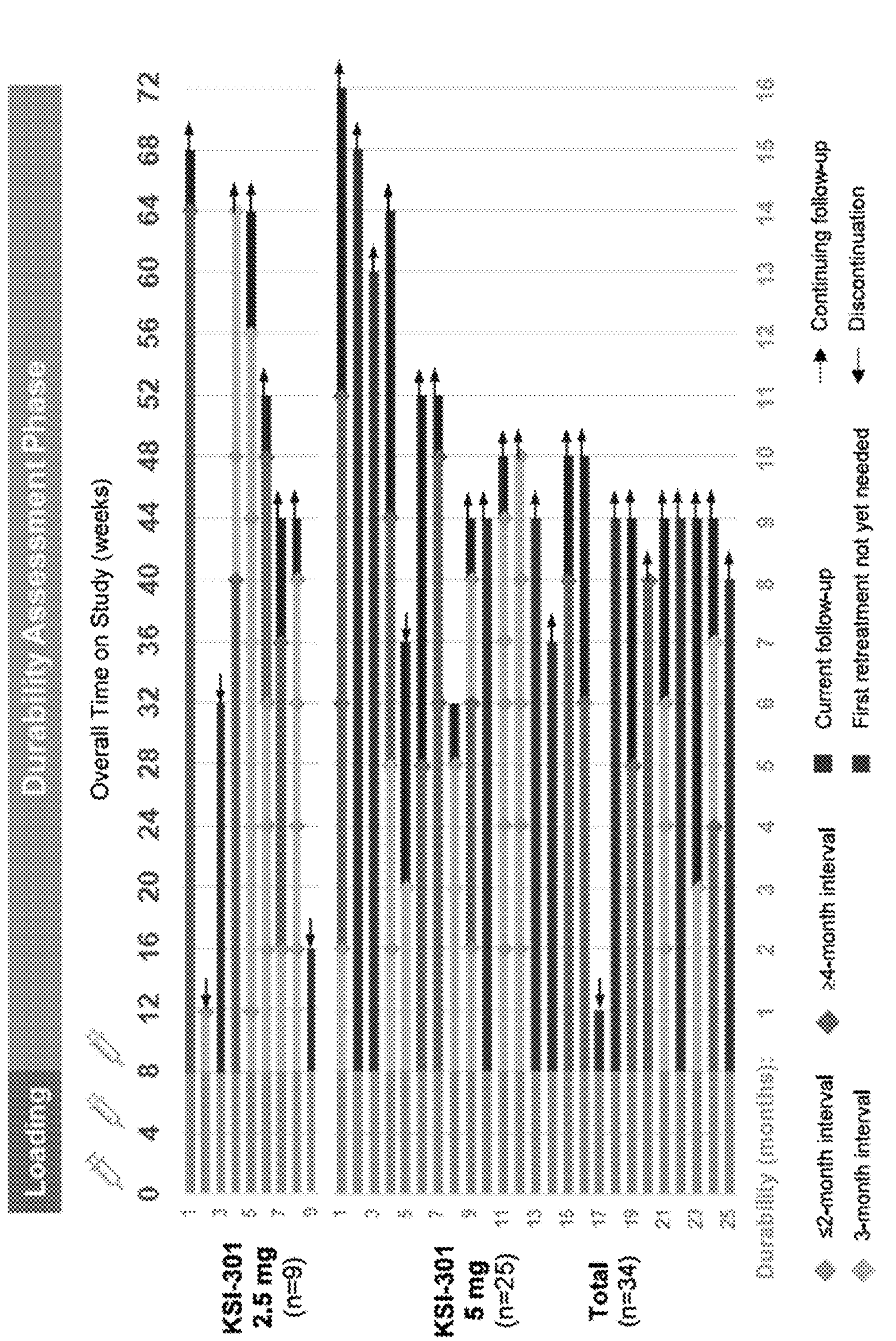

FIG. 54A is a set of graphs showing the schedule of intravitreal administration of KSI-301 received by individual patients treated for RVO, according to some embodiments of the present disclosure.

FIG. 54B is a table summarizing the administration interval of KSI-301 in RVO patients shown in FIG. 54A.

FIG. 55 is a graph showing benchmarking of KSI-301 in RVO against a standard-of-care treatment, according to some embodiments of the present disclosure.

Figure 56:
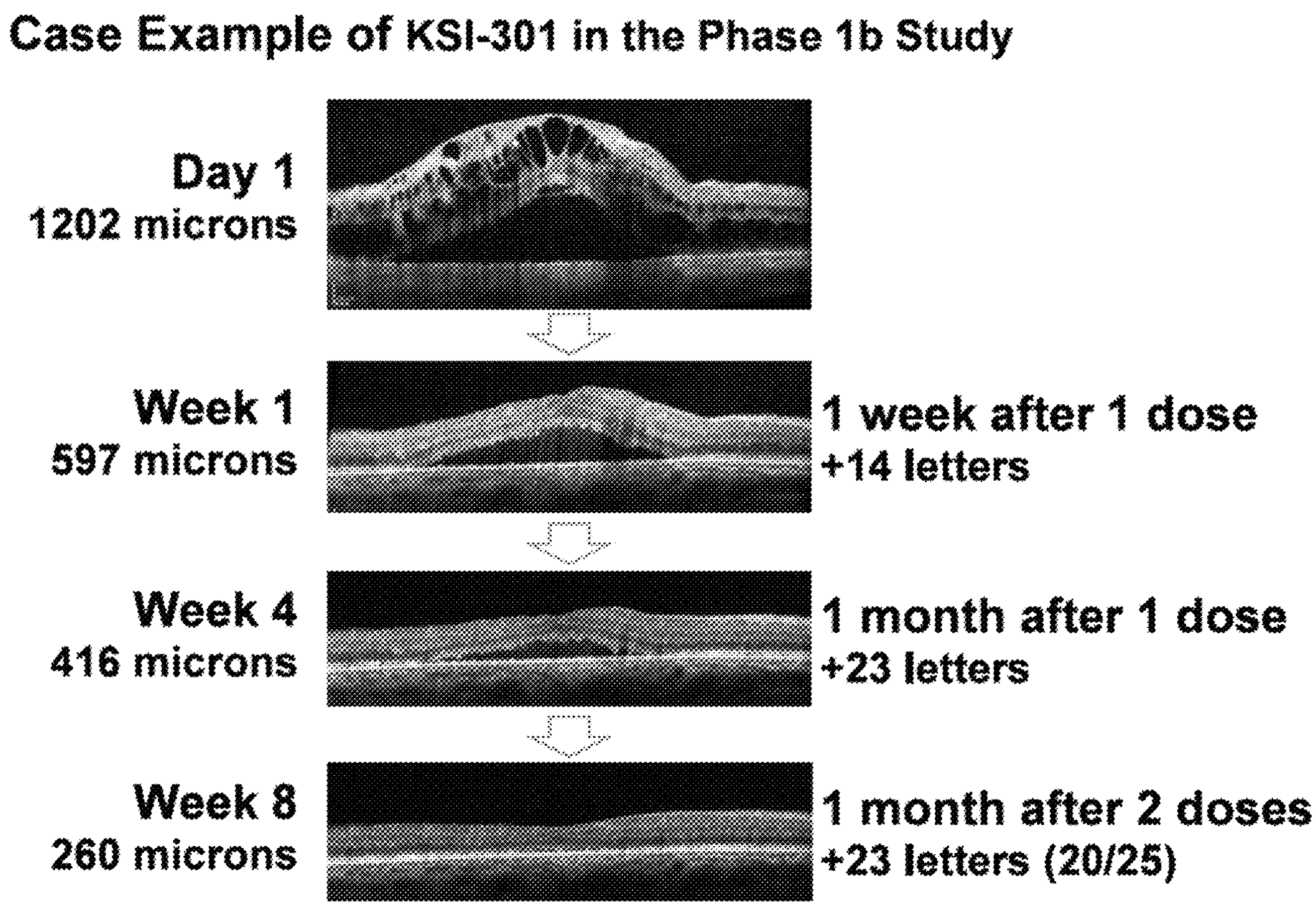

FIG. 56 is a collection of OCT images of a CRVO patient treated with KSI-301, according to some embodiments of the present disclosure.

Figure 57:
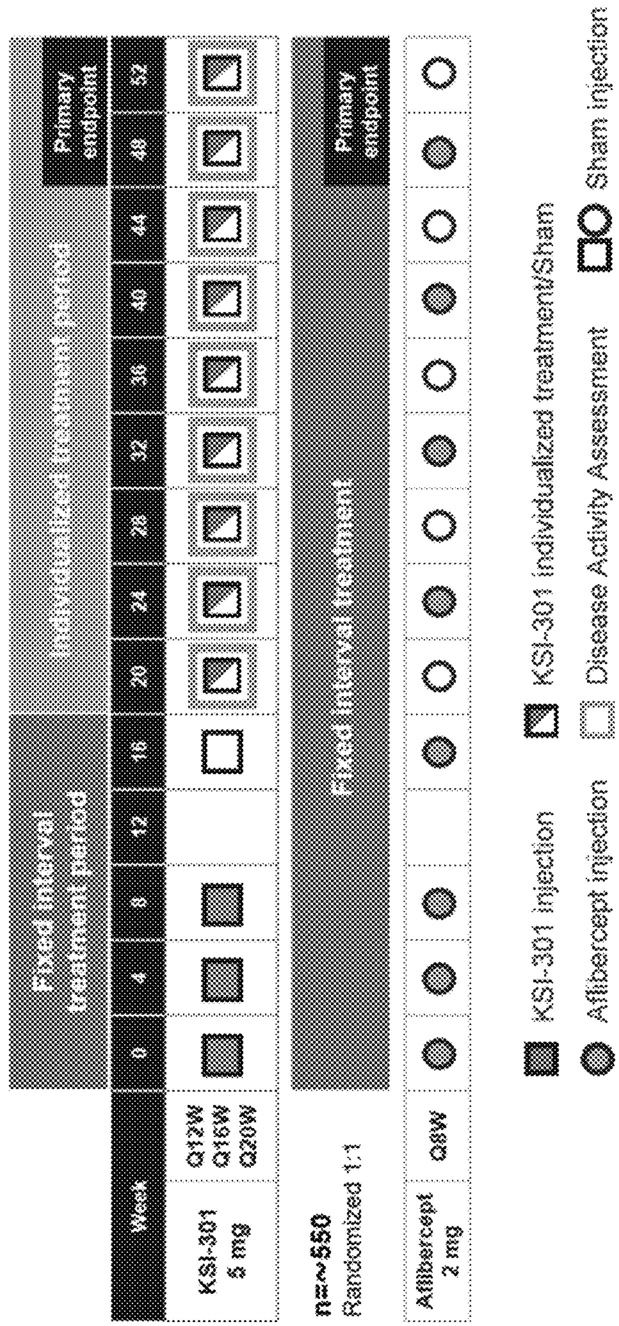

FIG. 57 is a schematic diagram representing an anti-VEGF antibody conjugate intravitreal administration schedule in age-related macular degeneration (wAMD), according to some embodiments of the present disclosure.

Figure 58:
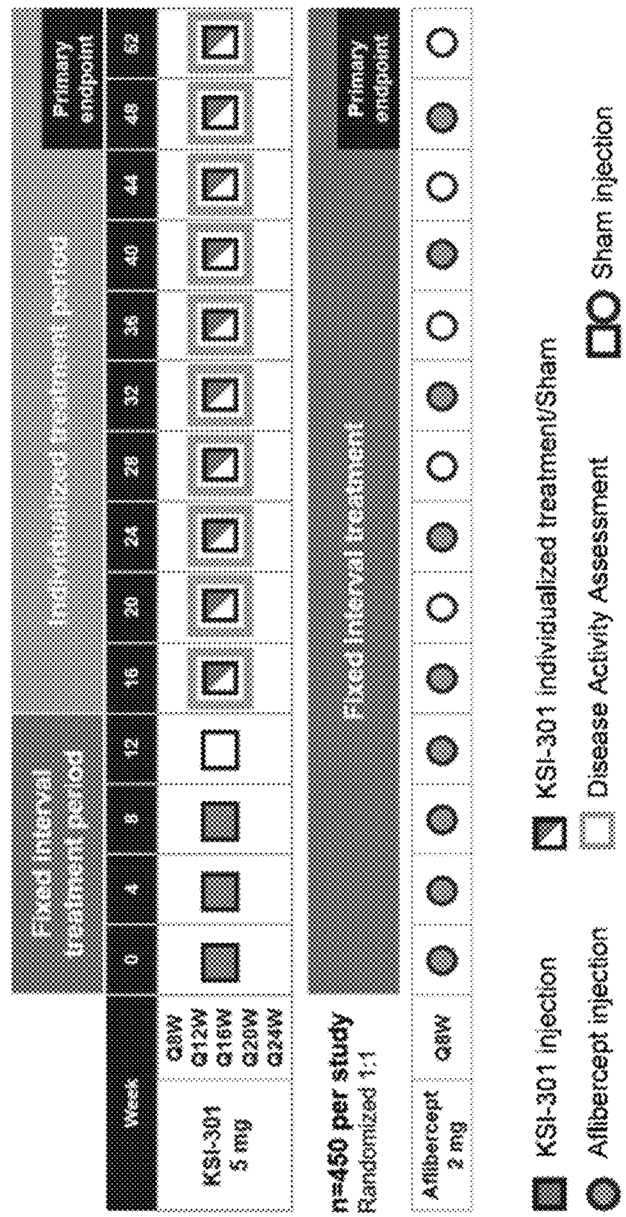

FIG. 58 is a schematic diagram representing an anti-VEGF antibody conjugate intravitreal administration schedule in diabetic macular edema (DME), according to some embodiments of the present disclosure.

Figure 59:
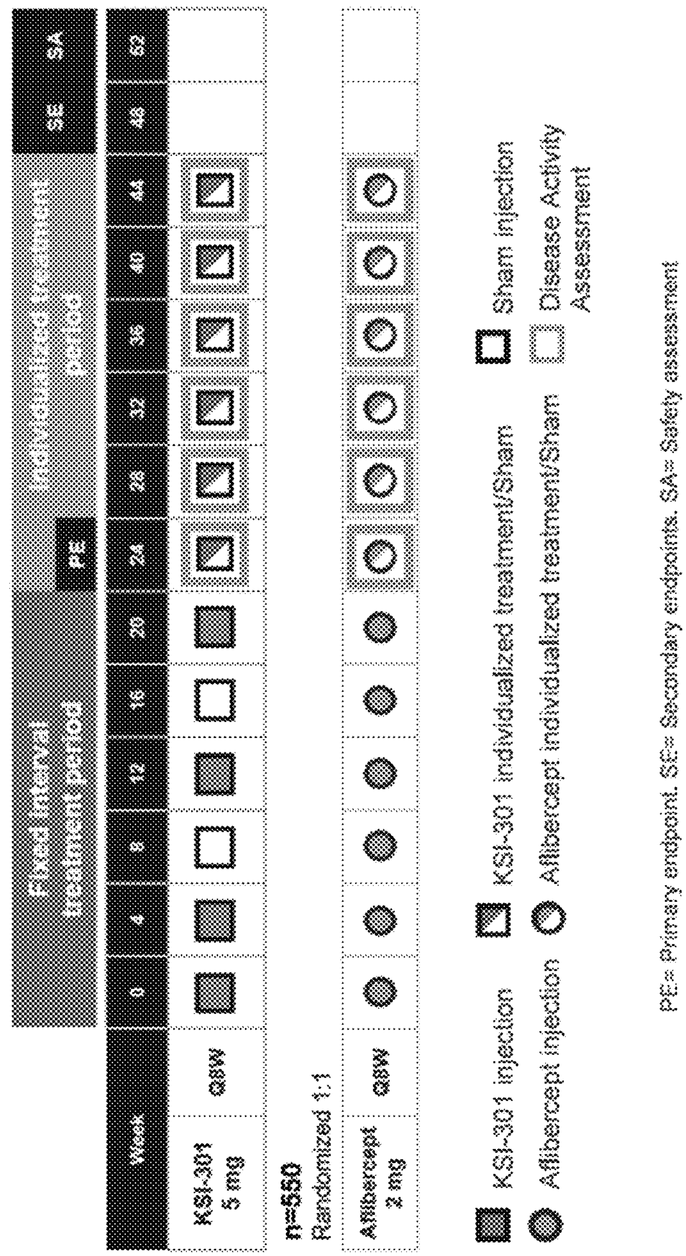

FIG. 59 is a schematic diagram representing an anti-VEGF antibody conjugate intravitreal administration schedule in retinal vein occlusion (RVO), according to some embodiments of the present disclosure.

DETAILED DESCRIPTION OF THE PREFERRED EMBODIMENT

Provided herein are methods of treating an eye disorder by administering an anti-VEGF antibody to a subject having an eye disorder. The anti-VEGF antibody of the present disclosure may be an anti-VEGF antibody conjugate (e.g., KSI-301) that includes a polymeric moiety that extends the half-life of the antibody when administered to a subject. The antibody conjugate may retain therapeutic efficacy after administration for a longer time period compared to an antibody without the polymeric moiety. Thus, the methods of the present disclosure may provide for a course of treatment for an eye disorder that includes fewer doses (e.g., less frequent administration) of the anti-VEGF antibody conjugates than conventional anti-VEGF antibody therapies, to achieve a therapeutic effect of the anti-VEGF therapy on the subject. The present methods may encourage better patient compliance with the treatment course especially when the eye disorder treatment involves intravitreal administration of the therapeutic agent.

Definitions

A "neovascular disorder" is a disorder or disease state characterized by altered, dysregulated or unregulated angiogenesis. Examples of neovascular disorders include neoplastic transformation (e.g. cancer) and ocular neovascular disorders including diabetic retinopathy and age-related macular degeneration.

An "ocular neovascular" disorder is a disorder characterized by altered, dysregulated or unregulated angiogenesis in the eye of a patient. Such disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

The term antibody includes intact antibodies and binding fragments thereof. A binding fragment refers to a molecule other than an intact antibody that comprises a portion of an intact antibody that binds the antigen to which the intact antibody binds. Examples of binding fragments include Fv, Fab', Fab'-SH, F(ab')2; diabodies; linear antibodies; single-chain antibody molecules (e.g. scFv); and multispecific antibodies formed from antibody fragments. scFv antibodies are described in Houston J S. 1991. Methods in Enzymol. 203:46-96. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

Specific binding of an antibody to its target antigen(s) means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcR binding.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai S, Lachmann P C. 1990. Bispecific antibody: a tool for diagnosis and treatment of disease. Clin Exp Immunol. 79:315-321; Kostelny S A, Cole M S, Tso J Y. 1992. Formation of bispecific antibody by the use of leucine zippers. J Immunol. 148: 1547-1553). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. For convenience, the variable heavy CDRs can be referred to as $CDR_H1$, $CDR_H2$ and $CDR_H3$; the variable light chain CDRs can be referred to as $CDR_L1$, $CDR_L2$ and $CDR_L3$. The assignment of amino acids to each domain is in accordance with the definitions of Kabat E A, et al. 1987 and 1991. Sequences of Proteins of Immunological Interest (National Institutes of Health, Bethesda, MD) or Chothia C, Lesk A M. 1987. Canonical Structures for the Hypervariable Regions of Immunoglobulins. J Mol Biol 196:901-917; Chothia C, et al. 1989. Conformations of Immunoglobulin Hypervariable Regions. Nature 342:877-883. Kabat also provides a widely used numbering convention (Kabat numbering) in which corresponding residues between different heavy chain variable regions or between different light chain variable regions are assigned the same number. Although Kabat numbering can be used for antibody constant regions, EU numbering is more commonly used, as is the case in this application. Although specific sequences are provided for exemplary antibodies disclosed herein, it will be appreciated that after expression of protein chains one to several amino acids at the amino or carboxy terminus of the light and/or heavy chain, particularly a heavy chain C-terminal lysine residue, may be missing or derivatized in a proportion or all of the molecules.

The term "epitope" refers to a site on an antigen to which an antibody or extracellular trap segment binds. An epitope on a protein can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody (or Fab fragment) bound to its antigen to identify contact residues.

Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50: 1495, 1990). A test antibody competes with a reference antibody if an excess of a test antibody (e.g., at least 2×, 5×, 10×, 20× or 100×) inhibits binding of the reference antibody by at least 50%. In some embodiments the test antibody inhibits binding of the reference antibody by 75%, 90%, or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, WI, using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcy receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component Clq which in turn activates the complement cascade leading to target cell death. Activation of complement may also result in deposition of complement components on the target cell surface that facilitate ADCC by binding complement receptors (e.g., CR3) on leukocytes.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. No. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (which can be as defined by Kabat) from a mouse antibody, they can also be made with less than all CDRs (e.g., at least 3, 4, or 5 CDRs from a mouse antibody) (e.g., De Pascalis R, Iwahashi M, Tamura M, et al. 2002. Grafting "Abbreviated" Complementary-Determining Regions Containing Specificity-Determining Residues Essential for Ligand Contact to Engineer a Less Immunogenic Humanized Monoclonal Antibody. J Immunol. 169:3076-3084; Vajdos F F, Adams C W, Breece T N, Presta L G, de Vos A M, Sidhu, S S. 2002. Comprehensive functional maps of the antigen-binding site of an anti-ErbB2 antibody obtained with shotgun scanning mutagenesis. J Mol Biol. 320: 415-428; Iwahashi M, Milenic D E, Padlan E A, et al. 1999. CDR substitutions of a humanized monoclonal antibody (CC49): Contributions of individual CDRs to antigen binding and immunogenicity. Mol Immunol. 36:1079-1091; Tamura M, Milenic D E, Iwahashi M, et al. 2000. Structural correlates of an anticarcinoma antibody: Identification of specificity-determining regions (SDRs) and development of a minimally immunogenic antibody variant by retention of SDRs only. J Immunol. 164:1432-1441).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan E A. 1991. A possible procedure for reducing the immunogenicity of antibody variable domains while preserving their ligand-binding properties. Mol Immunol. 28:489-98) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Östberg L, Pursch E. 1983. Human×(mouse×human) hybridomas stably producing human antibodies. Hybridoma 2:361-367; Östberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332.

"Polymer" refers to a series of monomer groups linked together. A polymer is composed of multiple units of a single monomer (a homopolymer) or different monomers (a heteropolymer). High MW polymers are prepared from monomers that include, but are not limited to, acrylates, methacrylates, acrylamides, methacrylamides, styrenes, vinylpyridine, vinyl-pyrrolidone and vinyl esters such as vinyl acetate. Additional monomers are useful in high MW polymers. When two different monomers are used, the two monomers are called "comonomers," meaning that the different monomers are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using monomers or comonomers. The polymerization can be a conventional free radical polymerization or a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments, the initiator contains one of more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

"Phosphorylcholine," also denoted as "PC," refers to the following:

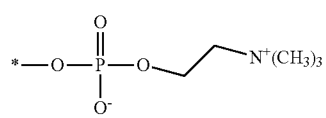

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate (HEA-PC shown below in Example 6) as monomer.

Poly(methacryloyloxyethyl phosphorylcholine) containing polymer refers to a polymer containing 2-(methacryloyloxy)ethyl-2-(trimethylammonium)ethyl phosphate (HEMA-PC or MPC) as monomer (see below):

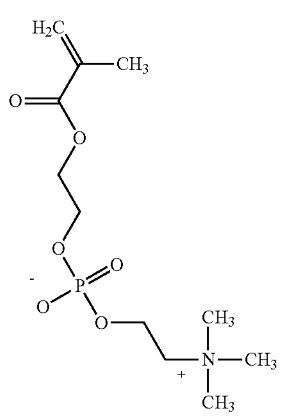

As used herein, "MPC" and "HEMA-PC" are interchangeable.

"Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In some embodiments, the molecular weight is measured by SEC-MALS (size exclusion chromatography—multi angle light scattering). In some embodiments, the polymeric reagents are typically polydisperse (i.e., number average molecular weight and weight average molecular weight of the polymers are not equal), and can possess low polydispersity values of, for example, less than about 1.5, as judged, for example, by the PDI value derived from the SEC-MALS measurement. In some embodiments, the polydispersities (PDI) are in the range of about 1.4 to about 1.2. In some embodiments the PDI is less than about 1.15, 1.10, 1.05, or 1.03.

The phrase "a" or "an" entity refers to one or more of that entity; for example, a compound refers to one or more compounds or at least one compound. As such, the terms "a" (or "an"), "one or more", and "at least one" can be used interchangeably herein.

"About" means variation one might see in measurements taken among different instruments, samples, and sample preparations.

"Protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," 3rd Edition, John Wiley and Sons, Inc., New York, 1999.

"Alkyl" refers to a straight or branched, saturated, aliphatic radical having the number of carbon atoms indicated. For example, C1-C6 alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7 or up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene.

For instance, a straight chain alkylene can be the bivalent radical of $-(CH_2)_n-$, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', $-CO_2R'$, —CONR'R", —OC(O)NR'R", —NR"C(O)R', —NR'—C(O)NR"R'", $-NR"C(O)_2R'$, $-NH-C(NH_2)=NH$, $-NR'C(NH_2)=NH$, $-NH-C(NH_2)=NR'$, —S(O)R', $-S(O)_2R'$, $-S(O)_2NR'R"$, —CN and $-NO_2$ in a number ranging from zero to (2m'+1), where m' is the total number of carbon atoms in such radical. R', R" and R'" each independently refer to hydrogen, unsubstituted (C1-C8)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. The term "alkyl" is include groups such as haloalkyl (e.g., $-CF_3$ and $-CH_2CF_3$) and acyl (e.g., $-C(O)CH_3$, $-C(O)CF_3$, $-C(O)CH_2OCH_3$, and the like). In some embodiments, the substituted alkyl and heteroalkyl groups have from 1 to 4 substituents. In some embodiments, the substituted alkyl and heteroalkyl groups have 1, 2 or 3 substituents. Exceptions are those perhalo alkyl groups (e.g., pentafluoroethyl and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', $-CO_2R'$, —CONR'R", —OC(O)NR'R", —NR"C(O)R', —NR'—C(O)NR"R'", $-NR"C(O)_2R'$, —NR—C(NR'R"R'")=NR"", —NR—C(NR'R")=NR'", —S(O)R', $-S(O)_2R'$, $-S(O)_2NR'R"$, $-NRSO_2R'$, —CN and $-NO_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $-CF_3$ and $-CH_2CF_3$) and acyl (e.g., $-C(O)CH_3$, $-C(O)CF_3$, $-C(O)CH_2OCH_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means a cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —$S(O)_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkyl ene-phenyl is 2,3-dihydrobenzofuran-5-yl.

In some embodiments the aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-m ethylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR" $C(O)_2$R', —NH—C($NH_2$)═NH, —NR' C($NH_2$)═NH, —NH—C($NH_2$)═NR', —S(O)R', —$S(O)_2$R', —$S(O)_2$NR'R", —$N_3$, —CH$(Ph)_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —$S(O)_2$—, —$S(O)_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2$NR'—. The substituent R' in —NR'— and —$S(O)_2$NR'— is selected from hydrogen or unsubstituted ($C_1$-$C_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. In some embodiments, quinolinyl represents 2-, 3- or 4-quinolinyl. In some embodiments, isoquinolinyl represents 1-, 3- or 4-isoquinolinyl. In some embodiments, benzopyranyl, benzothiopyranyl can represent 3-benzopyranyl or 3-benzothiopyranyl, respectively. In some embodiments, thiazolyl can represent 2- or 4-thiazolyl. In some embodiments, triazolyl can be 1-, 2- or 5-(1,2,4-triazolyl). In some embodiments, tetrazolyl can be 5-tetrazolyl.

In some embodiments, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —$S(O)_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

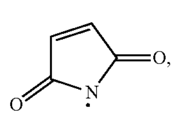

which upon reaction with a sulfhydryl (e.g., a thio alkyl) forms an —S-maleimido group having the structure

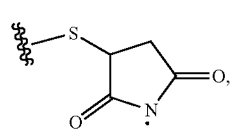

where "•" indicates the point of attachment for the maleimido group and "$\sim$" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as N-alpha-methyl amino acids (e.g. sarcosine), 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. In some embodiments, the halide is a bromine.

"Pharmaceutically acceptable excipient" refers to an excipient that can be included in compositions and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Therapeutic proteins are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The "biological half-life" of a substance is a pharmacokinetic parameter which specifies the time required for one half of the substance to be removed from a tissue or an organism following introduction of the substance.

"OG1786" is a 9-arm initiator used for polymer synthesis, which depicts that salt form of OG1786 with trifluororacetic acid. OG1786 may be used as other salts are used or as the free base.

"OG1801" is an approximately (+/−15%) 750 kDa polymer (either by Mn or Mp) made using OG1786 as an initiator for ATRP synthesis using the monomer HEMA-PC.

"OG1802" is OG1801 with a maleimide functionality added wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% Daltons.

"BCVA" denotes Best Corrected Visual Acuity.

"OCT-A" denotes OCT-Angiography.

"SD-OCT" denotes Spectral Domain Optical Coherence Tomography.

Multi-angle light scattering (MALS) is a technique of analyzing macromolecules where the laser light impinges on the molecule, the oscillating electric field of the light induces an oscillating dipole within it. This oscillating dipole will re-radiate light and can be measured using a MALS detector such as Wyatt miniDawn TREOS. The intensity of the radiated light depends on the magnitude of the dipole induced in the macromolecule which in turn is proportional to the polarizability of the macromolecule, the larger the induced dipole, and hence, the greater the intensity of the scattered light. Therefore, in order to analyze the scattering from a solution of such macromolecules, one should know their polarizability relative to the surrounding medium (e.g., the solvent). This may be determined from a measurement of the change, Δn, of the solution's refractive index n with the molecular concentration change, Δc, by measuring the dn/dc (=Δn/Δc) value using a Wyatt Optilab T-rEX differential refractometer. Two molar weight parameters that MALS determination employ are number average molecular weight (Mn) and weight average molecular weight (Mw) where the polydispersity index (PDI) equals Mw divided by Mn. SEC also allows another average molecular weight determination of the peak molecular weight Mp which is defined as the molecular weight of the highest peak at the SEC.

The PDI is used as a measure of the broadness of a molecular weight distribution of a polymer and bioconjugate which is derived from conjugation of a discrete protein (e.g. OG1950) to a polydisperse biopolymer (e.g., OG1802). For a protein sample, its polydispersity is close to 1.0 due to the fact that it is a product of translation where every protein molecule in a solution is expected to have almost the same length and molar mass. In contrast, due to the polydisperse nature of the biopolymer where the various length of polymer chains are synthesized during the polymerization process, it is very important to determine the PDI of the sample as one of its quality attribute for narrow distribution of molecular weight.

Size exclusion chromatography (SEC) is a chromatography technique in which molecules in solution are separated by their size. Typically an aqueous solution is applied to transport the sample through the column which is packed with resins of various pore sizes. The resin is expected to be inert to the analyte when passing through the column and the analytes separate from each other based on their unique size and the pore size characteristics of the selected column.

Coupling the SEC with MALS or SEC/MALS provides accurate distribution of molar mass and size (root mean square radius) as opposed to relying on a set of SEC calibration standards. This type of arrangement has many advantages over traditional column calibration methods. Since the light scattering and concentration are measured for each eluting fraction, the molar mass and size can be determined independently of the elution position. This is particularly relevant for species with non-globular shaped macromolecules such as the biopolymers (OG1802) or bioconjugates (e.g., KSI-301); such species typically do not elute in a manner that might be described by a set of column calibration standards.

In some embodiments, a SEC/MALS analysis includes a Waters HPLC system with Alliance 2695 solvent delivery module and Waters 2996 Photodiole Array Detector equipped with a Shodex SEC-HPLC column (7.8×300 mm). This is connected online with a Wyatt miniDawn TREOS and Wyatt Optilab T-rEX differential refractometer. The Empower software from Waters can be used to control the Waters HPLC system and the ASTRA V 6.1.7.16 software from Wyatt can be used to acquire the MALS data from the Wyatt miniDawn TREOS, dn/dc data from the T-rEX detector and the mass recovery data using the A280 absorbance signal from the Waters 2996 Photodiole Array detector. SEC can be carried out at 1 ml/min in 1×PBS pH 7.4, upon sample injection, the MALS and RI signals can be analyzed by the ASTRA software for determination of absolute molar mass (Mp, Mw, Mn) and polydisperse index (PDI). In addition, the calculation also involves the input dn/dc values for polymer and protein as 0.142 and 0.183, respectively. For KSI-301 dn/dc value, the dn/dc is calculated based on the weighted MW of the polymer and the protein to be about 0.148 using the formula below:

$$\text{Conjugate } dn/dc = 0.142\times[\text{MWpolymer}/(\text{MWpolymer}+\text{MWprotein})]+0.183\times[\text{MWprotein}/(\text{MWpolymer}+\text{MWprotein})]$$

where MWpolymer for OG1802 is 800 kDa and the MWprotein for OG1950 is 146 kDa.

"KSI-301" is a bioconjugate of a recombinant, mammalian cell expressed full-length humanized anti-VEGF monoclonal antibody which is covalently conjugated to a branched high molecular weight phosphorylcholine based biopolymer. In some embodiments, KSI-301 is supplied as a preservative free, sterile, aqueous solution in a single-use glass vial at a concentration of 50 mg/mL (based on antibody mass). FIG. 14 displays the amino acid sequence of the antibody portion of KSI-301. KSI-301 is an anti-vascular endothelial growth factor (VEGF) biopharmaceutical with an extended ocular half-life. KSI-301 is a bioconjugate of two intermediates: (1) OG1950 antibody intermediate, a recombinant, full-length humanized, anti-huVEGF A monoclonal antibody, and (2) OG1802 biopolymer intermediate, a phosphorylcholine biopolymer. The addition of OG1802, an inert biopolymer, increases the size of the biologic, thereby extending the ocular pharmacokinetics (PK) of KSI-301 beyond that of currently approved anti-huVEGF-A therapeutics. Nonclinical studies with KSI-301 indicate that it appropriately binds with high affinity to huVEGF-A whose binding to huVEGF Receptors 1 and 2 (huVEGFR) is then inhibited. This in turn abrogates huVEGF-A mediated function.

Pharmacokinetic studies have been conducted in rabbit which demonstrate that KSI-301 has extended ocular half-life, penetrates ocular tissues well and is distributed to the retina and choroid. In rabbit, KSI-301 has an ocular half-life of approximately 11 days, which is significantly longer than the reported rabbit half-life measured for aflibercept and ranibizumab, which are 4 to 5 and 3 to 4 days, respectively (CovanceStudy 8376321, Park 2016). A series of non-clinical GLP repeat dose (4-week dosing intervals) toxicology studies in cynomolgus monkeys testing the ocular and systemic safety of KSI-301 have been conducted through 26 weeks (7 intravitreal doses) and 10 weeks (3 intravenous doses), respectively. Results show that KSI-301 was well tolerated up to the maximum dose tested of 5 mg/eye (intravitreal) and 5 mg/kg (intravenous) in the ocular and systemic studies, respectively. Together, data extrapolated from non-clinical PK and toxicology studies indicate that KSI-301 can be safely and effectively dosed in human subjects. In some embodiments, the route of administration is via an intravitreal injection. In some embodiments, an anti-VEGF antibody conjugate (e.g., KSI-301) can be administered every 3-4 months, after a loading dose completion, or even less frequently.

In some embodiments, the molecule to be administered in any one or more of the methods provided herein is any one of the molecules disclosed in U.S. Pat. Pub. No. 2017/0190766, herein incorporated by reference in its entirety.

Methods of Treatment

Figure 13:
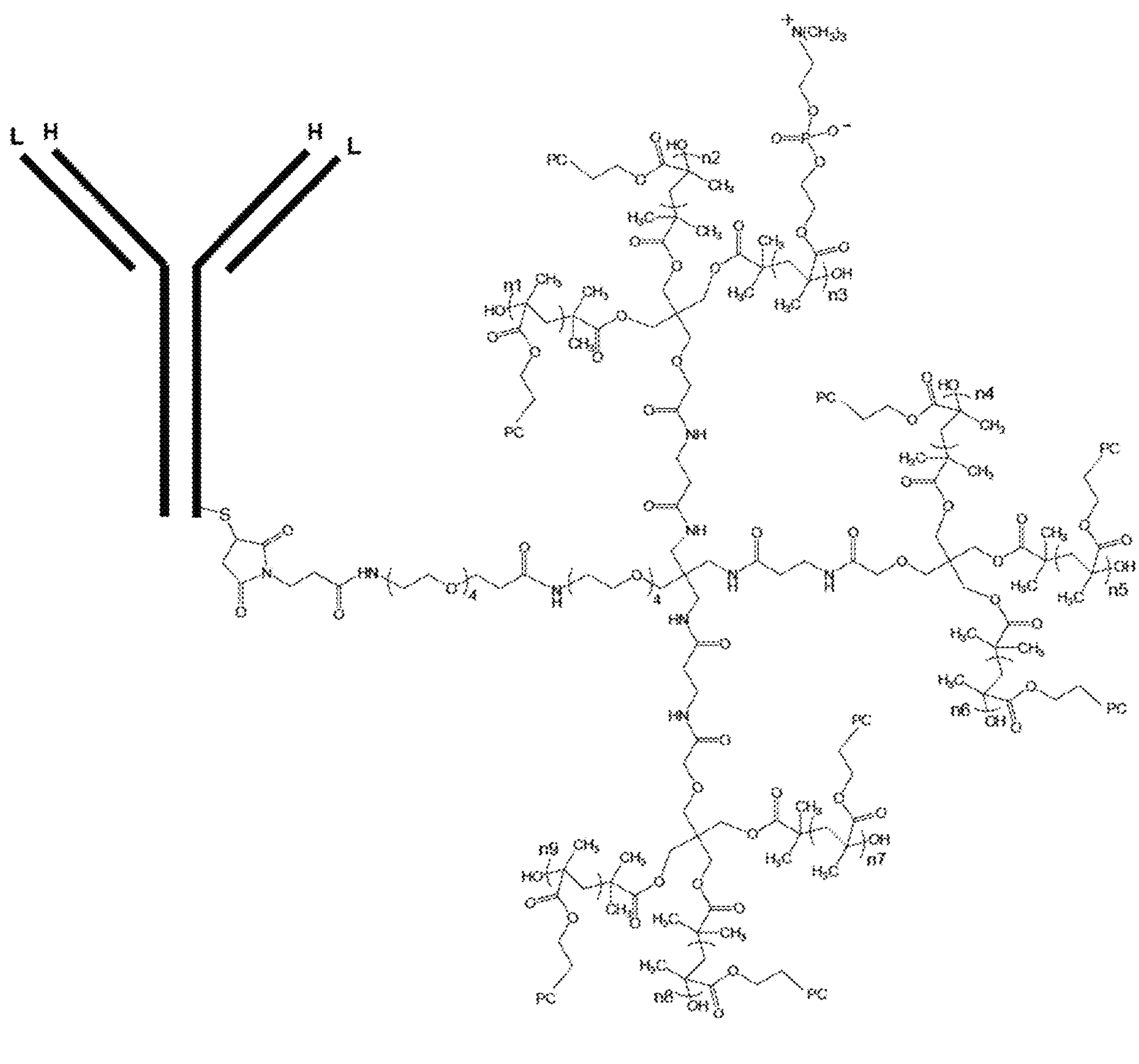
FIG. 13 is a schematic diagram of the structure of KSI-301, according to some embodiments of the present disclosure, where each heavy chain of the anti-VEGF-A antibody is denoted by the letter H, and each light chain of the anti-VEGF-A antibody is denoted by the letter L; the polymer is bonded to the anti-VEGF-A antibody through a sulfhydryl at C443 according to EU numbering, which bond is depicted on one of the heavy chains above; PC is

In general terms, a method of the present disclosure includes administering one or more doses of an anti-VEGF antibody conjugate (e.g., KSI-301, or the embodiment in FIG. 14 conjugated to a phosphorylcholine polymer, as provided herein, or the construct depicted in FIG. 13), or an anti-VEGF protein conjugate (e.g., aflibercept biopolymer conjugate) to a subject (e.g., human or other mammalian patient) in need of treating an eye disorder, to thereby treat the eye disorder. The anti-VEGF antibody conjugate or anti-VEGF protein conjugate, when administered to the subject, may provide a long-lasting therapeutic effect that allows for a dosing schedule with longer intervals between dosing than has been previously used with anti-VEGF therapies. In some embodiments, a therapeutic result of the anti-VEGF antibody conjugate therapy or anti-VEGF protein conjugate therapy, once achieved by administration of one or more doses (e.g., loading dose and/or maintenance dose) of the anti-VEGF antibody conjugate or anti-VEGF protein conjugate, is retained by the subject without requiring any additional dose thereafter, e.g., retained for the rest of the subject's life.

With reference to FIG. 42, an embodiment of a method of the present disclosure is described. The method 4200 can include administering 4210 an anti-VEGF antibody conjugate (e.g., KSI-301) to a subject in need of treating an eye disorder (e.g., wAMD, DME, or RVO) at a first loading dose. Then, the loading dose can be repeated 4220 at least once (e.g., repeated once, twice, three times, etc.). After administration of the loading doses, the therapeutic result of the anti-VEGF antibody conjugate, e.g., KSI-301, therapy can be retained by the subject for at least 8 weeks, e.g., at least 12 weeks, at least 16 weeks, at least 20 weeks, at least 24 weeks or longer, after the final loading dose. In some embodiments, the method includes administering 4230 one or more subsequent doses (e.g., maintenance doses) of the anti-VEGF antibody conjugate, e.g., KSI-301, to the subject at least 8 weeks, e.g., at least 12 weeks, at least 16 weeks, at least 20 weeks, at least 24 weeks, after administering the final loading dose. In some embodiments, the method includes administering an anti-VEGF protein, e.g., aflibercept, conjugate (in lieu of the anti-VEGF antibody conjugate) to a subject in need of treating an eye disorder, according to any of the methods disclosed herein.

In some embodiments, the method includes administering a first loading dose of an anti-VEGF antibody conjugate (e.g., KSI-301) or anti-VEGF protein conjugate (e.g., an aflibercept biopolymer conjugate) to a subject (e.g., human or other mammalian patient) in need of treating an eye disorder, and subsequently administering at least one more, but no more than two more of the loading doses to achieve a therapeutic result (e.g., improved vision, slowing disease progression, reduced symptoms, improved retinal health, etc.) of the anti-VEGF therapy that lasts for an extended period of time. In some embodiments, the patient may not require re-treatment of the eye disorder for an extended period of time upon receiving the final loading dose. In some embodiments, administration of the anti-VEGF antibody conjugate (or anti-VEGF protein conjugate (e.g., an aflibercept biopolymer conjugate)) may provide for a therapeutic result of the anti-VEGF therapy without any loading doses, to treat a subject having an eye disorder (e.g., non-proliferative diabetic retinopathy).

As used herein, any time "anti-VEGF antibody" or "anti-VEGF antibody conjugate" is referenced, an anti-VEGF protein, such as an anti-VEGF fusion protein, e.g., aflibercept, is also contemplated. Thus, as disclosed herein, any time "anti-VEGF antibody conjugate" is referenced, an anti-VEGF protein, e.g., aflibercept, covalently bonded to a phosphorylcholine containing biopolymer (e.g., OG1802) as disclosed herein, is also contemplated. In the various embodiments disclosed herein, any reference to an anti-VEGF antibody conjugate therapy, also contemplates an anti-VEGF protein, e.g., aflibercept, conjugate therapy. In the various embodiments of methods of treating an eye disorder, disclosed herein, any reference to an anti-VEGF antibody conjugate, also contemplates an aflibercept biopolymer conjugate.

A "loading dose" has its ordinary and customary meaning as understood by a person of ordinary skill in the art, in view of the present disclosure. A loading dose may refer to an amount of a therapeutic agent administered to a subject, either before a therapeutic effect of the agent is observed in the subject, or before a desired level of therapeutic effect of the agent is achieved in the subject. A loading dose is typically administered at the beginning of a course of treatment with the therapy. In some embodiments, the loading dose is administered more frequently or at shorter intervals compared to later doses that are for maintenance of a therapeutic result. The time period during which a subject receives one or more loading doses may be referred to as a loading phase. In some embodiments, a subject is not monitored for disease progression or status (e.g., not assessed for visual acuity, retinal thickness, etc.) during the loading phase. In some embodiments, a therapeutic result (as disclosed herein) of the anti-VEGF antibody conjugate therapy (e.g., KSI-301 therapy) has not reached a desired or threshold level during the loading phase. The loading dose may be one of a series of loading doses administered to the subject, e.g., during the loading phase. A "final loading dose" may refer to the last loading dose in a series of loading doses administered to the subject, at and/or after which a desired level of therapeutic effect of the agent is achieved. Thus, where the subject is given one loading dose, the final loading dose is the first loading dose. Where the subject is given two loading doses, the final loading dose is the second loading dose. Likewise, where the subject is given three loading doses, the final loading dose is the third loading dose, and so on. A dose of the therapeutic agent administered to a subject after the loading phase may be referred to as a maintenance dose or a retreatment dose. "Maintenance dose" and "retreatment dose" are used herein interchangeably. In some embodiments provided herein, the loading doses can be adequate without as frequent need for, or any need for, subsequent retreatment or maintenance doses. In some embodiments, a series of loading doses is administered to a subject at a higher frequency than a series of maintenance (or retreatment) doses administered to the subject. In some embodiment, the loading dose(s) given may be sufficient to keep disease activity under control in the subject, without requiring a maintenance (or retreatment) dose.

In some embodiments, the therapeutic result of the anti-VEGF therapy achieved by the methods disclosed herein is sufficiently retained so as not to require a maintenance dose at the scheduled time point in a predetermined dosing schedule. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of an anti-VEGF antibody conjugate (e.g. KSI-301), or anti-VEGF protein conjugate (e.g., an aflibercept biopolymer conjugate), until about 2 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 3 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 4 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 5 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 6 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 7 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 8 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 9 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 10 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 12 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 14 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 16 months or longer after receiving the last loading dose or the last maintenance dose. In some embodiments, a subject has at least 30%, at least 35%, at least 40%, at least 45%, at least 50%, at least 55%, at least 60%, at least 65%, at least 70%, at least 75%, at least 80%, at least 85%, at least 90%, at least 95%, or higher chance, or percentage between any two of the preceding values, of not requiring a subsequent dose, e.g., a maintenance dose, of the anti-VEGF antibody conjugate until about 18 months or longer after receiving the last loading dose or the last maintenance dose.

After receiving the last dose (e.g., the final loading dose, or any dosing that occurred last), the subject may retain a therapeutic result of the anti-VEGF therapy for a sustained period of time without the subject receiving a subsequent dose (e.g., a maintenance dose) of the antibody conjugate. A therapeutic result of the anti-VEGF therapy may include an improvement in one or more of visual acuity or retinal health (e.g., retinal thickness, extent of retinal perfusion, etc.) at or around the time of the final loading dose compared to before or at the time of the first loading dose. Any suitable therapeutic result of an anti-VEGF therapy may be used according to methods of the present disclosure. Suitable measures for determining therapeutic results include, e.g., visual acuity, retinal thickness, perfusion in at least one eye, diabetic retinopathy severity score (DRSS), disease activity of the eye disorder, or any combination thereof. In some embodiments, wAMD, DME, RVO, or DR disease activity includes one or more of increased intraretinal fluid, increased subretinal fluid, new intraretinal hemorrhage, new exudates.

In some embodiments, the therapeutic result includes an improvement, or at least a slowed decline, in visual acuity. Visual acuity may be monitored using any suitable method. In some embodiments, the visual acuity is measured by best corrected visual acuity (BCVA) using e.g., ETDRS letters or Snellen chart, etc. In some embodiments, the therapeutic result may include an improvement in BCVA measured by ETDRS letters of 3 letters or more, e.g., 4 letters or more, 5 letters or more, 6 letters or more, 7 letters or more, 8 letters or more, 9 letters or more, 10 letters or more, 12 letters or more, 15 letters or more, 18 letters or more, 20 letters or more, 22 letters, or more, including 25 letters or more, or by a number within a range defined by any two of the preceding values, compared to pre-treatment. In some embodiments, the therapeutic result may include a reduction in the rate of deterioration of BCVA by at least 10%, e.g., at least 15%, at least 25%, at least 50%, at least 75%, at least 90%, including about 100%, or any percentage in a range defined by any two of the preceding values, over pre-treatment.

In some embodiments, the therapeutic result includes a reduction, or at least a slowed increase, in retinal thickness (e.g., central subfield thickness). The retinal thickness may be measured using any suitable method, including, but not limited to, optical coherence tomography (OCT). In some embodiments, the therapeutic result may include a reduction in retinal thickness of about 25 μm or more, e.g., about 50 μm or more, about 75 μm or more, about 100 μm or more, about 125 μm or more, about 150 μm or more, about 175 μm or more, about 200 μm or more, about 225 μm or more, about 250 μm or more, about 275 μm or more, about 300 μm or more, about 325 μm or more, about 350 μm or more, about 375 μm or more, about 400 μm or more, or a reduction within a range defined by any two of the preceding values, compared to pre-treatment. In some embodiments, the therapeutic result may include a reduction in the rate of increase in retinal thickness by at least 10%, e.g., at least 15%, at least 25%, at least 50%, at least 75%, at least 90%, including about 100%, or any percentage in a range defined by any two of the preceding values, over pre-treatment.

In some embodiments, the therapeutic result includes improved perfusion, or at least a reduction in the rate of expansion of non-perfusion, of the retina. Perfusion may be monitored using any suitable method. Suitable methods include, without limitation, OCT-angiography (OCT-A), fluorescein angiogram or ultrawide-field fluorescein angiogram. The degree of perfusion, or non-perfusion, may be measured using any suitable measure. In some embodiments, non-perfusion area or area of capillary non-perfusion is measured. In some embodiments, an ischemic index is calculated by dividing the non-perfusion area by the total retinal area. In some embodiments, the presence or absence of retinal non-perfusion in retinal quadrants on the angiogram is measured. In some embodiments, the therapeutic result may include a reduction in the area of non-perfusion of at least 10%, e.g., at least 15%, at least 25%, at least 50%, at least 75%, at least 90%, including about 100%, or any percentage in a range defined by any two of the preceding values, over pre-treatment. In some embodiments, the therapeutic result may include a reduction in the rate of progressive non-perfusion of at least 10%, e.g., at least 15%, at least 25%, at least 50%, at least 75%, at least 90%, including about 100%, or any percentage in a range defined by any two of the preceding values, over pre-treatment.

In some embodiments, the therapeutic result includes improved, or prevented worsening of, diabetic retinopathy severity score (DRSS). In some embodiments, the therapeutic result may include an improved DRSS of 2 steps or more, or 3 steps or more compared to pre-treatment. In some embodiments, the therapeutic result may include preventing worsening of DRSS by 2 steps or more, or 3 steps or more compared to pre-treatment.

The therapeutic result is retained if the level of visual acuity or retinal health (e.g., retinal thickness, degree of non-perfusion, etc.) does not worsen by more than a predetermined amount compared to the improved level. In some embodiments, the therapeutic result is retained if the level of visual acuity or retinal health does not revert by 30% or more, e.g., 50% or more, 75% or more, 90% or more, including 100% or more to the pretreatment level of visual acuity or retinal health after the last dose (e.g., final loading dose). In some embodiments, the therapeutic result is retained if the rate of change of visual acuity or retinal health does not revert by 30% or more, e.g., 50% or more, 75% or more, 90% or more, including 100% or more to the pre-treatment level of the rate of change of visual acuity or retinal health after the last dose (e.g., final loading dose).

In some embodiments, the therapeutic result includes an improvement in visual acuity. In some embodiments the therapeutic result may be retained if BCVA does not fall by 3 letters or more, 4 letters or more, 5 letters or more, 6 letters or more, 7 letters or more, 8 letters or more, 9 letters or more, or 10 letters or more from the BCVA score at the time of the final loading dose (e.g., at Week 12 after three monthly loading doses). In some embodiments the therapeutic result may be retained if BCVA does not fall by 3 letters or more, 4 letters or more, 5 letters or more, 6 letters or more, 7 letters or more, 8 letters or more, 9 letters or more, or 10 letters or more from the BCVA score measured at the last assessment (e.g., 4 weeks ago). In some embodiments the therapeutic result may be retained if BCVA does not fall by 3 letters or more, 4 letters or more, 5 letters or more, 6 letters or more, 7 letters or more, 8 letters or more, 9 letters or more, or 10 letters or more from the best measured BCVA score, or the average of the 2 best measured BCVA scores, of the subject.

In some embodiments, the therapeutic result includes a reduction in retinal thickness (e.g., central subfield thickness). In some embodiments, the therapeutic result may be retained if retinal thickness (e.g., central subfield thickness) does not increase by 25 μm or more, 50 μm or more, 75 μm or more, 100 μm or more, 125 μm or more, or 150 μm or more from the retinal thickness at the time of the last dose (e.g., final loading dose) (e.g., at Week 12 after three monthly loading doses). In some embodiments, the therapeutic result may be retained if retinal thickness (e.g., central subfield thickness) does not increase by 25 μm or more, 50 μm or more, 75 μm or more, 100 μm or more, 125 μm or more, or 150 μm or more from the retinal thickness measured at the last assessment (e.g., 4 weeks ago). In some embodiments, a retained therapeutic result includes retinal thickness that is not greater than 150 μm, 125 μm, 100 μm, 75 μm, 50 μm, 40 μm, or 30 μm, compared to the lowest measured retinal thickness of the subject.

In some embodiments, the therapeutic result includes improved perfusion of the retina. In patients with DR, DME, and RVO, the retina can have an area of non-perfusion, or absence of blood flow. In some embodiments, non-perfusion is visualized on angiograms. In some embodiments, a therapeutic result of the anti-VEGF antibody conjugate, e.g., KSI-301, administration, or anti-VEGF protein conjugate (e.g., an aflibercept biopolymer conjugate) administration, according to methods of the present disclosure, includes regression of non-perfusion, or re-perfusion of the retina. In some embodiments, the therapeutic result may be retained if the area of non-perfusion is reduced by 10% or more, e.g., 15% or more, 25% or more, 50% or more, 75% or more, 90% or more, or about 100% relative to the area of non-perfusion at the time of the last dose (e.g., final loading dose). In some embodiments, the therapeutic result may be retained if the area of non-perfusion is not increased by 10% or more, e.g., 15% or more, 25% or more, 50% or more, 75% or more, 90% or more, or about 100% relative to the area of non-perfusion at the time of the last dose (e.g., final loading dose). In some embodiments, the therapeutic result may be retained if the area of non-perfusion is not increased by 10% or more, e.g., 15% or more, 25% or more, 50% or more, 75% or more, 90% or more, or about 100% relative to the area of non-perfusion measured at the last assessment (e.g., 4 weeks ago). In some embodiments, the therapeutic result may be retained if the area of non-perfusion is not increased by 10% or more, e.g., 15% or more, 25% or more, 50% or more, 75% or more, 90% or more, or about 100% relative to the smallest area of non-perfusion measured in the subject.

According to methods of the present disclosure, a therapeutic result of the anti-VEGF therapy after the last dose (e.g., final loading dose) may be retained for at least 8 weeks or more, e.g., at least 10 weeks or more, at least 12 weeks or more, at least 14 weeks or more, at least 16 weeks or more, at least 20 weeks or more, at least 24 weeks or more, at least 28 weeks or more, at least 32 weeks or more, at least 36 weeks or more, at least 40 weeks or more, at least 44 weeks or more, at least 48 weeks or more, including at least 52 weeks or more, after the last dose (e.g., final loading dose) was administered. In some embodiments, the therapeutic result may be retained for a time period of between 8 weeks to 1 year, e.g., between 8 weeks to 40 weeks, between 8 weeks to 32 weeks, including between 12 weeks to 28 weeks, after the final loading dose was administered. This can be for any one or more of the eye disorders provided herein, including, for example, RVO, DME, DR, and/or wAMD.

In some embodiments, the method includes administering one, two, or three loading doses of the anti-VEGF antibody conjugate (e.g., KSI-301), or anti-VEGF protein conjugate (e.g., an aflibercept biopolymer conjugate), to the subject, and administering one or more subsequent doses (e.g., maintenance doses) of the anti-VEGF antibody conjugate, e.g., KSI-301, (or anti-VEGF protein conjugate (e.g., an aflibercept biopolymer conjugate)) after the final loading dose. The subsequent doses may be administered to the subject no more frequently than once every 8 weeks, e.g., every 10 weeks, every 12 weeks, every 14 weeks, every 16 weeks, every 18 weeks, every 20 weeks, every 24 weeks, every 28 weeks, every 32 weeks, every 40 weeks, including every 52 weeks. Whether to administer a subsequent dose of the anti-VEGF antibody conjugate may be determined based on any convenient reason. In some embodiments, the subsequent dose may be administered based on a predetermined schedule (e.g., a schedule determined before the subject is administered any of the one or more of the loading doses). In some embodiments, the subsequent dose may be administered based on a predetermined schedule based on the severity of the eye disorder, the subject's previous response, or lack thereof, to other therapies for the eye disorder, or any other clinically relevant factors associated with the subject. In some embodiments, the subsequent dose may be administered based on the outcome of one or more assessment tests for ocular health and/or function carried out on the subject during the course of treatment with the anti-VEGF antibody conjugate. In some embodiments, the subsequent dose may be administered based on the outcome of one or more assessment tests carried out on the subject every 4 or more weeks, e.g., every 6 or more weeks, every 8 or more weeks, every 10 or more weeks, every 12 or more weeks, every 16 or more weeks, every 20 or more weeks, every 24 or more weeks, every 28 or more weeks, every 32 or more weeks, every 36 or more weeks, including every 40 or more weeks. In some embodiments, the subsequent dose may be administered if one or more assessment tests indicates a diminishment of the therapeutic result of the anti-VEGF therapy that is greater than a predetermined threshold.

As used herein, "Q4W", "Q8W" and the like refer to a dosing schedule, and have the ordinary and customary meaning to one of ordinary skill in the art. The number may indicate the number of the unit of time specified by the subsequent letter. "W" indicates a unit of a week; "M" specifies an interval of a month. Thus, Q4W refers to a dosing interval of 4 weeks, which also includes a dosing interval of one month; Q8W refers to a dosing interval of 8 weeks, which also includes a dosing interval of two months; and so on. As used herein, specification of a dosing schedule does not necessarily imply a number of doses beyond two, unless indicated otherwise. In some embodiments, a dosing schedule refers to the dosing schedule for maintenance doses (including the interval between the last loading dose, and the first maintenance dose). A reference to a dosing schedule being "longer" or "shorter" (e.g., "Q12W or longer") refers to the time interval between doses being longer than that specified (e.g., a dosing interval of 12 weeks or longer).

In some embodiments, the total number of injections (including loading and maintenance doses) of the anti-VEGF antibody conjugate (e.g., KSI-301) administered to the subject in the first year of treatment is 10 times or less, 9 times or less, 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject in the first two years of treatment is 10 times or less, 9 times or less, 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject in the first three years of treatment is 10 times or less, 9 times or less, 8 times or less, 7 times or less, 6 times or less, 5 times or less, 4 times or less, 3 times or less, 2 times or less, or once, in order to retain the therapeutic result of the anti-VEGF antibody conjugate therapy.

In some embodiments, the total number of maintenance doses of the anti-VEGF antibody conjugate (e.g., KSI-301)

administered to the subject in a one-year period for treatment is 7 times or less, 6 times or less, 5 times or less, 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject in a two-year period for treatment is 7 times or less, 6 times or less, 5 times or less, 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject in a three-year period for treatment is 7 times or less, 6 times or less, 5 times or less, 4 times or less, 3 times or less, 2 times or less, once or less, or zero, in order to retain the therapeutic result of the anti-VEGF antibody conjugate therapy.

In some embodiments, the total number of injections (including loading and maintenance doses) of the anti-VEGF antibody conjugate (e.g., KSI-301) administered to the subject with wAMD in the first year of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with wAMD in the first two years of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with wAMD in the first three years of treatment is 8 times or less, 7 times or less, 6 times or less, 5 times or less, 4 times or less, 3 times or less, 2 times or less, or once, in order to retain the therapeutic result of the anti-VEGF antibody conjugate therapy.

In some embodiments, the total number of maintenance doses of the anti-VEGF antibody conjugate (e.g., KSI-301) administered to the subject with wAMD in a one-year period for treatment is 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with wAMD in a two-year period for treatment is 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with wAMD in a three-year period for treatment is 4 times or less, 3 times or less, 2 times or less, once or less, or zero, in order to retain the therapeutic result of the anti-VEGF antibody conjugate therapy.

In some embodiments, the total number of injections (including loading and maintenance doses) of the anti-VEGF antibody conjugate (e.g., KSI-301) administered to the subject with DME in the first year of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with DME in the first two years of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with DME in the first three years of treatment is 8 times or less, 7 times or less, 6 times or less, 5 times or less, 4 times or less, 3 times or less, 2 times or less, or once, in order to retain the therapeutic result of the anti-VEGF antibody conjugate therapy.

In some embodiments, the total number of maintenance doses of the anti-VEGF antibody conjugate (e.g., KSI-301) administered to the subject with DME in a one-year period during treatment is 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with DME in a two-year period during treatment is 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with DME in a three-year period during treatment is 4 times or less, 3 times or less, 2 times or less, once or less, or zero, in order to retain the therapeutic result of the anti-VEGF antibody conjugate therapy.

In some embodiments, the total number of injections (including loading and maintenance doses) of the anti-VEGF antibody conjugate (e.g., KSI-301) administered to the subject with RVO in the first year of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with RVO in the first two years of treatment is 8 times or less, 7 times or less, 6 times or less, 5 times or less, 4 times or less, 3 times or less, 2 times or less, or once, in order to retain the therapeutic result of the anti-VEGF antibody conjugate therapy. In some embodiments, the total number of injections (including loading and maintenance doses) of the anti-VEGF antibody conjugate (e.g., KSI-301) administered to the subject with RVO in the first three years of treatment is 8 times or less, 7 times or less, 6 times or less, 5 times or less, 4 times or less, 3 times or less, 2 times or less, or once, in order to retain the therapeutic result of the anti-VEGF antibody conjugate therapy.

In some embodiments, the total number of maintenance doses of the anti-VEGF antibody conjugate (e.g., KSI-301) administered to the subject with DME in a one-year period during treatment is 5 times or less, 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with DME in a two-year period during treatment is 5 times or less, 4 times or less, 3 times or less, 2 times or less, once or less, or zero, in order to retain the therapeutic result of the anti-VEGF antibody conjugate therapy. In some embodiments, the total number of maintenance doses of the anti-VEGF antibody conjugate (e.g., KSI-301) administered to the subject with DME in a three-year period during treatment is 5 times or less, 4 times or less, 3 times or less, 2 times or less, once or less, or zero, in order to retain the therapeutic result of the anti-VEGF antibody conjugate therapy.

In some embodiments, a first subsequent dose is administered at a first time after the last loading dose, and a second subsequent dose is administered at a second period of time after the first subsequent dose, where no other dose is administered between the last loading dose and the first subsequent dose, or between the first subsequent dose and the second subsequent dose. The second period of time between the first and second subsequent doses may be the same or different from the first period of time between the last loading dose and the first subsequent dose. In some embodiments, the first time period is 8 weeks or more, e.g., 10 weeks or more, 12 weeks or more, 14 weeks or more, 16 weeks or more, 18 weeks or more, 20 weeks or more, 24 weeks or more, 28 weeks or more, 32 weeks or more, 36 weeks or more, 40 weeks or more, at least 44 weeks or more, at least 48 weeks or more, including 52 weeks or more. In some embodiments, the second period of time is longer than the first period of time by 0 weeks or more, e.g., by 4 weeks or more, by 6 weeks or more, by 8 weeks or more, by 10 weeks or more, by 12 weeks or more, by 16 weeks or more, by 20 weeks or more, including by 24 weeks or more. The timing for administering the second subsequent dose may depend on the outcome of one or more assessments for ocular health and/or function of the subject.

Any suitable amount of the anti-VEGF antibody conjugate, or anti-VEGF protein conjugate (e.g., an aflibercept biopolymer conjugate), may be administered to the subject in a subsequent dose (e.g., maintenance dose). In some embodiments, the subsequent dose includes about 1 mg or more, e.g., about 1.25 mg or more, about 1.5 mg or more, about 1.75 mg or more, about 2 mg or more, about 2.5 mg or more, about 3 mg or more, about 3.5 mg or more, about 4 mg or more, about 4.5 mg of more, including about 5 mg or more (by weight of the anti-VEGF antibody portion) of the anti-VEGF antibody conjugate. In some embodiments, the subsequent dose includes from about 1 mg to about 10 mg, e.g., about 1 mg to about 7.5 mg, about 1.25 mg to about 5 mg, including about 2 mg to about 5 mg (by weight of the anti-VEGF antibody portion) of the anti-VEGF antibody conjugate.

As the therapeutic result of the anti-VEGF therapy is retained for a sustained period of time after the last dose (e.g., final loading dose), the subject may not need to receive a dose of the anti-VEGF antibody conjugate, or anti-VEGF protein conjugate (e.g., an aflibercept biopolymer conjugate), while the therapeutic effect lasts. In some embodiments, no further administration of the anti-VEGF antibody conjugate, or anti-VEGF protein conjugate (e.g., an aflibercept biopolymer conjugate), is made to the subject within 4 weeks or more, e.g., within 6 weeks or more, within 8 weeks or more, within 10 weeks or more, within 12 weeks or more, within 14 weeks or more, within 16 weeks or more, within 20 weeks or more, within 24 weeks or more, within 28 weeks or more, within 32 weeks or more, within 36 weeks or more, within 40 weeks or more, within 44 weeks or more, within 48 weeks or more, including within 52 weeks or more, after the last dose (e.g., final loading dose).

A method of the present disclosure can include administering a fewer number of injections (of the anti-VEGF antibody conjugate, such as KSI-301, or anti-VEGF protein conjugate (e.g., an aflibercept biopolymer conjugate)) after the last loading dose compared to the number of injections in a standard of care treatment, to maintain a therapeutic result. In some embodiments, the average number of injections (e.g., of the anti-VEGF antibody conjugate) administered after the last loading dose is about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, about 0.18 or less, about 0.17 or less, or a number within a range defined by any two of the preceding values, over 16 weeks. In some embodiments, the average number of injections (e.g., of the anti-VEGF antibody conjugate) administered after the last loading dose is about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, about 0.18 or less, about 0.17 or less, or a number within a range defined by any two of the preceding values, over 12 weeks. In some embodiments, the average number of injections (of the anti-VEGF antibody conjugate, e.g., KSI-301) administered after the last loading dose is about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, about 0.18 or less, about 0.17 or less, or a number within a range defined by any two of the preceding values, over 8 weeks.

In some embodiments, the subject has DME, and the average number of injections (of the anti-VEGF antibody conjugate, e.g., KSI-301) administered after the last loading dose is about 1.75 or less, about 1.5 or less, about 1.25 or less, about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, or a number within a range defined by any two of the preceding values, over 16 weeks. In some embodiments, the subject has DME, and the average number of injections (of the anti-VEGF antibody conjugate, e.g., KSI-301) administered after the last loading dose is about 1.75 or less, about 1.5 or less, about 1.25 or less, about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, or a number within a range defined by any two of the preceding values, over 12 weeks. In some embodiments, the subject has DME, and the average number of injections (of the anti-VEGF antibody conjugate, e.g., KSI-301) administered after the last loading dose is about 1.75 or less, about 1.5 or less, about 1.25 or less, about 1 or less, about 0.9 or less, about 0.8 or less, about 0.7 or less, about 0.5 or less, about 0.45 or less, about 0.4 or less, about 0.35 or less, about 0.3 or less, about 0.25 or less, about 0.2 or less, or a number within a range defined by any two of the preceding values, over 8 weeks.

In some embodiments, the subject has RVO, and the average number of injections (of the anti-VEGF antibody conjugate, e.g., KSI-301) administered after the last loading dose is about 2.75 or less, about 2.5 or less, about 2.25 or less, about 2 or less, about 1.75 or less, about 1.5 or less, about 1.25 or less, about 1 or less, about 0.9 or less, about 0.8 or less, about 0.7 or less, about 0.5 or less, about 0.45 or less, or a number within a range defined by any two of the preceding values, over 16 weeks. In some embodiments, the subject has RVO, and the average number of injections (of the anti-VEGF antibody conjugate, e.g., KSI-301) administered after the last loading dose is about 2.75 or less, about 2.5 or less, about 2.25 or less, about 2 or less, about 1.75 or less, about 1.5 or less, about 1.25 or less, about 1 or less, about 0.9 or less, about 0.8 or less, about 0.7 or less, about 0.5 or less, about 0.45 or less, or a number within a range defined by any two of the preceding values, over 12 weeks. In some embodiments, the subject has RVO, and the average number of injections (of the anti-VEGF antibody conjugate, e.g., KSI-301) administered after the last loading dose is about 2.75 or less, about 2.5 or less, about 2.25 or less, about 2 or less, about 1.75 or less, about 1.5 or less, about 1.25 or less, about 1 or less, about 0.9 or less, about 0.8 or less, about 0.7 or less, about 0.5 or less, about 0.45 or less, or a number within a range defined by any two of the preceding values, over 8 weeks.

In some embodiments, the eye disorder treated by the present methods include one or more of age-related macular degeneration (AMD), diabetic macular edema (DME), retinal vein occlusion (RVO) (e.g., central retinal vein occlusion (CRVO) and branched central retinal vein occlusion (BRVO)), diabetic retinopathy (DR) (e.g., non-proliferative DR and proliferative DR) and presumed ocular histoplasmosis syndrome. In some embodiment, a subject to be treated by methods of the present disclosure has wet AMD. In some embodiments, the subject has wet AMD without a high pigment epithelial detachment (PED). In some embodiments, a subject has high PED when the baseline central subfield retinal thickness (CST) in an eye of the subject is 500 microns or greater.

In some embodiments, a subject with the eye disorder has, before receiving a treatment according to methods of the present disclosure, a CST of about 200 microns or more, about 250 microns or more, about 275 microns or more, about 300 microns or more, about 325 microns or more, about 350 microns or more, about 375 microns or more, about 400 microns or more, about 425 microns or more, about 450 microns or more, about 475 microns or more, about 500 microns or more, about 525 microns or more, about 550 microns or more, about 575 microns or more, about 600 microns or more, about 625 microns or more, about 650 microns or more, about 675 microns or more, about 700 microns or more, about 725 microns or more, about 750 microns or more, about 775 microns or more, about 800 microns or more, about 825 microns or more, about 850 microns or more, about 875 microns or more, about 900 microns or more, or a distance within a range defined by any two of the preceding values. The CST can be measured by, e.g., optical coherence tomography (OCT).

In some embodiments, a subject with the eye disorder has, before receiving a treatment according to methods of the present disclosure, a BCVA, in ETDRS letters, of about 80 or less, about 75 or less, about 70 or less, about 68 or less, about 66 or less, about 64 or less, about 62 or less, about 60 or less, about 58 or less, about 56 or less, about 54 or less, about 52 or less, about 50 or less, about 48 or less, about 46 or less, about 44 or less, about 42 or less, about 40 or less, or value within a range defined by any two of the preceding values.

In some embodiments, a method of the present disclosure includes administering a first loading dose of an anti-VEGF antibody conjugate (e.g., KSI-301) (or anti-VEGF protein conjugate (e.g., an aflibercept biopolymer conjugate)) to a subject (e.g., human or other mammalian patient) in need of treating wAMD or DME, and subsequently administering at least one more, but no more than two more of the loading doses to achieve a therapeutic result (e.g., improved vision, reduced symptoms, etc.) of the anti-VEGF therapy, where the therapeutic result is retained for at least 12 weeks after the final loading dose was administered. In some embodiments, the therapeutic result is retained for at least 14 weeks, e.g., at least 16 weeks, at least 20 weeks, at least 24 weeks, at least 28 weeks, at least 32 weeks, at least 36 weeks, at least 40 weeks, at least 44 weeks, at least 48 weeks, including at least 52 weeks after the final loading dose was administered.

In some embodiments, the eye disorder is wAMD and the method includes administering a subsequent dose of the anti-VEGF antibody conjugate, e.g., KSI-301, or anti-VEGF protein conjugate (e.g., an aflibercept biopolymer conjugate), after about 24 months of the final loading dose. In some embodiment, the eye disorder is wet AMD without a high pigment epithelial detachment (PED). In some embodiments, a subject has high PED when the baseline central subfield retinal thickness (CST) in an eye of the subject is 500 microns or greater.

In some embodiments, a subject treated by the present methods has RVO. In some embodiments, a method of the present disclosure includes administering a first loading dose of an anti-VEGF antibody conjugate (e.g., KSI-301), or anti-VEGF protein conjugate (e.g., an aflibercept biopolymer conjugate), to a subject (e.g., human patient) in need of treating RVO, and subsequently administering one more loading dose to achieve a therapeutic result (e.g., improved vision, reduced symptoms, etc.) of the anti-VEGF therapy, where the therapeutic result is retained for at least 8 weeks after the final loading dose was administered. In some embodiments, the therapeutic result is retained for at least 10 weeks, e.g., at least 12 weeks, at least 14 weeks, at least 16 weeks, at least 20 weeks, at least 24 weeks, at least 28 weeks, at least 32 weeks, at least 36 weeks, at least 40 weeks, including at least 52 weeks after the final loading dose was administered. In some embodiments, the method further includes administering one or more subsequent doses (e.g., maintenance doses) of the anti-VEGF antibody conjugate, e.g., KSI-301, after the final loading dose. The subsequent doses may be administered to the subject no more frequently than once every 8 weeks, e.g., every 10 weeks, every 12 weeks, every 14 weeks, every 16 weeks, every 18 weeks, every 20 weeks, every 24 weeks, every 28 weeks, every 32 weeks, every 36 weeks, every 40 weeks, every 44 weeks, every 48 weeks, including every 52 weeks.

Also provided herein are methods of treating a subject with an eye disorder, where the method includes administering between 1 to 3 loading doses, but no more than 3 loading doses, of an anti-VEGF antibody conjugate (e.g., KSI-301), or anti-VEGF protein conjugate (e.g., an aflibercept biopolymer conjugate), to a subject, and providing a follow-on application of the anti-VEGF antibody conjugate or anti-VEGF protein conjugate no sooner than 14 weeks after the last loading dose was administered. In some embodiments, the follow-on application of the anti-VEGF antibody conjugate or anti-VEGF protein conjugate is provided no sooner than 16 weeks, e.g., no sooner than 18 weeks, no sooner than 20 weeks, no sooner than 24 weeks, no sooner than 28 weeks, no sooner than 32 weeks, no sooner than 36 weeks, including no sooner than 40 weeks after the last loading dose was administered. In some embodiments, the eye disorder treated is DME.

Also provided are methods of treating a subject for an eye disorder, where the method includes administering to a subject in need of treating an eye disorder a monthly loading dose of an anti-VEGF antibody conjugate (e.g., KSI-301), or anti-VEGF protein conjugate (e.g., an aflibercept biopolymer conjugate), over one, two or three months, and administering one or more subsequent doses of the anti-VEGF antibody conjugate no less than every 8 weeks after the final loading dose. In some embodiments, the eye disorder is AMD (e.g., wAMD), DME, RVO or DR. In some embodiments, the eye disorder is RVO. In some embodiments, the eye disorder is wAMD, DME or DR, and the subsequent doses of the anti-VEGF antibody conjugate or anti-VEGF protein conjugate is administered no less than every 12 weeks, e.g., every 16 weeks, every 20 weeks, every 24 weeks, every 28 weeks, every 32 weeks, every 36 weeks, every 40 weeks, including every 52 weeks after the final loading dose. In some embodiments, the eye disorder is wAMD, and the subsequent doses of the anti-VEGF antibody conjugate or anti-VEGF protein conjugate is administered no less than every 12 weeks. In some embodiment, the eye disorder is wet AMD without a high pigment epithelial detachment (PED). In some embodiments, a subject has high PED when the baseline central subfield retinal thickness (CST) in an eye of the subject is 500 microns or greater.

In some embodiments, a method of the present disclosure includes administering at least one and up to three loading doses of an anti-VEGF antibody conjugate (e.g., KSI-301), or anti-VEGF protein conjugate (e.g., an aflibercept biopolymer conjugate), to a subject in need of treating an eye disorder, to thereby achieve a therapeutic result of the anti-VEGF therapy, assessing the ocular health of the subject after the final loading dose to determine whether the therapeutic result of the anti-VEGF therapy is retained, and not administering any subsequent doses of the anti-VEGF antibody conjugate or anti-VEGF protein conjugate for at least 8 weeks after the final loading dose until upon a determination that the anti-VEGF therapy is no longer retained. In some embodiments, the eye disorder is AMD (e.g., wAMD), DME or RVO. In some embodiments, the eye disorder is RVO. In some embodiments, the eye disorder is wAMD or DME, and the subsequent doses of the anti-VEGF antibody conjugate or anti-VEGF protein conjugate is administered at least 12 weeks after the final loading dose. In some embodiments, the eye disorder is wAMD and the method includes administering a subsequent dose of the anti-VEGF antibody conjugate, e.g., KSI-301, or anti-VEGF protein conjugate (e.g., an aflibercept biopolymer conjugate), after about 24 months of the final loading dose. In some embodiment, the eye disorder is wet AMD without a high pigment epithelial detachment (PED). In some embodiments, a subject has high PED when the baseline central subfield retinal thickness (CST) in an eye of the subject is 500 microns or greater.

In some embodiments, a method of the present disclosure includes administering at least one and up to three loading doses of an anti-VEGF antibody conjugate (e.g., KSI-301), or anti-VEGF protein conjugate (e.g., an aflibercept biopolymer conjugate), to a subject in need of treating an eye disorder, to achieve a therapeutic result (e.g., improved vision, reduced symptoms, etc.) of the anti-VEGF therapy, and administering one or more subsequent doses of the anti-VEGF antibody conjugate or anti-VEGF protein conjugate no less than every 8 weeks after the final loading dose, where the therapeutic result of the anti-VEGF therapy is retained as effectively as administering the one or more subsequent doses of the anti-VEGF antibody conjugate or anti-VEGF protein conjugate every 4 weeks after the final loading dose. In some embodiments, the eye disorder is AMD (e.g., wAMD), DME or RVO. In some embodiments, the eye disorder is RVO. In some embodiments, the eye disorder is wAMD or DME, and the subsequent doses of the anti-VEGF antibody conjugate is administered no less than every 12 weeks after the final loading dose, where the therapeutic result of the anti-VEGF therapy is retained as effectively as administering the one or more subsequent doses of the anti-VEGF antibody conjugate every 4 weeks after the final loading dose. In some embodiments, the eye disorder is wAMD and the method includes administering a subsequent dose of the anti-VEGF antibody conjugate, e.g., KSI-301, or anti-VEGF protein conjugate (e.g., an aflibercept biopolymer conjugate), after about 24 months of the final loading dose. In some embodiment, the eye disorder is wet AMD without a high pigment epithelial detachment (PED). In some embodiments, a subject has high PED when the baseline central subfield retinal thickness (CST) in an eye of the subject is 500 microns or greater.

According to some embodiments, a method of the present disclosure includes administering at least one and up to three loading doses of an anti-VEGF antibody conjugate (e.g., KSI-301), or anti-VEGF protein conjugate (e.g., an aflibercept biopolymer conjugate), to a subject in need of treating an eye disorder, to achieve a therapeutic result (e.g., improved vision, reduced symptoms, etc.) of the anti-VEGF therapy, and administering one or more subsequent doses of the anti-VEGF antibody conjugate no less than every 12 weeks after the final loading dose, where the therapeutic result of the anti-VEGF therapy is retained as effectively as the therapeutic result a standard or care treatment for the eye disorder, where the standard of care treatment includes administering three monthly loading doses of a standard of care therapeutic, and administering one or more subsequent doses of the standard of care therapeutic every 8 weeks, or every 4 weeks, after the final loading dose of the standard of care therapeutic. In some embodiments, the eye disorder is wAMD. In some embodiment, the eye disorder is wet AMD without a high pigment epithelial detachment (PED). In some embodiments, a subject has high PED when the baseline central subfield retinal thickness (CST) in an eye of the subject is 500 microns or greater. In some embodiments, the standard of care therapeutic is aflibercept. In some embodiments, the subsequent doses of the anti-VEGF antibody conjugate is administered no less than every 16 weeks, e.g., no less than every 20 weeks, no less than every 24 weeks, no less than every 28 weeks, including no less than every 32 weeks, after the final loading dose of the anti-VEGF antibody conjugate.

Also provided herein are methods of reperfusion of an eye in a subject suffering from DME, where the method includes identifying the subject with DME, DR or RVO, administering at least 2 loading doses of an anti-VEGF antibody conjugate (e.g., KSI-301), or anti-VEGF protein conjugate (e.g., an aflibercept biopolymer conjugate), to the subject, and providing one or more further doses of the anti-VEGF antibody conjugate or anti-VEGF protein conjugate to the subject until the subject displays reperfusion in at least one eye. Reperfusion of an eye may be monitored using any suitable measure. In some embodiments, reperfusion of the eye is determined by an increase in blood vessel count, e.g., in retinal tissue, compared to a pretreatment state. The reperfusion of the eye may be monitored using any suitable method, including, but not limited to, OCT-angiography (OCT-A), fluorescein angiogram or ultrawide-field fluorescein angiogram. In some embodiments, the method provides for improved perfusion of an eye as measured by reduction in the area of non-perfusion of at least 10%, e.g., at least 20%, at least 30%, at least 50%, at least 75%, at least 90%, including about 100%, over a pre-treatment area of non-perfusion. In some embodiments, the method provides for reperfusion of an eye as measured by a reduction in the area of non-perfusion of between 10% and 100%, e.g., between 10% and 75%, between 10% and 50%, including between 10% and 30%, over a pre-treatment area of non-perfusion. In some embodiments, the improved perfusion provides at least 10% recovery, e.g., at least 20% recovery, at least 30% recovery, at least 50% recovery, at least 75% recovery, at least 90% recovery, including approximately 100% recovery of visual acuity in the subject over the pretreatment level. In some embodiments, the improved perfusion provides between 10% and 100% recovery, e.g., between 10% and 90% recovery, between 10% and 75% recovery, between 10% and 50% recovery, including between 10% and 30% recovery of visual acuity in the subject over the pretreatment level.

The loading doses may be administered to the subject at any suitable time interval to achieve the desired therapeutic result. In some embodiments, the loading doses are administered with 3 weeks or more, e.g., 4 weeks or more, one month or more, 5 weeks or more, 6 weeks or more, 8 weeks or more, 12 weeks or more, including 16 weeks or more between each loading dose. Where there are more than two loading doses, the time period between each loading dose may be the same or may be different. In some embodiments, some of the loading doses may be administered at the same interval, and some other loading doses may be administered at a different interval.

Any suitable amount of the anti-VEGF antibody conjugate or anti-VEGF protein conjugate may be administered to the subject in a loading dose. In some embodiments, the loading dose includes about 1 mg or more, e.g., about 1.25 mg or more, about 1.5 mg or more, about 1.75 mg or more, about 2 mg or more, about 2.5 mg or more, about 3 mg or more, about 3.5 mg or more, about 4 mg or more, about 4.5 mg of more, including about 5 mg or more (by weight of the anti-VEGF antibody portion) of the anti-VEGF antibody conjugate. In some embodiments, the loading dose includes from about 1 mg to about 10 mg, e.g., about 1 mg to about 7.5 mg, about 1.25 mg to about 5 mg, including about 2 mg to about 5 mg (by weight of the anti-VEGF antibody portion) of the anti-VEGF antibody conjugate.

Also provided herein are methods of treating an eye disorder by administering an anti-VEGF antibody conjugate (e.g., KSI-301), or anti-VEGF protein conjugate (e.g., an aflibercept biopolymer conjugate), to a subject in need of treating an eye disorder, where a single dose of the anti-VEGF antibody conjugate or anti-VEGF protein conjugate is sufficient to obtain a therapeutic effect of the anti-VEGF therapy. In some embodiments, a lasting therapeutic effect is obtained by a single dose of the anti-VEGF antibody conjugate or anti-VEGF protein conjugate, without administering any loading dose (e.g., without having a loading phase with monthly loading doses in the treatment schedule). In some embodiments, the eye disorder is non-proliferative DR. In some embodiments, the VEGF antibody conjugate or anti-VEGF protein is administered to a patient having non-proliferative DR to improve perfusion in at least one eye of the subject.

Any suitable amount of the anti-VEGF antibody conjugate or anti-VEGF protein conjugate may be administered to the subject in a dose. In some embodiments, the dose includes 1 mg or more, e.g., 1.25 mg or more, 1.5 mg or more, 1.75 mg or more, 2 mg or more, 2.5 mg or more, 3 mg or more, 3.5 mg or more, 4 mg or more, 4.5 mg of more, including 5 mg or more (by weight of the anti-VEGF antibody portion) of the anti-VEGF antibody conjugate. In some embodiments, the dose includes from 1 mg to 10 mg, e.g., 1 mg to 7.5 mg, 1.25 mg to 5 mg, including 2 mg to 5 mg (by weight of the anti-VEGF antibody portion) of the anti-VEGF antibody conjugate.

In some embodiments, methods of the present disclosure provide for an anti-VEGF therapy for an eye disorder, where there is reduced risk of intraocular inflammation (e.g., blepharitis, infectious conjunctivitis, keratitis, scleritis, endophthalmitis). In some embodiments, intravitreal administration of the anti-VEGF antibody conjugate (e.g., KSI-301), or anti-VEGF protein conjugate (e.g., an aflibercept biopolymer conjugate), is associated with a reduced risk of intraocular inflammation, e.g., compared to a standard of care treatment for the eye disorder. In some embodiments, intravitreal administration of the anti-VEGF antibody conjugate (e.g., KSI-301), or anti-VEGF protein conjugate (e.g., an aflibercept biopolymer conjugate), does not cause intraocular inflammation.

In some embodiments, retreating wAMD involves one or more of:

- Increase in CST≥75 μm with a decrease in BCVA of ≥5 letters compared to Week 12, OR
- Decrease in BCVA of >5 letters compared to Day 1, due to worsening wAMD activity, OR
- Decrease in BCVA of ≥10 letters compared to the best prior BCVA, due to worsening wAMD activity.

In some embodiments, retreating wAMD involves one or more of:

- Increase in CST≥50 μm with a decrease in BCVA of ≥5 letters compared to Week 12, OR
- Decrease in BCVA of >10 letters compared to the best prior BCVA, due to worsening wAMD activity, OR
- Increase of ≥75 microns compared to Week 12, OR
- New Macular Hemorrhage In some embodiments, retreating DME and RVO involves one or more of:

- Increase in CST≥75 μm with a decrease in BCVA of ≥5 letters compared to Week 12 or the prior visit, OR
- Decrease in BCVA of ≥10 letters compared to the best prior BCVA, due to worsening DME/RVO disease activity In some embodiments, no more than 0, 1, 2, 3, 4, 5, or 6 retreatment events is required for a one year duration for a subject, including, over a 1, 2, 3 or 4 year duration.

In some embodiments, retreatment occurs when one or more of the above criteria occurs. In some embodiments, a retreatment is a treatment that follows the last loading dose or treatment for a subject. A loading dose is a dose that is provided initially to bring the amount of drug in the patient or subject up to a desired level to have an initial therapeutic effect. In contrast, a retreatment dose, or maintenance dose, is a dose that is provided to return the therapeutic effect of the drug to the subject, after a prior dose (last loading dose or retreatment/maintenance dose) has degraded in effectiveness, or on a predetermined interval.

In some embodiments, the method involves administering a re-treatment with intravitreal injection of an antibody or conjugate thereof (e.g., KSI-301) if at least one of the following re-treatment criteria is met. In some embodiments, the criteria are related to signs of disease recurrence and/or vision loss due to disease recurrence. In some embodiments, the subject has wAMD and the criteria is one or more of: increase in OCT central subfield retinal thickness (CST)≥75 μm with a decrease in BCVA of ≥5 letters compared to Week 12; decrease in BCVA of ≥10 letters compared to Day 1, due to worsening wAMD disease activity (e.g. increased intraretinal fluid, increased subretinal fluid, new intraretinal hemorrhage, new subretinal hemorrhage); and/or decrease in BCVA of ≥10 letters compared to the best prior BCVA, due to worsening wAMD disease activity. In some embodiments, the subject has DME or RVO, and the criteria is one or more of: increase in OCT central subfield retinal thickness (CST)≥75 μm with a decrease in BCVA of ≥5 letters compared to Week 12 or the prior visit (4-week span between visits); and/or decrease in BCVA of ≥10 letters compared to the best prior BCVA, due to worsening DME/RVO disease activity (e.g. increased intraretinal fluid, increased subretinal fluid, new intraretinal hemorrhage, new exudates).

In some embodiments, the method involves administering a re-treatment with intravitreal injection of an antibody or conjugate thereof (e.g., KSI-301) if at least one of the following re-treatment criteria is met. In some embodiments, the criteria are related to signs of disease recurrence and/or vision loss due to disease recurrence. In some embodiments, the subject has wAMD, and the criteria is one or more of: increase in OCT central subfield retinal thickness (CST)≥50 μm with a decrease in BCVA of ≥5 letters compared to Week 12; decrease in BCVA of ≥10 letters compared to the best prior BCVA, due to worsening wAMD disease activity (e.g. increased intraretinal fluid, increased subretinal fluid, new intraretinal hemorrhage, new subretinal hemorrhage); increase in OCT central subfield retinal thickness (CST)≥75 μm; and/or new macular hemorrhage.

In some embodiments, no retreatment dose is given to a subject for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the last loading dose. In some embodiments, 1 loading dose is administered and no retreatment dose is given to a subject for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the loading dose. In some embodiments, 2 loading doses are given to a subject and no retreatment dose is given for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the last loading dose. In some embodiments, 3 loading doses are given to a subject and no retreatment dose is given for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the last loading dose. In some embodiments, 1-2 loading doses are given to a subject and no retreatment dose is given for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the last loading dose. In some embodiments, 1-3 loading doses are given to a subject and 1, 2, 3, or 4 retreatment dose are given for at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or more weeks following the last loading dose. In some embodiments, no more than 2, 3, 4, or 5 loading doses are administered to a subject. In some embodiments, no $4^{th}$ loading dose is provided to the subject. In some embodiments, the above treatment approaches allow for the subject's vision to stay improved at or close to the level achieved following the $1^{st}$ $2^{nd}$ or $3^{rd}$ loading dose. In some embodiments, the above treatment approaches allow for the subject's vision to stay improved to the point of not requiring a retreatment of the subject.

In some embodiments, the methods of the present disclosure can provide a long dosing interval and still sustain a therapeutic result of the anti-VEGF antibody conjugate (e.g., KSI-301) therapy, or anti-VEGF protein conjugate (e.g., an aflibercept biopolymer conjugate) therapy. In some embodiments, at least 75% of patients treated according to methods of the present disclosure can be on a Q4M dosing interval. In some embodiments, at least 90% of patients treated according to methods of the present disclosure can be on a Q4M dosing interval. In some embodiments, at least 50%, at least 55%, at least 60%, at least 65%, at least 70%, at least 75%, at least 80%, at least 85%, at least 90% of patients treated according to methods of the present disclosure can be on a Q4M dosing interval. In some embodiments, between about 40 to about 95%, e.g., between about 45 to about 90%, between about 50 to about 85%, between about 55 to about 85%, between about 60 to about 85%, between about 65 to about 85%, including between about 70 to about 80% of patients treated according to methods of the present disclosure can be on a Q4M dosing interval. In some embodiments, at least 75% of patients treated according to methods of the present disclosure can be on a Q5M dosing interval. In some embodiments, at least 50%, at least 55%, at least 60%, at least 65%, at least 70%, at least 75%, at least 80%, at least 85%, at least 90% of patients treated according to methods of the present disclosure can be on a Q5M dosing interval. In some embodiments, between about 40 to about 95%, e.g., between about 45 to about 90%, between about 50 to about 85%, between about 55 to about 85%, between about 60 to about 85%, between about 65 to about 85%, including between about 70 to about 80% of patients treated according to methods of the present disclosure can be on a Q5M dosing interval. In some embodiments, at least 55% of patients treated according to methods of the present disclosure can be on a Q6M dosing interval. In some embodiments, at least 70% of patients treated according to methods of the present disclosure can be on a Q6M dosing interval. In some embodiments, at least 75% of patients treated according to methods of the present disclosure can be on a Q6M dosing interval. In some embodiments, at least 30%, at least 35%, at least 40%, at least 45%, at least 50%, at least 55%, at least 60%, at least 65%, at least 70%, at least 75%, or at least 80% of patients treated according to methods of the present disclosure can be on a Q6M dosing interval. In some embodiments, between about 30 to about 85%, e.g., between about 30 to about 80%, between about 35 to about 75%, between about 40 to about 70%, between about 45 to about 65%, between about 50 to about 65%, including between about 50 to about 60% of patients treated according to methods of the present disclosure can be on a Q6M dosing interval.

In some embodiments, a patient (e.g., patient having an eye disorder, such as, but not limited to wAMD, RVO or DME) treated according to methods of the present disclosure has at least 75% chance of maintaining a therapeutic result of anti-VEGF therapy on a Q5M dosing interval. In some embodiments, a patient (e.g., patient having an eye disorder, such as, but not limited to wAMD, RVO or DME) treated according to methods of the present disclosure has at least 50%, at least 55%, at least 60%, at least 65%, at least 70%, at least 75%, or at least 80% chance of maintaining a therapeutic result of anti-VEGF therapy on a Q5M dosing interval. In some embodiments, a patient (e.g., patient having an eye disorder, such as, but not limited to wAMD, RVO or DME) treated according to methods of the present disclosure has between about 40 to about 95%, e.g., between about 45 to about 90%, between about 50 to about 85%, between about 55 to about 85%, between about 60 to about 85%, between about 65 to about 85%, including between about 70 to about 80% chance of maintaining a therapeutic result of anti-VEGF therapy on a Q5M dosing interval. In some embodiments, a patient (e.g., patient having an eye disorder, such as, but not limited to wAMD, RVO or DME) treated according to methods of the present disclosure has at least 55% chance of maintaining a therapeutic result of anti-VEGF therapy on a Q6M dosing interval. In some embodiments, a patient (e.g., patient having an eye disorder, such as, but not limited to wAMD, RVO or DME) treated according to methods of the present disclosure has at least 70% chance of maintaining a therapeutic result of anti-VEGF therapy on a Q6M dosing interval. In some embodiments, a patient (e.g., patient having an eye disorder, such as, but not limited to wAMD, RVO or DME) treated according to methods of the present disclosure has at least 80% chance of maintaining a therapeutic result of anti-VEGF therapy on a Q6M dosing interval. In some embodiments, a patient (e.g., patient having an eye disorder, such as, but not limited to wAMD, RVO or DME) treated according to methods of the present disclosure has at least 30%, at least 35%, at least 40%, at least 45%, at least 50%, at least 55% chance of maintaining a therapeutic result of anti-VEGF therapy on a Q6M dosing interval. In some embodiments, a patient (e.g., patient having an eye disorder, such as, but not limited to wAMD, RVO or DME) treated according to methods of the present disclosure has between about 30 to about 85%, e.g., between about 30 to about 80%, between about 35 to about 75%, between about 40 to about 70%, between about 45 to about 65%, between about 50 to about 65%, including between about 50 to about 60% chance of maintaining a therapeutic result of anti-VEGF therapy on a Q6M dosing interval.

In some embodiments, a patient having RVO treated according to methods of the present disclosure has at least 75% chance of maintaining a therapeutic result of anti-VEGF therapy on a Q4M dosing interval. In some embodiments, a patient having RVO treated according to methods of the present disclosure has at least 80% chance of maintaining a therapeutic result of anti-VEGF therapy on a Q5M dosing interval. In some embodiments, a patient having RVO treated according to methods of the present disclosure has at least 90% chance of maintaining a therapeutic result of anti-VEGF therapy on a Q5M dosing interval. In some embodiments, a patient having RVO treated according to methods of the present disclosure has at least 50%, at least 55%, at least 60%, at least 65%, at least 70%, at least 75%, at least 80% or at least 900% chance of maintaining a therapeutic result of anti-VEGF therapy on a Q4M dosing interval. In some embodiments, a patient having RVO treated according to methods of the present disclosure has between about 40 to about 95%, e.g., between about 45 to about 95%, between about 50 to about 95%, between about 55 to about 95%, between about 60 to about 95%, between about 65 to about 95%, including between about 70 to about 90% chance of maintaining a therapeutic result of anti-VEGF therapy on a Q4M dosing interval.

In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 1, 2, 3, 4, 5, or 6 loading doses (loading doses of an anti-VEGF antibody conjugate, e.g., KSI-301), according to some methods of the present disclosure, do not receive a retreatment dose (e.g., due to disease activity meeting one or more retreatment criteria) for at least about 28 weeks after the last loading dose, or after the last retreatment dose. In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 3 loading doses (loading doses of the anti-VEGF antibody conjugate, e.g., KSI-301), according to some methods of the present disclosure, do not receive a retreatment dose (e.g., due to disease activity meeting one or more retreatment criteria) for at least about 28 weeks after the last loading dose, or after the last retreatment dose.

In some embodiments, a subject (e.g., a subject having an eye disorder, such as, but not limited to wAMD, RVO or DME) who has been administered 1, 2, 3, 4, 5, or 6 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 28 weeks after the last loading dose, or after the last retreatment dose (and in the alternative, for at least 0.5, 0.6, 0.7, 0.8, 0.9. 1, 11.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 years or more can pass without a subsequent need for another injection of KSI-301 (or in the alternative an anti-VEGF protein therapeutic, such as an aflibercept bioconjugate). In some embodiments, a subject having wAMD, who has been administered 3 loading doses (of the anti-VEGF antibody conjugate, e.g., KSI-301), according to some methods of the present disclosure, has a chance of about 70% or higher of not receiving a retreatment dose (e.g., due to disease activity meeting one or more retreatment criteria) for at least about 28 weeks after the last loading dose, or after the last retreatment dose. In some embodiments, a subject (e.g., a subject having an eye disorder, such as, but not limited to wAMD, RVO or DME) who has been administered 3 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 28 weeks after the last loading dose, or after the last retreatment dose.

In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 1, 2, 3, 4, 5, or 6 loading doses (loading doses of an anti-VEGF antibody conjugate, e.g., KSI-301), according to some methods of the present disclosure, do not receive a retreatment dose (e.g., due to disease activity meeting one or more retreatment criteria) for at least about 24 weeks after the last loading dose, or after the last retreatment dose. In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 3 loading doses (loading doses of the anti-VEGF antibody conjugate, e.g., KSI-301), according to some methods of the present disclosure, do not receive a retreatment dose (e.g., due to disease activity meeting one or more retreatment criteria) for at least about 24 weeks after the last loading dose, or after the last retreatment dose.

In some embodiments, a subject (e.g., a subject having an eye disorder, such as, but not limited to wAMD, RVO or DME) who has been administered 1, 2, 3, 4, 5, or 6 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 24 weeks after the last loading dose, or after the last retreatment dose. In some embodiments, a subject (e.g., a subject having an eye disorder, such as, but not limited to wAMD, RVO or DME) who has been administered 3 loading doses (e.g., of KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 24 weeks after the last loading dose, or after the last retreatment dose.

In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 1, 2, 3, 4, 5, or 6 loading doses (loading doses of an anti-VEGF antibody conjugate, e.g., KSI-301), according to some methods of the present disclosure, do not receive a retreatment dose (e.g., due to disease activity meeting one or more retreatment criteria) for at least about 20 weeks after the last loading dose, or after the last retreatment dose. In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 3 loading doses (e.g., loading doses of anti-VEGF antibody conjugate, e.g., KSI-301), according to some methods of the present disclosure, do not receive a retreatment dose (e.g., due to disease activity meeting one or more retreatment criteria) for at least about 20 weeks after the last loading dose, or after the last retreatment dose.

In some embodiments, a subject (e.g., a subject having an eye disorder, such as, but not limited to wAMD, RVO or DME) who has been administered 1, 2, 3, 4, 5, or 6 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 20 weeks after the last loading dose, or after the last retreatment dose. In some embodiments, a subject (e.g., a subject having an eye disorder, such as, but not limited to wAMD, RVO or DME) who has been administered 3 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 20 weeks after the last loading dose, or after the last retreatment dose.

In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 1, 2, 3, 4, 5, or 6 loading doses (loading doses of an anti-VEGF antibody conjugate, e.g., KSI-301), according to some methods of the present disclosure, do not receive a retreatment dose (e.g., due to disease activity meeting one or more retreatment criteria) for at least about 16 weeks after the last loading dose, or after the last retreatment dose. In some embodiments, 50% or more, 55% or more, 60% or more, 65% or more, 70% or more, 75% or more, 80% or more, 85% or more, 90% or more, 95% or more, or about 100%, or a percentage within a range defined by any two of the preceding values, of subjects (e.g., subjects having an eye disorder, such as, but not limited to wAMD, RVO or DME) administered 3 loading doses (loading doses of the anti-VEGF antibody conjugate, e.g., KSI-301), according to some methods of the present disclosure, do not receive a retreatment dose (e.g., due to disease activity meeting one or more retreatment criteria) for at least about 16 weeks after the last loading dose, or after the last retreatment dose.

In some embodiments, a subject (e.g., a subject having an eye disorder, such as, but not limited to wAMD, RVO or DME) who has been administered 1, 2, 3, 4, 5, or 6 loading doses (of the anti-VEGF antibody conjugate, e.g., KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 16 weeks after the last loading dose, or after the last retreatment dose. In some embodiments, a subject (e.g., a subject having an eye disorder, such as, but not limited to wAMD, RVO or DME) who has been administered 3 loading doses (e.g., of KSI-301), according to some methods of the present disclosure, has a chance of 50% or more, 55% or more, 60% or more, 65% or more, 70% or more, 75% or more, 80% or more, 85% or more, 90% or more, 95% or more, or about 100%, or a percentage within a range defined by any two of the preceding values, of not receiving a retreatment dose (e.g., due to disease activity meeting one or more retreatment criteria) for at least about 16 weeks after the last loading dose, or after the last retreatment dose.

In some embodiments, for any of the eye disorders provided herein (e.g., wAMD, RVO and/or DME), 2 or 3 loading doses will provide for permanent resolution of the disorder, such that no further retreatment or maintenance doses are required. In some embodiments, for any of the eye disorders provided herein (e.g., wAMD, RVO and/or DME), 2 or 3 loading doses will provide for 1, 2, 3, 4, 5, 6, 7, 8, 9, 10 years or longer of effective suppression of the disorder such that no further retreatment of maintenance doses are required during that time period.

In some embodiments, any of the above dosing schedules is from any ocular disorder. In some embodiments, it is for the treatment and/or prevention of RVO, AMD, wAMD, and/or DME, and/or any of the other disorders provided herein.

In some embodiments, wAMD patients achieve 3 to 6 months of durability via the use of an anti-VEGF antibody conjugate, e.g., KSI-301, or anti-VEGF protein conjugate (e.g., an aflibercept biopolymer conjugate).

In some embodiments, DME patients achieve 3 to 5+ months of durability with only 3 loading doses via the use of the anti-VEGF antibody conjugate, e.g., KSI-301, or anti-VEGF protein conjugate (e.g., an aflibercept biopolymer conjugate). In some embodiments, DME patients achieve 3 to 6+ months of durability with only 3 loading doses via the use of the anti-VEGF antibody conjugate, e.g., KSI-301, or anti-VEGF protein conjugate (e.g., an aflibercept biopolymer conjugate).

In some embodiments, RVO patients achieving 2 to 4+ months of durability with only 3 loading doses via the use of the anti-VEGF antibody conjugate, e.g., KSI-301, or anti-VEGF protein conjugate (e.g., an aflibercept biopolymer conjugate). In some embodiments, RVO patients achieve 2 to 5+ months of durability with only 3 loading doses via the use of the anti-VEGF antibody conjugate, e.g., KSI-301, or anti-VEGF protein conjugate (e.g., an aflibercept biopolymer conjugate).

In some embodiments, sustained improvement in PDR with 3 loading doses via the use of the anti-VEGF antibody conjugate, e.g., KSI-301, or anti-VEGF protein conjugate (e.g., an aflibercept biopolymer conjugate).

In some embodiments, a reduced number of loading doses in DME and RVO is achieved via the use of the anti-VEGF antibody conjugate, e.g., KSI-301, or anti-VEGF protein conjugate (e.g., an aflibercept biopolymer conjugate). In some embodiments, a dosing schedule for wet AMD is: every 3 to 5 months (although some wAMD patients may benefit from dosing every 8 weeks). In some embodiments, a dosing schedule for DME is every 3 to 6 months. In some embodiments, a dosing schedule for RVO is every 8 weeks or longer (e.g., 6 months). In some embodiments, a dosing schedule for diabetic retinopathy (without diabetic macular edema) is every 3 months or longer (e.g., every 4 months or every 6 months). In some embodiments, the dosing schedule can be applied to treat diabetic retinopathy (non-proliferative diabetic retinopathy and proliferative diabetic retinopathy).

In some embodiments, an RVO patient that has received more than one retreatment after the loading dose, the time to the second retreatment is longer than the time to the first retreatment. This is also surprising and unexpected.

In some embodiments, the amount of the antibody administered to the subject will be between 1 and 5 mg, e.g., 1.25 (25 microliters), 2.5 (50 microliters) or 5 mg (100 microliters).

In some embodiments, one applies only two loading doses and then a re-treatment dose every eight weeks (e.g., for RVO). In the case of RVO using only two loading doses or even three loading doses and having as good outcome as with monthly is surprising and unexpected (as data shows that Lucentis, Eylea, and Avastin all need monthly dosing for the primary results). In some embodiments, for DME using an anti-VEGF antibody conjugate, e.g., KSI-301, or anti-VEGF protein conjugate (e.g., an aflibercept biopolymer conjugate), it is possible to obtain good results with 3 loading doses whereas other antibody systems require 4 or 5 monthly loading doses.

In some embodiments, for non-proliferative DR, one can avoid any loading dose or only include a single loading dose to obtain the treatment.

In some embodiments, one can decrease the severity of diabetic retinopathy in patients with either non-proliferative or proliferative diabetic retinopathy. One can achieve this using the same treatment regimen as DME (3 loading doses and then q12w or less frequent), or with the 'no loading doses or 2 loading doses and then every 3, 4, or 6 months'). In some embodiments, the outcome measures there are 1) improvement in 2 or more steps of diabetic retinopathy severity status on standard color photos of the retina or 2) prevention of 2 or more steps worsening of DRSS using photo. In some embodiments, retreatment is done less frequently than once every 8 weeks.

In some embodiments, the dosing schedule can be applied to non-proliferative DR with 1 to 2 loading doses, or just 1 loading dose and not more than that. The retreatment can occur no sooner than 12 or 16 or 24 weeks thereafter.

In some embodiments, for proliferative DR, 3 monthly loading doses can be applied followed by every 12 weeks or longer.

In some embodiments, a method of administering an anti-VEGF antibody conjugate or anti-VEGF protein conjugate is provided in which the patient gets a loading phase (for example, 2 loading doses q4 weeks), then a retreatment at 8 weeks, then the time to a second retreatment is longer that the time to the first retreatment (for example, 16+ weeks). In some embodiments, this reflects a 'disease modification'.

In some embodiments, an anti-VEGF antibody conjugate, e.g., KSI-301, or anti-VEGF protein conjugate (e.g., an aflibercept biopolymer conjugate), can be administered to a subject with diabetes for a 'reperfusion' of ischemic areas: giving a dose of the anti-VEGF antibody conjugate, e.g., KSI-301 (or a loading phase of the anti-VEGF antibody conjugate, e.g., KSI-301, for example, 3 loading doses every 4 weeks three times, so day 0, week 4, week 8) then retreatments as need.

In some embodiments, a method of disease modification of an eye disorder is provided. The method comprises: administering an anti-VEGF antibody conjugate, e.g., KSI-301, or anti-VEGF protein conjugate (e.g., an aflibercept biopolymer conjugate), to a subject having an eye disorder at a first loading dose, whereby the eye disorder is thereby modified in a beneficial manner to the subject.

In some embodiments, a method of treating an eye disorder is provided. The method comprises identifying a subject with DME, DR or RVO; administering 1-6 loading doses of an anti-VEGF antibody conjugate, e.g., KSI-301, or anti-VEGF protein conjugate (e.g., an aflibercept biopolymer conjugate), to the subject; providing a first retreatment dose of the anti-VEGF antibody conjugate, e.g., KSI-301, or anti-VEGF protein conjugate (e.g., aflibercept biopolymer conjugate), to the subject following a first amount of time from the last loading dose; and providing a second retreatment dose of the anti-VEGF antibody conjugate, e.g., KSI-301, or anti-VEGF protein conjugate (e.g., aflibercept biopolymer conjugate), to the subject, following a second amount of time from the first retreatment dose of the anti-VEGF antibody conjugate, e.g., KSI-301, or anti-VEGF protein conjugate (e.g., aflibercept biopolymer conjugate), wherein the second amount of time is greater than the first amount of time. In some embodiments, the second amount of time is 10, 20, 30, 40, 50, 60, 70, 80, 90, 100% or greater than the first amount of time. In some embodiments, the second amount of time is 1, 2, 3, 4, 5, 6, 7, 8, 9, 10, 11, 12, 13, 14, 15, 16 or more weeks longer than the first amount of time. In some embodiments, the loading doses include 3 doses of the anti-VEGF antibody conjugate, e.g., KSI-301, or anti-VEGF protein conjugate (e.g., aflibercept biopolymer conjugate), administered to the subject.

In some embodiments, an anti-VEGF antibody conjugate, e.g., KSI-301, or anti-VEGF protein conjugate (e.g., an aflibercept biopolymer conjugate), can be applied in a method of treating DME or proliferative diabetic retinopathy or non-proliferative diabetic retinopathy with an anti-VEGF antibody conjugate, e.g., KSI-301, or anti-VEGF protein conjugate (e.g., an aflibercept biopolymer conjugate), that results in reperfusion (of ischemic tissue), and therefore represents improvement of underlying disease. The terms perfusion and reperfusion are used interchangeably herein.

In some embodiments, following the loading injections and the first retreatment injection, each subsequent retreatment injection will be less frequent than the first retreatment injection. That is, the amount of time between retreatment injections can be increased, give the properties of the present method. In particular, the amount of time can increase by 1, 2, 3, 4, 5, 6, 7, 8, 9, 10, 11, 12, 13, 14, 15, 16, 17, 18, 19, 20 or more weeks for each subsequent retreatment injection. In some embodiments, the amount of time increases by 1, 2, 3, 4, 5, 6, 7, 8, 90, 10, 15, 20, 25, 30, 35, 40, 45, 50, 100, 500, 1000, 5000, 10,000 percent or more between each retreatment.

In some embodiments, a method of treating an eye disorder can include: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is diabetic macular edema (DME); and repeating the loading dose at least once, but not more than twice, whereby the subject retains a therapeutic result of the anti-VEGF antibody conjugate, e.g., KSI-301, or anti-VEGF protein conjugate (e.g., aflibercept biopolymer conjugate), therapy for at least 8 weeks after a final loading dose. In some embodiments, the subject retains the therapeutic result of the anti-VEGF antibody conjugate, e.g., KSI-301, therapy, or anti-VEGF protein conjugate (e.g., aflibercept biopolymer conjugate) therapy, for at least 8, 9, 10, 11, 12, 13, 14, 15, 16, 17, 18, 19, 20, 21, 22, 23, 24, 25, 26, 27, 28, 29, 30, 32, 34, 36, 38, 40, 44, 48, 52, 56, or 60 or more weeks after the final loading dose. In some embodiments, the loading dose is administered twice, or three times. In some embodiments, the loading dose is administered monthly or every other month.

In some embodiments, the method further includes administering one or more subsequent doses of the anti-VEGF antibody conjugate, e.g., KSI-301, or anti-VEGF protein conjugate (e.g., an aflibercept biopolymer conjugate), to the subject after the final loading dose. In some embodiments, the subsequent doses of the anti-VEGF antibody conjugate is administered at a dosing schedule of Q8W, Q12W, Q16W, Q20W, or Q24W, or longer. In some embodiments, the dosing schedule is between Q8W and Q24W. In some embodiments, no subsequent dose of the anti-VEGF antibody conjugate is administered to the subject within at least about one year, about two years, or about three years, after the first loading dose. In some embodiments, no more than one subsequent dose of the anti-VEGF antibody conjugate is administered to the subject within at least about one year, about two years, or about three years, after the first loading dose. In some embodiments, no more than two subsequent dose of the anti-VEGF antibody conjugate is administered to the subject within at least about one year, about two years, or about three years, after the first loading dose. In some embodiments, no more than three subsequent dose of the anti-VEGF antibody conjugate is administered to the subject within at least about one year, about two years, or about three years, after the first loading dose.

In some embodiments, a method of treating an eye disorder includes: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is wet age-related macular degeneration (wAMD); and repeating the loading dose at least once, but not more than twice, whereby the subject retains a therapeutic result of the anti-VEGF antibody conjugate therapy, or anti-VEGF protein conjugate therapy for at least 12 weeks after a final loading dose. In some embodiments, the subject retains the therapeutic result of the anti-VEGF antibody conjugate, e.g., KSI-301, therapy for at least 12, 13, 14, 15, 16, 17, 18, 19, 20, 21, 22, 23, 24, 25, 26, 27, 28, 29, 30, 32, 34, 36, 38, 40, 44, 48, 52, 56, or 60 or more weeks after the final loading dose. In some embodiments, the loading dose is administered twice, or three times. In some embodiments, the loading dose is administered monthly or every other month.

In some embodiments, the method further includes administering one or more subsequent doses of the anti-VEGF antibody conjugate, e.g., KSI-301, or anti-VEGF protein conjugate (e.g., aflibercept biopolymer conjugate), to the subject after the final loading dose. In some embodiments, the subsequent doses of the anti-VEGF antibody conjugate or anti-VEGF protein conjugate is administered at a dosing schedule of Q2W, Q4W, Q8W, Q12W, Q16W, Q20W, or Q24W, or longer. In some embodiments, the dosing schedule is between Q12W and Q20W. In some embodiments, no more than one, two, three, or four subsequent doses, or no subsequent dose of the anti-VEGF antibody conjugate or anti-VEGF protein conjugate is administered to the subject within about one year of the first loading dose. In some embodiments, the dosing schedule is between Q12W and Q20W. In some embodiments, no more than one, two, three, or four subsequent doses, or no subsequent dose of the anti-VEGF antibody conjugate or anti-VEGF protein conjugate is administered to the subject within about two years of the first loading dose. In some embodiments, no more than one, two, three, or four subsequent doses, or no subsequent dose of the anti-VEGF antibody conjugate or anti-VEGF protein conjugate is administered to the subject within about three years of the first loading dose.

In some embodiments, a method of treating an eye disorder includes: administering an anti-VEGF antibody conjugate, e.g., KSI-301, or anti-VEGF protein conjugate (e.g., an aflibercept biopolymer conjugate), to a subject in need of treating an eye disorder at a first loading dose, wherein the eye disorder is retinal vein occlusion (RVO), e.g., CRVO or BRVO; and repeating the loading dose at least once, but not more than twice, whereby the subject retains a therapeutic result of the anti-VEGF antibody conjugate, e.g., KSI-301, therapy, or anti-VEGF protein conjugate (e.g., aflibercept biopolymer conjugate) therapy, for at least 8 weeks after a final loading dose. In some embodiments, the subject retains the therapeutic result of the anti-VEGF antibody conjugate, e.g., KSI-301, therapy, or anti-VEGF protein conjugate (e.g., aflibercept biopolymer conjugate) therapy, for at least 8, 9, 10, 11, 12, 13, 14, 15, 16, 17, 18, 19, 20, 21, 22, 23, 24, 25, 26, 27, 28, 29, 30, 32, 34, 36, 38, 40, 44, 48, 52, 56, or 60 or more weeks after the final loading dose. In some embodiments, the loading dose is administered twice, or three times. In some embodiments, the loading dose is administered monthly or every other month.

In some embodiments, the method further includes administering one or more subsequent doses of the anti-VEGF antibody conjugate, e.g., KSI-301, or anti-VEGF protein conjugate (e.g., aflibercept biopolymer conjugate), to the subject after the final loading dose. In some embodiments, the subsequent doses of the anti-VEGF antibody conjugate is administered at a dosing schedule of Q8W, Q12W, Q16W, Q20W, or Q24W, or longer. In some embodiments, the dosing schedule is Q8W or longer. In some embodiments, no subsequent dose of the anti-VEGF antibody conjugate is administered to the subject within at least about one year, about two years, or about three years, after the first loading dose. In some embodiments, no more than one subsequent dose of the anti-VEGF antibody conjugate is administered to the subject within at least about one year, about two years, or about three years, after the first loading dose. In some embodiments, no more than two subsequent dose of the anti-VEGF antibody conjugate is administered to the subject within at least about one year, about two years, or about three years, after the first loading dose. In some embodiments, no more than three subsequent dose of the anti-VEGF antibody conjugate is administered to the subject within at least about one year, about two years, or about three years, after the first loading dose.

In some embodiments, a method of treating an eye disorder includes administering to a subject in need of treating an eye disorder a therapeutically effective amount of an anti-VEGF antibody conjugate, e.g., KSI-301, or anti-VEGF protein conjugate (e.g., an aflibercept biopolymer conjugate), wherein the eye disorder is diabetic retinopathy (DR), thereby treating the eye disorder. In some embodiments, the anti-VEGF antibody conjugate is administered according to a dosing schedule of Q12W, Q16W, Q20W, or Q24W, or longer. In some embodiments, the dosing schedule is between Q12W and Q24W. In some embodiments, the method further comprises administering to the subject at least one loading dose, but no more than two loading doses, of the anti-VEGF antibody conjugate. In some embodiments, the time between any two consecutive loading doses is about 4 or 8 weeks (once a month or once every other month).

In some embodiments, a method of treating an eye disorder includes administering to a subject in need of treating an eye disorder a first dose of a plurality of doses of an anti-VEGF antibody conjugate, e.g., KSI-301, or anti-VEGF protein conjugate (e.g., an aflibercept biopolymer conjugate), in a dosing schedule comprising: a loading dosing schedule comprising 1-3 loading doses of the anti-VEGF antibody conjugate, wherein the first dose is a loading dose; followed by a maintenance dosing schedule comprising one or more subsequent doses of the anti-VEGF antibody conjugate after a final loading dose, wherein the maintenance dosing schedule comprises a predetermined dosing schedule of Q8W or longer. In some embodiments, the predetermined dosing schedule is Q8W, Q12W, Q16W, Q20W, or Q24W, or longer. In some embodiments, the eye disorder is wAMD, and the predetermined dosing schedule is Q12W or longer, e.g., Q16W, Q20W, or Q24W, or longer. In some embodiments, the eye disorder is DME, DR, or RVO.

In some embodiments, the method includes an individualized dosing schedule. A method of treating an eye disorder with an individualized dosing schedule can include: evaluating a therapeutic result of the anti-VEGF antibody conjugate, e.g., KSI-301, therapy, or anti-VEGF protein conjugate (e.g., an aflibercept biopolymer conjugate) therapy, in the subject at one or more time points after the first dose (e.g., a loading dose or a maintenance dose); and administering a subsequent dose of the anti-VEGF antibody conjugate, or anti-VEGF protein conjugate, to the subject at a subsequent time point specified by the predetermined dosing schedule, unless the therapeutic result is retained by the subject, in which case extending the time interval until administering the subsequent dose. In some embodiments, a subject's eye health, e.g. retinal health, may be evaluated or assessed at a follow-up visit 4, 8, or 12 weeks, or any time point within a range defined by the above values, after the last dose, e.g., last loading dose, or last maintenance dose. In some embodiments, the therapeutic result of the anti-VEGF antibody conjugate therapy or anti-VEGF protein conjugate therapy may be assessed by any suitable option as disclose herein (e.g., visual acuity, retinal thickness, etc.). In some embodiments, if the therapeutic result of the anti-VEGF antibody conjugate therapy or anti-VEGF protein conjugate therapy is retained, as disclosed herein, no subsequent dose, e.g., maintenance dose, is needed, and the actual dosing schedule may deviate from the predetermined dosing schedule. In some embodiments, the next subsequent dose, e.g., maintenance dose, is postponed as long as the therapeutic result of the anti-VEGF antibody conjugate therapy or anti-VEGF protein conjugate therapy is retained. In some embodiments, for example, an actual dosing schedule may deviate from a predetermined Q8W dosing schedule if at 8 weeks after the last loading dose or the last maintenance dose, the subject's treated eye retains the therapeutic result of the anti-VEGF antibody conjugate therapy, the anti-VEGF antibody conjugate is not administered at the scheduled time. In some embodiments, the next maintenance dose may be postponed indefinitely as long as the therapeutic result of the anti-VEGF antibody conjugate therapy is retained.

In some embodiments, a method of treating an eye disorder includes: identifying a subject in need of treating an eye disorder, wherein the eye disorder is presumed ocular histoplasmosis syndrome; and intravitreally administering to the subject a therapeutically effective amount of the anti-VEGF antibody conjugate, e.g., KSI-301, or anti-VEGF protein conjugate (e.g., an aflibercept biopolymer conjugate), thereby treating the eye disorder. In some embodiments, the therapeutically effective amount comprises about 1 mg to about 5 mg, about 1.25 mg to about 5 mg, or about 2.5 mg to about 5 mg (by weight of the anti-VEGF antibody portion) of the anti-VEGF antibody conjugate. In some embodiments, no more than one injection of the anti-VEGF antibody conjugate or anti-VEGF protein conjugate is required to treat the eye disorder.

In some embodiments, administering to the subject in need of treating an eye disorder no more than three loading doses of the anti-VEGF antibody conjugate (e.g., KSI-301) provides a therapeutic result that lasts at least 24 weeks or longer. In some embodiments, administering to the subject in need of treating an eye disorder no more than two doses of the anti-VEGF antibody conjugate (e.g., KSI-301) provides a therapeutic result that lasts at least 24 weeks or longer. In some embodiments, administering to the subject in need of treating an eye disorder no more than one dose of the anti-VEGF antibody conjugate (e.g., KSI-301) provides a therapeutic result that lasts at least 24 weeks or longer. In some embodiments, after the final loading dose, no additional dose (e.g., maintenance dose) of the anti-VEGF antibody conjugate is administered to the subject for at least 24 weeks (i.e., it is effective for that period of time such that additional maintenance or retreatment doses are not required during that time). In some embodiments, after administering one loading dose, no additional dose (e.g., maintenance dose) of the anti-VEGF antibody conjugate is administered to the subject for at least 24 weeks. In some embodiments, after administering two loading doses, no additional dose (e.g., maintenance dose) of the anti-VEGF antibody conjugate is administered to the subject for at least 24 weeks. In some embodiments, after administering three loading dose, no additional dose (e.g., maintenance dose) of the anti-VEGF antibody conjugate is administered to the subject for at least 24 weeks. In some embodiments, an interval between loading doses is about one month to about two months. In some embodiments, an interval between loading doses is about one month or about two months. In some embodiments, the anti-VEGF antibody conjugate (e.g., KSI-301) is administered to the subject at a dosing schedule (e.g., maintenance dosing schedule) of Q24W or longer. In some embodiments, the eye disorder is wAMD. In some embodiments, the eye disorder is RVO. In some embodiments, the eye disorder is DME. In some embodiments, the eye disorder is DR.

Antibody Conjugates

Provided herein are anti-VEGF antibodies (including anti-VEGF proteins, e.g., afliberccept) and conjugates thereof. In some embodiments, the antibodies themselves are different from other anti-VEGF agents and provide superior results over other anti-VEGF agents. In some embodiments, the anti-VEGF antibody conjugate displays a surprising superiority over other antibodies and/or the expectation of the activity other antibody conjugates.

In some embodiments, the anti-VEGF antibody conjugate is KSI-301, which is an antibody conjugate comprising:

(1) an anti-VEGF-A antibody; and (2) a phosphorylcholine containing polymer, wherein the polymer is covalently bonded to the anti-VEGF-A antibody at a cysteine outside a variable region of the anti-VEGF-A antibody, and wherein said cysteine replaces a non-cysteine amino acid that occurs in a same position in sequence, wherein the anti-VEGF-A antibody comprises a light chain and heavy chain, said heavy chain comprising an Fc region, wherein the cysteine is in the Fc region of the heavy chain, wherein the sequence of a heavy chain comprises SEQ ID NO: 1, and wherein the sequence of a light chain comprises SEQ ID NO: 2, wherein the antibody conjugate has the following structure:

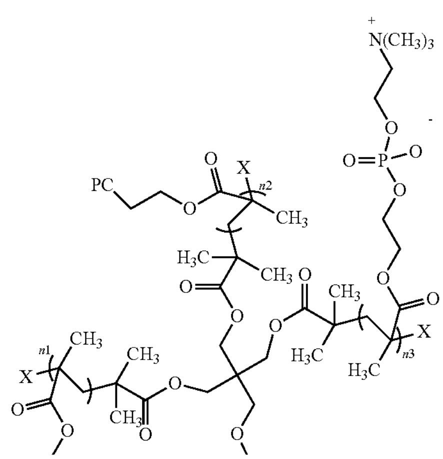

-continued

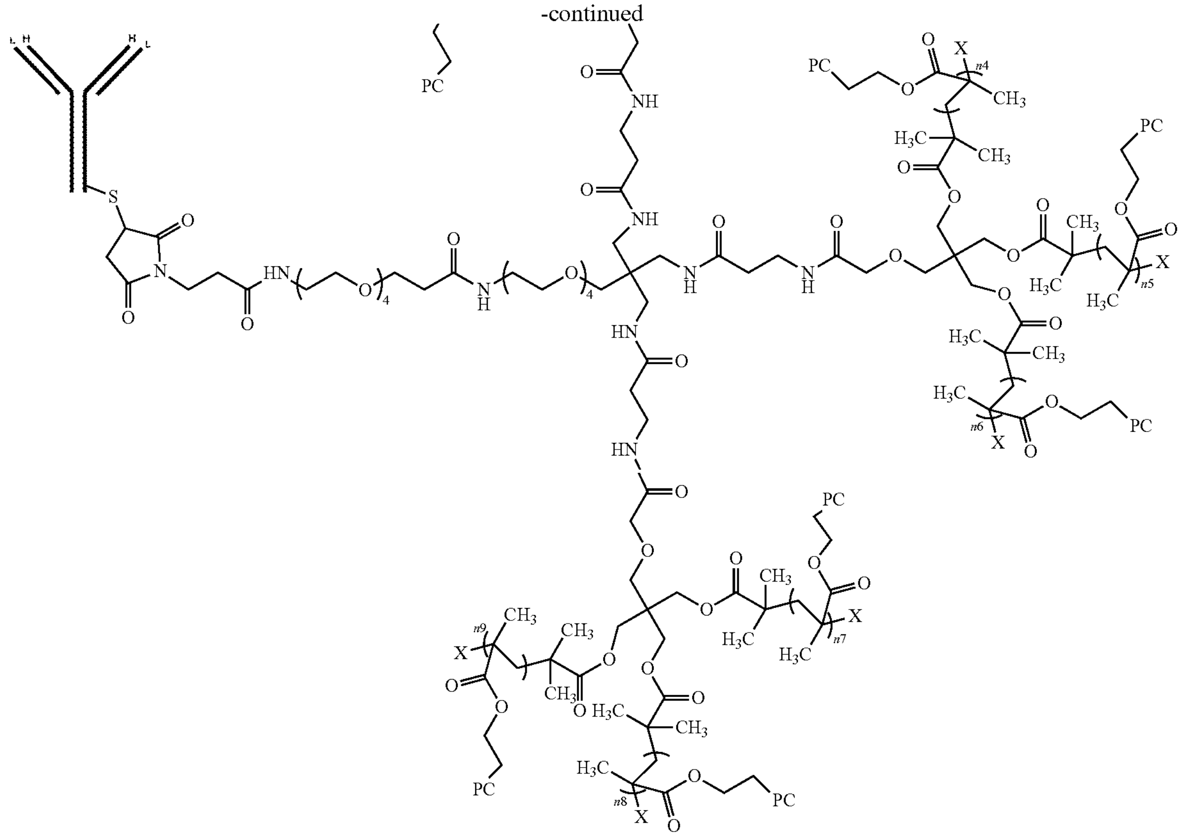

wherein:

each heavy chain of the anti-VEGF-A antibody is denoted by the letter H, and each light chain of the anti-VEGF-A antibody is denoted by the letter L;

the polymer is bonded to the anti-VEGF-A antibody through a sulfhydryl at C443 according to EU numbering, which bond is depicted on one of the heavy chains above;

PC is

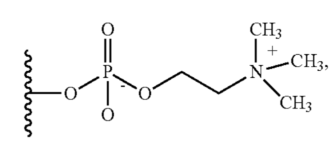

where the curvy line indicates the point of attachment to the rest of the polymer; and n1, n2, n3, n4, n5, n6, n7, n8 and n9 are the same or different such that the sum of n1, n2, n3, n4, n5, n6, n7, n8 and n9 is 2500 plus or minus 15%.

Historically, conjugating a molecule to a protein often resulted in a decrease in the protein's binding interaction to its intended target. In some embodiments of the present disclosure, when conjugating to a location that is outside of the active site, the same level of decrease as might have been expected is not necessarily observed. The evidence provided herein shows the opposite effect as to what may have been expected. In some embodiments, and without intending to be limited by theory, the conjugate can be superior to the antibody alone. For example, the interaction of a ligand and its specific receptor is often driven through the stereospecific interaction of the ligand and the receptor, as directed by the interactions of the hydrophilic amino acids on the ligand with the hydrophilic amino acids on the receptor, and water molecules are front and center in those interactions. At the same time, this hydrophilic stereospecificity is further enhanced by de-emphasizing and/or suppressing non-specific hydrophobic interactions that might generally be mediated/created by hydrophobic-to-hydrophobic amino acids.

In some embodiments, an anti-VEGF antibody conjugate is provided that is capable of blocking at least 90% of an interaction between a VEGF ligand ("VEGFL") and a VEGF-receptor ("VEGFR"). For example, it can block at least 90, 91, 92, 93, 94, 95, 96, 97, 98, 99, or effectively all of the interaction between VEGFR and VEGFL. In some embodiments, the noted blocking occurs at saturating concentrations. In some embodiments, an anti-VEGF antibody conjugate is provided that blocks at least 95% of an interaction between a VEGF ligand and a VEGF-receptor. An example of such superiority of blocking is the ability of the anti-VEGF antibody bioconjugate (an antibody conjugate provided herein, e.g., KSI-301) to block to a higher degree than Lucentis® (ranibizumab) or Avastin® (bevacizumab) or even the antibody OG1950 (unconjugated). Indeed, this result was unexpected in that while the addition of a polymer to an antibody (to form an antibody conjugate), could be expected to have some or no detrimental impact on binding/activity of the antibody, it was unexpected that it would actually improve the blocking ability of the antibody in this manner.

In some embodiments, the antibodies or conjugates thereof inhibit at least 70, 80, 85, 86, 87, 88, 89, 90, 91, 92, 93, 94, 95, 96, 97, 98, 99, or 100% of the activity and/or interaction between VEGFR and VEGFL. In some embodiments, the IC50 value can be 0.1, 1, 2, 3, 4, 5, 6, 7, 8, 9, 10, 20, 30, 40, 50, 100 nM or less than any one or more of the preceding values. In some embodiments, the KD can be 2*10^-13, 1*10^-13, 1*10^-12, 1*10^-11, 1*10^-10M or less than any one of the preceding values. In some embodiments, the IC50 value can be 1, 5, 10, 20, 30, 40, 50, 60, 70 80, 90, 100, 200, 300, 400, 500, 600, 700, 800, 900, 1,000, 1,100, 1,200, 1,300, or less than any one of the preceding values.

In some embodiments, an anti-VEGF antibody is provided that blocks at least 90% of an interaction between a VEGF ligand and a VEGF-receptor. For example, it can block at least 91, 92, 93, 94, 95, 96, 97, 98, 99, or effectively all of the interaction between VEGFR and VEGFL. As example of such superiority of blocking, is the ability of of OG1950 (and antibody provided herein) to block to a higher degree than Lucentis® (ranibizumab) or Avastin® (bevacizumab).

In some embodiments, other antibodies, such as Lucentis® (ranibizumab) or Avastin® (bevacizumab) can be conjugated to one or more of the polymers as described herein, by one or more of the processes described herein. In some embodiments, any antibody, or fragment thereof, can be conjugated to one or more of the polymers as described herein, by one or more of the processes described herein.

In some embodiments the antibody comprises a heavy chain amino acid variable region that comprises SEQ ID NO 1 and a light chain amino acid variable region that comprises SEQ ID NO. 2. In some embodiments, the antibody is conjugated to one or more of the polymers provided herein. In some embodiments, the conjugated antibody is at least 90% identical to SEQ ID NO: 1 and/or 2. In some embodiments, the antibody contains the 6 CDRs within SEQ ID NO:1 and SEQ ID NO: 2, as well as a point mutation of L443C (EU numbering, or 449C in SEQ ID NO: 1). In some embodiments, the conjugated antibody is at least 90% identical to SEQ ID NO: 1 and/or 2 and includes the following mutations: L234A, L235A, and G237A (EU numbering), and at least one of the following mutations: Q347C (EU numbering) or L443C (EU numbering).

In some embodiments an antibody that binds to VEGF-A is provided. The antibody comprises: a $CDR_H1$ that is the $CDR_H1$ in SEQ ID NO: 1, a $CDR_H2$ that is the $CDR_H2$ in SEQ ID NO: 1, a $CDR_H3$ that is the $CDR_H3$ in SEQ ID NO: 1, a $CDR_L1$ that is the $CDR_L1$ in SEQ ID NO: 2, a $CDR_L2$ that is the $CDR_L2$ in SEQ ID NO: 2, a $CDR_L3$ that is the $CDR_L3$ in SEQ ID NO: 2, at least one of the following mutations: L234A, L235A, and G237A (EU numbering), and at least one of the following mutations: Q347C (EU numbering) or L443C (EU numbering).

As will be appreciated by one of skill in the art, in light of the present specification, any of the antibodies provided herein can be conjugated to any of the polymers provided herein and/or any antibody provided herein can have a cysteine added such that it allows for site specific conjugation to a polymer.

"VEGF" or "vascular endothelial growth factor" is a human vascular endothelial growth factor that affects angiogenesis or an angiogenic process. In particular, the term VEGF means any member of the class of growth factors that (i) bind to a VEGF receptor such as VEGFR-1 (Flt-1), VEGFR-2 (KDR/Flk-1), or VEGFR-3 (FLT-4); (ii) activates a tyrosine kinase activity associated with the VEGF receptor; and (iii) thereby affects angiogenesis or an angiogenic process.

The VEGF family of factors is made up of five related glycoproteins: VEGF-A (also known as VPE), -B, -C, -D and PGF (placental growth factor). Of these, VEGF-A is the most well studied and is the target of anti-angiogenic therapy. Ferrara et al, (2003) Nat. Med. 9:669-676. VEGF-A exists as a number of different isotypes which are generated both by alternative splicing and proteolysis: VEGF-$A_{206}$, VEGF-$A_{189}$, VEGF-$A_{165}$, and VEGF-$A_{121}$. The isoforms differ in their ability to bind heparin and non-signaling binding proteins called neuropilins. The isoforms are all biologically active as dimers.

The various effects of VEGF are mediated by the binding of a VEGF, e.g., VEGF-A (P15692), -B (P49766), -C(P49767) and -D (Q43915), to receptor tyrosine kinases (RTKs). The VEGF family receptors belong to class V RTKs and each carry seven Ig-like domains in the extracellular domain (ECD). In humans, VEGF binds to three types of RTKs: VEGFR-1 (Flt-1) (P17948), VEGFR-2 (KDR, Flk-1) (P935968) and VEGFR-3 (Flt-4) (P35916). Unless otherwise apparent from the context reference to a VEGF means any of VEGF-A, -B, -C, -D, and PGF, in any of the natural isoforms or natural variants or induced variants having at least 90, 95, 98 or 99% or 100% sequence identity to a natural form. In some embodiments, such VEGFs are human VEGFs. Likewise reference to a VEGFR means any of VEGR-1, R-2 or R-3, including any natural isoform or natural variant, or an induced variant having at least 90, 95, 98 or 99% or 100% sequence identity to a natural sequences.

VEGF antagonist therapies have been approved for the treatment of certain cancers and wet AMD. Bevacizumab (AVASTIN, Genentech/Roche) is a humanized mouse monoclonal antibody that binds to and neutralizes human VEGF, in particular to all isoforms of VEGF-A and to bioactive proteolytic fragments of VEGF-A. See, e.g., Ferrara N, Hillan K J, Gerber H P, Novotny W. 2004. Discovery and development of bevacizumab, an anti-VEGF antibody for treating cancer. Nat Rev Drug Discov. 3(5):391-400. Bevacizumab has been approved for the treatment of certain cancers. The protein sequence of the heavy and light chains of bevacizumab (DrugBank DB00112) are set forth in SEQ ID NO. 3 (heavy) and SEQ ID NO. 4 (light).

Bevacizumab variable light chain CDRs are $CDR_L1$: SASQDISNYLN (SEQ ID NO: 12), $CDR_L2$: FTSSLHS (SEQ ID NO: 13) and $CDR_L3$: QQYSTVPWT (SEQ ID NO: 14). Bevacizumab variable heavy chain CDRs are $CDR_H1$: GYTFTNYGMN, $CDR_H2$: WINTYTGEPTYAADFKR (SEQ ID NO: 10), and $CDR_H3$: YPHYYGSSHWYFDV. CDRs are defined by Kabat except $CDR_H1$ uses the composite Kabat/Chothia definition. In some embodiments, a cysteine can be added to the Bevacizumab sequence and the antibody (and/or a variant that includes the 6 CDRs of Bevacizumab) can be conjugated to any one or more of the polymers provided herein.

Another anti-VEGF molecule, derived from the same mouse monoclonal antibody as bevacizumab has been approved as a treatment for wet AMD: ranibizumab (LUCENTIS® (ranibizumab), Genentech/Roche). Ranibizumab is an antibody fragment or Fab. Ranibizumab was produced by affinity maturation of the variable heavy and light chains of bevacizumab. The sequence of the heavy and light chains of ranibizumab (as published by Novartis) is set forth in SEQ ID NO. 5 and 6 respectively. In some embodiments, a cysteine can be added to the ranibizumab sequence and the antibody (and/or a variant that includes the 6 CDRs of ranibizumab) can be conjugated to any one or more of the polymers provided herein.

The Ranibizumab CDRS are the same as Bevacizumab except where an improvement was added after affinity maturation: Ranibizumab variable light chain CDRs are $CDR_L1$: SASQDISNYLN (SEQ ID NO: 12), $CDR_L2$:

FTSSLHS (SEQ ID NO: 13) and $CDR_L3$: QQYSTVPWT (SEQ ID NO: 14). Ranibizumab variable heavy chain CDRs are $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11).

In some embodiments, an antibody conjugate is presented having an anti-VEGF-A antibody bonded at a cysteine outside a variable region of the antibody to a phosphorylcholine containing polymer, wherein the cysteine has been added via recombinant DNA technology. In some embodiments, the polymer is bonded to a single cysteine. In some embodiments, "added by recombinant DNA technology" means that the cysteine residue replaces a non-cysteine amino acid that occurs in the same position in a known or existing antibody or in a consensus antibody sequence. Thus, for example where the antibody is an IgG1 and the heavy chain possess a leucine at EU position 443, the leucine is replaced via recombinant DNA technology with a cysteine (L443C, EU numbering, or 449C in SEQ ID NO: 1). Correspondingly, the native IgG1 sequence at EU position 347 is Q (glutamine) and the Q is replaced with cysteine via recombinant DNA technology to yield Q347C.

In some embodiments, the anti-VEGF-A antibody comprises a light chain and a heavy chain where the heavy chain has an Fc region. In some embodiments, the cysteine is in the Fc region and the anti-VEGF-A antibody is an immunoglobulin G (IgG). In some embodiments, the anti-VEGF-A heavy chain has $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and position 221 (via sequential counting as in SEQ ID NO. 3) is T, and the anti-VEGF-A light chain has $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L.

In some embodiments, the anti-VEGF-A heavy chain isotype is IgG1. In some embodiments, the IgG1 constant domain has one or more mutations relative to an IgG1 constant domain (e.g. constant region of SEQ ID NO. 3) to modulate effector function. In some embodiments, the effector function mutations are one or more of the following: (EU numbering) E233X, L234X, L235X, G236X, G237X, A327X, A330X, and P331X wherein X is any natural or unnatural amino acid. In some embodiments, the mutations are selected from the group consisting of (EU numbering): E233P, L234V, L234A, L235A, G237A, A327G, A330S, and P331S. In some embodiments, the antibody conjugate has the following mutations (EU numbering): L234A, L235A, and G237A.

In some embodiments, the cysteine residue is in the anti-VEGF-A heavy chain and is Q347C (EU numbering) or L443C (EU numbering). In some embodiments, the cysteine residue is L443C (EU numbering, or 449C in SEQ ID NO: 1). In some embodiments, the sequence of the anti-VEGF-A heavy chain is SEQ ID NO. 1 and the sequence of the anti-VEGF-A light chain is SEQ ID NO. 2.

In some embodiments, the phosphorylcholine containing polymer comprises 2-(methacryloyloxyethyl)-2'-(trimethylammonium)ethyl phosphate (MPC) monomers as set forth below:

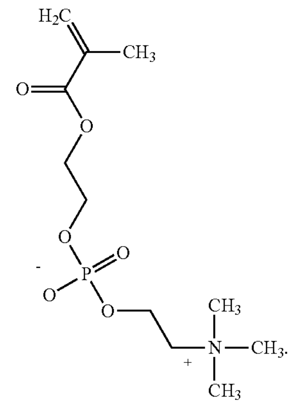

Such that the polymer comprises the following repeating units:

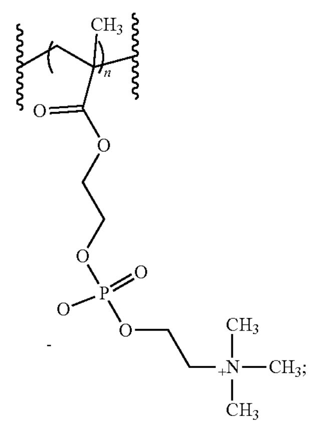

where n is an integer from 1 to 3000 and the wavy lines indicate the points of attachment between monomer units in the polymer.

In some embodiments, the polymer has three or more arms, or is synthesized with an initiator comprising 3 or more polymer initiation sites. In some embodiments, the polymer has 2, 3, 4, 5, 6, 7, 8, 9, 10, 11 or 12 arms, or is synthesized with an initiator comprising 2, 3, 4, 5, 6, 7, 8, 9, 10, 11, or 12 polymer initiation sites. More preferably, the polymer has 3, 6, or 9 arms, or is synthesized with an initiator comprising 3, 6, or 9 polymer initiation sites. In some embodiments, the polymer has 9 arms, or is synthesized with an initiator comprising 9 polymer initiation sites.

In some embodiments, the polymer that is added has a molecular weight between about 300,000 and about 1,750,000 Da (SEC-MALs). In some embodiments, the polymer has a molecular weight between about 500,000 and about 1,000,000 Da. In some embodiments, the polymer has a molecular weight of between about 600,000 to about 900,000 Da. In some embodiments, the polymer has a molecular weight of between about 750,000 to about 850,000 Da. In some embodiments, the polymer has a molecular weight of between about 800,000 to about 850,000 Da. In some embodiments, the polymer has a molecular weight of between about 750,000 to about 800,000 Da.

In some embodiments, any of the antibodies described herein can be further conjugated to a polymer to form a bioconjugate. The molecular weight of the bioconjugate (in total, SEC-MALs) can be between about 350,000 and 2,000,000 Daltons, for example, between about 450,000 and 1,900,000 Daltons, between about 550,000 and 1,800,000 Daltons, between about 650,000 and 1,700,000 Daltons, between about 750,000 and 1,600,000 Daltons, between about 850,000 and 1,500,000 Daltons, between about 900,000 and 1,400,000 Daltons, between about 950,000 and 1,300,000 Daltons, between about 900,000 and 1,000,000 Daltons, between about 1,000,000 and 1,300,000 Daltons, between about 850,000 and 1,300,000 Daltons, between about 850,000 and 1,000,000 Daltons, and between about 1,000,000 and 1,200,000 Daltons.

In some embodiments, the antibody conjugate is purified. In some embodiments, the polymer is aspect of the antibody conjugate is polydisperse, i.e. the polymer PDI is not 1.0. In some embodiments, the PDI is less than 1.5. In some embodiments, the PDI is less than 1.4. In some embodiments, the PDI is less than 1.3. In some embodiments the PDI is less than 1.2. In some embodiments the PDI is less than 1.1.

In some embodiments, the antibody conjugate has an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C449 in SEQ ID NO. 1 to the polymer. In some embodiments, the polymer has 9 arms and has a molecular weight of between about 600,000 to about 1,000,000 Da.

In some embodiments, the antibody conjugate has an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C443 (EU numbering, or 449C in SEQ ID NO: 1) to the polymer. In some embodiments, the polymer has 9 arms and has a molecular weight of between about 600,000 to about 1,000,000 Da.

In some embodiments, the antibody conjugate has the following structure:

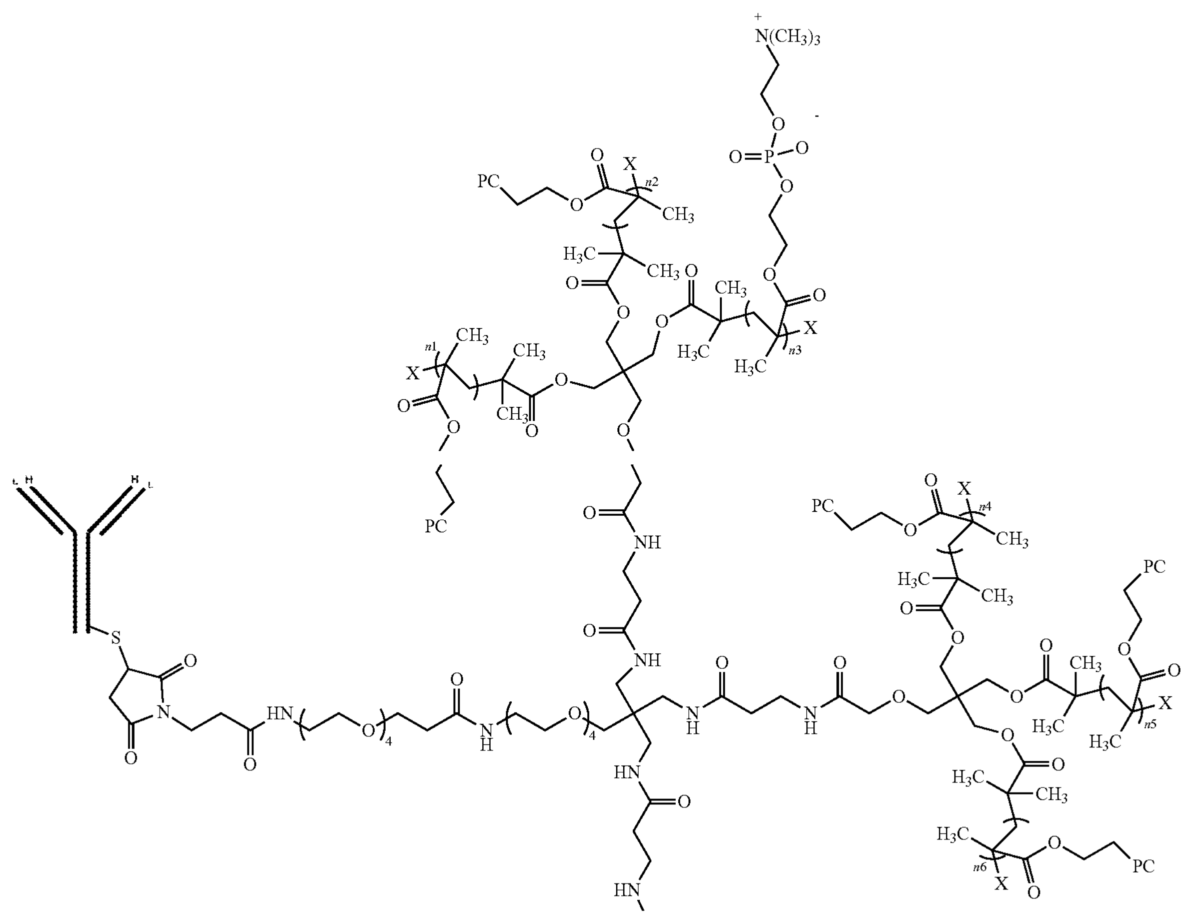

-continued

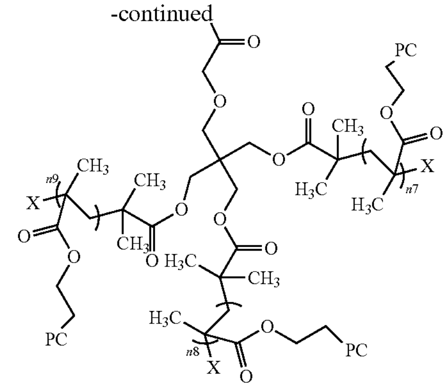

wherein: each heavy chain of the anti-VEGF-A antibody is denoted by the letter H, and each light chain of the anti-VEGF-A antibody is denoted by the letter L;

the polymer is bonded to the anti-VEGF-A antibody through the sulfhydryl of C449 of SEQ ID NO: 1, which bond is depicted on one of the heavy chains; PC is,

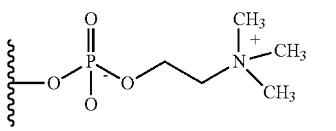

where the curvy line indicates the point of attachment to the rest of the polymer; wherein X is a) —OR where R is H, methyl, ethyl, propyl, or isopropyl, b) —H, c) any halogen, including —Br, —Cl, or —I, d) —SCN, or e) —NCS; and n1, n2, n3, n4, n5, n6, n7, n8 and n9 are the same or different such that the sum of n1, n2, n3, n4, n5, n6, n7, n8 and n9 is 2500 plus or minus 10%. In some embodiments, n1, n2, n3, n4, n5, n6, n7, n8 and n9 are the same or different and are integers from 0 to 3000. In some embodiments, n1, n2, n3, n4, n5, n6, n7, n8 and n9 are the same or different and are integers from 0 to 500. In some embodiments, X is —OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

In some embodiments, the antibody conjugate has the following structure:

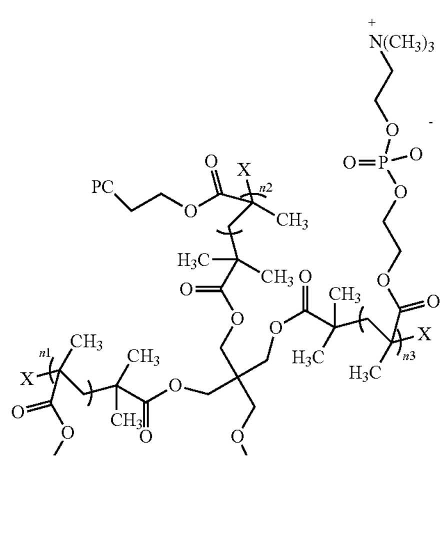

-continued

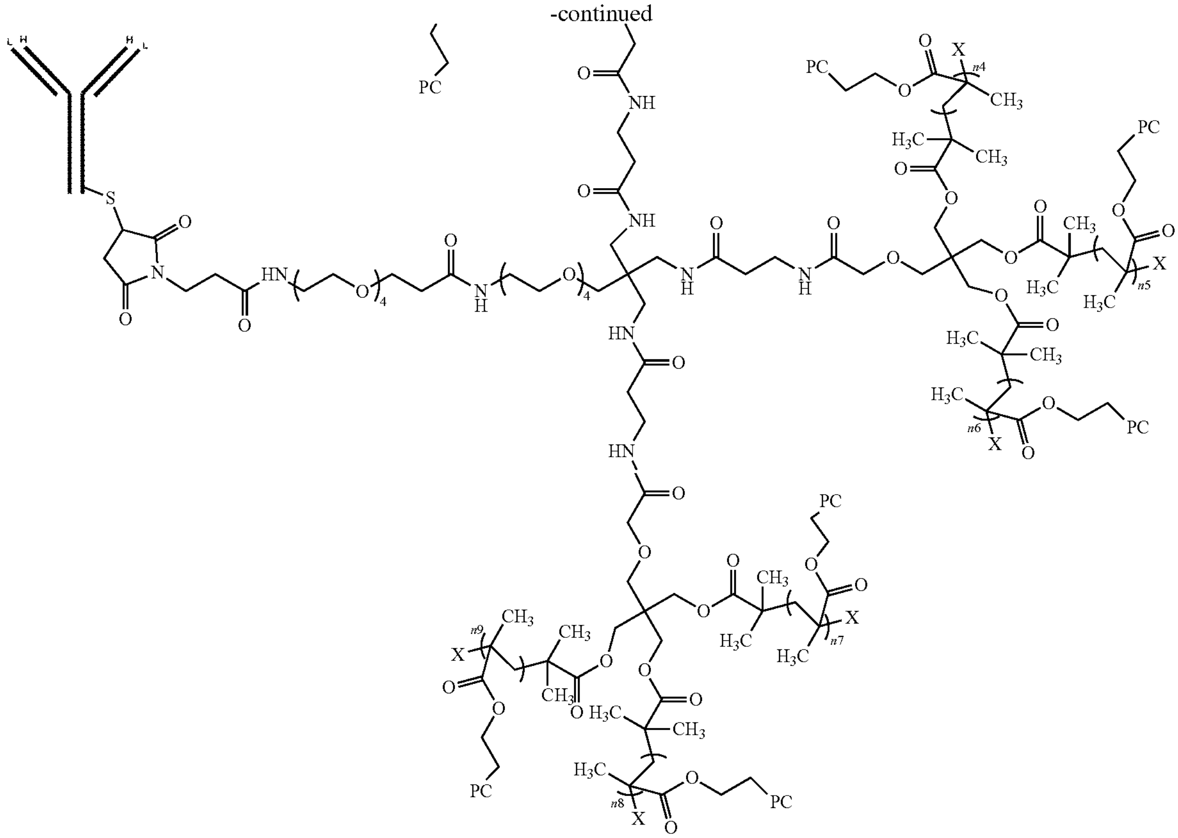

wherein: each heavy chain of the anti-VEGF-A antibody is denoted by the letter H, and each light chain of the anti-VEGF-A antibody is denoted by the letter L;

the polymer is bonded to the anti-VEGF-A antibody through the sulfhydryl of C443 (EU numbering, or 449C in SEQ ID NO: 1), which bond is depicted on one of the heavy chains; PC is,

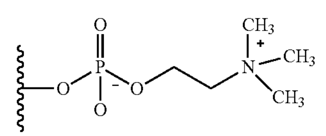

where the curvy line indicates the point of attachment to the rest of the polymer; wherein X is a) —OR where R is H, methyl, ethyl, propyl, or isopropyl, b) —H, c) any halogen, including Br, —Cl, or —I, d) —SCN, or e) —NCS; and n1, n2, n3, n4, n5, n6, n7, n8 and n9 are the same or different such that the sum of n1, n2, n3, n4, n5, n6, n7, n8 and n9 is 2500 plus or minus 10%. In some embodiments, n1, n2, n3, n4, n5, n6, n7, n8 and n9 are the same or different and are integers from 0 to 3000. In some embodiments, n1, n2, n3, n4, n5, n6, n7, n8 and n9 are the same or different and are integers from 0 to 500. In some embodiments, X is —OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl—CCO—$R_7$, —CO——$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring. In some embodiments, this construct is designated as KSI-301.

In some embodiments, the antibody conjugate is present in a liquid formulation. In some embodiments, the antibody conjugate is combined with a pharmaceutically acceptable carrier.

In some embodiments, an anti-VEGF-A antibody is presented. The anti-VEGF-A antibody heavy chain has at least the following CDR sequences: $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11). In some embodiments, the anti-VEGF-A heavy chain has those CDRs and in addition has threonine (T) at position 221 (via sequential counting as in SEQ ID NO. 3). In some embodiments, the anti-VEGF-A light chain has at least the following CDRs: $CDR_L1$: SASQDISNYLN (SEQ ID NO: 12), $CDR_L2$: FTSSLHS (SEQ ID NO: 13) and $CDR_L3$: QQYSTVPWT (SEQ ID NO: 14). In some embodiments, the anti-VEGF-A antibody has those CDRs and in addition has leucine (L) at Kabat position 4. In some embodiments, the isotype of the anti-VEGF-A antibody heavy chain, is IgG1 and has a $CH_1$, hinge, $CH_2$ and $CH_3$ domains. In some embodiments the light chain isotype is kappa. In some embodiments, the anti-VEGF antibody conjugate (e.g., KSI-301) construct will have one or more of these CDRs.

In some embodiments, the IgG1 domain of the anti-VEGF-A antibody has one or more mutations to modulate effector function, such as ADCC, ADCP, and CDC. In some embodiments, the IgG1 mutations reduce effector function. In some embodiments the amino acids to use for effector function mutations include (EU numbering) E233X, L234X, L235X, G236X, G237X, G236X, D270X, K322X, A327X, P329X, A330X, A330X, P331X, and P331X, in which X is any natural or non-natural amino acid. In some embodiments, the mutations include one or more of the following: E233P, L234V, L234A, L235A, G237A, A327G, A330S and P331S (EU numbering). In some embodiments, the anti-VEGF-A heavy chain has the following mutations (EU numbering): L234A, L235A and G237A. In some embodiments, the number of effector function mutations relative to a natural human IgG1 sequence is no more than 10. In some embodiments the number of effector function mutations relative to a natural human IgG1 sequence is no more than 5, 4, 3, 2 or 1. In some embodiments, the antibody has decreased Fc gamma binding and/or complement Clq binding, such that the antibody's ability to result in an effector function is decreased. This can be especially advantageous for ophthalmic indications/disorders.

In some embodiments, the anti-VEGF-A antibody comprises one or more of the following amino acid mutations: L234A, L235A, G237A (EU numbering), and L443C (EU numbering, or 449C in SEQ ID NO: 1).

In some embodiments, the anti-VEGF-A antibody is or is part of a human immunoglobulin G (IgG1).

In some embodiments, the VEGF-A antibody comprises a heavy chain constant domain that comprises one or more mutations that reduce an immune-mediated effector function.

In some embodiments an anti-VEGF-A antibody is provided. The anti-VEGF-antibody comprises a heavy chain that comprises a $CDR_H1$ comprising the sequence GYDFTHYGMN (SEQ ID NO: 9), a $CDR_H2$ comprising the sequence WINTYTGEPTYAADFKR (SEQ ID NO: 10), a $CDR_H3$ comprising the sequence YPYYYGTSHWYFDV (SEQ ID NO: 11), a $CDR_L1$ comprising the sequence SASQDISNYLN (SEQ ID NO: 12), a $CDR_L2$ comprising the sequence FTSSLHS (SEQ ID NO: 13), and a $CDR_L3$ comprising the sequence QQYSTVPWT (SEQ ID NO: 14).

Alternatively, the IgG domain can be IgG2, IgG3 or IgG4 or a composite in which a constant regions is formed from more than one of these isotypes (e.g., CH1 region from IgG2 or IgG4, hinge, $CH_2$ and $CH_3$ regions from IgG1). Such domains can contain mutations to reduce and/or modulate effector function at one or more of the EU position mentioned for IgG1. Human IgG2 and IgG4 have reduced effector functions relative to human IgG1 and IgG3.

The anti-VEGF-A heavy chain has a cysteine residue added as a mutation by recombinant DNA technology which can be used to conjugate a half-life extending moiety. In some embodiments, the mutation is (EU numbering) Q347C (EU numbering) and/or L443C (EU numbering, or 449C in SEQ ID NO: 1). In some embodiments, the mutation is L443C (EU numbering, or 449C in SEQ ID NO: 1). In some embodiments, the stoichiometry of antibody to polymer is 1:1; in other words, a conjugate has one molecule of antibody conjugated to one molecule of polymer.

The half-life of the anti-VEGF-A antibodies can be extended by attachment of a "half-life ("half life") extending moieties" or "half-life ("half life") extending groups". Half-life extending moieties include peptides and proteins which can be expressed in frame with the biological drug of issue (or conjugated chemically depending on the situation) and various polymers which can be attached or conjugated to one or more amino acid side chain or end functionalities such as —SH, —OH, —COOH, —CONH2, —NH2, or one or more N- and/or O-glycan structures. Half-life extending moieties generally act to increase the in vivo circulatory half-life of biologic drugs.

Examples of peptide/protein half-life extending moieties include Fc fusion (Capon D J, Chamow S M, Mordenti J, et al. Designing CD4 immunoadhesions for AIDS therapy. Nature. 1989. 337:525-31), human serum albumin (HAS) fusion (Yeh P, Landais D, Lemaitre M, et al. Design of yeast-secreted albumin derivatives for human therapy: biological and antiviral properties of a serum albumin-CD4 genetic conjugate. Proc Natl Acad Sci USA. 1992. 89:1904-08), carboxy terminal peptide (CTP) fusion (Fares F A, Suganuma N. Nishimori K, et al. Design of a long-acting follitropin agonist by fusing the C-terminal sequence of the chorionic gonadotropin beta subunit to the follitropin beta subunit. Proc Natl Acad Sci USA. 1992. 89:4304-08), genetic fusion of non-exact repeat peptide sequence (XTEN) fusion (Schellenberger V, Wang C W, Geething N C, et al. A recombinant polypeptide extends the in vivo half-life of peptides and proteins in a tunable manner. Nat Biotechnol. 2009. 27:1186-90), elastin like peptide (ELPylation) (MCpherson D T, Morrow C, Minehan D S, et al. Production and purification of a recombinant elastomeric polypeptide, G(VPGVG19-VPGV, from *Escherichia coli*. Biotechnol Prog. 1992. 8:347-52), human transferrin fusion (Prior C P, Lai C-H, Sadehghi H et al. Modified transferrin fusion proteins. Patent WO2004/020405. 2004), proline-alanine-serine (PASylation) (Skerra A, Theobald I, Schlapsky M. Biological active proteins having increased in vivo and/or vitro stability. Patent WO2008/155134 A1. 2008), homo-amino acid polymer (HAPylation) (Schlapschy M, Theobald I, Mack H, et al. Fusion of a recombinant antibody fragment with a homo-amino acid polymer: effects on biophysical properties and prolonged plasma half-life. Protein Eng Des Sel. 2007. 20:273-84) and gelatin like protein (GLK) fusion (Huang Y-S, Wen X-F, Zaro J L, et al. Engineering a pharmacologically superior form of granulocyte-colony-stimulating-factor by fusion with gelatin-like protein polymer. Eur J. Pharm Biopharm. 2010. 72:435-41).

Examples of polymer half-life extending moieties include polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anhydride, polystyrene-co-maleic acid anhydride, poly(1-hydroxymethyethylene hydroxymethylformal) (PHF), a zwitterionic polymer, a phosphorylcholine containing polymer and a polymer comprising MPC, Poly ($Gly_x$-$Ser_y$), Hyaluronic acid (HA), Heparosan polymers (HEP), Fleximers, Dextran, and Poly-sialic acids (PSA).

In one embodiment a half-life extending moiety can be conjugated to an antibody via free amino groups of the protein using N-hydroxysuccinimide (NETS) esters. Reagents targeting conjugation to amine groups can randomly react to ϵ-amine group of lysines, α-amine group of N-terminal amino acids, and δ-amine group of histidines.

However, the anti-VEGF-A antibodies disclosed herein have many amine groups available for polymer conjugation. Conjugation of polymers to free amino groups, thus, might negatively impact the ability of the antibody proteins to bind to VEGF.

In some embodiments, a half-life extending moiety is coupled to one or more free SH groups using any appropriate thiol-reactive chemistry including, without limitation, maleimide chemistry, or the coupling of polymer hydrazides or polymer amines to carbohydrate moieties of the antibody after prior oxidation. In some embodiments maleimide coupling is used. In some embodiments, coupling occurs at cysteines naturally present or introduced via genetic engineering.

In some embodiments, polymers are covalently attached to cysteine residues introduced into anti-VEGF-A antibodies by site directed mutagenesis. In some embodiments, the cysteine residues are employed in the Fc portion of the antibody. In some embodiments, the sites to introduce cysteine residues into an Fc region are provided in WO 2013/093809, U.S. Pat. No. 7,521,541, WO 2008/020827, U.S. Pat. Nos. 8,008,453, 8,455,622 and US2012/0213705, incorporated herein by reference for all purposes. In some embodiments, the cysteine mutations are Q347C (EU numbering) and L443C referring to the human IgG heavy chain by EU numbering.

In some embodiments, conjugates of antibody and high MW polymers serving as half-life extenders are provided. In some embodiments, a conjugate comprises an antibody that is coupled to a zwitterionic polymer wherein the polymer is formed from one or more monomer units and wherein at least one monomer unit has a zwitterionic group is provided. In some embodiments, the zwitterionic group is phosphorylcholine.

In some embodiments, one of the monomer units is HEMA-PC. In some embodiments, a polymer is synthesized from a single monomer which is HEMA-PC.

In some embodiments, some antibody conjugates have 2, 3, or more polymer arms wherein the monomer is HEMA-PC. In some embodiments, the conjugates have 2, 3, 4, 5, 6, 7, 8, 9, 10, 11, or 12 polymer arms wherein the monomer is HEMA-PC. In some embodiments, the conjugates have 3, 6 or 9 arms. In some embodiments, the conjugate has 9 arms.

In some embodiments, polymer-antibody conjugates have a polymer portion with a molecular weight of between 100,000 and 1,500,000 Da. In some embodiments, the conjugate has a polymer portion with a molecular weight between 500,000 and 1,000,000 Da. In some embodiments, the conjugate has a polymer portion with a molecular weight between 600,000 to 800,000 Da. In some embodiments, the conjugate has a polymer portion with a molecular weight between 600,000 and 850,000 Da and has 9 arms. When a molecular weight is given for an antibody conjugated to a polymer, the molecular weight will be the addition of the molecular weight of the protein, including any carbohydrate moieties associated therewith, and the molecular weight of the polymer.

In some embodiments, an anti-VEGF-A antibody has a HEMA-PC polymer which has a molecular weight measured by Mw of between about 100 kDa and 1650 kDa is provided. In some embodiments, the molecular weight of the polymer as measured by Mw is between about 500 kDa and 1000 kDa. In some embodiments, the molecular weight of the polymer as measured by Mw is between about 600 kDa to about 900 kDa. In some embodiments, the polymer molecular weight as measured by Mw is 750 kDa plus or minus 15%.

In some embodiments, the polymer is made from an initiator suitable for ATRP having one or more polymer initiation sites. In some embodiments, the polymer initiation site has a 2-bromoisobutyrate site. In some embodiments, the initiator has 3 or more polymer initiation sites. In some embodiments, the initiator has 3, 4, 5, 6, 7, 8, 9, 10, 11 or 12 polymer initiation sites. In some embodiments, the initiator has 3, 6 or 9 polymer initiation sites. In some embodiments, the initiator has 9 polymer initiation sites. In some embodiments, the initiator is OG1786.

The anti-VEGF-A antibodies can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing antibody, e.g. constitutively or on induction, and (v) isolating the antibody, e.g. from the culture medium or by harvesting the transformed cells, in order to (vi) obtain purified antibody.

The anti-VEGF-A antibodies can be produced by expression in a suitable prokaryotic or eukaryotic host system characterized by producing a pharmacologically acceptable antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the antibodies disclosed herein and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

Method of Conjugating Proteins to Polymers

In some embodiments, a method is presented of preparing a therapeutic protein-half life extending moiety conjugate having the step of conjugating a therapeutic protein which has a cysteine residue added via recombinant DNA technology to a half-life extending moiety having a sulfhydryl specific reacting group selected from the group consisting of maleimide, vinylsulfones, orthopyridyl-disulfides, and iodoacetamides to provide the therapeutic protein-half life extending moiety conjugate.

In some embodiments a method of preparing the anti-VEGF antibody conjugate, e.g., KSI-301, from OG1950 is provided. The method comprises reducing the OG1950 protein with a 50× molar excess of the TCEP reducing agent. After reduction, the antibody is oxidized to produce a decapped OG1950 antibody where the inter- and intra-light and heavy chain disulfide bonds naturally occurring in the antibody are formed, but the engineered Cysteine on the heavy chain position L443C (EU numbering, or 449C in SEQ ID NO: 1) remains to be decapped. The OG1950 is then conjugated by adding an excipient and adding 5-10× molar excess of a maleimide biopolymer. The biopolymer links to the OG1950 antibody through a covalent thiolether linkage. After conjugation, the anti-VEGF antibody conjugate, e.g., KSI-301, is purified with both unconjugated antibody and polymer removed.

The protein and process described above can be varied as well. Thus, in some embodiments, a process for preparing a conjugated protein (which need not be an antibody or an anti-VEGF antibody) is provided. The process includes reducing one or more cysteines in a protein to form a decapped protein in a solution. After reducing the one or more cysteines the decapped protein is reoxidized to restore at least one disulfide linkage in the reduced protein while ensuring that an engineered cysteine residue in the protein remains in a free thiol form to form a reoxidized decapped protein in the solution. At least one excipient is then added to the solution. The excipient reduces a polymer induced protein precipitation. After the excipient is added, a polymer is added to the solution, which is conjugated to the reoxidized decapped protein at the engineered cysteine residue to form a conjugated protein.

In some embodiments, the molar excess of the reducing agent can be altered to any amount that functions. In some embodiments 10, 20, 30, 40, 50, 60, 70, 80, 90× molar excess of the reducing agent (which need not be TCEP in all embodiments) can be employed. In some embodiments, any antibody (therapeutic or otherwise) can be employed. In some embodiments, 1, 2, 3, 4, 5, 6, 7, 8, 9, 10, 11, 12, 13, 14, 15× molar excess of a maleimide biopolymer can be employed. In some embodiments, there is an excess of decapped protein to polymer. In some embodiments, the amount of the reduced protein is less than the amount of the polymer. In some embodiments, the amount of the reduced protein is 90%, 80%, 70%, 60%, 50%, 40%, 30%, 20%, 10%, 5%, 4%, 3%, 2%, 1% of the amount of the polymer. In some embodiments, 10-15 times as much polymer is used as protein. In some embodiments the amount of the reduced antibody is greater than the amount of the polymer. In some embodiments the amount of the polymer is greater than the amount of the reduced antibody.

In some embodiments, the purification step is optional.

In some embodiments, the method of making an antibody conjugate comprises conjugating an anti-VEGF-A antibody to a phosphorylcholine containing polymer. In some embodiments the method comprises the steps of conjugating an anti-VEGF-A antibody to a phosphorylcholine containing polymer. The anti-VEGF-A antibody comprises an amino residue added via recombinant DNA technology. In some embodiments, the added amino acid residue is a cysteine residue. In some embodiments, the cysteine residue is added outside a variable region of the antibody. The cysteine residue can be added to either the heavy chain or light chain of the antibody.

In some embodiments, the polymer comprises or consists of a phosphorylcholine containing polymer. In some embodiments, the phosphorylcholine containing polymer comprises a sulfhydryl specific reacting group selected from the group consisting of a maleimide, a vinylsulfone, an orthopyridyl-disulfide, and an iodoacetamide. In some embodiments, the sulfhydryl specific reacting group on the phosphorylcholine containing polymer reacts with the cysteine residue on the anti-VEGF-A antibody to make the antibody conjugate.

In some embodiments, the protein to be conjugated can be an antibody, an antibody protein fusion, or a binding fragment thereof. In some embodiments, the protein is not an antibody but is an enzyme, a ligand, a receptor, or other protein or mutants or variants thereof. In some embodiments, the native protein contains at least one disulfide bond and at least one non-native cysteine.

In some embodiments, the excipient can be an acid or a base. In some embodiments, the excipient is a detergent, a sugar, or a charged amino acid. In some embodiments, the excipient assists in keeping the protein in solution during the conjugation to the polymer. In some embodiments, the excipient is added to the solution containing the protein, prior to the addition of the polymer to the solution that contains the protein.

In some embodiments, the reaction occurs under aqueous conditions between about pH 5 to about pH 9. In some embodiments, the reaction occurs between 6.0 and 8.5, between 6.5 and 8.0 or between 7.0 and 7.5.

In some embodiments, the polymer is conjugated to the protein at 2-37 degrees Celsius. In some embodiments, the conjugation occurs at 0-40 degrees Celsius, 5-35 degrees Celsius, 10-30 degrees Celsius, and 15-25 degrees Celsius.

In some embodiments, the conjugated proteins described herein can be contacted to an ion exchange medium or hydrophobic interaction chromatography or affinity chromatography medium for purification (to remove the conjugated from the unconjugated). In some embodiments, the ion exchange medium, hydrophobic interaction chromatography, and/or affinity chromatography medium separates the conjugated protein from the free polymer and from the reoxidized decapped protein.

In some embodiments, the processes described herein and outlined in FIG. 18 involves an excipient that is capable of facilitating and/or maintaining a solubility system. In some embodiments, the process allows the solution to maintain the solubility of the two components meant to interact. This can include the solubility of the protein and the polymer and then the end conjugate as well. In some embodiments, without the excipient approach, the issue can be that while the protein is soluble, when the biopolymer is added, the solubility of the solution (e.g., protein) drops and it crashes/precipitates out of solution. Of course, when the protein crashes out, it is not available to conjugate efficiently with the biopolymer. Thus, an excipient can be employed to maintain the solubility of the protein in the presence of the biopolymer so the two can couple to form the protein conjugate (or as depicted in FIG. 18, an antibody conjugate). This also allows for the solubility of the conjugate to be maintained.

In some embodiments, the polymers disclosed herein can comprise one or more of the following: a zwitterion, a phosphorylcholine, or a PEG linker bridging a center of a polymer branching point to the maleimide functional group. In some embodiments, any of the polymers provided herein can be added to a protein via the methods provided herein.

In some embodiments, any of the proteins provided herein can be conjugated to any of the polymers provided herein via one or more of the methods provided herein.

In some embodiments, the process(es) provided herein allow(s) for larger scale processing to make and purify protein and/or antibody conjugates. In some embodiments, the volume employed is at least 1 liter, for example 1, 10, 100, 1,000, 5,000, 10,000, liters or more. In some embodiments, the amount of the antibody conjugate produced and/or purified can be 0.1, 1, 10, 100, 1000, or more grams.

In some embodiments, the therapeutic protein may be any of the anti-VEGF-A antibodies described herein having a cysteine residue added via recombinant DNA technology. In some embodiments, the anti-VEGF antibody heavy chain has the following CDRs: $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11). The heavy chain can also have threonine (T) at position 221 (via sequential counting as in SEQ ID NO. 3). In some embodiments, the anti-VEGF light chain has the following CDRs: $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14). The anti-VEGF-A light chain can also have leucine (L) at Kabat position 4.

In some embodiments, the anti-VEGF-A antibody is IgG1. In some embodiments, the heavy chain has one or more mutations to modulate effector function. In some embodiments, the mutations are to one or more of the following amino acid positions (EU numbering): E233, L234, L235, G236, G237, A327, A330, and P331. In some embodiments, the mutations are selected from the group consisting of: E233P, L234V, L234A, L235A, G237A, A327G, A330S and P331S (EU numbering). In some embodiments, the mutations are (EU numbering) L234A, L235A and G237A.

In some embodiments, the cysteine residue added to the therapeutic protein via recombinant DNA technology should not be involved in Cys-Cys disulfide bond pairing. In this regard, therapeutic proteins may be dimeric. So for example, an intact anti-VEGF-A antibody has two light chains and two heavy chains. If a Cys residue is introduced into the heavy chain for instance, the intact antibody will have two such introduced cysteines at identical positions and the possibility exists that these cysteine residues will form intra-chain disulfide bonds. If the introduced cysteine residues form Cys-Cys disulfide bonds or have a propensity to do so, that introduced Cys residue will not be useful for conjugation. It is known in the art how to avoid positions in the heavy and light chains that will give rise to intra-chain disulfide pairing. See, e.g., U.S. Patent Application No. 2015/0158952.

In some embodiments, the cysteine residue introduced via recombinant DNA technology is selected from the group consisting of (EU numbering) Q347C and L443C. In some embodiments, the cysteine residue is L443C (EU numbering, or 449C in SEQ ID NO: 1). In some embodiments, the heavy chain the antibody has the amino acid sequence set forth in SEQ ID NO. 1 and the light chain has the amino acid sequence of SEQ ID NO. 2.

In some embodiments, the sulfhydral specific reacting group is maleimide.

In some embodiments, the half-life extending moiety is selected from the group consisting of polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(1-hydroxymethyethylene hydroxymethylformal) (PHF), a zwitterionic polymer, a phosphorylcholine containing polymer and a polymer comprising 2-methacryloyloxy-2'-ethyltrimethylammoniumphosphate (MPC).

In some embodiments, the half-life extending moiety is a zwitterionic polymer. In some embodiments, the zwitterion is phosphorylcholine, i.e. a phosphorylcholine containing polymer. In some embodiments, the polymer is composed of MPC units.

In some embodiments, the MPC polymer has three or more arms. In some embodiments, the MPC polymer has 2, 3, 4, 5, 6, 7, 8, 9, 10, 11 or 12 arms. In some embodiments, the MPC polymer has 3, 6, or 9 arms. In some embodiments, the MPC polymer has 9 arms. In some embodiments, the polymer is synthesized with an initiator comprising 2, 3, 4, 5, 6, 7, 8, 9, 10, 11, 12, or more polymer initiation sites In some embodiments, the MPC polymer has a molecular weight between about 300,000 and 1,750,000 Da. In some embodiments, the MPC polymer has a molecular weight between about 500,000 and 1,000,000 Da or between about 600,000 to 900,000 Da.

In some embodiments, the method of preparing a therapeutic protein-half life extending moiety conjugate has an additional step of contacting the therapeutic protein with a thiol reductant under conditions that produce a reduced cysteine sulfhydryl group. As discussed above, it is preferable that the cysteine residue added via recombinant DNA technology are unpaired, i.e. are not involved in Cys-Cys intra chain disulfide bonds or are not substantially involved in such bonding. However, Cys residues which are not involved in such Cys-Cys disulfide bonding and are free for conjugation are known to react with free cysteine in the culture media to form disulfide adducts. See, e.g., WO 2009/052249. A cysteine so derivatized will not be available for conjugation. To free the newly added cysteine from the disulfide adduct, the protein after purification is treated with a reducing agent, e.g., dithiothreitol. However, such treatment with a reducing agent will reduce all of the cysteine residues in the therapeutic protein, including native cysteines many of which are involved in inter and intra chain Cys-Cys disulfides bonds. The native Cys-Cys disulfides are generally crucial to protein stability and activity and they should be reformed. In some embodiments, all native (e.g., inter and intra) Cys-Cys disulfides are reformed.

To reform native inter and intra-chain disulfide residues, after reduction to remove the cysteine disulfide adducts, the therapeutic protein is exposed to oxidizing conditions and/or oxidizing agents for a prescribed period of time, e.g., overnight. In some embodiments, ambient air exposure overnight can be used to achieve reformation of the native disulfide bonds. In some embodiments, an oxidizing agent is employed to restore the native disulfides. In some embodiments, the oxiding agent is selected from the group consisting of acqueous CuSO4 and dehydroascorbic acid (DHAA). In some embodiments, the oxidizing agent is DHAA. In some embodiments, the range of DHAA used is in the range of 5-30 equivalents. In some embodiments, the range is 10-20 equivalents. In some embodiments, the range is 15 equivalents.

In some embodiments, the thiol reductant is selected from the group consisting of: Tris[2-carboxyethyl]phosphine hydrochloride (TCEP), dithiothreitol (DTT), dithioerythritol (DTE), sodium borohydride ($NaBH_4$), sodium cyanoborohydride ($NaCNBH_3$), β-mercaptoethanol (BME), cysteine hydrochloride and cysteine. In some embodiments, the thiol reductant is TCEP.

In some embodiments, the thiol reductant concentration is between 1 and 100 fold molar excess relative to the therapeutic protein concentration. In some embodiments, the thiol reductant concentration is between 20 to 50 fold molar excess relative to the therapeutic protein concentration. In some embodiments, the thiol reductant is removed following incubation with the therapeutic protein prior to oxidation of the therapeutic protein.

In some embodiments, the method for conjugating a therapeutic protein to a half-life extending moiety has a further step of purifying the therapeutic protein conjugate after conjugation. In some embodiments, the therapeutic protein conjugate is purified using a technique selected from the group consisting of ion exchange chromatography, hydrophobic interaction chromatography, size exclusion chromatography, and affinity chromatography or combinations thereof.

In some embodiments, the therapeutic protein conjugate retains at least 20% biological activity relative to unconjugated therapeutic protein. In some embodiments, the therapeutic protein conjugate retains at least 50% biological activity relative to unconjugated therapeutic protein. In some embodiments, the therapeutic protein conjugate retains at least 90% biological activity relative to native therapeutic protein.

In some embodiments, the therapeutic protein conjugate has an increased half-life relative to unconjugated therapeutic protein. In some embodiments, the therapeutic protein conjugate has at least a 1.5 fold increase in half-life relative to unconjugated therapeutic protein. In some embodiments, the therapeutic protein conjugate has at least a 5 fold increase in half-life relative to unconjugated therapeutic protein.

In some embodiments, the zwitterionic polymer of the method of conjugating a therapeutic protein to a half-life extending moiety is a radically polymerizable monomer having a zwitterionic group and the method has a further step of polymerizing the free radically polymerizable zwitterionic monomer in a polymerization medium to provide a polymer, the medium comprising: the radically polymerizable zwitterionic monomer; a transition metal catalyst $M_t^{(q-1)+}$ wherein M t is a transition metal, q is a higher oxidation state of the metal and q−1 is a lower oxidation state of the metal, wherein the metal catalyst is supplied as a salt of the form $Mt^{(q-1)+}X'_{(q-1)}$ wherein X' is a counterion or group or the transition metal catalyst is supplied in situ by providing the inactive metal salt at its higher oxidation state $M_t^{q+}X'_q$ together with a reducing agent that is capable of reducing the transition metal from the oxidized inactive state to the reduced active state; a ligand; and an initiator.

To function as an ATRP transition metal catalyst, the transition metal should have at least two readily accessible oxidation states separated by one electron, a higher oxidation state and a lower oxidation state. In ATRP, a reversible redox reaction results in the transition metal catalyst cycling between the higher oxidation state and the lower oxidation state while the polymer chains cycle between having propagating chain ends and dormant chain ends. See, e.g., U.S. Pat. No. 7,893,173.

In some embodiments, the radically polymerizable zwitterionic monomer is selected from the group consisting of

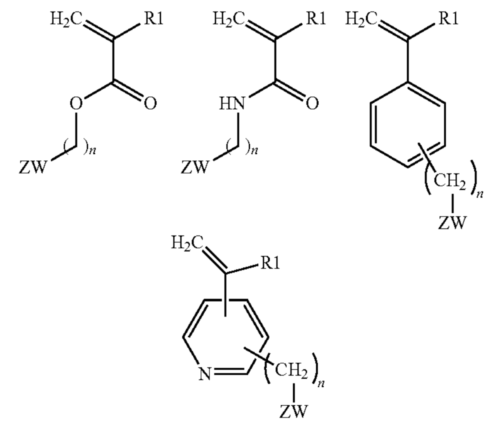

wherein R1 is H or $C_{1-6}$ alkyl, ZW is a zwitterion and n is an integer from 1-6.

In some embodiments, the radically polymerizable monomer is

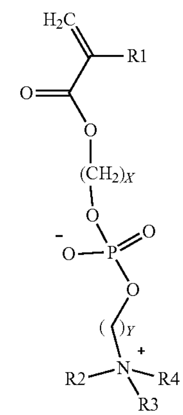

wherein R1 is H or $C_{1-6}$ alkyl, R2, R3, R4 are the same or different and are H or $C_{1-4}$ alkyl and X and Y are the same or different and are integers from 1-6. In some embodiments, R1, R2, R3 and R4 are each methyl and X and Y are each 2.

In some embodiments, the radically polymerizable monomer is

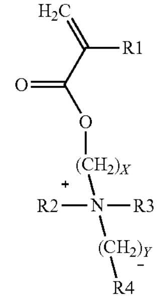

wherein R1 is H or $C_{1-6}$ alkyl, R2 and R3 are the same or different and are H or $C_{1-4}$ alkyl, R4 is $PO_4$—, $SO_3$— or $CO_2$— and X and Y are the same or different and are integers from 1-6. In some embodiments, R1, R2 and R3 are methyl, R4 is $PO_4$— and X and Y are each 2.

In some embodiments, the monomer is

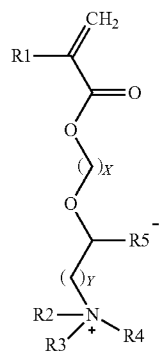

wherein R1 is H or $C_{1-6}$ alkyl, R2, R3 and R4 are the same or different and are H or $C_{1-4}$ alkyl, R5 is $PO_4$—, $SO_3$— or $CO_2$— and X and Y are the same or different and are integers from 1-6. In some embodiments, R1, R2, R3 and R4 are methyl, R5 is $PO_4$— and X and Y are 2.

In some embodiments, the transition metal Mt is selected from the group consisting of Cu, Fe, Ru, Cr, Mo, W, Mn, Rh, Re, Co, V, Zn, Au, and Ag. In some embodiments, the metal catalyst is supplied as a salt of the form $Mt^{(q-1)+}X'_{(q-1)}$. $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^{+}$, $V^{2+}$, $Zn^{+}$, $Au^{+}$, and $Ag^{+}$ and X' is selected from the group consisting of halogen, $C_{1-6}$ alkoxy, $(SO_4)_{1/2}$, $(PO_4)_{1/3}$, $(R7PO_4)_{1/2}$, $(R7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. In some embodiments, $M_t^{(q-1)+}$ is $Cu^{1+}$ and X' is Br.

In some embodiments, $M_t^{(q-1)+}$ is supplied in situ. In some embodiments, $M_t^{q+}X_q$ is $CuBr_2$. In some embodiments, the reducing agent is an inorganic compound. In some embodiments, the reducing agent is selected from the group consisting of a sulfur compound of a low oxidation level, sodium hydrogen sulfite, an inorganic salt comprising a metal ion, a metal, hydrazine hydrate and derivatives of such compounds. In some embodiments, the reducing agent is a metal. In some embodiments, the reducing agent is Cu °.

In some embodiments, the reducing agent is an organic compound. In some embodiments, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

In some embodiments, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, N,N,N',N',N"-Pentamethyldiethylenetriamine, 1,1,4,7,10,10-Hexamethyltriethylenetetramine, Tris(2-dimethylaminoethyl)amine, N,N-bis(2-pyridylmethyl)octadecylamine, N,N,N',N'-tetra[(2-pyridal)methyl] ethylenediamine, tris[(2-pyridyl)methyl]amine, tris(2-aminoethyl)amine, tris(2-bis(3-butoxy-3-oxopropyl) aminoethyl)amine, tris(2-bis(3-(2-ethylhexoxy)-3-oxopropyl)aminoethyl)amine and Tris(2-bis(3-dodecoxy-3-oxopropyl)aminoethyl)amine. In some embodiments, the ligand is 2,2'-bipyridine.

In some embodiments the initiator has the structure:

$$R1—R2—(R3)_s$$

wherein R1 is a nucleophilic reactive group, R2 comprises a linker, and R3 comprises a polymer synthesis initiator moiety having the structure

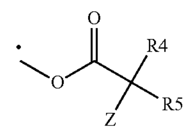

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof; Z is a halogen, —OR (where R is —H, methyl, ethyl, propyl, or isopropyl), —SCN or —NCS; and s is an integer between 1 and 20.

In some embodiments, Z is Br and R4 and R5 are each methyl. In some embodiments, R1 is selected from the group consisting of —$NH_2$, —OH, and —SH.

In some embodiments R2 is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. In some embodiments, R2 is

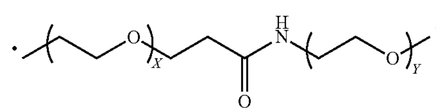

wherein X and Y are the same or different and are integers from 1-20. In some embodiments, X and Y are each 4.

In some embodiments, R3 is

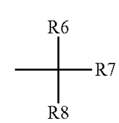

wherein R6, R7 and R8 are the same or different and are selected from the group consisting of

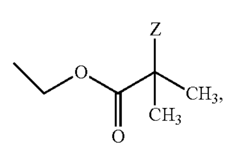

-continued
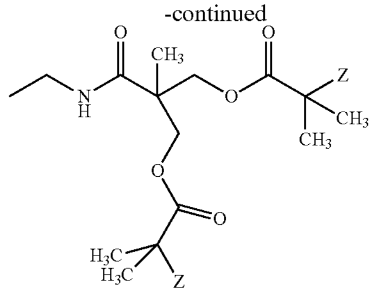
and
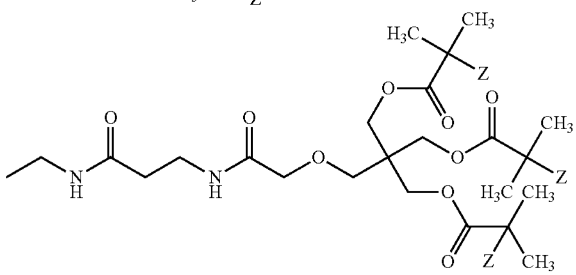
wherein Z is —OR (where R is —H, methyl, ethyl, propyl, or isopropyl), —SCN, —NCS, —F, —Cl, —Br or —I. In some embodiments, Z is —Br and R6, R7 and R8 are each
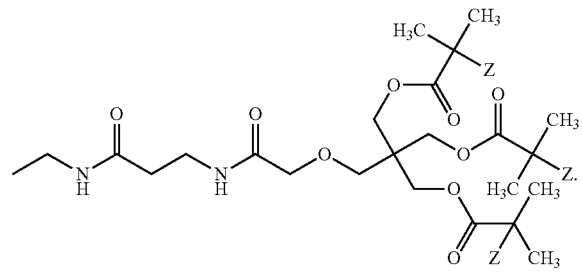
In some embodiments, the initiator has the structure:
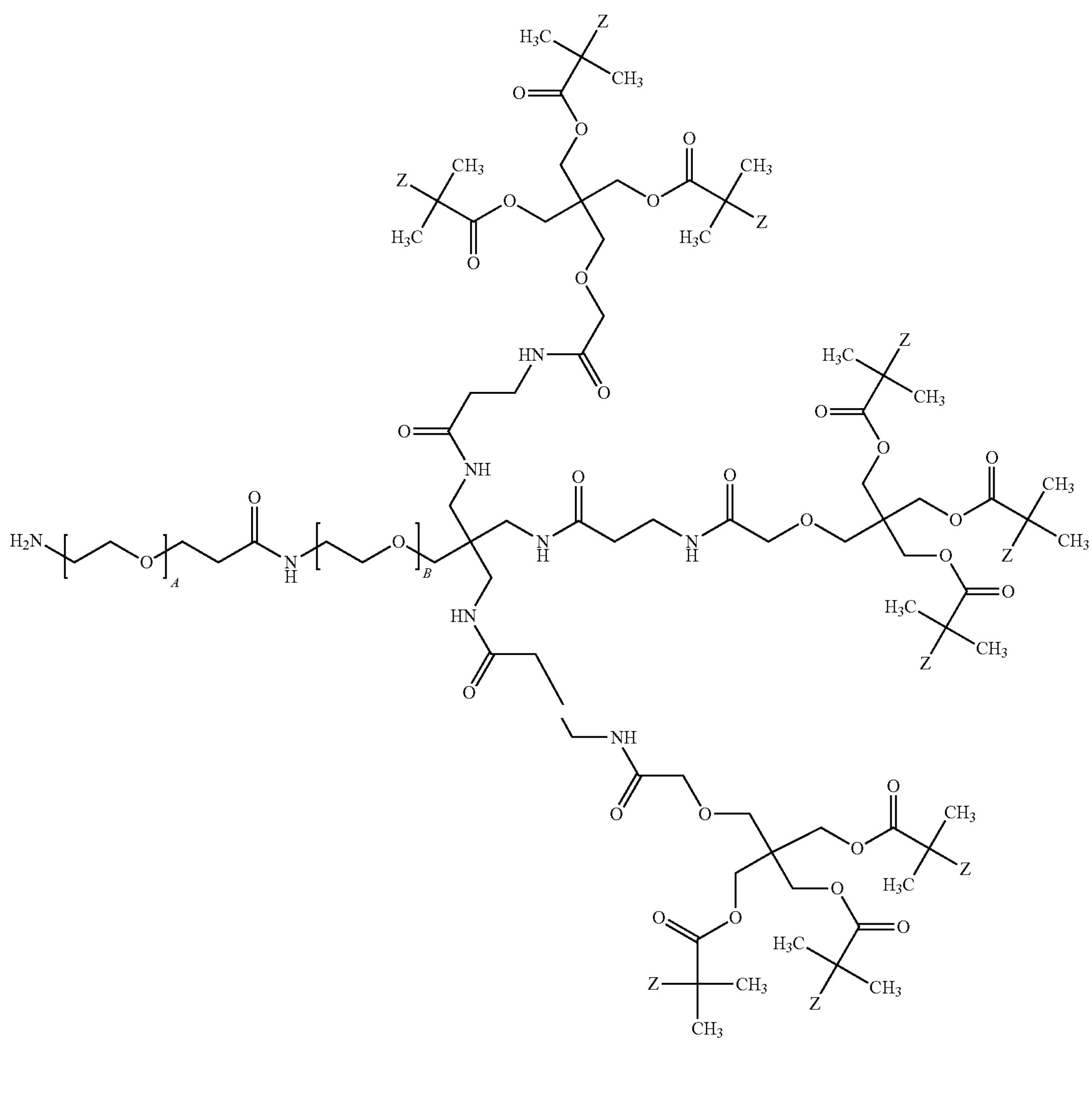

wherein A and B are the same or different and are integers from 2 to 12 and Z is any halide, for example Br. In some embodiments, A and B are each 4.

In some embodiments, the method further has the step of reacting the polymer with a maleimide reagent to provide a polymer having a terminal maleimide. In some embodiments, the maleimide compound is

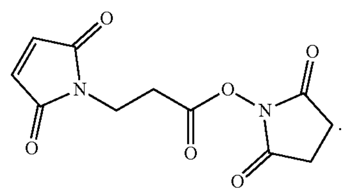 [SMILES: O=C(CCN1C(=O)C=CC1=O)ON1C(=O)CCC1=O]

Method of Treatment

In some embodiments, a method is presented for the treatment or prophylaxis of an ocular disease having the step of administering a therapeutic protein selected from the group consisting of an anti-VEGF-A antibody (and conjugates thereof), and anti-VEGF protein conjugate (e.g., an aflibercept biopolymer conjugate). In some embodiments, any one or more of the antibodies or antibody conjugates or protein conjugates provided herein can be used as treatment and/or prophylaxis for an ocular disease. The method includes administering to the subject any one or more of the antibodies or antibody conjugates provided herein.

In some embodiments a method for treatment or prophylaxis of an ocular disease is provided. The method comprises administering an effective dose of any of the an antibody and/or antibody conjugates and/or protein conjugates described herein to a subject in need thereof. In some embodiments, the disease can be age-related macular degeneration (AMD) or diabetic macular edema (DME). In some embodiments, the disease can be wet AMD. In some embodiment, the eye disorder is wet AMD without a high pigment epithelial detachment (PED). In some embodiments, a subject has high PED when the baseline central subfield retinal thickness (CST) in an eye of the subject is 500 microns or greater.

In some embodiments, the ocular disease is selected from one or more of the group consisting of diabetic retinopathy, choroidal neovascularization (CNV), age-related macular degeneration (AMD), diabetic macular edema (DME), pathological myopia, von Hippel-Lindau disease, histoplasmosis of the eye, central retinal vein occlusion (CRVO), branched central retinal vein occlusion (BRVO), corneal neovascularization, retinal neovascularization, retinopathy of prematurity (ROP), subconjunctival hemorrhage, and hypertensive retinopathy. In some embodiments, the ocular disease is diabetic retinopathy.

In some embodiments, the antibody or antibody conjugate or protein conjugate is administered no more frequently than once a month. In some embodiments, the antibody or conjugate thereof is administered two times per month or weekly. In some embodiments, the antibody or conjugate thereof is administered once every two months, once every three months, once every four months, once every five months, once every six months, once every seven months, once every eight months, once every nine months, once every ten months, once every eleven months, or once every twelve months.

In some embodiments, one or more of the compositions provided herein can allow for a reduction in the consequences of high treatment burdens from the use of intravitreal injection of anti-VEGF agents for the treatment of the wet (proliferative) form of age related macular degeneration (AMD). Real world outcomes for patients with wet AMD lag behind the clinical outcomes demonstrated in the phase 3 clinical studies such as the MARINA and ANCHOR studies with Lucentis® (ranibizumab) and the VIEW 1 and VIEW 2 studies with Eylea® (aflibercept). An anti-VEGF therapeutic with a longer ocular residence time such that it can be administered less frequently and therefore with a more patient-tolerable profile can bring real world outcomes closer to phase 3 clinical outcomes for more patients.

In some embodiments, compounds, including antibody conjugates and anti-VEGF-A antibodies, and anti-VEGF protein conjugates (e.g., an aflibercept biopolymer conjugates), described herein are used to treat patients who have background or nonproliferative diabetic retinopathy but have little or no vision impairment. In some embodiments, such patients are dosed less than once a month via intravitreal injection. In some embodiments, such patients are dosed six times a year. In some embodiments, such pateints are dosed no more than four times a year. In some embodiments, the patients are dose no more than three times a year. In some embodiments, the patients are dosed no more than twice a year. In some embodiments, the patients are dosed no more than once a year. In some embodiments, the subject receives the antibody or antibody conjugate or protein conjugate via intravitreal injection.

The therapeutic proteins (e.g., both antibodies and antibody conjugates) described herein can be employed by expression of such polypeptides in vivo in a patient, i.e., gene therapy.

There are two major approaches to getting the nucleic acid (optionally contained in a vector) into the patient's cells: in vivo and ex vivo. For in vivo delivery the nucleic acid is injected directly into the patient, usually at the sites where the therapeutic protein is required, i.e., where biological activity of the therapeutic protein is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g, U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (including retroviral) particle with a cellular receptor, followed by introduction of the nucleic acids contained by the particle into the cell. A commonly used vector for ex vivo delivery of the gene is a retrovirus.

In some embodiments, the in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinison et al., Cancer Investigation, 14(1): 54-65 (1996)). In some embodiments the vectors for use in gene therapy are viruses, which include adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the therapeutic protein, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO polypeptide from a host cell in which it is placed. In some embodiments, the signal sequence for this purpose is a mammalian signal sequence. In some embodiments, the signal is the native signal sequence for the therapeutic protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414(1990). For a review of the currently known gene marking and gene therapy protocols, see, Anderson et al., Science, 256: 808-813 (1992). See also WO 93/25673 and the references cited therein.

Suitable gene therapy and methods for making retroviral particles and structural proteins can be found in, e.g., U.S. Pat. No. 5,681,746.

In some embodiments, a method for treatment or prophylaxis of an ocular disease in a mammal is presented in which a nucleic acid molecule that encodes a therapeutic protein selected from the group consisting of an anti-VEGF-A antibody is administered.

In some embodiments, the heavy chain is that set forth in SEQ ID NO. 1 and the light chain is that set forth in SEQ ID NO. 2. In some embodiments, the nucleic acid molecule is administered via ex vivo gene therapy.

Methods of preparing an antibody conjugate suitable for use in methods of the present disclosure is found, e.g., in PCT publication number WO2017117464, which is incorporated by reference herein in its entirety.

Pharmaceutical Compositions

Therapeutic proteins can be incorporated into a pharmaceutical composition with a pharmaceutically acceptable excipient. Pharmaceutical compositions adapted for oral administration may be presented as discrete units such as capsules, as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions can be adapted for nasal administration wherein the excipient is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the excipient is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-400 mOsm/kg water.

The pharmaceutical compositions may contain preserving agents, solubilizing agents, stabilizing agents, wetting agents, emulsifiers, sweeteners, colorants, odorants, salts (substances may themselves be provided in the form of a pharmaceutically acceptable salt), buffers, coating agents or antioxidants. They may also contain therapeutically active agents in addition to the substance. The pharmaceutical compositions may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The antibodies and pharmaceutical compositions containing them may be administered in an effective regime for treating or prophylaxis of a patient's disease including, for instance, administration by oral, intravitreal, intravenous, subcutaneous, intramuscular, intraosseous, intranasal, topical, intraperitoneal, and intralesional administration. Parenteral infusions include intramuscular, intravenous, intraarterial, intraperitoneal, or subcutaneous administration or routes among others. In therapy or as a prophylactic, the active agent may be administered to an individual as an injectable composition, for example as a sterile aqueous dispersion In some embodiments the agent is isotonic or substantially isotonic.

For administration to mammals, and particularly humans, it is expected that the dosage of the active agent is from 0.01 mg/kg body weight, typically around 1 mg/kg. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited. In some embodiments, the dosage can be 0.5 to 20 mg/eye, e.g., 1, 2, 3, 4, 5, 6, 7, 8, 9, 10, 11, 12, 13, 14, 15, 16, 17, 18, or 19 mg.

This dosage may be repeated as often as appropriate (e.g., weekly, fortnightly, monthly, once every two months, quarterly, twice a year, yearly). If side effects develop the amount and/or frequency of the dosage can be reduced, in accordance with normal clinical practice. In one embodiment, the pharmaceutical composition may be administered once every one to thirty days. In one embodiment, the pharmaceutical composition may be administered twice every thirty days. In one embodiment, the pharmaceutical composition may be administered once a week.

The antibodies and pharmaceutical compositions can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

The antibodies and pharmaceutical compositions disclosed herein can be used for treatment or prophylaxis of disease, particularly the ocular diseases or conditions described herein.

The anti-VEGF antibody conjugates, or anti-VEGF protein conjugates, and pharmaceutical compositions containing them may be formulated for and administered by ocular, intraocular, and/or intravitreal injection, and/or juxtascleral injection, and/or subretinal injection and/or subtenon injection, and/or superchoroidal injection and/or subconjunctival and/or topical administration in the form of eye drops and/or ointment. Such antibodies and compositions can be delivered by a variety of methods, e.g. intravitreally as a device and/or a depot that allows for slow release of the compound into the vitreous, including those described in references such as Intraocular Drug Delivery, Jaffe, Ashton, and Pearson, editors, Taylor & Francis (March 2006). In one example, a device may be in the form of a minipump and/or a matrix and/or a passive diffusion system and/or encapsulated cells that release the compound for a prolonged period of time (Intraocular Drug Delivery, Jaffe, Ashton, and Pearson, editors, Taylor & Francis (March 2006)).

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMID and CNV, is direct intravitreal injection. Intravitreal injections are usually repeated at intervals which depend on the patient's condition, and the properties and half-life of the drug delivered.

Therapeutic antibodies and related conjugates generally are placed into a container having a sterile access port, for example, an intravenous solution bag or vial having a stopper pierceable by a hypodermic injection needle. Such compositions may also be supplied in the form of pre-filled syringes.

A "stable" formulation is one in which the protein or protein conjugated to a polymer of other half-life extending moiety therein essentially retains its physical stability and/or chemical stability and/or biological activity upon storage. By "stable" is also meant a formulation which exhibits little or no signs of instability, including aggregation and/or deamidation. For example, the formulations provided may remain stable for at least two year, when stored as indicated at a temperature of 5-8° C. Suitable formulations for an anti-VEGF antibody conjugate of the present disclosure is described in e.g., PCT publication number WO2017117464, which is incorporated by reference herein in its entirety.

Various analytical techniques for measuring protein stability are available in the art and are reviewed in Peptide and Protein Drug Delivery, 247-301 (Vincent Lee ed., New York, N.Y., 1991) and Jones, 1993 Adv. Drug Delivery Rev. 10: 29-90, for examples. Stability can be measured at a selected temperature for a selected time period. In some embodiments the storage of the formulations is stable for at least 6 months, 12 months, 12-18 months, or for 2 or more years.

A protein, such as an antibody or fragment thereof, "retains its physical stability" in a pharmaceutical formulation if it shows no signs of aggregation, precipitation, deamidation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

A protein-polymer conjugate "retains its chemical stability" the chemical bond between the protein and the polymer is maintained intact, e.g., it is not hydrolyzed or otherwise disrupted. The protein part of the conjugate retains its chemical stability as described above.

By "isotonic" is meant that the formulation of interest has essentially the same osmotic pressure as human blood or the vitreous for intravitreal injections. Isotonic formulations will generally have an osmotic pressure from about 250 to 400 mOsm. Isotonicity can be measured using a vapor pressure or ice-freezing type osmometer, for example.

As used herein, "buffer" refers to a buffered solution that resists changes in pH by the action of its acid-base conjugate components. In some embodiments, the buffer has a pH from about 3.0 to about 8.0; for example from about 4.5 to 8; or about pH 6 to about 7.5; or about 6.0 to about 7.0, or about 6.5-7.0, or about pH 7.0 to about 7.5; or about 7.1 to about 7.4. A pH of any point in between the above ranges is also contemplated.

In some embodiments, "PBS" phosphate buffered saline, Tris based buffers and histidine based buffers are used.

In some embodiments, the PBS buffer is made up of at least $Na_2HPO_4$, $KH_2PO_4$ and NaCl adjusted so as to provide the appropriate pH. In some embodiments, the buffer may contain other pharmaceutical excipients such as KCl and other salts, detergents and/or preservatives so as to provide a stable storage solution.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In some embodiments, formulations, to be safe for human use or for animal testing, should have sufficiently low levels of endotoxin. "Endotoxin" is lipopolysaccharide (LPS) derived from the cell membrane of Gram-negative bacteria. Endotoxin is composed of a hydrophilic polysaccharide moiety covalently linked to a hydrophobic lipid moiety (lipid A). Raetz C R, Ulevitch R J, Wright S D, Sibley C H, Ding A, Nathan CF. 1991. Gram-negative endotoxin: an extraordinary lipid with profound effects on eukaryotic signal transduction. FASEB J. 5(12):2652-2660. Lipid A is responsible for most of the biological activities of endotoxin, i.e., its toxicity. Endotoxins are shed in large amount upon bacterial cell death as well as during growth and division. They are highly heat-stable and are not destroyed under regular sterilizing conditions. Extreme treatments with heat or pH, e.g., 180-250° C. and over 0.1 M of acid or base must be used (Petsch D, Anspach F. 2000. Endotoxin removal from protein solutions. J Biotechnol. 76: 97-119). Such conditions of course would be highly detrimental to biological drugs.

In the biotech and pharmaceutical industries, it is possible to find endotoxin during both production processes and in final products. As bacteria can grow in nutrient poor media, including water, saline and buffers, endotoxins are prevalent unless precautions are taken. Endotoxin injection into an animal or human causes a wide variety of pathophysiological effects, including endotoxin shock, tissue injury and even death. Ogikubo Y, Ogikubo Y, Norimatsu M, Noda K, Takahashi J, Inotsume M, Tsuchiya M, Tamura Y. 2004. Evaluation of the bacterial endotoxin test for quantifications of endotoxin contamination of porcine vaccines. Biologics 32:88-93.

Pyrogenic reactions and shock are induced in mammals upon intravenous injection of endotoxin at low concentrations (1 ng/mL) (Fiske J M, Ross A, VanDerMeid R K, McMichael J C, Arumugham. 2001. Method for reducing endotoxin in *Moraxella catarrhalis* UspA2 protein preparations. J Chrom B. 753:269-278). The maximum level of endotoxin for intravenous applications of pharmaceutical and biologic product is set to 5 endotoxin units (EU) per kg of body weight per hour by all pharmacopoeias (Daneshiam M, Guenther A, Wendel A, Hartung T, Von Aulock S. 2006. In vitro pyrogen test for toxic or immunomodulatory drugs. J Immunol Method 313:169-175). EU is a measurement of the biological activity of an endotoxin. For example, 100 pg of the standard endotoxin EC-5 and 120 pg of endotoxin from *Escherichia coli O*111:B4 have activity of 1 EU (Hirayama C, Sakata M. 2002. Chromatographic removal of endotoxin from protein solutions by polymer particles. J Chrom B 781:419-432). Meeting this threshold level has always been a challenge in biological research and pharmaceutical industry (Berthold W, Walter J. 1994. Protein Purification: Aspects of Processes for Pharmaceutical Products. Biologicals 22:135-150; Petsch D, Anspach F B. 2000. Endotoxin removal from protein solutions. J Biotech 76:97-119).

The presence of endotoxin in drugs to be delivered via intravitreal injection is of particular concern. Intravitreal injection of drug (penicillin) was first performed in 1945 by Rycroft. Rycroft B W. 1945. Penicillin and the control of deep intra-ocular infection. British J Ophthalmol 29 (2): 57-87. The vitreous is a chamber where high level of drug can be introduced and maintained for relatively long periods of time. The concentration of drug that can be achieved via intravitreal injection far exceeds what can be generated by topical administration or by systemic administration (e.g. intravenous).

One of the most dangerous complications potentially arising from intravitreal injections is endophthalmitis. Endophthalmitis falls into two classes: infectious and sterile. Infectious endophthalmitis is generally cause by bacteria, fungi or parasites. The symptoms of infectious endophthalmitis include severe pain, loss of vision, and redness of the conjunctiva and the underlying episclera. Infectious endophthalmitis requires urgent diagnosis and treatment. Possible treatments include intravitreal injection of antibiotics and pars plana vitrectomy in some cases. Enucleation may be called for to remove a blind and painful eye. See, e.g., Christy N E, Sommer A. 1979. Antibiotic prophylaxis of postoperative endophthalmitis. Ann Ophthalmol 11 (8): 1261-1265.

Sterile endophthalmitis in contrast does not involve an infectious agent and can be defined as the acute intraocular inflammation of the vitreous cavity that resolves without the need of intravitreal antibiotics and/or vitreoretinal surgery. If a vitreous microbiological study has been done, it needs to be negative culture proven to sustain a diagnosis of sterile endophthalmitis. Marticorena J, Romano V, Gomez-Ulla F. 2012 "Sterile Endophthalmitis after Intravitreal Injections" Med Inflam. 928123.

It has been observed that intravitreal injection of biological drugs contaminated with endotoxin can result in sterile endophthalmitis. Marticorena, et al. Bevacizumab (Avastin) is approved by the Food and Drug Administration for the treatment of glioblastoma and of metastatic colorectal cancer, advanced nonsquamous non-small-cell lung cancer and metastatic kidney cancer. Bevacizumab is also widely used off label as a treatment for wet AMD. Bevacizumab comes from the manufacturer as a 100 mg/4 ml. This solution cannot be directly used for intravitreal injection and should be compounded by a pharmacist. Clusters of sterile endophthalmitis have been observed and are theorized to be cause by inadvertent contamination of bevacizumab by endotoxin by the compounding pharmacist.

Given the dire clinical results of intravitreal injection of endotoxin, the total amount of endotoxin that can be given to a patient via intravitreal dosing is highly limited. In some embodiments, a solution having an antibody or antibody-conjugate is provided having an endotoxin level that does not exceed 5.0 EU/ml. In some embodiments, the endotoxin level does not exceed 1.0 EU/ml. In some embodiments, the endotoxin level does not exceed 0.5 EU/ml. In some embodiments, the endotoxin level does not exceed 0.2 EU/ml. In some embodiments, the endotoxin level does not exceed 2, 1, 0.5, 0.2, 0.1, 0.09, 0.08, 0.07, 0.06, 0.05, 0.04, 0.03, 0.02 or 0.01 EU/ml.

Two commonly used FDA-approved tests for the presence of endotoxin are the rabbit pyrogen test and Limulus Amoebodyte Lysate (LAL) assay (Hoffman S, et al. 2005. International validation of novel pyrogen tests based on human monocytoid cells J. Immunol. Methods 298:161-173; Ding J L, Ho B A. 2001. New era in pyrogen testing. Biotech. 19:277-281). The rabbit pyrogen test was developed in the 1920s and involves monitoring the temperature rise in a rabbit injected with a test solution. However, use of the rabbit pyrogen test has greatly diminished over the years due to expense and long turnaround time. Much more common is the LAL test. LAL is derived from the blood of a horseshoe crab and clots upon exposure to endotoxin.

One of the simplest LAL assays is the LAL gel-clot assay. Essentially, the LAL clotting assay is combined with a serial dilution of the sample in question. Formation of the gel is proportional to the amount of endotoxin in the sample. Serial dilutions are prepared from the sample and each dilution assayed for its ability to form LAL gel. At some point a negative reaction is contained. The amount of endotoxin in the original sample can be estimated from the dilution assay.

Other LAL tests have also been developed, including the turbidimetric LAL assay (Ong K G, Lelan J M, Zeng K F, Barrett G, Aourob M, Grimes C A. 2006. A rapid highly-sensitive endotoxin detection system. Biosensors and Bioelectronics 21:2270-2274) and the chromogenic LAL assay (Haishima Y, Hasegawa C, Yagami T, Tsuchiya T, Matsuda R, Hayashi Y. 2003. Estimation of uncertainty in kinetic-colorimetric assay of bacterial endotoxins. J Pharm Biomed Analysis. 32:495-503). The turbidimetric and chromogenic assays are much more sensitive and quantitative than the simple gel-clot dilution assay.

In some embodiments a method of reducing the amount of endotoxin in a composition having an antibody disclosed herein is provided. The method having the steps of contacting the composition with an affinity chromatography resin that binds to the antibody; eluting the antibody from the affinity chromatography resin to form an affinity chromatography eluent having the antagonist; contacting the affinity chromatography eluent with an ion-exchange resin that binds the antibody; and eluting the antibody from the ion-exchange resin, wherein the antibody eluted from the ion-exchange resin is substantially free from endotoxin.

The above method for reducing the amount of endotoxin, or other method or process recited herein, can be performed in the order described in the steps above or it can optionally be performed by varying the order of the steps or even repeating one or more of the steps. In one embodiment, the method of reducing the amount of endotoxin in a composition is performed in the order of the described steps. In some embodiments, the affinity chromatography resin contacting, washing and eluting steps are repeated in the same order more than one time before contacting the affinity chromatography eluent with the ion exchange resin. The method can also include a filtering step using, for example, a 0.1 micron, 0.22 micron, or 0.44 micron filter, that can be performed on either one or more of the eluents removed after each resin binding step.

In certain instances, the steps of contacting the composition with affinity chromatography resin, washing and eluting the antibody from the affinity chromatography resin can be repeated more than one time before contacting the first eluent with an ion-exchange resin. In one embodiment, the affinity chromatography resin comprises a recombinant Protein A ("rProteinA") resin. One example of a suitable recombinant Protein A resin is rProteinA Sepharose FF® resin (Amersham, Piscataway, N.J.). In another embodiment, a suitable affinity chromatography resin would comprise a protein G chromatography resin. In other embodiments, a suitable affinity chromatography resin comprises a mixed Protein A/Protein G resin. In other embodiments, a suitable affinity chromatography resin comprises a hydrophobic charge induction resin that comprises a 4-mercaptoethylpyridine ligand such as a MEP HyperCel® resin (BioSepra, Cergy, Saint Christophe, France).

In some embodiments, the ion exchange resin comprises an anion-exchange resin. As will be known by the person skilled in the art, ion exchangers may be based on various materials with respect to the matrix as well as to the attached charged groups. For example, the following matrices may be used, in which the materials mentioned may be more or less cross-linked: MacroCap Q (GE Healthcare Biosciences, Piscataway, NJ), agarose based (such as Sepharose CL-6B®, Sepharose Fast Flow® and Sepharose High Performance 0), cellulose based (such as DEAE Sephacel®), dextran based (such as Sephadex®), silica based and synthetic polymer based. For the anion exchange resin, the charged groups, which are covalently attached to the matrix, may, for example, be diethylaminoethyl, quaternary aminoethyl, and/or quaternary ammonium. In some embodiments the anion-exchange resin comprises a quaternary amine group. An exemplarily anion-exchange resin that has a quaternary amine group for binding the anti-M-CSF antibody is a Q Sepharose® resin (Amersham, Piscataway, N.J.).

In other aspects, if the endotoxin levels are higher than desired after subjecting the composition to the aforementioned anion-exchange chromatography step, the composition may in the alternative be subjected to a cation exchange resin. In some embodiments, any endotoxin in the composition should have a differential binding to the ion-exchange resin than the protein in question to allow purification of the protein from the endotoxin. In this regard, endotoxin is negatively charged and will generally bind to an anion exchange resin. If both the protein and the endotoxin bind to the anion exchange resin, purification of one from the other may be effectuated by using a salt gradient to elute the two into different fractions. The relative binding of the protein to a particular resin may also be effected by changing the pH of the buffer relative to the pI of the protein. In some embodiments, cation-exchange chromatography is the sole ion-exchange chromatography employed.

In some embodiments, if the endotoxin levels are too high after the anion exchange resin, the composition may be further subjected to a second ion-exchange step, for example, by contacting the compositions with a cation exchange resin and followed by a wash step, then elution from the ion-exchange resin. In some embodiments, the cation exchange resin comprises a sulfonic group for binding. Exemplary cation exchange resins are SP Sepharose® resin FF (Amersham, Piscataway, N.J.) Poros XS (CEX) (Life Technology, Grand Island, New York).

In some embodiments, after the solution of antibody protein is produced having the specified level of endotoxin, there are a number of steps prior to final formulation of the protein. In some embodiments, a half-life extending moiety is conjugated to the protein. The conjugate is then formulated into a final drug formulation which is injected into the patients. In some embodiments, the conjugate is again purified on an ion-exchange resin which can be a cation-exchange resin. In other embodiments, the protein is formulated. In all cases, normal laboratory procedures should be employed to prevent the introduction of endotoxin contaminants into the protein sample or into the protein-polymer conjugate.

EXAMPLES

Example 1: Retinal Half-Life, Retinal Bioavailability and Systemic Clearance of KSI-301

Figure 1:
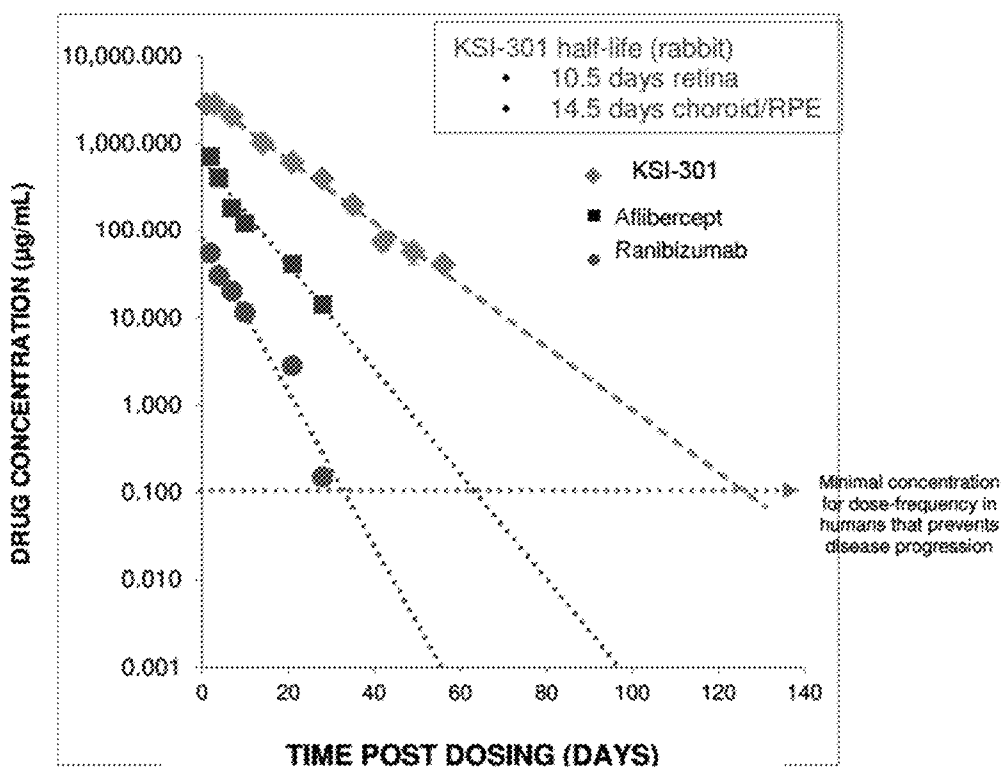
FIG. 1 is a graph showing extended half-life of KSI-301 in vivo.

KSI-301 administered intravitreally showed extended half-life in the retina and choroid/retinal pigment epithelium (RPE) in a rabbit model (FIG. 1). Comparison of the KSI-301 data with published results for Aflibercept and Ranibizumab indicated that KSI-301 exhibited superior durability compared to the other anti-VEGF therapeutics. Data are from a rabbit model. Ranibizumab data: Gaudrealt et al (2007) IOVS 46(2) 726, Gaudrealt et al (2007) Retina 27(9) 1260, Bakri et al (2007) Ophthalmol 114(12) 2179; Aflibercept data: EVER Congress Portoroz Slovenia (2008) Struble (Covance) Koehler-Stec (Regeneron). Aflibercept data was adjusted arithmetically to reflect 2,000 μg dose administered (based on rabbit in vivo dosing of 500 μg); KSI-301 data was adjusted arithmetically to reflect 5,000 μg dose administered (based on rabbit in vivo dosing of 725 μg). Error bars reflects standard error of the mean.

Figure 2:
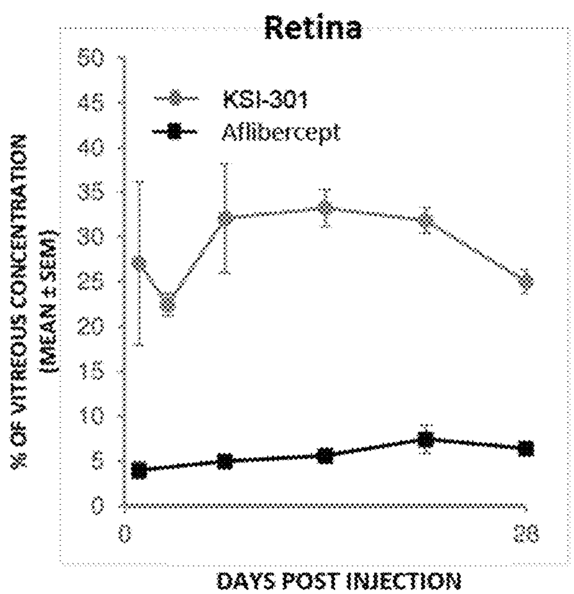
FIG. 2 is a graph showing in vivo retinal bioavailability of KSI-301.

KSI-301 administered intravitreally showed excellent retinal bioavailability (FIG. 2). Comparison of the KSI-301 data with published results for Aflibercept indicated better bioavailability of KSI-301. The data from FIG. 2 are from a covance rabbit ADME (absorption, distribution, metabolism, elimination) model. Aflibercept data (2008): EVER Congress Portoroz Slovenia Struble (Covance), Koehler-Stec (Regeneron). Error bars reflects standard error of the mean.

Figure 3:
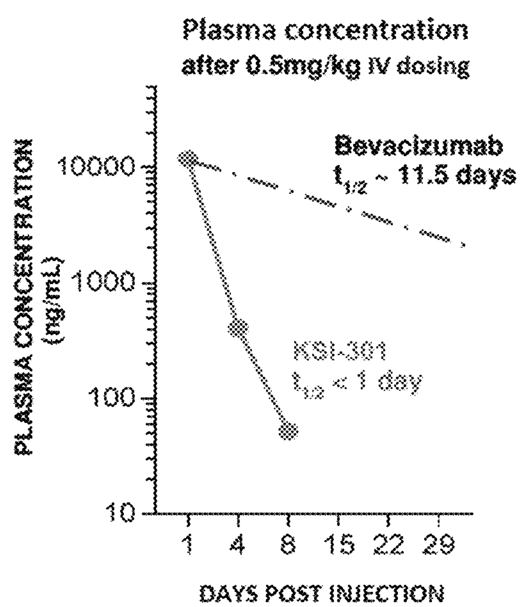
FIG. 3 is a graph showing rapid systemic clearance of intravenously administered KSI-301.

Intravenously administered KSI-301 showed rapid systemic clearance (FIG. 3). Comparison of the KSI-301 data with published results for Bevacizumab indicated faster systemic clearance for KSI-301. The Bevacizumab data was from Yeung et al 2010 Cancer Research.

Example 2: Ascending Dose Escalation Study of Intravitreal Administrations of KSI-301 in Subjects with Diabetic Macular Edema (DME)

Study Design

An ascending dose escalation study was carried out to assess ocular and systemic safety, tolerability, and establish a maximum tolerated dose (MTD) of KSI-301. One of three doses, 1.25 mg, 2.5 mg, and 5 mg (by weight of protein), were given to each subject as a single injection. Three subjects were enrolled at each dose level. Subjects were followed for a total of 12 weeks at the following time points; Day 2, Week 1, Week 2, Week 4, Week 8, and final follow up at Week 12.

At the study onset, the first 3 subjects were enrolled into the 1st dosing cohort (1.25 mg of KSI-301) and treated with a single intravitreal dose of KSI-301. Subjects were sequentially assessed with a waiting period of at least 24 hours between subjects to allow sufficient time for safety review for each subject before approving injection of the next subject.

Dose groups were enrolled in an escalating fashion once the 3rd subject at the preceding dose level completed a safety period of one week after their dose of KSI-301. Subject enrollment and dose escalation were based upon review of safety information and the occurrence of dose limiting toxicities (DLTs).

Eight of the nine enrolled subjects were previously treated with limited to no response despite multiple prior anti-VEGF treatments and severe disease (BCVA median 3, range 0-7 in the year prior)

Results

Figure 4:
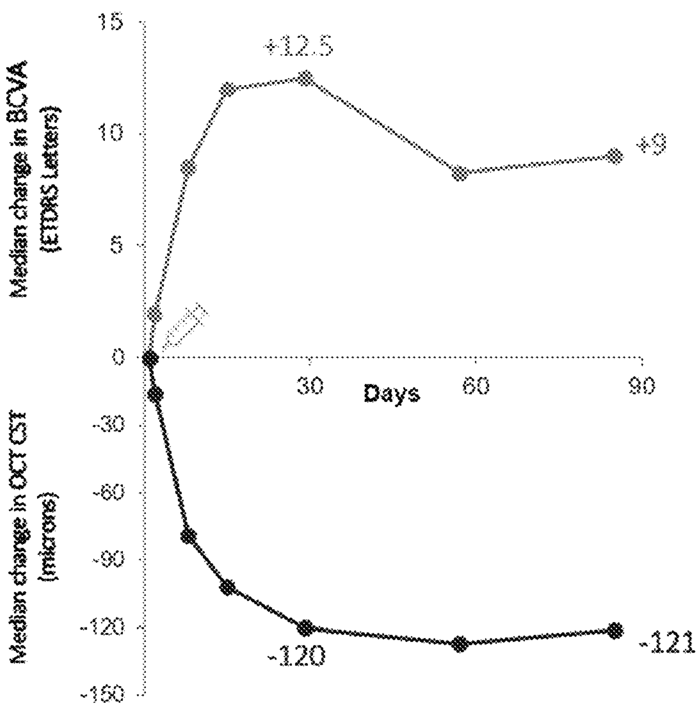
FIG. 4 is a graph showing the therapeutic effect of a single intravitreal administration of KSI-301 in patients with diabetic macular edema (DME), according to some embodiments of the present disclosure.

A single injection of KSI-301 resulted in rapid, high-magnitude responses durable to 12 weeks (FIG. 4). No intraocular inflammation and no drug-related adverse events were observed. FIG. 4: Application of 1.25 mg, 2.5 mg, or 5 mg (by weight of protein) of KSI-301 administered intravitreally to subjects with diabetic macular edema (DME). BCVA and OCT CST was measured after intravitreal injection of KSI-301. Median changes from baseline to week 12, pooled across 3 dose groups (n=9 patients total, 3 patients per dose group). Do D V, Angiogenesis 2019; Patel et al., ARVO 2019.

The results show the effectiveness of KSI-301 as a single injection in patients, most of whom had previously been treated for their DME with other anti-VEGF agents (bevacizumab, aflibercept, and/or ranibizumab). The results indicate that KSI-301 when administered intravitreally provides an improvement in visual acuity and retinal thickness (measured on OCT) in a stable fashion through 12 weeks. The experiment examined diabetic macular edema (DME) patients with severe disease (n=9). Some patients were previously treated (8/9) with limited to no response despite multiple prior anti-VEGF treatments and severe disease (median 3, range 0-7 in the year prior). The results demonstrated that a single injection of KSI-301 resulted in rapid, high-magnitude responses durable to 12 weeks. No intraocular inflammation and no drug-related adverse events were observed.

The results were obtained from application of 1.25 mg, 2.5 mg, or 5 mg (by weight of protein) of KSI-301 administered intravitreally to subjects with diabetic macular edema. The results show the effectiveness of KSI-301 as a single injection in patients, most of whom had previously been treated for their DME with other anti-VEGF agents (bevacizumab, aflibercept, and/or ranibizumab). The results indicate that KSI-301 when administered in a single dose, as done here, had unexpected therapeutic effects because the visual acuity and retinal thickness (measured on OCT) improved in a stable fashion through 12 weeks.

Example 3: Open Label, Multi-center Exploratory Study to Investigate Multiple Intravitreal Administrations of KSI-301 in Subjects with Wet Age-Related Macular Degeneration (wAMD)

The following study design and methods were followed in Examples 3, 4 and 5, unless indicated otherwise. In general, patients who were anti-VEGF treatment naïve and with either wAMD, DME, or RVO were randomly assigned to receive three monthly loading doses of either 2.5 mg or 5 mg (by weight of antibody) KSI-301 and then were followed every month or more often thereafter, and re-treated when either the physician determined that re-treatment due to disease activity was required or the patient met any re-treatment criteria.

Overall Study Design

In this study, patients who were anti-VEGF treatment naïve and with either wAMD, DME, or RVO were randomly assigned to receive three monthly loading doses of either 2.5 mg or 5 mg (by weight of antibody) KSI-301 and then were followed every month or more often thereafter, and retreated when either the physician determined that re-treatment due to disease activity is required or the patient meets any of the re-treatment criteria. These criteria were related to signs of disease recurrence and/or vision loss due to disease recurrence.

Figure 5:
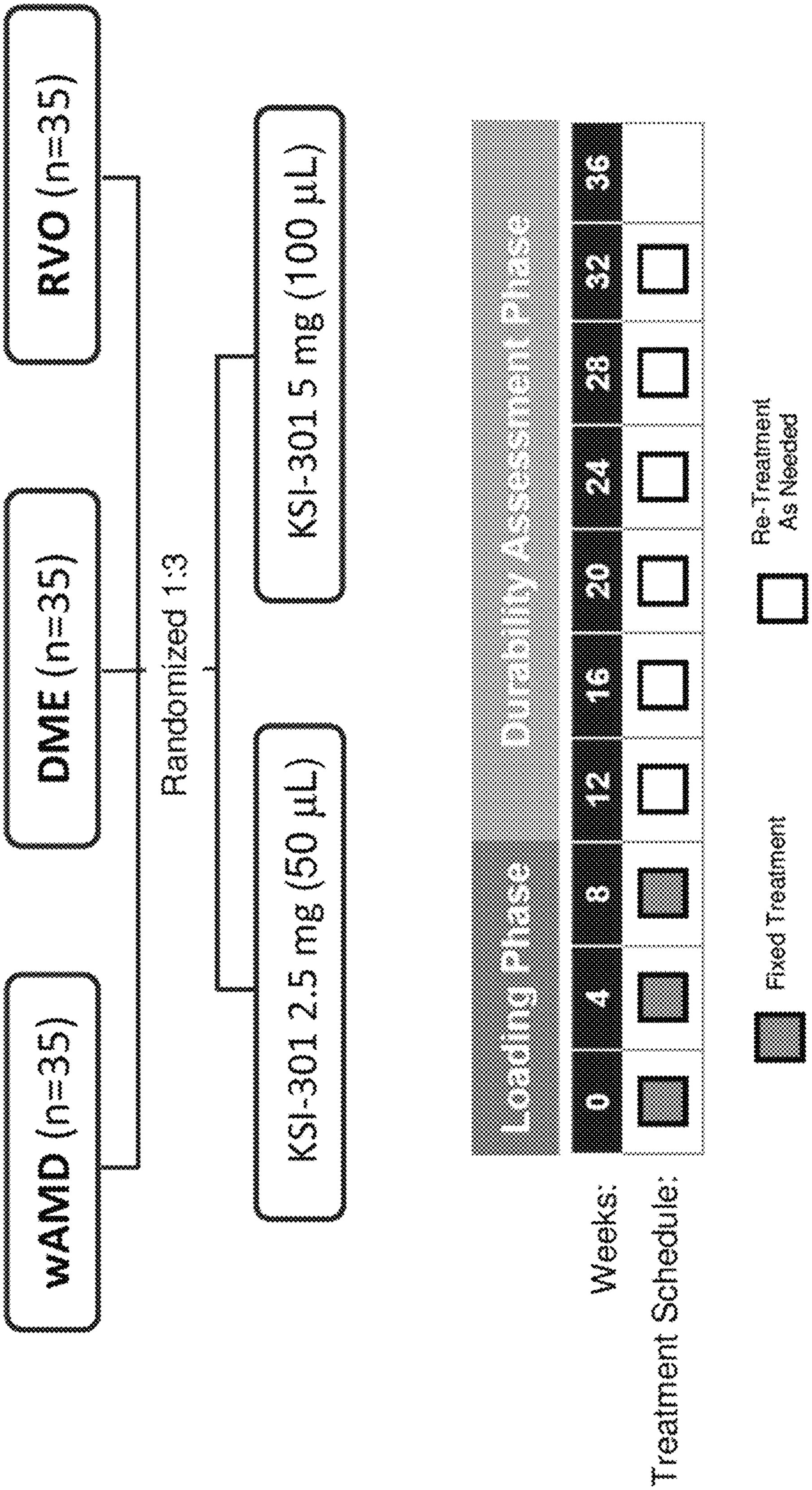
FIG. 5 is a schematic diagram representing a KSI-301 intravitreal administration schedule in age-related macular degeneration (wAMD), diabetic macular edema (DME), and retinal vein occlusion (RVO), according to some embodiments of the present disclosure.

Two dose levels of KSI-301, 2.5 mg (50 μL) and 5 mg (100 μL) (by weight of protein) were evaluated in a multiple-dose study. Each subject received 3 initial intravitreal injections of KSI-301, the first at Day 1, the second at Week 4 and the third at Week 8 (FIG. 5). All cohorts were randomized 1:3 to the 2.5 mg or 5 mg dose.

FIG. 5: Study design for a randomized, open label study to evaluate multidose safety, efficacy and durability of intravitreal administration of KSI-301.

Subjects were evaluated every 4 weeks and may have received additional administration of the study drug starting at Week 16, if specific re-treatment criteria were met. There were no mandatory injections at assessment visits, except in the case of the wet AMD cohort, where a mandatory intravitreal injection was given at a visit if it had been 24 weeks since the last injection.

Eligible subjects were selected based on predetermined inclusion and exclusion criteria. Subjects were treatment naïve with respect to the eye disorder to be treated, and had no history of retinal disease other than the condition under investigation.

KSI-301 was formulated in approximately 12.5 mM sodium phosphate and 0.025% polysorbate 20 as a aqueous solution at 50 mg/mL (based on antibody mass) and filled into single-use 2.0 mL vials.

During the study, multiple-dose exposure of KSI-301 was well-tolerated and no intraocular inflammation was observed. 113 subjects were dosed, with 308 total doses given (104 doses at day 1, 96 doses at week 4, 84 doses at week 8). The following were observed:

- No intraocular inflammation or ocular SAEs in the study eye were reported to date;
- No drug-related adverse events (AEs) or drug-related serious adverse events (SAEs) were reported to date;
- Most AEs were assessed as mild and were consistent with profile of intravitreal anti-VEGFs;
- 8 non-ocular SAEs that were not drug-related were reported in 4 subjects:
  - One 92 y/o RVO subject with hospitalization related to a pre-existing condition that resulted in death
  - One 66 y/o RVO subject with hospitalization related to dizziness
  - One 43 y/o DME subject with hospitalization related to a pre-existing condition
  - One 56 y/o DME subject with hospitalization related to a pre-existing condition wAMD Cohort Patients included in the wAMD cohort: were ≥50 years of age; had treatment naïve wet age-related macular degeneration involving the fovea; had a lesion area <30 mm 2 (12 disc areas) of any lesion type; had a BCVA ETDRS letter score ≤78 and ≥23 (~20/25 to ~20/320 Snellen equivalent) in the study eye at Screening and confirmed at Day 1; and had a decrease in vision in the study eye determined to be primarily the result of wAMD.

The average characteristics of the study population is show in Table 1.

TABLE 1

Study population characteristics

| Variable | wAMD cohort (n = 35) | DME cohort (n = 35) | RVO cohort (n = 35) |
|---|---|---|---|
| Age (years, mean) | 76 | 60 | 64 |
| Gender (Female, %) | 71.4 | 40.7 | 37.1 |
| Race, n (%), White | 32 (91.4) | 28 (82.4) | 31 (88.6) |
| BCVA (ETDRS letters, mean) | 66 | 70 | 59 |
| BCVA, Snellen 20/40 or better, n (%) | 14 (40.0) | 16 (47.1) | 6 (17.1) |
| OCT CST (microns, mean) | 380 | 402 | 630 |

Trial Assessments

The following assessments were made every 4 weeks after the 3 initial intravitreal injections of KSI-301: Best Corrected Visual Acuity (BCVA) by the Early treatment diabetic retinopathy study (ETDRS) visual acuity test; Spectral Domain Optical Coherence Tomography (SD-OCT); OCT angiography (OCT-A).

Re-Treatment Criteria (Non-Loading Dose)

Re-treatment with intravitreal injection of KSI-301 was performed if at least one of the following re-treatment criteria were met. These criteria are related to signs of disease recurrence and/or vision loss due to disease recurrence.

- Increase in OCT central subfield retinal thickness (CST) ≥75 μm with a decrease in BCVA of ≥5 letters compared to Week 12;
- Decrease in BCVA of >5 letters compared to Day 1, due to worsening wAMD disease activity (e.g. increased intraretinal fluid, increased subretinal fluid, new intraretinal hemorrhage, new subretinal hemorrhage);
- Decrease in BCVA of ≥10 letters compared to the best prior BCVA, due to worsening wAMD disease activity (e.g. increased intraretinal fluid, increased subretinal fluid, new intraretinal hemorrhage, new subretinal hemorrhage); or
- 24 weeks/6 months have elapsed since the previous injection.

Results

Figure 6:
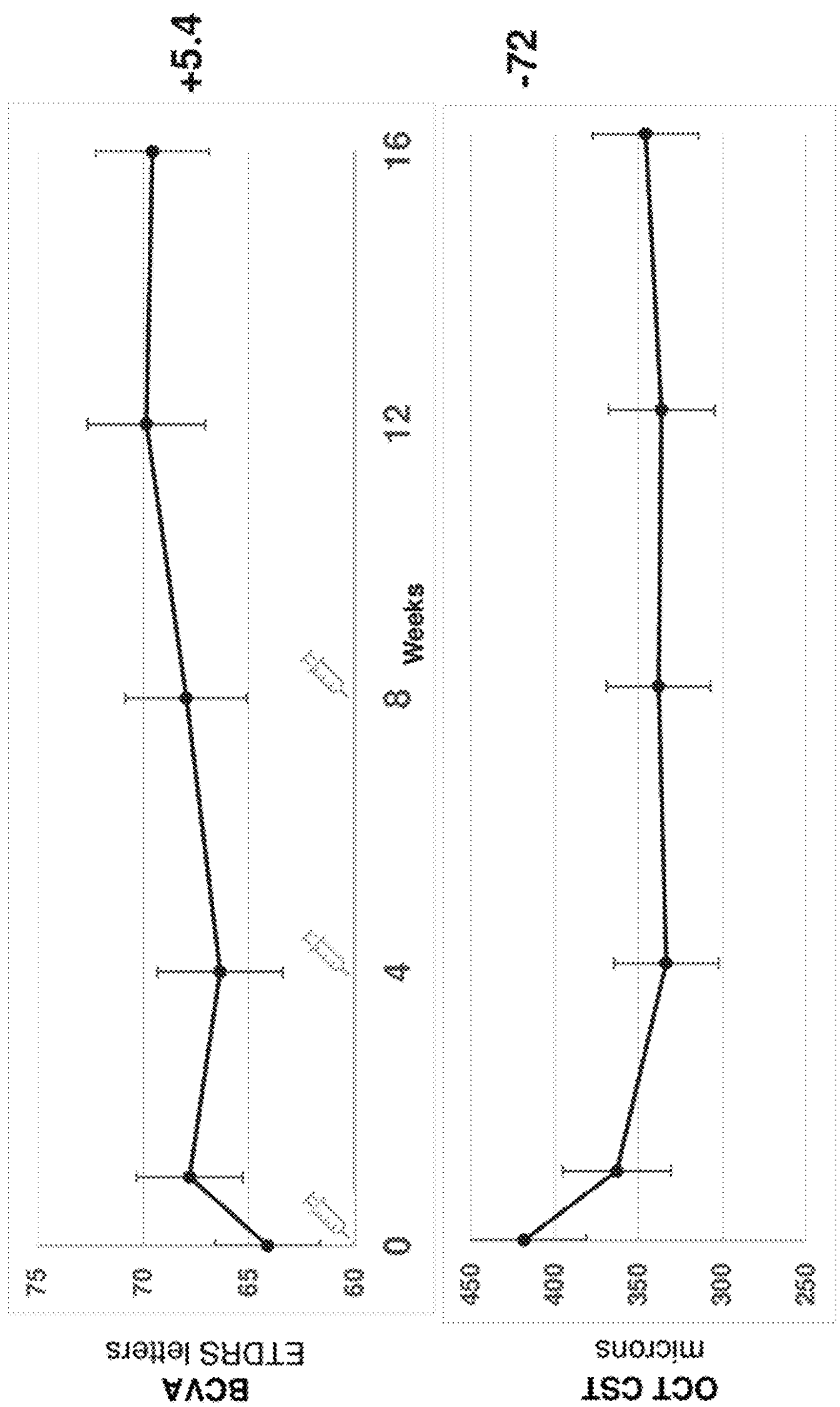
FIG. 6 is a set of graphs showing sustained therapeutic effects of KSI-301 after intravitreal administration of loading doses of KSI-301 to patients with wet age-related macular degeneration (wAMD), according to some embodiments of the present disclosure.
Figure 12:
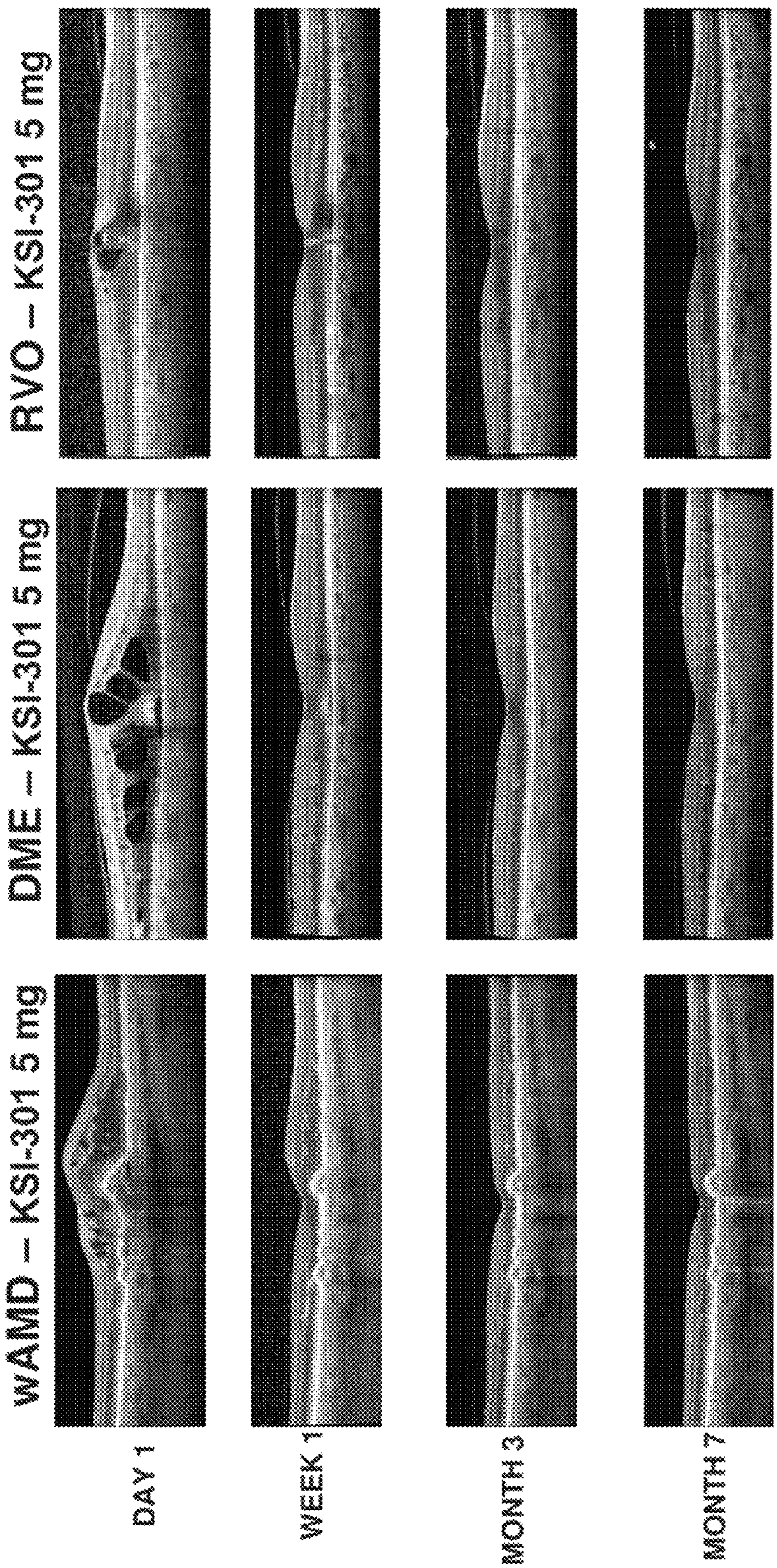
FIG. 12 is a collection of images showing sustained improvement in retinal health after intravitreal administration of loading doses of KSI-301 to patients with wAMD (left column), DME (middle column), and RVO (right column), according to some embodiments of the present disclosure.

Improvement in BCVA and OCT CST were observed in patients after the first loading dose administered on Day 1 (FIG. 6; FIG. 12, left column). The improved BCVA and OCT CST values were comparable to a standard of care anti-VEGF therapy. The therapeutic effect of KSI-301 was sustained during the loading phase, and continued for at least 8 weeks after the final loading dose administered at Week 8 (FIG. 6). Reduction in CST was sustained for 7 months without re-treatment in a representative patient (FIG. 12, left column).

FIG. 6: Initial improvements in best corrected vision (BCVA) and retinal thickness (OCT) in patients with wet AMD. BCVA and CST assessment for wAMD cohort. N=25. Includes randomized patients that reached Week 16 visit by the data cutoff date; 2.5 and 5 mg doses were pooled. BCVA=best corrected visual acuity; OCT=optical coherence tomography; CST=central subfield thickness.

FIG. 12: Durability of therapy in patients from the wAMD cohort. OCT scan of individual retinas at day 1 (row 1), week 1 (row 2), month 3 (row 3), and month 7 (row 4) of treatment with KSI-301. Left column: wAMD patient; middle column: DME patient; right column: RVO patient.

Figure 7:
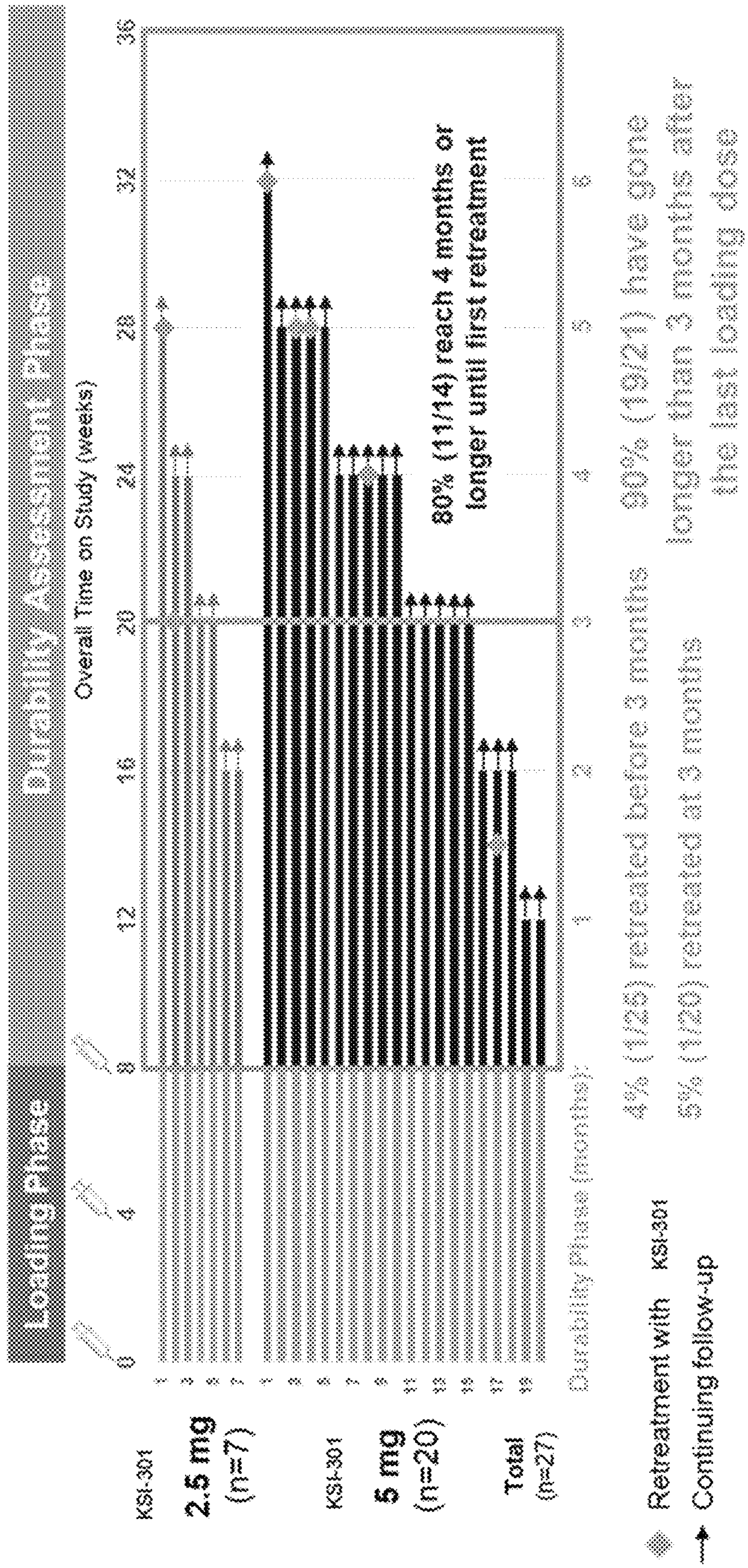
FIG. 7 is a set of graphs showing the schedule of intravitreal administration of KSI-301 received by individual patients treated for wAMD, according to some embodiments of the present disclosure. 4% (1/25) retreated before 3 months; 5% (1/20) retreated at 3 months; 90% (19/21) have gone longer than 3 months after the last loading dose; and 80% (11/14) reach 4 months or longer until first retreatment.

The results show the durability of therapy in patients from the wAMD cohort to date (FIG. 7). The data indicate that KSI-301 provide therapeutic effects that are unexpected relative to the current agents, and may provide better results because only 1 patient has been re-treated before week 20 (or about 3 months since the last loading dose), 1 patient has been re-treated at 3 months since the last loading dose, and $^{11}/_{14}$ (80%) have reached 4 months or longer until the first re-treatment. This indicates that the target dosing interval of 3 to 5 months in wAMD is possible.

In summary, only 1 patient out of 25 (4%) was re-treated before 3 months (FIG. 7). Only 1 patient out of 20 (5%) was re-treated at 3 months. 86% ($^{18}/_{21}$) of the patients reached 3 months or longer after the last loading dose without re-treatment, and 80% ($^{11}/_{14}$) of the patients reached 4 months or longer after the last loading dose without re-treatment. This indicates that the target dosing interval in wAMD can be 3 to 5 months.

FIG. 7: Treatment durability of KSI-301 in the wAMD cohort. Includes randomized patients that reached the first re-treatment opportunity (Week 12 visit) by the data cutoff date. Each bar represents an individual patient. Re-treatment is indicated by (+). All depicted patients were followed beyond the indicated last assessment time point (indicated by a right arrow). The results can be summarized as follows:

- 18.5% have received re-treatment ($^{5}/_{27}$), Among patients reaching week 20, 95% ($^{20}/_{21}$) have not received re-treatment for greater than 12-weeks after last loading dose
- 81.5% have not required re-treatment ($^{22}/_{27}$)
- Among patients reaching week 20, 95% ($^{20}/_{21}$) have not received re-treatment for at least 12-weeks after the $3^{rd}$ loading dose
- Retreatment up to 6 months after the loading phase has been achieved in the KSI-301 5 mg dose.

Example 4: Open Label, Multi-Center Exploratory Study to Investigate Multiple Intravitreal Administrations of KSI-301 in Subjects with Diabetic Macular Edema (DME)

The overall study design and trial assessment were as described in Example 3.

DME Cohort

Patients included in the DME cohort had: treatment naïve diabetic macular edema; a BCVA ETDRS letter score ≤78 and ≥23 (~20/25 to ~20/320 Snellen equivalent) in the study eye at Screening and confirmed at Day 1; Central subfield thickness (CST) of ≥300 microns on SD-OCT (Heidelberg Spectralis or equivalent); and a decrease in vision in the study eye determined to be primarily the result of DME.

The average characteristics of the study population is show in Table 1, above.

Re-Treatment Criteria (Non-Loading Dose)

Re-treatment with intravitreal injection of KSI-301 was performed if at least one of the following re-treatment criteria were met. These criteria are related to signs of disease recurrence and/or vision loss due to disease recurrence.

- Increase in OCT central subfield retinal thickness (CST) ≥75 μm with a decrease in BCVA of ≥5 letters compared to Week 12 or the prior visit (4-week span between visits); or
- Decrease in BCVA of ≥10 letters compared to the best prior BCVA, due to worsening DME/RVO disease activity (e.g. increased intraretinal fluid, increased subretinal fluid, new intraretinal hemorrhage, new exudates).

Results

Figure 8:
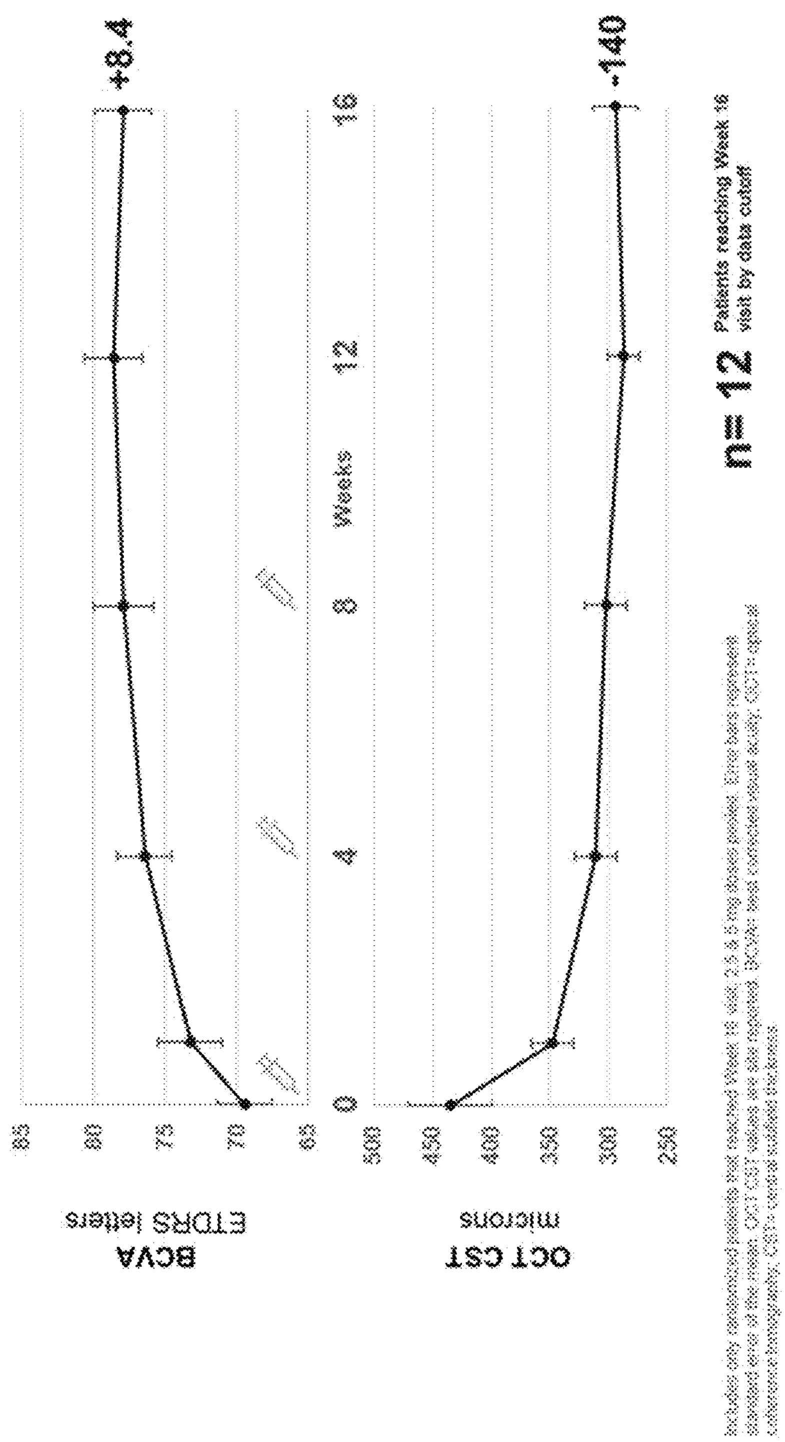
FIG. 8 is a set of graphs showing sustained therapeutic effects of KSI-301 after intravitreal administration of loading doses of KSI-301 to patients with diabetic macular edema (DME), according to some embodiments of the present disclosure.

Improvement in BCVA and OCT CST were observed in patients after the first loading dose administered on Day 1 (FIG. 8; FIG. 12, middle column). Therapeutic effect of KSI-301 was sustained during the loading phase, and continued for at least 8 weeks after the final loading dose administered at Week 8 (FIG. 8). Reduction in CST was sustained for 7 months without re-treatment in a representative patient (FIG. 12, middle column).

The data demonstrates the effect of KSI-301 after 3 monthly doses in patients with DME (FIG. 8). The data are unexpected because current products require either monthly therapy or 5 monthly loading doses, whereas KSI-301 provided high levels of improvement after only 3 loading doses.

FIG. 8: BCVA and CST assessment for DME cohort. N=12. Includes randomized patients that reached Week 16 visit by the data cutoff date; 2.5 and 5 mg doses were pooled. BCVA=best corrected visual acuity; OCT=optical coherence tomography; CST=central subfield thickness.

No patient required re-treatment before 3 months after the last loading dose, and no patient required a $4^{th}$ or $5^{th}$ monthly loading dose. (FIG. 9). 18% ($^{2}/_{11}$) of patients were re-treated at 3 months. Among patients reaching week 20, 81.8% ($^{9}/_{11}$) did not require re-treatment for over 12-weeks after the 3rd loading dose. Some patients reached 4, 5, or 6 months without re-treatment.

Figure 9:
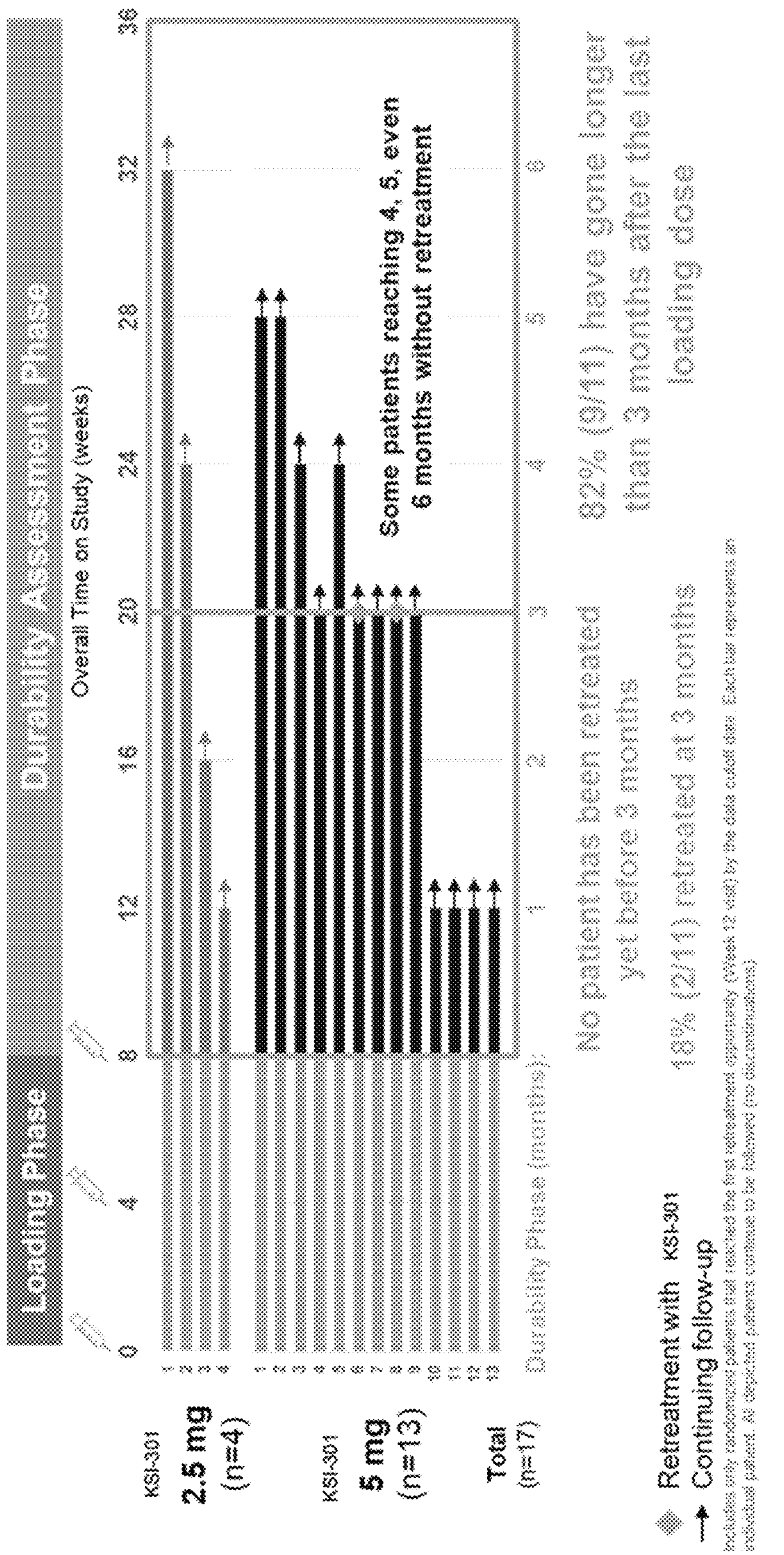
FIG. 9 is a set of graphs showing the schedule of intravitreal administration of KSI-301 received by individual patients treated for DME, according to some embodiments of the present disclosure.

The data indicate the potential for 3+ month dosing interval in patients with DME after only 3 loading doses (FIG. 9). Furthermore, the data are unexpected because no DME patient has yet been re-treated before 3 months. Additionally over 80% have gone longer than 3 months after the last loading dose before they needed to be re-treated. This is unexpected because with conventional therapies, as many as 9-10 injections are administered in the first 12 months of therapy.

FIG. 9: Treatment durability of KSI-301 in the DME cohort. Includes randomized patients that reached the first re-treatment opportunity (Week 12 visit) by the data cutoff date. Each bar represents an individual patient. Re-treatment is indicated by (+). All depicted patients were followed beyond the indicated last assessment time point (indicated by a right arrow). The results can be summarized as follows:

- 11.8% have received re-treatment ($^{2}/_{17}$)
- Among patients reaching week 20, 80% ($^{8}/_{10}$) have not received re-treatment for greater than 12-weeks after last loading dose
- 88.2% have not received re-treatment ($^{15}/_{17}$)
- Among patients reaching week 20, 81.8% ($^{9}/_{11}$) have not received re-treatment for greater than 12-weeks after only 3 loading doses
- No patient has required a $4^{th}$ or $5^{th}$ monthly loading dose.

FIG. 16 depicts the Diabetic Retinopathy Severity results (DRSS). The figure shows the proportion of patients with differing levels of diabetic retinopathy severity, measured on a standardized photographic reading scale by an independent expert reading center. DR can be described as different levels of severity, from mild to moderate to severe non-proliferative diabetic retinopathy, for example, or mild to high-risk proliferative DR. In this case, the majority of patients had level 47 disease (moderate NPDR) at baseline. After 12 weeks (3 loading doses and then one month), 27% of the patients had an improvement in DR severity by >=2 steps on the severity scale, 13% had a one-step improvement, and 60% maintained the same level of DR severity. (DR severity is known to improve following the application of anti-VEGF therapy but with other agents it takes 1 to 2 years to reach peak effect, and the effect is lost in many patients, and the disease worsens again, if the anti-VEGF therapy is stopped). The images show a patient with proliferative (level 65) disease who had disease modification and improved to non-proliferative (level 53, 2 steps on the standard grading scale) at week 12. With no additional doses given, the effect on DR severity was maintained for an additional 14 weeks which was the maximal follow-up time available for that patient. In some embodiments, a patient with non-proliferative DR can be treated using an anti-VEGF antibody conjugate (e.g., KSI-301) with no or potentially only a few loading doses (e.g., 1 dose, 2 doses, or 3 initiating doses) and then retreated every 3 to 6 months for the treatment of non-proliferative DR.

Example 4.5

A patient with non-proliferative DR is identified. The patient is treated with no loading dose, but treated every 3-6 months with a single injection of an anti-VEGF antibody conjugate (e.g., KSI-301) and the non-proliferative DR is treated. In the alternative, the patient is treated with 1, 2, or 3 loading doses first.

Example 5: Open Label, Multi-Center Exploratory Study to Investigate Multiple Intravitreal Administrations of KSI-301 in Subjects with Retinal Vein Occlusion (RVO)

The overall study design and trial assessment were as described in Example 3.

RVO Cohort

Patients included in the RVO cohort had: treatment naïve retinal vein occlusion with macular edema and secondary visual impairment; a BCVA ETDRS letter score ≤78 and ≥23 (~20/25 to ~20/320 Snellen equivalent) in the study eye at Screening and confirmed at Day 1; Central subfield thickness (CST) of ≥300 microns on SD-OCT (Heidelberg Spectralis or equivalent); Branch retinal vein occlusion (BRVO) or central retinal vein occlusion (CRVO); and a decrease in vision in the study eye determined by the investigator to be primarily the result of macular edema secondary to RVO.

The average characteristics of the study population is show in Table 1.

Re-Treatment Criteria

Re-treatment with intravitreal injection of KSI-301 was performed if at least one of the following re-treatment criteria were met. These criteria are related to signs of disease recurrence and/or vision loss due to disease recurrence.

- Increase in OCT central subfield retinal thickness (CST) ≥75 μm with a decrease in BCVA of ≥5 letters compared to Week 12 or the prior visit (4-week span between visits); or
- Decrease in BCVA of ≥10 letters compared to the best prior BCVA, due to worsening DME/RVO disease activity (e.g. increased intraretinal fluid, increased subretinal fluid, new intraretinal hemorrhage, new exudates).

Results

Figure 10:
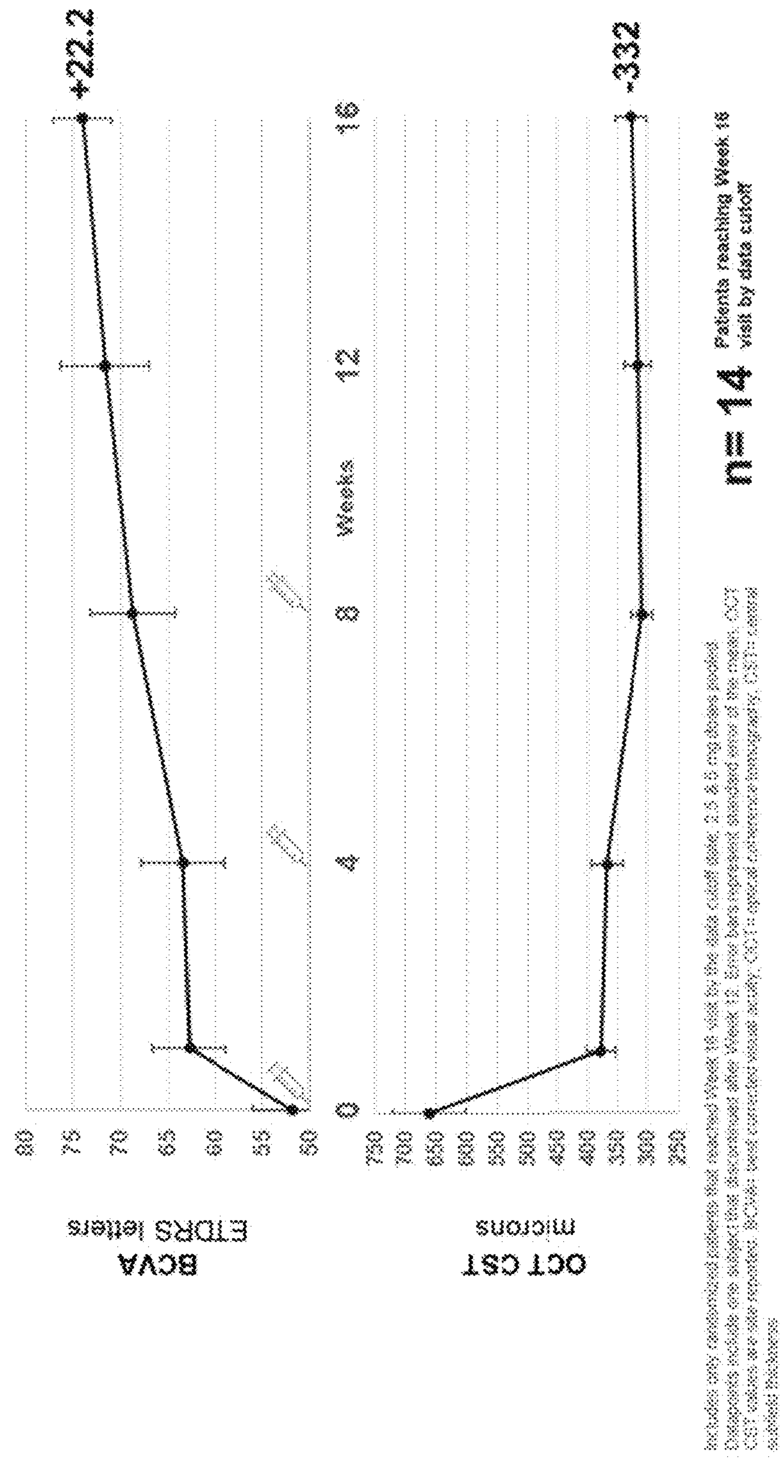
FIG. 10 is a set of graphs showing sustained therapeutic effects of KSI-301 after intravitreal administration of loading doses of KSI-301 to patients with retinal vein occlusion (RVO), according to some embodiments of the present disclosure.

Improvement in BCVA and OCT CST were observed in patients after the first loading dose administered on Day 1 (FIG. 10; FIG. 12, right column). Therapeutic effect of KSI-301 was sustained during the loading phase, and continued for at least 8 weeks after the final loading dose administered at Week 8 (FIG. 10). Reduction in CST was sustained for 7 months without re-treatment in a representative patient (FIG. 12, right column).

The data demonstrate the effect of KSI-301 after 3 monthly doses in patients with RVO (FIG. 10). The data are unexpected because a continued improvement in visual acuity is observed from 8 weeks to 16 weeks. In studies of ranibizumab, aflibercept, and bevacizumab in RVO, switching from monthly therapy to less than monthly therapy results in worsening of visual acuity and OCT CST.

FIG. 10: BCVA and CST assessment for RVO cohort. N=14. Includes randomized patients that reached Week 16 visit by the data cutoff date; 2.5 and 5 mg doses were pooled. BCVA=best corrected visual acuity; OCT=optical coherence tomography; CST=central subfield thickness.

75% (18/24) of patients in the RVO cohort did not require re-treatment (FIG. 11). 8% (2/24) of patients had first retreatment at 1 month; 23% (3/13) of patients had first re-treatment at 2 months; and 11% (1/9) of patients had first re-treatment at 3 months. Among patients reaching week 20, 56% (5/9) did not require re-treatment for over 12-weeks after the 3rd loading dose. 100% (18/18) patients in the 5 mg cohort did not require a $4^{th}$ or $5^{th}$ monthly loading dose, and if any, received re-treatment at 9 weeks or later after the last loading doses. Moreover, only 2 of 8 patients on 5 mg had received first re-treatment at 2 months, and both then had a longer time before the next treatment. Thus, of the patients who have received more than one re-treatment, the time between the first and second re-treatment was extended compared to the time between the last loading dose and the first re-treatment.

Figure 11:
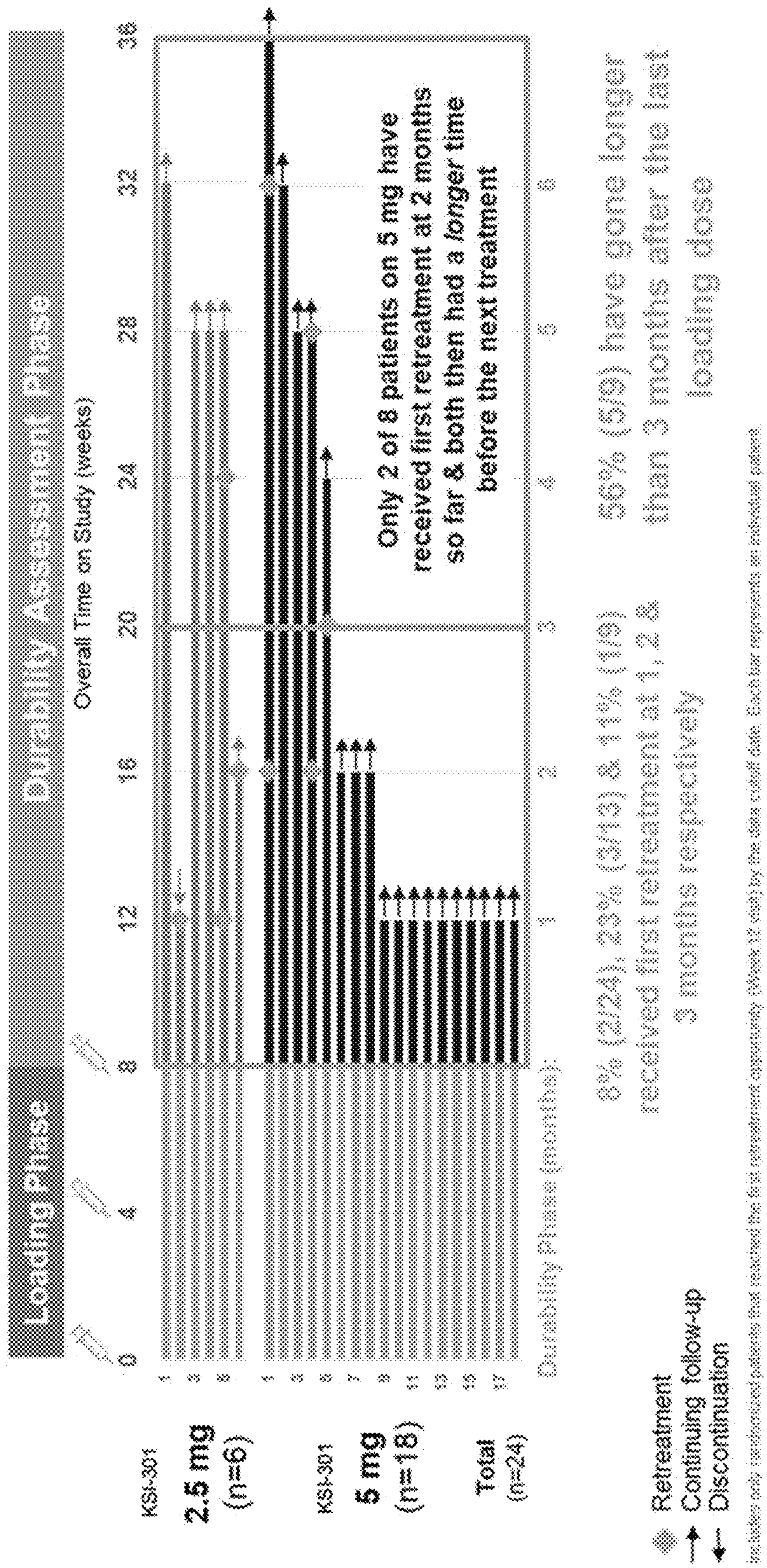
FIG. 11 is a graph showing the schedule of intravitreal administration of KSI-301 received by individual patients treated for RVO, according to some embodiments of the present disclosure.

The data shows that in the 5 mg dose group, the RVO patients were receiving first retreatment at 8 weeks or later (FIG. 11). This result is unexpected because conventional therapy requires monthly dosing to treat RVO. Moreover, of the patients who had received more than one retreatment, the time between first and second retreatment was extended, which was also unexpected because typically patients with RVO have disease recurrence on a particular pattern, or regular intervals. Finally, over half the patients (5/9) have gone for longer than 3 months since the last loading dose, which was also unexpected given the high intraocular VEGF load of RVO.

FIG. 11: Treatment durability of KSI-301 in the RVO cohort. Includes randomized patients that reached the first re-treatment opportunity (Week 12 visit) by the data cutoff date. Each bar represents an individual patient. Re-treatment is indicated by (+). Patients followed beyond the indicated last assessment time point are indicated by a right arrow. Discontinuation is indicated by a left arrow. Further results shown in FIG. 11 can be summarized as follows:

- 25% have received re-treatment (6/24)
- Among patients reaching week 20, 56% (5/9) have not received re-treatment for greater than 12-weeks after last loading dose
- 75% have not received re-treatment (18/24)
- Among patients reaching week 20, 56% (5/9) have not received re-treatment for greater than 12-weeks after only 3 loading doses
- 18/18 patients in the KSI-301 5 mg cohort didn't require a $4^{th}$ monthly loading dose

Example 6

One first identifies a subject in need of having an eye disorder treated (either prophylactically or otherwise). Then one administers between 1 and 5 mg of antibody of an anti-VEGF antibody conjugate (e.g., KSI-301) to the subject in a first loading dose, and optionally a second loading dose and optionally a third loading dose (within about one month of each other). Following the last loading dose, the subject will retain a therapeutic benefit of the anti-VEGF therapy for at least 12 weeks. This can be applied to diabetic macular edema (DME), retinal vein occlusion (RVO), wet age-related macular degeneration (AMD), and/or in the alternative diabetic retinopathy (DR).

Example 6.5

One first identifies a subject in need of having an eye disorder treated (either prophylactically or otherwise). Then one administers between 1 and 5 mg of antibody of an anti-VEGF antibody conjugate (e.g., KSI-301) to the subject in a first loading dose, and optionally a second loading dose and optionally a third loading dose (within about one month of each other). Following the last loading dose, the subject will retain a therapeutic benefit of the anti-VEGF antibody conjugate therapy for at least 16 weeks. Alternatively, following the last loading dose, the subject will retain a therapeutic benefit of the anti-VEGF antibody conjugate therapy for at least 20 weeks. Alternatively, following the last loading dose, the subject will retain a therapeutic benefit of the anti-VEGF antibody conjugate therapy for at least 24 weeks. Alternatively, following the last loading dose, the subject will retain a therapeutic benefit of the anti-VEGF antibody conjugate therapy for at least 30 weeks. Alternatively, following the last loading dose, the subject will retain a therapeutic benefit of the anti-VEGF antibody conjugate therapy for at least 36 weeks. Alternatively, following the last loading dose, the subject will retain a therapeutic benefit of the anti-VEGF antibody conjugate therapy for at least 42 weeks. Alternatively, following the last loading dose, the subject will retain a therapeutic benefit of the anti-VEGF antibody conjugate therapy for at least 48 weeks. Alternatively, following the last loading dose, the subject will retain a therapeutic benefit of the anti-VEGF antibody conjugate therapy for at least 54 weeks. Alternatively, following the last loading dose, the subject will retain a therapeutic benefit of the anti-VEGF antibody conjugate therapy for at least 60 weeks. This can be applied to diabetic macular edema (DME), retinal vein occlusion (RVO), wet age-related macular degeneration (AMD), and/or in the alternative diabetic retinopathy (DR).

Example 7

The present example provides a method of treating retinal vein occlusion (RVO). The method comprises administering an anti-VEGF antibody conjugate (e.g., KSI-301) to a subject with RVO at a first loading dose. One can then repeat the loading dose, once or in the alternative two times. This results in the subject retaining a therapeutic result of the anti-VEGF antibody conjugate therapy for at least 8 weeks after a final loading dose. In the alternative, this results in the subject retaining a therapeutic result of the anti-VEGF antibody bioconjugate, e.g., KSI-301, therapy for at least 12 weeks after a final loading dose. In the alternative, this results in the subject retaining a therapeutic result of the anti-VEGF antibody bioconjugate, e.g., KSI-301, therapy for at least 20 weeks after a final loading dose.

Example 7.5

The present example provides a method of treating retinal vein occlusion (RVO). The method comprises administering an anti-VEGF antibody conjugate (e.g., KSI-301) to a subject with RVO at a first loading dose. One can then repeat the loading dose, once or in the alternative two times. This results in the subject retaining a therapeutic result of the anti-VEGF antibody conjugate therapy for at least 24 weeks after a final loading dose. In the alternative, this results in the subject retaining a therapeutic result of the anti-VEGF antibody conjugate therapy for at least 30 weeks after a final loading dose. In the alternative, this results in the subject retaining a therapeutic result of the anti-VEGF antibody conjugate therapy for at least 36 weeks after a final loading dose. In the alternative, this results in the subject retaining a therapeutic result of the anti-VEGF antibody conjugate therapy for at least 42 weeks after a final loading dose. In the alternative, this results in the subject retaining a therapeutic result of the anti-VEGF antibody conjugate therapy for at least 48 weeks after a final loading dose. In the alternative, this results in the subject retaining a therapeutic result of the anti-VEGF antibody conjugate therapy for at least 54 weeks after a final loading dose. In the alternative, this results in the subject retaining a therapeutic result of the anti-VEGF antibody conjugate therapy for at least 60 weeks after a final loading dose.

Example 8

The present example provides a method of improving perfusion of an eye, the method comprises identifying a subject with DME, DR or RVO. One then administers at least 2 loading doses of an anti-VEGF antibody conjugate (e.g., KSI-301) to the subject at 1.25-5 mg, with one month between each injection. One does not administer more than 2 injections. One then provides one or more further doses (retreatments) of the anti-VEGF antibody conjugate, e.g., KSI-301, to the subject, until the subject displays improved perfusion in at least one eye.

Example 9

The present example provides a method of improving perfusion of an eye. The method involves identifying a subject with non-proliferative DR and administering an initial dose of an anti-VEGF antibody conjugate (e.g., KSI-301) to the subject (between 1 and 5 mg of antibody), to provide improved perfusion in at least one eye. The dose is repeated until perfusion is achieved within the subject's treated eye.

Example 10

The present example provides a method of treating a subject with DME, DR or RVO. The method comprises administering 1-3 loading doses of an anti-VEGF antibody conjugate (e.g., KSI-301) (at 1-5 mg of antibody on a once monthly basis) to a subject with DME, DR or RVO. One does not administer more than 3 loading doses to the subject. To the extent required, if at all, one provides a follow-on application of the anti-VEGF antibody conjugate (retreatment) at a point in time no sooner than 12 weeks after a last loading dose.

Example 10.5

The present example provides a method of treating a subject with DME, DR or RVO. The method comprises administering 1-3 loading doses of an anti-VEGF antibody conjugate (e.g., KSI-301) (at 1-5 mg of antibody on a once monthly basis) to a subject with DME, DR or RVO. One does not administer more than 3 loading doses to the subject. To the extent required, if at all, one provides a follow-on application of the anti-VEGF antibody conjugate (retreatment) at a point in time no sooner than 16 weeks after a last loading dose. Alternatively, one provides a follow-on application of the anti-VEGF antibody conjugate (retreatment) at a point in time no sooner than 20 weeks after a last loading dose. Alternatively, one provides a follow-on application of the anti-VEGF antibody conjugate (retreatment) at a point in time no sooner than 24 weeks after a last loading dose. Alternatively, one provides a follow-on application of the anti-VEGF antibody conjugate (retreatment) at a point in time no sooner than 30 weeks after a last loading dose. Alternatively, one provides a follow-on application of the anti-VEGF antibody conjugate (retreatment) at a point in time no sooner than 36 weeks after a last loading dose. Alternatively, one provides a follow-on application of the anti-VEGF antibody conjugate (retreatment) at a point in time no sooner than 42 weeks after a last loading dose. Alternatively, one provides a follow-on application of the anti-VEGF antibody conjugate (retreatment) at a point in time no sooner than 48 weeks after a last loading dose. Alternatively, one provides a follow-on application of the anti-VEGF antibody conjugate (retreatment) at a point in time no sooner than 54 weeks after a last loading dose. Alternatively, one provides a follow-on application of the anti-VEGF antibody conjugate (retreatment) at a point in time no sooner than 60 weeks after a last loading dose.

Example 11

The present example provides a method of treating a subject with non-proliferative DR. One identifies a patient in need of therapy and administers 1 or 2 loading doses of an anti-VEGF antibody conjugate (e.g., KSI-301) (1-5 mg, once a month) to a subject with non-proliferative DR. One does not administer more than 2 loading doses to the subject. Optionally, one can provide a follow-on administration of the anti-VEGF antibody conjugate, e.g., KSI-301, (retreatment) at a point in time no sooner than 12 weeks after a last loading dose.

Example 11.5

The present example provides a method of treating a subject with non-proliferative DR. One identifies a patient in need of therapy and administers 1 or 2 loading doses of an anti-VEGF antibody conjugate (e.g., KSI-301) (1-5 mg, once a month) to a subject with non-proliferative DR. One does not administer more than 2 loading doses to the subject. Optionally, one can provide a follow-on administration of the anti-VEGF antibody conjugate (retreatment) at a point in time no sooner than 16 weeks after a last loading dose. Alternatively, one can provide a follow-on administration of the anti-VEGF antibody conjugate (retreatment) at a point in time no sooner than 20 weeks after a last loading dose. Alternatively, one can provide a follow-on administration of the anti-VEGF antibody conjugate (retreatment) at a point in time no sooner than 24 weeks after a last loading dose. Alternatively, one can provide a follow-on administration of the anti-VEGF antibody conjugate (retreatment) at a point in time no sooner than 30 weeks after a last loading dose. Alternatively, one can provide a follow-on administration of the anti-VEGF antibody conjugate (retreatment) at a point in time no sooner than 36 weeks after a last loading dose. Alternatively, one can provide a follow-on administration of the anti-VEGF antibody conjugate (retreatment) at a point in time no sooner than 42 weeks after a last loading dose. Alternatively, one can provide a follow-on administration of the anti-VEGF antibody conjugate (retreatment) at a point in time no sooner than 48 weeks after a last loading dose. Alternatively, one can provide a follow-on administration of the anti-VEGF antibody conjugate (retreatment) at a point in time no sooner than 54 weeks after a last loading dose. Alternatively, one can provide a follow-on administration of the anti-VEGF antibody conjugate (retreatment) at a point in time no sooner than 60 weeks after a last loading dose.

Example 12

The present example provides a method of treating a subject with RVO. The method comprises administering 1 or 2 loading doses of an anti-VEGF antibody conjugate (e.g., KSI-301) (1-5 mg, once monthly) to a subject with RVO. No additional loading doses are administered to the 3 subject. One then, optionally, provides a follow-on administration of the anti-VEGF antibody conjugate (retreatment) at a point in time no sooner than 8 weeks after a last loading dose. In the alternative, the retreatment occurs no sooner than 12 weeks. In the alternative, the retreatment occurs no sooner than 16 weeks. In the alternative, the retreatment occurs no sooner than 20 weeks. In the alternative, the retreatment occurs no sooner than 24 weeks.

Example 12.5

The present example provides a method of treating a subject with RVO. The method comprises administering 1 or 2 loading doses of an anti-VEGF antibody conjugate (e.g., KSI-301) (1-5 mg, once monthly) to a subject with RVO. No additional loading doses are administered to the 3 subject. One then, optionally, provides a follow-on administration of the anti-VEGF antibody conjugate (retreatment) at a point in time no sooner than 30 weeks after a last loading dose. In the alternative, the retreatment occurs no sooner than 36 weeks. In the alternative, the retreatment occurs no sooner than 42 weeks. In the alternative, the retreatment occurs no sooner than 48 weeks. In the alternative, the retreatment occurs no sooner than 54 weeks. In the alternative, the retreatment occurs no sooner than 60 weeks.

Example 13

The present example provides a method of treating RVO. One administers an anti-VEGF antibody conjugate (e.g., KSI-301) (1-5 mg, once a month) to a subject in need of treating RVO at 1-3 loading doses. The subject thereby retains a therapeutic result of the anti-VEGF antibody conjugate therapy for RVO for at least 8 weeks after a final loading dose. The subject will retain at least one, if not most or all of the therapeutic benefits over this period of time, such that the subject will not substantially benefit from another retreatment for at least 14 weeks following the last application of the anti-VEGF antibody conjugate.

Example 13.5

The present example provides a method of treating RVO. One administers an anti-VEGF antibody conjugate (e.g., KSI-301) (1-5 mg, once a month) to a subject in need of treating RVO at 1-3 loading doses. The subject thereby retains a therapeutic result of the anti-VEGF antibody conjugate therapy for RVO for at least 12 weeks after a final loading dose. The subject will retain at least one, if not most or all of the therapeutic benefits over this period of time, such that the subject will not substantially benefit from another retreatment for at least 18 weeks following the last application of the anti-VEGF antibody bioconjugate. Alternatively, the subject retains at least one, if not most or all of the therapeutic benefits over this period of time, such that the subject will not substantially benefit from another retreatment for at least 24 weeks following the last application of the anti-VEGF antibody bioconjugate. Alternatively, the subject retains at least one, if not most or all of the therapeutic benefits over this period of time, such that the subject will not substantially benefit from another retreatment for at least 30 weeks following the last application of the anti-VEGF antibody bioconjugate. Alternatively, the subject retains at least one, if not most or all of the therapeutic benefits over this period of time, such that the subject will not substantially benefit from another retreatment for at least 36 weeks following the last application of the anti-VEGF antibody bioconjugate. Alternatively, the subject retains at least one, if not most or all of the therapeutic benefits over this period of time, such that the subject will not substantially benefit from another retreatment for at least 42 weeks following the last application of the anti-VEGF antibody bioconjugate. Alternatively, the subject retains at least one, if not most or all of the therapeutic benefits over this period of time, such that the subject will not substantially benefit from another retreatment for at least 48 weeks following the last application of the anti-VEGF antibody bioconjugate. Alternatively, the subject retains at least one, if not most or all of the therapeutic benefits over this period of time, such that the subject will not substantially benefit from another retreatment for at least 54 weeks following the last application of the anti-VEGF antibody bioconjugate. Alternatively, the subject retains at least one, if not most or all of the therapeutic benefits over this period of time, such that the subject will not substantially benefit from another retreatment for at least 60 weeks following the last application of the anti-VEGF antibody bioconjugate.

Example 14

One first identifies a subject in need of having an eye disorder treated (either prophylactically or otherwise). Then one administers between 1 and 5 mg of antibody of an anti-VEGF antibody conjugate (e.g., KSI-301) to the subject in a first loading dose, and optionally a second loading dose and optionally a third loading dose (within about one month of each other). Following the last loading dose, the subject will retain a therapeutic benefit of the anti-VEGF antibody conjugate therapy for at least 12 weeks. This can be applied to diabetic macular edema (DME), retinal vein occlusion (RVO), wet age-related macular degeneration (AMD), and/or in the alternative diabetic retinopathy (DR). Following any retreatment application, the duration between any subsequent retreatment events will increase, as the subject will need less and less treatment for each retreatment administered.

Example 14.5

One first identifies a subject in need of having an eye disorder treated (either prophylactically or otherwise). Then one administers between 1 and 5 mg of antibody of an anti-VEGF antibody conjugate (e.g., KSI-301) to the subject in a first loading dose, and optionally a second loading dose and optionally a third loading dose (within about one month of each other). Following the last loading dose, the subject will retain a therapeutic benefit of the anti-VEGF antibody conjugate therapy for at least 18 weeks. Alternatively following the last loading dose, the subject will retain a therapeutic benefit of the anti-VEGF antibody conjugate therapy for at least 24 weeks. Alternatively following the last loading dose, the subject will retain a therapeutic benefit of the anti-VEGF antibody conjugate therapy for at least 30 weeks. Alternatively following the last loading dose, the subject will retain a therapeutic benefit of the anti-VEGF antibody conjugate therapy for at least 36 weeks. Alternatively following the last loading dose, the subject will retain a therapeutic benefit of the anti-VEGF antibody conjugate therapy for at least 42 weeks. Alternatively following the last loading dose, the subject will retain a therapeutic benefit of the anti-VEGF antibody conjugate therapy for at least 48 weeks. Alternatively following the last loading dose, the subject will retain a therapeutic benefit of the anti-VEGF antibody conjugate therapy for at least 54 weeks. Alternatively following the last loading dose, the subject will retain a therapeutic benefit of the anti-VEGF antibody conjugate therapy for at least 60 weeks.

This can be applied to diabetic macular edema (DME), retinal vein occlusion (RVO), wet age-related macular degeneration (AMD), and/or in the alternative diabetic retinopathy (DR). Following any retreatment application, the duration between any subsequent retreatment events will increase, as the subject will need less and less treatment for each retreatment administered.

Example 15

The present example summarizes the safety and characteristics observed for the use of KSI-301 through repeated administration. 113 subjects were dosed over phase 1a and 1b. 308 total doses were administered. The following was observed with respect to safety:

- No intraocular inflammation or ocular SAEs in the study eye reported to date
- No drug-related AEs or drug-related SAEs reported to date
- Most AEs were assessed as mild and are consistent with profile of intravitreal anti-VEGFs
- 8 non-ocular SAEs that were not drug-related have been reported in 4 subjects:
  - One 92 y/o RVO subject with hospitalization related to a pre-existing condition that resulted in death
  - One 66 y/o RVO subject with hospitalization related to dizziness
  - One 43 y/o DME subject with hospitalization related to a pre-existing condition
  - One 56 y/o DME subject with hospitalization related to a pre-existing condition.

The above examples demonstrate that Antibody Biopolymer Conjugate (ABC) constructs are a new design platform for long durability intravitreal medicines. KSI-301 has achieved important development results, including:

- Excellent Safety: zero cases of intraocular inflammation after 300+ doses
- Strong Efficacy: across 3 major phenotypically variable retinal diseases wet AMD, DME/DR & RVO
- Remarkable Biological Durability: majority of treated eyes extended to 4 months or beyond without retreatment after 3 loading doses. It is anticipated that potential is being demonstrated for:

3 to 5+ month interval in wAMD
3 to 5+ month interval in DME
2 to 3+ month interval in RVO Example 16

FIGS. 17A and 17B depict OCT and OCT angiography of a wet AMD patient that has been treated with 3 loading doses of 5 mg KSI-301 at baseline, week 4 and week 8. In additional to diminishing fluid on the OCT images, there's a direct effect on the choroidal neovascular membrane in both flow and size as represented with the spot reduction in the center of the panels. The choroidal neovascular membrane is the core feature of wet AMD, and having a direct effect in this membrane is believed to be a sign of disease modification.

Example 17

Figure 18A:
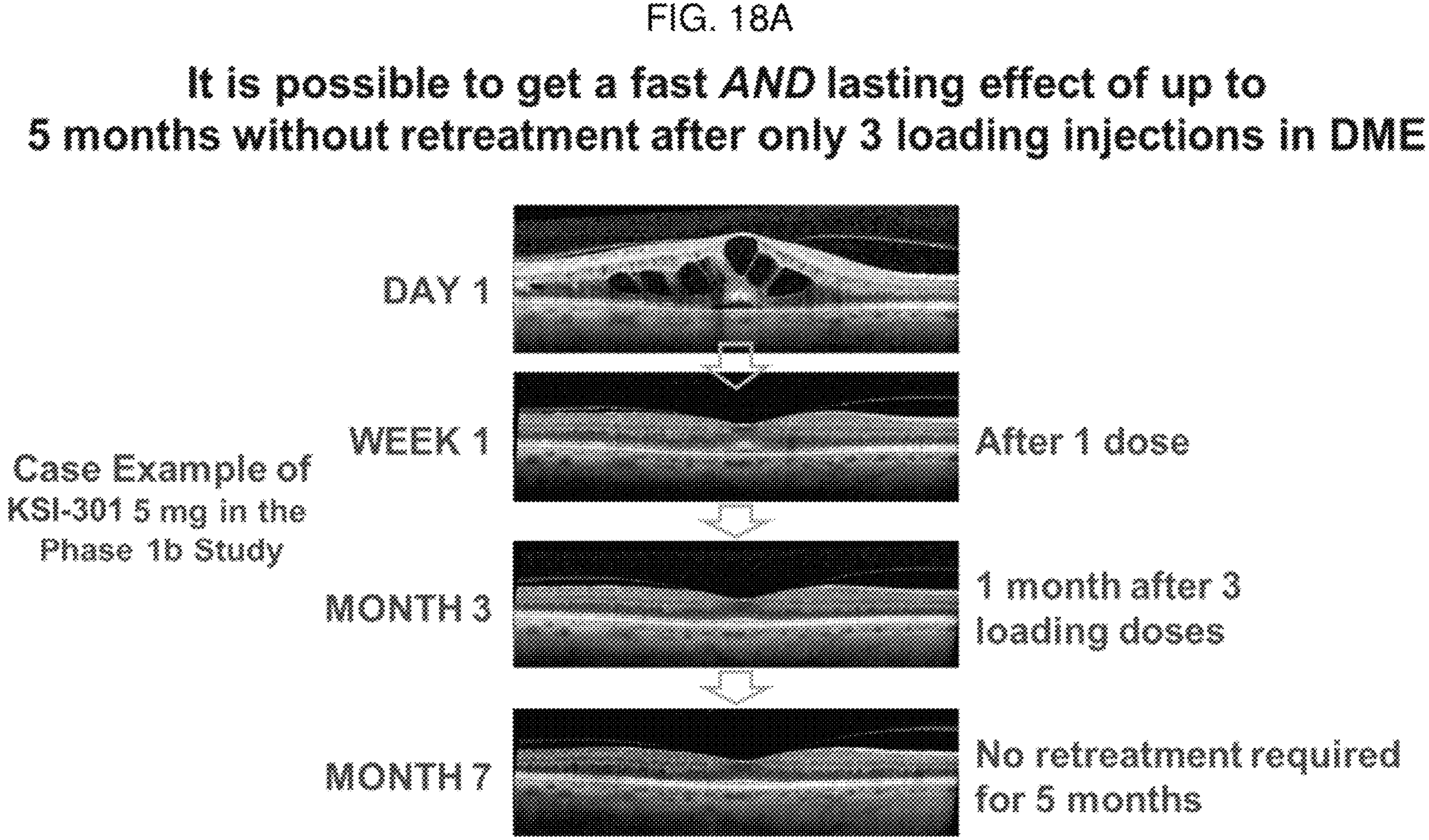
Figure 18B:
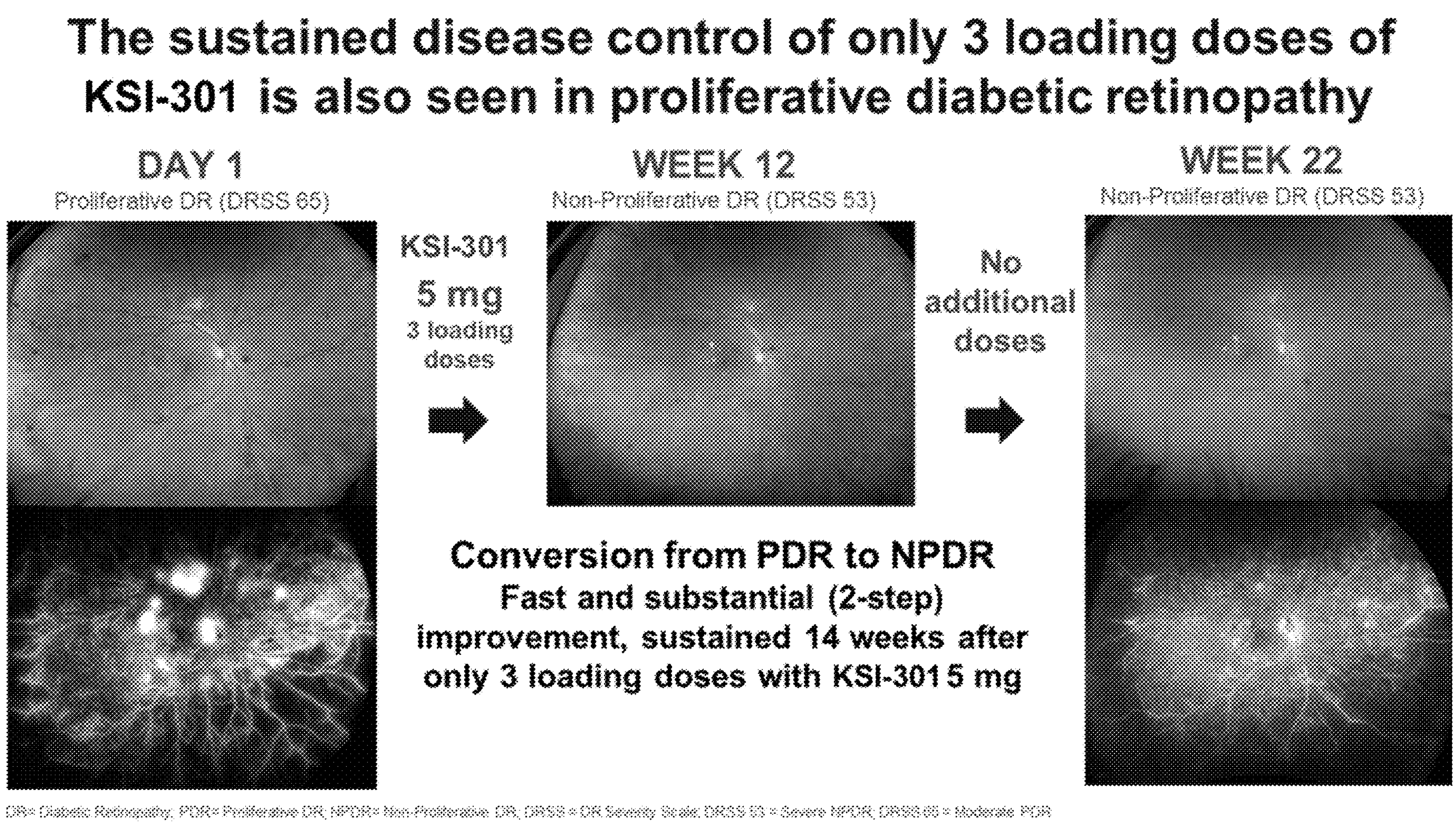
Figure 18C:
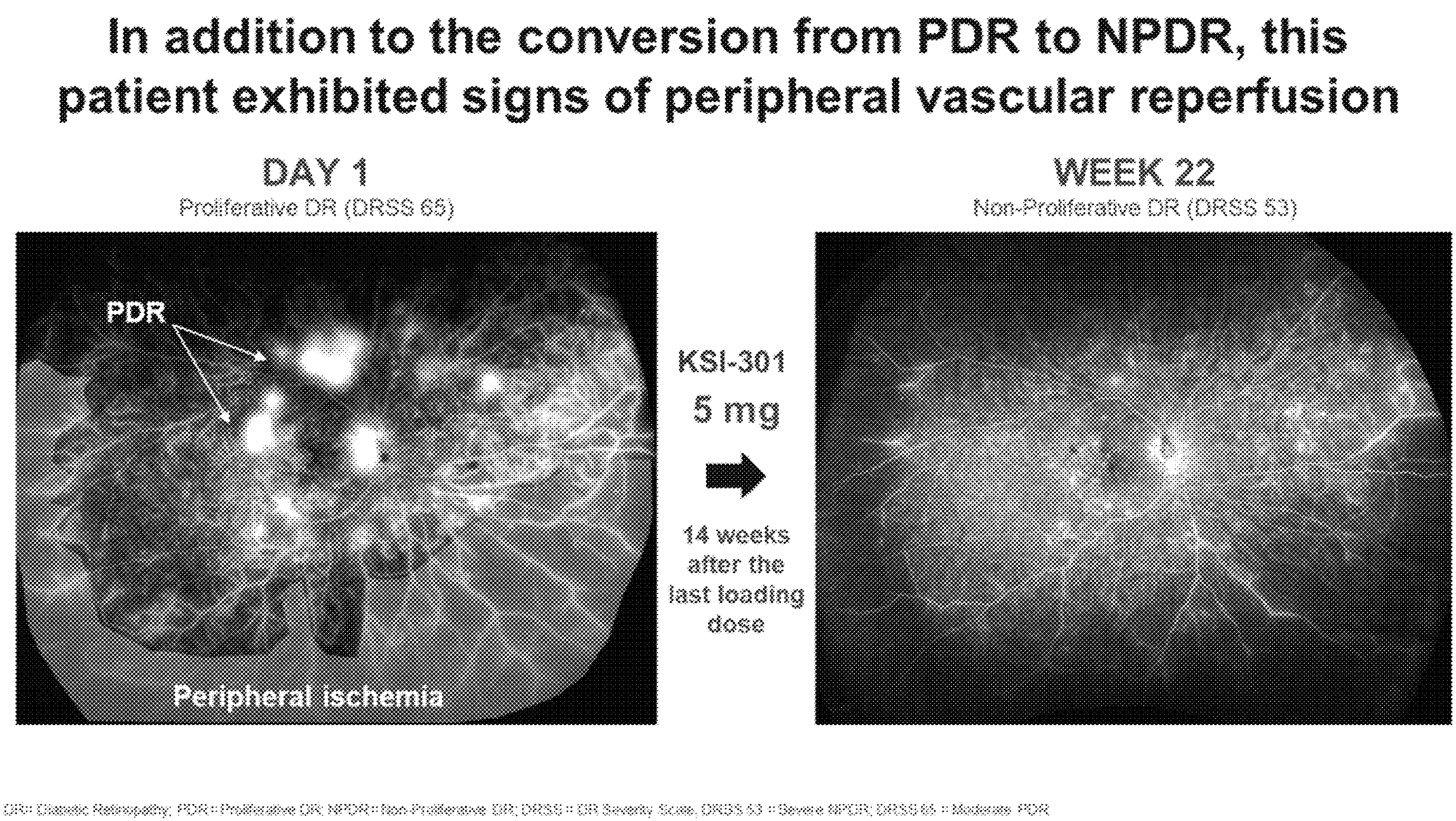
Figure 18D:
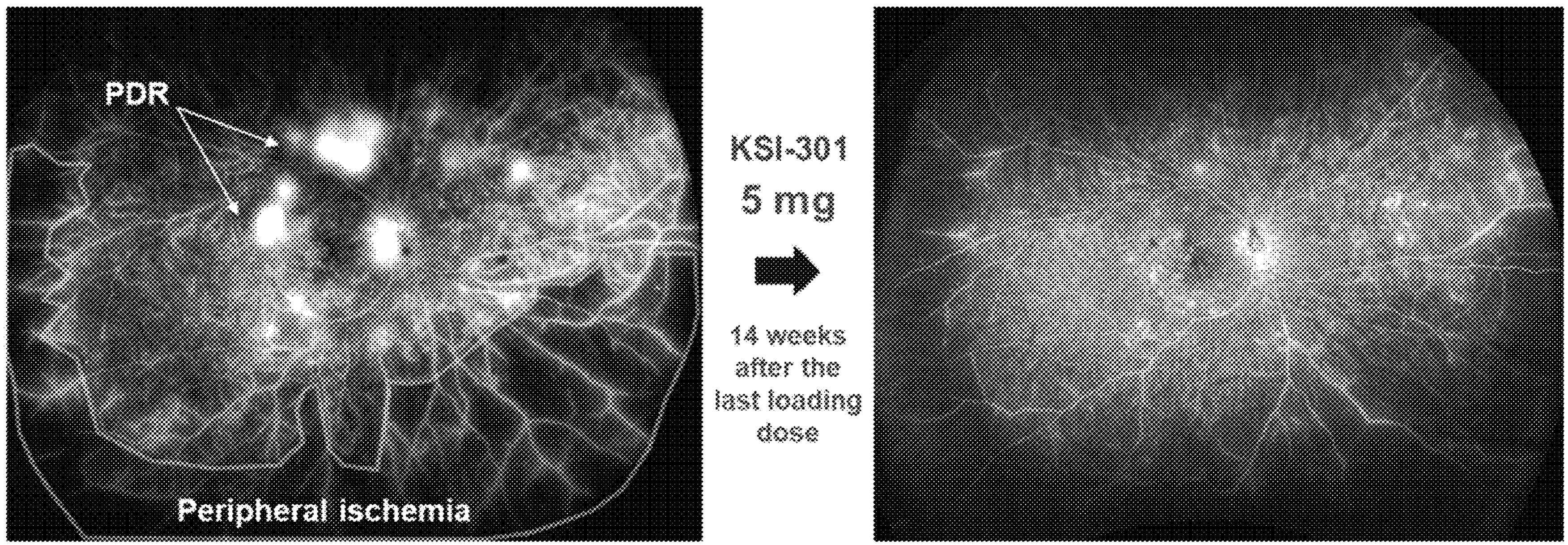

FIGS. 18A-18D show an example of a DME with disease modification post 3 loading doses, with significant DRSS improvement and reperfusion representing disease modification. FIG. 18A shows a time course revealing that it is possible to get both fast and long lasting effect in DME with only 3 loading doses (no retreatment required for at least 5 months). FIG. 18B demonstrates that the effectiveness of only three loading doses of KSI-301 is present in proliferative diabetic retinopathy. As shown, there was a fast and substantial (2 steep) improvement, sustained 14 weeks after 3 loading doses of KSI-301. In addition to the conversion from PDR to NPDR, the subject also displayed signs of peripheral vascular reperfusion (FIGS. 18C and 18D).

Thus, use of KSI-301 in the manner provided herein can be used to achieve fast and prolonged results and reperfusion.

Example 18

FIG. 19 displays the results in an RVO patient, that after 3 loading doses, no additional doses were required for at least 5 months, representing what is believed to be disease modification. Thus, use of KSI-301 in the manner provided herein can be used to achieve disease modification.

Example 19

FIG. 20 displays a set of OCT images of a patient showing the effect of 3 loading doses lasting 8 weeks until diseases recurs and the patient receives retreatment. The effect of that 4th dose lasts 16 weeks until the patient requires retreatment, effectively doubling the retreatment interval from 8 to 16 weeks, which could be a sign of disease modification. Thus, this demonstrates that additional effectiveness is achieved through the retreatment process as well, allowing for more time between subsequent required retreatments.

Example 20

FIG. 21A-21C Show the results of a single injection of KSI-301. Phase 1 Single Dose Study—Summary:

Rapid high-magnitude and durable treatment responses were seen at all dose levels tested.

Twelve weeks after a single dose, median BCVA improvement from baseline of +9 ETDRS chart letters and median improvement in retinal edema of −121 microns (OCT CST) were observed.

No dose-limiting toxicities, drug-related adverse events, or intraocular inflammation were observed through each patients' last visit at 12 weeks.

FIG. 21A show a graph of the median changes from baseline to week 12. It demonstrates a rapid, high response that is durable for KSI-301 administration. Case study 1 results are shown in FIG. 21B, which demonstrates the effectiveness of KSI-301 administration on chronic macular edema in a subject with prior suboptimal response. FIG. 21C displays the results from Case study 2, which shows the resolution of subretinal fluid through 12 weeks in a subject with chronic edema and extensive foveal lipid exudates.

These results provide two cases where after a single injection, in previously treated and failed patients, a single injection of KSI-301 has long lasting benefit. In case 2, the effect slow manifested and increased over time after KSI-301 injection, demonstrating a form of disease modification.

Example 21

Follow-up assessments of patients enrolled in the study described in Example 3 were performed. The results show durability of KSI-301 treatment in patients from the wAMD cohort that extended to 3 to 5 or more months (FIG. 22). 83% (20/24) of patients reached 4 months or longer before first retreatment. 85% (22/26) of patients did not receive retreatment for longer than 3 months after the last loading dose. 6% (2/31) were retreated before 3 months after the last loading dose, and 8% (2/25) were retreated at 3 months after the last loading dose. These results indicate that the target dosing interval in wAMD can be 3 to 5 or more months after the loading dose.

FIG. 22: Treatment durability of KSI-301 in the wAMD cohort. Includes randomized patients that reached the first re-treatment opportunity (Week 12 visit) by the data cutoff date. Each bar represents an individual patient. Re-treatment is indicated by (♦). Patients followed beyond the indicated last assessment time point (indicated by a right arrow). One discontinued patient is indicated by left arrow.

Improvement in BCVA and OCT CST continued to be observed in patients at week 20, 12 weeks after the last loading dose (FIG. 23). The improved BCVA and OCT CST values were comparable to a standard of care anti-VEGF therapy. The therapeutic effect of KSI-301 was sustained during the loading phase, and continued for at least 12 weeks after the final loading dose administered at Week 8 (FIG. 23). Improvement in BCVA and OCT CST was observed in a larger cohort of patients that reached Week 12 (FIG. 25).

FIG. 23: Improvements in best corrected vision (BCVA) and retinal thickness (OCT) in patients with wet AMD. BCVA and CST assessment for wAMD cohort. N=25. Includes randomized patients that reached Week 20 visit by the data cutoff date; 2.5 and 5 mg doses were pooled. BCVA=best corrected visual acuity; OCT=optical coherence tomography; CST=central subfield thickness. Error bars represent standard error of the mean.

FIG. 25: Improvements in BCVA and OCT in wet AMD patients treated with KSI-301. N=31. Includes randomized patients that reached Week 12 visit by the data cutoff date; 2.5 and 5 mg doses were pooled. BCVA=best corrected visual acuity; OCT=optical coherence tomography; CST=central subfield thickness. Error bars represent standard error of the mean.

Improvement in BCVA and OCT CST of a subset of patients from the wAMD cohort that did not have high pigment epithelial detachment (PED) were analyzed. These patients also showed sustained improvement in BCVA and OCT CST values, and the therapeutic effect of KSI-301 was sustained during the loading phase, and continued for at least 12 weeks after the final loading dose administered at Week 8 (FIG. 24). Improvement in BCVA and OCT CST was observed in a larger cohort of wAMD patients without high PED that reached Week 12 (FIG. 26).

FIG. 24: Improvements in best corrected vision (BCVA) and retinal thickness (OCT) in wet AMD patients without high PED. BCVA and CST assessment for wAMD cohort. N=23. High PED defined as presence of a PED with baseline CST≥500 microns. Includes randomized patients that reached Week 20 visit by the data cutoff date; 2.5 and 5 mg doses were pooled. BCVA=best corrected visual acuity; OCT=optical coherence tomography; CST=central subfield thickness. Error bars represent standard error of the mean.

FIG. 26: Improvements in BCVA and OCT in wet AMD patients with high PED, treated with KSI-301. N=29. High PED defined as presence of a PED with baseline CST≥500 microns. Includes randomized patients that reached Week 12 visit by the data cutoff date; 2.5 and 5 mg doses were pooled. BCVA=best corrected visual acuity; OCT=optical coherence tomography; CST=central subfield thickness. Error bars represent standard error of the mean.

Example 22

Follow-up assessments of patients enrolled in the study described in Example 4 were performed. The results show durability of KSI-301 treatment in patients from the DME cohort that extended more than 4 months (FIG. 27). 72% (8/11) of patients reached 4 months or longer without retreatment. 81% (13/16) did not require retreatment more than 3 months after the last loading dose. One patient was retreated before 3 months, and 13% (2/15) of patients were retreated at 3 months. These results indicate that the target dosing interval in DME can be 3 or more months after the loading dose.

FIG. 27: Treatment durability of KSI-301 in the DME cohort. Includes randomized patients that reached the first re-treatment opportunity (Week 12 visit) by the data cutoff date. Each bar represents an individual patient. Re-treatment is indicated by (+). All depicted patients were followed beyond the indicated last assessment time point (indicated by a right arrow).

Improvement in BCVA and OCT CST were observed in DME patients at Week 20, 12 weeks after the last loading dose (FIG. 28). Therapeutic effect of KSI-301 was sustained during the loading phase, and continued for at least 12 weeks after the final loading dose administered at Week 8. Improvement in BCVA and OCT CST was observed in a larger cohort of DME patients that reached Week 12 (FIG. 29).

FIG. 28: BCVA and CST assessment for DME cohort. N=15. Includes randomized patients that reached Week 20 visit by the data cutoff date; 2.5 and 5 mg doses were pooled. BCVA=best corrected visual acuity; OCT=optical coherence tomography; CST=central subfield thickness. Error bars represent standard error of the mean.

FIG. 29: BCVA and CST assessment for DME cohort. N=19. Includes randomized patients that reached Week 12 visit by the data cutoff date; 2.5 and 5 mg doses were pooled. BCVA=best corrected visual acuity; OCT=optical coherence tomography; CST=central subfield thickness. Error bars represent standard error of the mean.

Example 23

Follow-up assessments of patients enrolled in the study described in Example 5 were performed. The results show durability of KSI-301 treatment in patients from the RVO cohort that extended more than 3 months (FIG. 30). Only 3 patients received more than 1 retreatment, and in those 3 patients, each retreatment occurred at a longer interval than the first interval until retreatment. 50% (9/18) of patients reached 3 months or longer without retreatment. 6% (2/32), 30% (7/23) and 14% (2/14) of patients received first retreatment at 1, 2 and 3 months, respectively. These results indicate that the target dosing interval in RVO can be 2 to 3 months or longer.

FIG. 30: Treatment durability of KSI-301 in the RVO cohort. Includes randomized patients that reached the first re-treatment opportunity (Week 12 visit) by the data cutoff date. Each bar represents an individual patient. Re-treatment is indicated by (♦). Patients followed beyond the indicated last assessment time point are indicated by a right arrow. Discontinuation is indicated by a left arrow.

Improvement in BCVA and OCT CST were observed in RVO patients at Week 20, 12 weeks after the last loading dose (FIG. 31). Therapeutic effect of KSI-301 was sustained during the loading phase, and continued for at least 12 weeks after the final loading dose administered at Week 8 (FIG. 31). Improvement in BCVA and OCT CST was observed in a larger cohort of RVO patients that reached Week 12 (FIG. 32).

FIG. 31: BCVA and CST assessment for RVO cohort. N=15.

Includes randomized patients that reached Week 20 visit by the data cutoff date; 2.5 and 5 mg doses were pooled. BCVA=best corrected visual acuity; OCT=optical coherence tomography; CST=central subfield thickness. Error bars represent standard error of the mean.

FIG. 32: BCVA and CST assessment for RVO cohort. N=32. Includes randomized patients that reached Week 12 visit by the data cutoff date; 2.5 and 5 mg doses were pooled. BCVA=best corrected visual acuity; OCT=optical coherence tomography; CST=central subfield thickness. Error bars represent standard error of the mean.

Example 24

During the study described in Examples 22-23, multiple-dose exposure of KSI-301 was well-tolerated and no intraocular inflammation was observed. 116 subjects were dosed, with 338 total doses given (107 doses at day 1, 103 doses at week 4, 96 doses at week 8). The following were observed:

- No intraocular inflammation or ocular SAEs in the study eye were reported to date;
- No drug-related adverse events (AEs) or drug-related serious adverse events (SAEs) were reported to date;
- Most AEs were assessed as mild and were consistent with profile of intravitreal anti-VEGFs;
- 12 non-ocular SAEs that were not drug-related were reported in 7 subjects:
  - One 92 y/o RVO subject with hospitalization related to a pre-existing condition that resulted in death;
  - One 66 y/o RVO subject with hospitalization related to dizziness;
  - One 43 y/o RVO subject with a broken leg related to a motorcycle accident;
  - One 85 y/o RVO subject with hospitalization related to a pre-existing condition.

Example 24

The study described in Examples 3-5, 15-23 was further extended to up to 72 weeks, as shown in FIG. 33.

FIG. 33: Updated study design for a randomized, open label study to evaluate multidose safety, efficacy and durability of intravitreal administration of KSI-301.

The updated average characteristics of the study population is show in Table 2.

TABLE 2

Updated study population characteristics

| Variable | wAMD cohort (n = 51) | DME cohort (n = 35) | RVO cohort (n = 35) |
|---|---|---|---|
| Age, mean (SD), years | 77.9 (10.5) | 59.7 (11.7) | 63.6 (12.6) |
| Gender, n (%), female | 32 (62.7) | 14 (40.0) | 13 (37.1) |
| Race, n (%), White | 48 (94.1) | 28 (80.0) | 31 (88.6) |
| BCVA, mean (SD), ETDRS letters | 63.3 (13.3) | 66.8 (10.2) | 54.9 (15.4) |
| Snellen equivalent | ~20/50 | ~20/50 | 20/80 |
| BCVA, Snellen 20/40 or better, n (%) | 20 (39.2) | 16 (45.7) | 6 (17.1) |
| OCT CST, mean (SD), microns | 430 (162) | 453 (110) | 675 (237) |

SD = standard deviation;
BCVA = best corrected visual acuity;
OCT = optical coherence tomography;
CST = central subfield thickness Further follow-up assessments of patients enrolled in the study described in Example 21 were performed. The results show durability of KSI-301 treatment in patients from the wAMD cohort that extended to 3 to 6 or more months (FIG. 34). In 55% (16/29) of patients, the first retreatment was at 6 months after the last loading dose, which was a mandatory retreatment in the study design for the wAMD cohort. 72% (21/29) of patients did not receive retreatment for 5 months or longer after the last loading dose. 84% (27/32) of patients did not receive retreatment for 4 months or longer after the last loading dose. 86% (30/35) of patients did not receive retreatment for 3 months or longer after the last loading dose. 14% (5/35) were retreated at or before 3 months after the last loading dose. These results indicate that the target dosing interval in wAMD can be 3 to 6 or more months after the last loading dose.

FIG. 34: Treatment durability of KSI-301 in the wAMD cohort. Includes randomized patients that reached the first re-treatment opportunity (Week 12 visit) by the data cutoff date. Each bar represents an individual patient. Re-treatment is indicated by (♦). Patients followed beyond the indicated last assessment time point are indicated by a right arrow. One discontinued patient is indicated by the left arrow.

Improved BCVA and OCT CST was maintained in patients at week 24, 16 weeks after the last loading dose (FIG. 35). The baseline (pre-treatment) BCVA for this cohort was 64.1 ETDRS letters. The average improvement in BCVA at Week 24 was +5.9 letters (corresponding to 20/40 Snellen VA). The improved BCVA and OCT CST values were comparable to reported improvements in a standard of care anti-VEGF therapy (baseline of 60.8 letters, gain of ~6 letters; or baseline of 61.5, gain of ~5.2 letters at Week 20). The average improvement in OCT CST was −58 microns at Week 24. The therapeutic effect of KSI-301 was sustained during the loading phase, and continued for at least 16 weeks after the final loading dose administered at Week 8 (FIG. 35).

Over the 16 weeks after the final loading dose, a patient received on average 0.16 injections of KSI-301 for retreatment. (FIG. 35). This is in comparison to the standard of care treatments, aflibercept or brolucizumab, which require a mean number of injections of 1.0 over the same time period, per the respective labels.

FIG. 35: Improvements in best corrected vision (BCVA) and retinal thickness (OCT) in patients with wet AMD. BCVA and CST assessment for wAMD cohort. N=31. Includes randomized patients that reached Week 24 visit by the data cutoff date; 2.5 and 5 mg doses were pooled. BCVA=best corrected visual acuity; OCT=optical coherence tomography; CST=central subfield thickness. Error bars represent standard error of the mean.

Example 25

Further follow-up assessments of patients enrolled in the study described in Example 22 were performed. The DME cohort population characteristics were as described in Table 2. The results show durability of KSI-301 treatment in patients from the DME cohort that extended more than 6 months (FIG. 36). 69% (9/13) of patients reached 6 months or longer without retreatment. 73% (11/15) did not require retreatment more than 5 months after the last loading dose. 80% (16/20) did not require retreatment more than 4 months after the last loading dose. 83% (20/24) did not require retreatment more than 3 months after the last loading dose. 17% (4/24) of patients were retreated during the first 3 months. These results indicate that the target dosing interval in DME can be 3 to 6 or more months after the last loading dose.

FIG. 36: Treatment durability of KSI-301 in the DME cohort. Includes randomized patients that reached the first re-treatment opportunity (Week 12 visit) by the data cutoff date. Each bar represents an individual patient. Re-treatment is indicated by (+). All depicted patients were followed beyond the indicated last assessment time point (indicated by a right arrow).

Improvement in BCVA and OCT CST were observed in DME patients at Week 24, 16 weeks after the last loading dose (FIG. 37). The average improvement in BCVA at Week 24 was +6.8 letters (corresponding to ~$20/32^{+2}$ Snellen VA). The average improvement in OCT CST was −133 microns at Week 24. Therapeutic effect of KSI-301 was sustained during the loading phase, and continued for at least 16 weeks after the final loading dose administered at Week 8.

Over the 16 weeks after the loading dose a patient on average received 0.21 injections of KSI-301. (FIG. 37). This is in comparison to the standard of care treatment, aflibercept or brolucizumab, which requires a mean number of injections of 2.0 over the same time period, per the label (aflibercept), or based on a pivotal study design (brolucizumab).

FIG. 37: BCVA and CST assessment for DME cohort. N=19. Includes randomized patients that reached Week 24 visit by the data cutoff date; 2.5 and 5 mg doses were pooled. BCVA=best corrected visual acuity; OCT=optical coherence tomography; CST=central subfield thickness. Error bars represent standard error of the mean.

Example 26

Follow-up assessments of patients enrolled in the study described in Example 23 were performed. The RVO cohort population characteristics were as described in Table 2. The results show durability of KSI-301 treatment in patients from the RVO cohort that extended more than 4 months (FIG. 38). 53% (16/30) of patients reached 4 months or longer without retreatment. 55% (17/31) of patients reached 3 months or longer without retreatment. 34% (11/32) of patients received retreatment during the first 2 months after the last loading dose, while 45% (14/31) received retreatment during the first 3 months after the last loading dose. These results indicate that the target dosing interval in RVO can be 2 to 4 months or longer.

FIG. 38: Treatment durability of KSI-301 in the RVO cohort. Includes randomized patients that reached the first re-treatment opportunity (Week 12 visit) by the data cutoff date. Each bar represents an individual patient. Re-treatment is indicated by (♦). Patients followed beyond the indicated last assessment time point are indicated by a right arrow. Discontinuation is indicated by a left arrow.

Improvement in BCVA and OCT CST continued to be observed in RVO patients at Week 24, 16 weeks after the last loading dose (FIG. 39). The average improvement in BCVA at Week 24 was +22.2 letters (corresponding to 20/32 Snellen VA). The average improvement in OCT CST was −350 microns at Week 24. The therapeutic effect of KSI-301 was sustained during the loading phase, and continued for at least 16 weeks after the final loading dose administered at Week 8 (FIG. 39).

Over the 16 weeks after the final loading dose a patient received on average 0.46 injections of KSI-301 for retreatment. (FIG. 39). This is in comparison to the standard of care treatments, aflibercept or brolucizumab, which require a mean number of injections of 3.0 over the same time period, per the label (aflibercept), or based on a pivotal study design (brolucizumab).

FIG. 39: BCVA and CST assessment for RVO cohort. N=30. Includes randomized patients that reached Week 24 visit by the data cutoff date; 2.5 and 5 mg doses were pooled. BCVA=best corrected visual acuity; OCT=optical coherence tomography; CST=central subfield thickness. Error bars represent standard error of the mean.

Example 27

During the study described in Examples 3-5, and 15-26, multiple-dose exposure of KSI-301 was well-tolerated and no intraocular inflammation was observed. 130 subjects were dosed, with 420 total doses given (121 doses at day 1, 112 doses at week 4, 105 doses at week 8). The following were noted:

- No intraocular inflammation or ocular SAEs in the study eye were reported to date;
- No drug-related adverse events (AEs) or drug-related serious adverse events (SAEs) were reported to date;
- Most AEs were assessed as mild and were consistent with profile of intravitreal anti-VEGFs;
- 16 non-ocular SAEs that were not drug-related were reported in 10 subjects:
  - One 92 y/o RVO subject with hospitalization related to a pre-existing condition that resulted in death;
  - Six (43, 56, 62, 66, 70 and 72 y/o, respectively) DME subjects with hospitalization related to a pre-existing condition;
  - One 66 y/o RVO subject with hospitalization related to dizziness;
  - One 43 y/o RVO subject with a broken leg related to a motorcycle accident;
  - One 85 y/o RVO subject with hospitalization related to a pre-existing condition.

Example 28: Phase 2 Randomized Study of KSI-301 and a Standard of Care Treatment in wAMD About 550 treatment naïve wAMD patients participate in a randomized study comparing treatment with KSI-301 with treatment with a standard of care therapeutic (aflibercept). The standard of care treatment includes 3 loading doses of the therapeutic (at 2 mg per administration) administered at 4-week intervals, followed by alternating administration of a maintenance dose or sham injection every 4 weeks, starting at 16 weeks after initial treatment (FIG. 40). Thus, the standard of care therapeutic is administered to the patient every 8 weeks.

KSI-301 is administered (at 5 mg per administration) to another patient cohort with 3 loading doses at 4-week intervals. After the final loading dose (Week 8), patients receive at least a sham injection every 4 weeks, starting at 16 weeks after initial treatment (FIG. 40). One cohort of KSI-301-treated patients are assessed for disease activity every 12 weeks (Q12W) after the last loading dose (Week 8). Another cohort of KSI-301-treated patients are assessed for disease activity every 16 weeks (Q16W) after the last loading dose (Week 8). A patient is retreated with KSI-301 if the assessed disease activity meets pre-specified retreatment criteria. A third cohort of KSI-301-treated patients are administered KSI-301 every 20 weeks (Q20W) after the last loading dose (Week 8). All patients are administered KSI-301 at 20 weeks after the last loading dose (Week 8).

FIG. 40: Study design for randomized study to evaluate KSI-301 against Aflibercept in treating treatment naïve wAMD patients. KSI-301 is dosed as infrequently as every 20 weeks.

Re-Treatment Criteria (Non-Loading Dose)

Re-treatment with intravitreal injection of KSI-301 is performed if at least one of the following re-treatment criteria is met. These criteria are related to signs of disease recurrence and/or vision loss due to disease recurrence.

- Increase in OCT central subfield retinal thickness (CST) ≥50 μm with a decrease in BCVA of ≥5 letters compared to Week 12;
- Decrease in BCVA of ≥10 letters compared to the best prior BCVA, due to worsening wAMD disease activity (e.g. increased intraretinal fluid, increased subretinal fluid, new intraretinal hemorrhage, new subretinal hemorrhage);
  - Increase in OCT central subfield retinal thickness (CST)≥75 μm;
  - New macular hemorrhage.

The disease activity observed during assessments of wAMD patients treated with KSI-301 in the Phase 1b study, as described in Examples 3, 15, 21 and 24, was used to construct a hypothetical schedule of retreatment for each patient, under the stricter retreatment criteria specified in the Phase 2 clinical trial (FIG. 41A). Out of 32 total patients, 24 patients (or 75%) would have reached the 5-month cap for retreatment without any earlier need for retreatment (FIGS. 41A and 41B). Only 12.5% of the patients would have required a first retreatment at 12 weeks, and another 12.5% would have required a first retreatment at 16 weeks (FIGS. 41A and 41B).

FIGS. 41A and 41B: Treatment durability of KSI-301 in the wAMD cohort under hypothetical retreatment criteria in a Phase 2 clinical trial (FIG. 41), and hypothetical probability of a patient remaining on Q20W dosing (FIG. 41B). Includes randomized patients that would have met retreatment criteria before or at Week 28 by the data cutoff date. Each bar represents an individual patient.

Example 29

The study described in Examples 3-5, 15-24 was further extended to Weeks 76 to 148 (Months 19 to 36) (FIG. 43).

FIG. 43 shows an updated study design for a randomized, open label study to evaluate multidose safety, efficacy and durability of intravitreal administration of KSI-301. The number of patients for the wAMD, DME and RVO arms of the study were 51, 35 and 35, respectively.

Example 30

This example shows further follow-up assessments of the clinical study of KSI-301 for wAMD described in Examples 21 and 24. The results showed improved average BCVA and OCT CST was maintained in patients at week 44, 36 weeks after the last loading dose (FIG. 44). The therapeutic effect of the anti-VEGF antibody conjugate was sustained during the loading phase, and continued for at least 36 weeks after the final loading dose administered at Week 8. 58% of patients received their first retreatment dose at Week 32 (Q6M dosing), which was a mandated retreatment dose for any patient who had not been retreated since the last loading dose. Further, a patient received on average 1.32 injections of the anti-VEGF antibody conjugate between Week 12 and 40, of which 44% were mandated Q6M doses. In contrast, the mean number of injections according to the label for a conventional treatment (aflibercept) over the same time period would be 4.

FIG. 45A shows the individual break down of the follow-up assessment. Durability of the anti-VEGF antibody conjugate treatment in patients from the wAMD cohort extended to 3 to 6 or more months. FIG. 45B summarizes the results shown in FIG. 45A. In 72% of patients, the patient achieved at least one treatment interval of 6 months (Q6M—the mandated cap for the interval between treatment doses) sometime after the last loading dose (FIG. 45B). 49% (20/41) of patients did not receive retreatment for 6 months after the last loading dose. 66% (27/41) of patients did not receive retreatment for 5 months or longer after the last loading dose. 82% (40/49) of patients did not receive retreatment for 4 months or longer after the last loading dose. 92% (45/49) of patients did not receive retreatment for 3 months or longer after the last loading dose. Only 8% (4/49) were retreated at or before 2 months after the last loading dose. These results indicate that the target dosing interval of the anti-VEGF antibody conjugate in wAMD can be 3 to 6 or more months after the last loading dose.

Thus, nearly half of wAMD patients were on time to first retreatment of 6 months, and >60% wAMD patients achieved a 6 month interval at least once during follow up. These results were unexpected on the basis of the half-life of KSI-301 alone.

FIG. 46 shows a case example of a wAMD patient in the Phase 1b study described above, treated with KSI-301 with 6-month dosing through 1 year. OCT images were taken at the indicated time points. BCVA was also assessed (indicated by the change in ETDRS Letters value under the Week label). OCT and BCVA improvement was observed as early as 1 month (Week 12) after the last loading dose, and was sustained for at least 6 months (Week 32) after the last loading dose. At 6 months (Week 32), a mandatory retreatment dose was administered. 6 months (Week 56) after retreatment, the patient maintained the OCT and BCVA improvement. In total, the patient received 4 intravitreal injections in the first year of treatment.

In some embodiments, a wAMD patient is administered intravitreally an effective amount of an anti-VEGF antibody conjugate, e.g., KSI-301, at a dosing interval of about 3 months, about 4 months, about 5 months, or about 6 months, or any time interval between any two of the above values, at any time period after the patient is administered the last loading dose. In some embodiments, a wAMD patient is not administered a maintenance dose of the anti-VEGF antibody conjugate until at least about 3 months, at least about 4 months, at least about 5 months, or at least about 6 months or more, or until any time point between any two of the above values, after the last loading dose. In some embodiments, a wAMD patient has about 40%, about 50%, about 55%, about 60%, or about 65% or higher chance of not requiring a maintenance dose of the anti-VEGF antibody conjugate until about 6 months or more after the last loading dose or the last maintenance dose. In some embodiments, a wAMD patient has about 50%, about 55%, about 60%, about 65%, or about 70% or higher chance of not requiring a maintenance dose of the anti-VEGF antibody conjugate until about 5 months or more after the last loading dose or the last maintenance dose. In some embodiments, a wAMD patient has about 50%, about 60%, about 70%, or about 80% or higher chance of not requiring a maintenance dose of the anti-VEGF antibody conjugate until about 4 months or more after the last loading dose or the last maintenance dose. In some embodiments, a wAMD patient has about 60%, about 70%, about 80%, or about 90% or higher chance of not requiring a maintenance dose of the anti-VEGF antibody conjugate until about 3 months or more after the last loading dose or the last maintenance dose. In some embodiments, a subject receives 8 or fewer, 7 or fewer, 6 or fewer, 5 or fewer, 4 or fewer intravitreal injections of the anti-VEGF antibody conjugate in the first year of treatment for wAMD, including the loading doses. In some embodiments, a subject receives 4 or fewer, 3 or fewer, 2 or fewer, or 1 maintenance doses of the anti-VEGF antibody conjugate per year for treatment of wAMD.

Example 31

This example shows benchmarking of KSI-301 durability compared to aflibercept (Eylea®) long-interval RCT data for treatment-naïve wAMD (FIG. 47) and Eylea real-world data for wAMD (FIG. 48). FIG. 47 shows the distribution of treatment intervals among treatment-naïve wAMD patients in the KSI-301 Phase 1b study described above was compared to that in a treat-and-extend randomized clinical trial for Ranibizumab and Aflibercept, a combination of two conventional anti-VEGF treatments. Almost 50% of patients receiving the conventional anti-VEGF treatments had treatment interval of 4 weeks, and the treatment interval extended to a maximum interval of 12 weeks (3 months) for about 15% of the patients. In contrast, about 50% of patients treated with KSI-301 had treatment interval of 24 weeks (6 months)—the maximum interval permitted under the study. Over 80% of the patient receiving KSI-301 treatment had a treatment interval of 16 weeks or more, and exceeded the maximum treatment interval achieved by the conventional anti-VEGF treatments.

FIG. 48 shows a comparison of the mean treatment interval for patients treated with KSI-301 in the Phase 1b study described above and the mean treatment interval from real-world data for aflibercept (Eylea®) treat-and-extend. Patients treated with aflibercept had a mean treatment interval of 8 weeks, and a mean maximum treatment interval of 9.6 weeks. In contrast, patients on KSI-301 had a mean first interval (mean interval to first retreatment after last loading dose) of 19.3 weeks, and a mean maximum interval of 20.6 weeks. These results demonstrate the superior duration of the therapeutic effect of the anti-VEGF antibody conjugate compared to conventional anti-VEGF treatments for treating wAMD.

In some embodiments, the mean maximum interval for treating wAMD with the anti-VEGF antibody conjugate, e.g., KSI-301, is at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 170% or at least about 200% longer than the mean maximum interval for a conventional anti-VEGF treatment. In some embodiments, the anti-VEGF antibody conjugate is administered to a wAMD patient at a frequency that is at most about 80%, at most about 70%, at most about 60%, at most about 50%, at most about 40%, at most about 30%, at most about 20%, at most about 10% or less than the frequency of administration of a conventional anti-VEGF treatment to treat wAMD.

Example 32

This example shows further follow-up assessments of the clinical study of KSI-301 for DME described in Examples 22 and 25. FIG. 49 shows that the therapeutic effect of KSI-301 was sustained during the loading phase, and continued for at least 36 weeks after the final loading dose administered at Week 8. A patient received on average 0.61 injections of the anti-VEGF antibody conjugate between Week 12 and 40, and 67% of patients required no retreatment injections. In contrast, the mean number of injections according to the label for a conventional treatment (aflibercept) over the same time period would be 5.

FIG. 50A shows the individual break down of the follow-up assessment. Durability of the KSI-301 treatment in patients from the DME cohort extended to 3 to 6 or more months. FIG. 50B summarizes the results shown in FIG. 50A. 45% (15/33) of the patients to date (more than 6 months since the last loading dose) have not required a retreatment dose after the loading doses. In 79% of patients, the patient achieved at least one treatment interval of 6 months or longer sometime after the last loading dose. In 67% (22/33) of patients time to retreatment was 6 months or longer after the last loading dose. 70% (23/33) of patients did not receive retreatment for 5 months or longer after the last loading dose. 76% (25/33) of patients did not receive retreatment for 4 months or longer after the last loading dose. 97% (32/33) of patients did not receive retreatment for 3 months or longer after the last loading dose. Only 3% (1/33) of patients were retreated at 2 months after the last loading dose. No patients were retreated before 2 months after the last loading dose.

These results indicate that the target dosing interval of the anti-VEGF antibody conjugate, e.g., KSI-301, in DME can be 3 to 6 or more months after the last loading dose.

In summary, 2/3 of DME patients have required no additional treatment more than 6 months after the 3 loading doses. These results would not have been expected based on the high treatment need in DME with marketed anti-VEGF treatments (e.g., the median number of injections in the first year based on DRCR.net treatment algorithm is 9-10).

FIG. 51 shows a case example of a DME patient in the Phase 1b study described above, treated with KSI-301 with no treatment after the loading phase. OCT images were taken at the indicated time points. BCVA was also assessed (indicated by the change in ETDRS Letters value under the Week label). OCT and BCVA improvement was observed as early as 1 month (Week 12) after the last loading dose, and was sustained for at least 12 months (Week 56) after the last loading dose. No retreatment doses were required for over 12 months after the last loading dose. In total, the patient received 3 intravitreal injections in the first year of treatment.

In some embodiments, a DME patient is administered intravitreally an effective amount of an anti-VEGF antibody conjugate, e.g., KSI-301, at a dosing interval of about 3 months, about 4 months, about 5 months, about 6 months, about 7 months, about 8 months, about 9 months, or about 10 months, about 11 months, about 12 months, about 13 months, or about 14 months or more, or any time interval between any two of the above values, at any time period after the patient is administered the last loading dose. In some embodiments, a DME patient is not administered a maintenance dose of the anti-VEGF antibody conjugate until at least about 3 months, at least about 4 months, at least about 5 months, at least about 6 months, at least about 7 months, at least about 8 months, at least about 9 months, at least about 10 months, at least about 11 months, at least about 12 months, at least about 13 months, or at least about 14 months or more, or until any time point between any two of the above values, after the last loading dose. In some embodiments, a DME patient has about 30%, about 35%, about 40%, about 45%, or about 50% or higher chance of not requiring a maintenance dose of the anti-VEGF antibody conjugate until about 7 months or more after the last loading dose or the last maintenance dose. In some embodiments, a DME patient has at least about 40%, at least about 50%, at least about 55%, at least about 60%, or at least about 65% chance of not requiring a maintenance dose of the anti-VEGF antibody conjugate until about 6 months or more after the last loading dose or the last maintenance dose. In some embodiments, a DME patient has at least about 50%, at least about 55%, at least about 60%, at least about 65%, or at least about 70% chance of not requiring a maintenance dose of the anti-VEGF antibody conjugate until about 5 months or more after the last loading dose or the last maintenance dose. In some embodiments, a DME patient has at least about 50%, at least about 60%, at least about 70%, or at least about 75% chance of not requiring a maintenance dose of the anti-VEGF antibody conjugate until about 4 months or more after the last loading dose or the last maintenance dose. In some embodiments, a DME patient has at least about 60%, at least about 70%, at least about 80%, at least about 90%, or at least about 95% chance of not requiring a maintenance dose of the anti-VEGF antibody conjugate until about 3 months or more after the last loading dose or the last maintenance dose. In some embodiments, a subject receives 8 or fewer, 7 or fewer, 6 or fewer, 5 or fewer, 4 or fewer, or 3 or fewer, intravitreal injections of the anti-VEGF antibody conjugate in the first year of treatment for DME, including the loading doses. In some embodiments, a subject receives 4 or fewer, 3 or fewer, 2 or fewer, or 1 or fewer, or no maintenance doses of the anti-VEGF antibody conjugate per year for treatment of DME.

Example 33

This example shows benchmarking of KSI-301 durability compared to Eylea in DME. FIG. 52 shows the mean number of injections required in one-year interval for patients with DME treated with KSI-301 (right) in the Phase 1b study described above, or with Eylea (aflibercept) (left), a conventional anti-VEGF treatment. Patients on conventional anti-VEGF treatment required on average 6 monthly loading doses, and 3.2 maintenance doses, for a total of 9.2 injections in the first year of treatment. In contrast, patients treated with KSI-301 required only on average 3 monthly loading doses, and 1 maintenance dose, for a total of 4 injections in the first year of treatment. Thus, KSI-301 allowed for treatment of DME at half the number of loading and maintenance doses compared to a conventional anti-VEGF treatment. These results demonstrate the superior duration of the therapeutic effect of the anti-VEGF antibody conjugate compared to conventional anti-VEGF treatments for treating DME.

In some embodiments, the number of loading doses (e.g., monthly loading doses) required for treatment of DME with the anti-VEGF antibody conjugate, e.g., KSI-301, is at most about 75%, at most about 70%, at most about 65%, at most about 60%, at most about 55%, at most about 50%, at most about 45%, or at most about 40% of the number of loading doses required for treatment with a conventional anti-VEGF treatment. In some embodiments, the number of maintenance doses required for treatment of DME with the anti-VEGF antibody conjugate is at most about 75%, at most about 70%, at most about 65%, at most about 60%, at most about 55%, at most about 50%, at most about 45%, or at most about 40% of the number of maintenance doses required for treatment with a conventional anti-VEGF treatment. In some embodiments, the total number of doses per year required for treatment of DME with the anti-VEGF antibody conjugate is at most about 75%, at most about 70%, at most about 65%, at most about 60%, at most about 55%, at most about 50%, at most about 45%, or at most about 40% of the total number of doses required per year for treatment with a conventional anti-VEGF treatment.

Example 34

This example shows further follow-up assessments of the clinical study of KSI-301 for RVO described in Examples 23 and 26. FIG. 53 shows that the therapeutic effect of the anti-VEGF antibody conjugate was sustained during the loading phase, and continued for at least 36 weeks after the final loading dose administered at Week 8. A patient received on average 1.33 injections of the anti-VEGF antibody conjugate between Week 12 and 40, and only 36% of patients required more than one retreatment dose. In contrast, the mean number of injections according to the label for a conventional treatment (aflibercept) over the same time period would be 8.

FIG. 54A shows the individual break down of the follow-up assessment. Durability of KSI-301 treatment in patients from the RVO cohort extended to 2 to 4 or more months after 3 monthly loading doses. FIG. 54B summarizes the results shown in FIG. 54A. 81% of the patients achieved at least one treatment interval of 4 months or longer sometime after the last loading dose. In 56% (18/32) of patients time to retreatment was 4 months or longer after the last loading dose. 66% (21/32) of patients did not receive retreatment for 3 months or longer after the last loading dose. 94% (31/33) of patients did not receive retreatment for 2 months or longer after the last loading dose. Only 6% (2/34) of patients were retreated at 1 month after the last loading dose.

These results indicate that the target dosing interval of the anti-VEGF antibody conjugate, e.g., KSI-301, in RVO can be 2 to 4 months or more after the last loading dose.

FIG. 56 shows a case example of a CRVO patient in the Phase 1b study described above, treated with KSI-301. OCT images were taken at the indicated time points and thickness measurement is indicated below the Week labels on the left. BCVA was also assessed (indicated by the change in ETDRS Letters value on the right). The OCT measurement before treatment indicated the patient had the most severe CRVO. OCT and BCVA improvement was observed as early as 1 week after the first loading dose, and continued to improve over the following 3 weeks until the next monthly loading dose. OCT continued to improve and BCVA was maintained one month after the second loading dose. These results indicated that it can be possible to control the most severe CRVO cases with only 2 loading doses of the anti-VEGF antibody conjugate.

In some embodiments, a RVO (e.g., BRVO, CRVO) patient is administered intravitreally an effective amount of an anti-VEGF antibody conjugate, e.g., KSI-301, at a dosing interval of about 2 months, about 3 months, about 4 months, about 5 months, about 6 months, about 7 months, about 8 months, about 9 months, about 10 months, about 11 months, about 12 months, about 13 months, about 14 months, or about 15 months or more, or any time interval between any two of the above values, at any time period after the last loading dose. In some embodiments, a RVO patient is not administered a maintenance dose of the anti-VEGF antibody conjugate until at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, or at least about 15 months or more, or any time point between any two of the above values, after the last loading dose. In some embodiments, a RVO patient has about 45%, about 50%, about 55%, about 60%, about 65%, or about 70% or higher chance of not requiring a maintenance dose of the anti-VEGF antibody conjugate until about 4 months or more after the last loading dose or the last maintenance dose. In some embodiments, a RVO patient has about 50% or higher, about 55% or higher, about 60% or higher, about 65% or higher, or about 70% or higher chance of not requiring a maintenance dose of the anti-VEGF antibody conjugate until about 3 months or more after the last loading dose or the last maintenance dose. In some embodiments, a RVO patient has about 60%, about 70%, about 80%, about 85%, about 90%, or about 95% or higher chance of not requiring a maintenance dose of the anti-VEGF antibody conjugate until about 2 months or more after the last loading dose or the last maintenance dose. In some embodiments, a subject receives 8 or fewer, 7 or fewer, 6 or fewer, 5 or fewer, 4 or fewer intravitreal injections of the anti-VEGF antibody conjugate in the first year of treatment for RVO, including the loading doses. In some embodiments, a subject receives 5 or fewer, 4 or fewer, 3 or fewer, 2 or fewer, or 1 maintenance doses of the anti-VEGF antibody conjugate per year for treatment of RVO. In some embodiments, an RVO patient (e.g., a CRVO patient) receives 2 or 3 loading doses of the anti-VEGF antibody conjugate.

Example 35

This example shows benchmarking of KSI-301 durability compared to Eylea in RVO. FIG. 55 shows the mean number of injections required in one-year interval for patients with RVO treated with KSI-301 (right) in the Phase 1b study described above, or with Eylea (aflibercept) (left), a conventional anti-VEGF treatment. Patients on conventional anti-VEGF treatment required on average 6 monthly loading doses, and 2.6 maintenance doses, for a total of 8.6 injections in the first year of treatment. In contrast, patients treated with KSI-301 required only on average 3 monthly loading doses, and 1.7 maintenance doses, for a total of 4.7 injections in the first year of treatment. Thus, KSI-301 allowed for treatment of RVO at half the number of loading doses, and about ⅔ the number of maintenance doses compared to a conventional anti-VEGF treatment. These results demonstrate the superior duration of the therapeutic effect of the anti-VEGF antibody conjugate compared to conventional anti-VEGF treatments for treating RVO.

In some embodiments, the number of loading doses (e.g., monthly loading doses) required for treatment of RVO with the anti-VEGF antibody conjugate, e.g., KSI-301, is at most about 75%, at most about 70%, at most about 65%, at most about 60%, at most about 55%, at most about 50%, at most about 45%, or at most about 40% of the number of loading doses required for treatment with a conventional anti-VEGF treatment. In some embodiments, the number of maintenance doses required for treatment of RVO with the anti-VEGF antibody conjugate is at most about 80%, at most about 75%, at most about 70%, at most about 65%, or at most about 60% of the number of maintenance doses required for treatment with a conventional anti-VEGF treatment. In some embodiments, the total number of doses per year required for treatment of RVO with the anti-VEGF antibody conjugate is at most about 80%, at most about 75%, at most about 70%, at most about 65%, at most about 60%, at most about 55%, or at most about 50% of the total number of doses required per year for treatment with a conventional anti-VEGF treatment.

Example 36

This example provides a Phase 2b/3 wAMD study with KSI-301 dosed as infrequently as once every 20 weeks (after the loading doses). FIG. 57 shows a schematic view of the study design. Patients in the KSI-301 treatment arm of the study are on Q12W, Q16W or Q20W dosing schedule, unless a disease activity assessment criteria (below) are met at any follow up assessment, at which time the patient is administered a maintenance dose.

Disease Activity Assessment Criteria (Non-Loading Dose)

These criteria are related to signs of disease recurrence and/or vision loss due to disease recurrence.

- Increase in OCT central subfield retinal thickness (CST) ≥50 μm with a decrease in BCVA of ≥5 letters compared to Week 12;
- Decrease in BCVA of ≥10 letters compared to the best prior BCVA, due to worsening wAMD activity (e.g. increased intraretinal fluid, increased subretinal fluid, new intraretinal hemorrhage, new subretinal hemorrhage);
- Increase in OCT central subfield retinal thickness (CST) ≥75 μm compared to Week 12;
- New macular hemorrhage.

Example 37

This example provides a Phase 3 DME studies with KSI-301 that is dosed as infrequently as once every 24 weeks (after the loading doses). FIG. 58 shows a schematic view of the study design. Patients in the KSI-301 treatment arm of the study are on Q8W, Q12W, Q16W, Q20W, Q24W dosing schedule, unless a disease activity assessment criteria (below) are met at any follow up assessment, at which time the patient is administered a maintenance dose.

Disease Activity Assessment Criteria (Non-Loading Dose)

These criteria are related to signs of disease recurrence and/or vision loss due to disease recurrence.

- Increase in OCT central subfield retinal thickness (CST) ≥50 μm compared to lowest previous measurement with a decrease in BCVA of ≥5 letters compared to the average of the 2 best previous BCVA assessments due to worsening of DME disease activity;
- Increase in OCT CST≥75 μm compared to lowest previous measurement due to worsening of DME disease activity;
- New or worsening proliferative DR (PDR).

Example 38

This example provides Phase 3 RVO studies with KSI-301 that is dosed once 8 weeks (after the loading doses). FIG. 58 shows a schematic view of the study design. Patients in the KSI-301 treatment arm of the study receive two monthly loading doses followed by two every 8-week dosing, then every 8 week dosing with disease activity assessment to individualize dosing. If disease activity assessment criteria (below) are met at any follow up assessment, the patient is administered a maintenance dose.

Disease Activity Assessment Criteria (Non-Loading Dose)

These criteria are related to signs of disease recurrence and/or vision loss due to disease recurrence.

- Increase in OCT central subfield retinal thickness (CST) ≥75 μm compared to lowest previous measurement due to worsening of RVO disease activity;
- Increase in OCT CST≥75 μm compared to lowest previous measurement due to worsening of RVO disease activity.

Example 39

This example shows a clinical study for Non-proliferative diabetic retinopathy (NPDR) with KSI-301 dosed as infrequently as once every 6 months (after the loading doses). Patients in the KSI-301 treatment arm of the study receive two loading doses 8 weeks apart. Then patients receive maintenance doses every 4 or 6 months. The endpoint is not only perfusion but using the ETDRS DRSS (Diabetic retinopathy severity score) % patients with >=2 or 3 step improvement and 2 or 3 step worsening.

Example 40

During the study described in Examples 3-5, 15-26, and 29-35, multiple-dose exposure of KSI-301 was well-tolerated and no intraocular inflammation was observed. 130 subjects were dosed, with 546 total doses given. 121 subjects completed the loading phase in Phase 1b, and 81 received at least one additional retreatment at Week 12 or later. The following were noted:

- Most adverse events (AEs) were assessed as mild and are consistent with profile of conventional intravitreal anti-VEGF treatment;
- To date, 29 serious adverse events (SAEs) have been reported in 16 subjects—none drug related;
- One ocular SAE in the study eye (worsening DME secondary to systemic fluid overload, not drug related);
- Only two AEs of intraocular inflammation, both trace to 1+ vitreous cells, with complete resolution
  - Rate of 0.37% on per-injection basis (2/546 injections), 1.5% on per-patient basis (2/130 patients)
  - No vasculitis or retinitis in either patient.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect disclosed herein can be used in combination with any other unless specifically indicated otherwise. Although some embodiments have been described in some detail by way of illustration and example for purposes of clarity and understanding, it will be apparent that certain changes and modifications may be practiced within the scope of the appended claims.

```
                              SEQUENCE LISTING


Sequence total quantity: 14
SEQ ID NO: 1            moltype = AA  length = 453
FEATURE                 Location/Qualifiers
REGION                  1..453
                        note = Anti-VEGF-A heavy chain
source                  1..453
                        mol_type = protein
                        organism = synthetic construct
SEQUENCE: 1
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSCS PGK                              453

SEQ ID NO: 2            moltype = AA  length = 214
FEATURE                 Location/Qualifiers
REGION                  1..214
                        note = Anti-VEGF-A light chain
source                  1..214
                        mol_type = protein
                        organism = synthetic construct
SEQUENCE: 2
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 3            moltype = AA  length = 453
FEATURE                 Location/Qualifiers
REGION                  1..453
                        note = Antigen binding protein components
source                  1..453
                        mol_type = protein
                        organism = synthetic construct
SEQUENCE: 3
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 4            moltype = AA  length = 214
FEATURE                 Location/Qualifiers
REGION                  1..214
                        note = Antigen binding protein components
source                  1..214
                        mol_type = protein
                        organism = synthetic construct
SEQUENCE: 4
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 5            moltype = AA  length = 231
FEATURE                 Location/Qualifiers
REGION                  1..231
                        note = Antigen binding protein components
```

-continued

```
source                  1..231
                        mol_type = protein
                        organism = synthetic construct
SEQUENCE: 5
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH L           231

SEQ ID NO: 6            moltype = AA  length = 214
FEATURE                 Location/Qualifiers
REGION                  1..214
                        note = Antigen binding protein components
source                  1..214
                        mol_type = protein
                        organism = synthetic construct
SEQUENCE: 6
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 7            moltype = DNA  length = 1413
FEATURE                 Location/Qualifiers
misc_feature            1..1413
                        note = Heavy chain
source                  1..1413
                        mol_type = other DNA
                        organism = synthetic construct
SEQUENCE: 7
atgaaagctg tggtgctggc cgtggctctg gtcttcctga cagggagcca ggctgaggtg  60
cagctggtgg aatccggcgg aggcctggtc cagcctggcg gatccctgag actgtcctgt  120
gccgcctccg gctacgactt cacccattac ggcatgaact gggtccgaca ggcccctggc  180
aagggcctgg aatgggtcgg atggatcaac acctacaccg gcgagcccac ctacgccgcc  240
gacttcaagc ggcggttcac cttctccctg gacacctcca agtccaccgc ctacctgcag  300
atgaactccc tgcgggccga ggacaccgcc gtgtactact gcgccaagta cccctactac  360
tacggcacct cccactggta cttcgacgtg tggggccagg gcaccctggt caccgtgtcc  420
tccgcctcta ccaagggccc ctccgtgttc cctctggccc cctccagcaa gtccacctct  480
ggcggcaccg ccgctctggg ctgcctggtc aaggactact tccccgagcc cgtgaccgtg  540
tcctggaact ctggcgccct gacctccggc gtgcacacct tccagccgt gctgcagtcc  600
tccggcctgt actccctgtc ctccgtcgtg accgtgccct ccagctctct gggcacccag  660
acctacatct gcaacgtgaa ccacaagccc tccaacacca aggtggacaa gaaggtggaa  720
cccaagtcct gcgacaagac ccacacctgt ccccccctgcc ctgcccctga agcagccggt  780
gcacccagcg tgttcctgtt cccccccaaag cccaaggaca ccctgatgat ctcccggacc  840
cccgaagtga cctgcgtggt ggtggacgtg tcccacgagg accctgaagt gaagttcaat  900
tggtacgtgg acggcgtgga agtgcacaat gccaagacca agcccagaga ggaacagtac  960
aactccacct accgggtggt gtccgtgctg accgtgctgc atcaggactg gctgaacggc  1020
aaagagtaca agtgcaaggt ctccaacaag gccctgcctg cccccatcga aaagaccatc  1080
tccaaggcca agggccagcc ccgcgagcct caggtgtaca cactgccacc cagccgggaa  1140
gagatgacca agaaccaggt ctccctgacc tgtctggtca agggcttcta cccctccgat  1200
atcgccgtcg aatgggagtc caacggccag cccgagaaca actacaagac caccccccct  1260
gtgctggact ccgacggctc attcttcctg tactccaagc tgaccgtgga caagtcccgg  1320
tggcagcagg gcaacgtgtt ctcctgctcc gtgatgcacg aggccctgca caaccactac  1380
acccagaagt ccctgtcctg cagccccggc aag                              1413

SEQ ID NO: 8            moltype = DNA  length = 702
FEATURE                 Location/Qualifiers
misc_feature            1..702
                        note = Light chain
source                  1..702
                        mol_type = other DNA
                        organism = synthetic construct
SEQUENCE: 8
atgggatgga gctgtatcat cctcttcttg gtggcaacag ctacaggcgt gcactccgac  60
atccagctga cccagtcccc ctccagcctg tccgcctctg tgggcgacag agtgaccatc  120
acctgttccg ccagccagga catctccaac tacctgaact ggtatcagca gaagcccggc  180
aaggccccca aggtgctgat ctacttcacc tcctccctgc actccggcgt gccctccaga  240
ttctccggct ctggctccgg caccgacttt accctgacca tctccagcct gcagcccgag  300
gacttcgcca cctactactg ccagcagtac tccaccgtgc cctggacctt cggccagggc  360
accaaggtgg aaatcaagcg gaccgtggcc gctccctccg tgttcatctt cccaccctcc  420
gacgagcagc tgaagtccgg aaccgcctcc gtcgtgtgcc tgctgaacaa cttctacccc  480
cgcgaggcca aggtgcagtg gaaggtggac aacgccctgc agagcggcaa ctcccaggaa  540
tccgtcaccg agcaggactc caaggacagc acctactccc tgtccagcac cctgaccctg  600
tccaaggccg actacgagaa gcacaaggtg tacgcctgcg aagtgaccca ccagggcctc  660
agctccccag tgaccaagtc cttcaaccgg ggcgagtgct ag                    702

SEQ ID NO: 9            moltype = AA  length = 10
FEATURE                 Location/Qualifiers
REGION                  1..10
```

-continued

```
                          note = Antigen binding protein components
source                    1..10
                          mol_type = protein
                          organism = synthetic construct
SEQUENCE: 9
GYDFTHYGMN                                                          10

SEQ ID NO: 10             moltype = AA  length = 17
FEATURE                   Location/Qualifiers
REGION                    1..17
                          note = Antigen binding protein components
source                    1..17
                          mol_type = protein
                          organism = synthetic construct
SEQUENCE: 10
WINTYTGEPT YAADFKR                                                  17

SEQ ID NO: 11             moltype = AA  length = 14
FEATURE                   Location/Qualifiers
REGION                    1..14
                          note = Antigen binding protein components
source                    1..14
                          mol_type = protein
                          organism = synthetic construct
SEQUENCE: 11
YPYYYGTSHW YFDV                                                     14

SEQ ID NO: 12             moltype = AA  length = 11
FEATURE                   Location/Qualifiers
REGION                    1..11
                          note = Antigen binding protein components
source                    1..11
                          mol_type = protein
                          organism = synthetic construct
SEQUENCE: 12
SASQDISNYL N                                                        11

SEQ ID NO: 13             moltype = AA  length = 7
FEATURE                   Location/Qualifiers
REGION                    1..7
                          note = Antigen binding protein components
source                    1..7
                          mol_type = protein
                          organism = synthetic construct
SEQUENCE: 13
FTSSLHS                                                             7

SEQ ID NO: 14             moltype = AA  length = 9
FEATURE                   Location/Qualifiers
REGION                    1..9
                          note = Antigen binding protein components
source                    1..9
                          mol_type = protein
                          organism = synthetic construct
SEQUENCE: 14
QQYSTVPWT                                                           9
```

What is claimed is:

1. A method of treating an eye disorder, comprising:

administering an anti-VEGF antibody conjugate to a subject in need of treating an eye disorder at a first loading dose, wherein the eye disorder is retinal vein occlusion (RVO), wherein the anti-VEGF antibody conjugate comprises:

an anti-VEGF-A antibody comprising a light chain and a heavy chain, wherein the heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and the light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14); and a phosphorylcholine-containing polymer covalently bonded to the heavy chain, wherein the phosphorylcholine-containing polymer is formed by 2-(methacryloyloxyethyl)-2'-(trimethylammonium) ethyl phosphate (MPC) monomers, and has a molecular weight from about 600,000 to about 1,000,000 Da; and repeating the loading dose at least once, but not more than twice, whereby the subject retains a therapeutic result of the anti-VEGF antibody conjugate therapy for at least 8 weeks after a final loading dose.

2. The method of claim 1, wherein the therapeutic result of the anti-VEGF antibody conjugate therapy lasts for at least 12 weeks past a final loading dose.

3. The method of claim 1, wherein the therapeutic result of the anti-VEGF antibody conjugate therapy lasts for at least 14 weeks past a final loading dose.

4. The method of claim 3, wherein no further administration of the anti-VEGF antibody conjugate is provided to the subject within 14 weeks of a final loading dose.

5. The method of claim 1, wherein no further administration of the anti-VEGF antibody conjugate is provided to the subject within four weeks of a final loading dose.

6. The method of claim 1, wherein no further administration of the anti-VEGF antibody conjugate is provided to the subject within ten weeks of a final loading dose.

7. The method of claim 1, further comprising administering one or more subsequent doses of the anti-VEGF antibody conjugate to the subject after the final loading dose.

8. The method of claim 7, comprising administering the one or more subsequent doses of the anti-VEGF antibody conjugate at a dosing schedule of Q8W or longer.

9. The method of claim 8, comprising:

administering a first subsequent dose of the anti-VEGF antibody conjugate at a first time period after the final loading dose; and administering a second subsequent dose at a second time period after the first subsequent dose, wherein the anti-VEGF antibody conjugate is not administered between the first subsequent dose and the second subsequent dose, wherein the first time period is shorter than the second time period.

10. The method of claim 7, wherein any subsequent dose of the anti-VEGF antibody conjugate is administered no more frequently than once every 12 weeks.

11. The method of claim 10, wherein at least 1.25 mg of antibody per loading dose is administered to the subject in the form of the anti-VEGF antibody conjugate.

12. The method of claim 1, wherein the loading doses are administered with about one to two months between each loading dose.

13. The method of claim 12, wherein about 5 mg of antibody per loading dose is administered to the subject in the form of the anti-VEGF antibody conjugate.

14. The method of claim 13, wherein no dose is administered until at least 20 weeks following the last loading dose.

15. The method of claim 13, wherein the therapeutic result comprises one or more of improved visual acuity, reduced retinal thickness, improved retinal perfusion, improved diabetic retinopathy severity score (DRSS), or reduced disease activity of the eye disorder, compared to a pre-treatment level.

16. The method of claim 1, wherein the anti-VEGF antibody conjugate is administered via intravitreal injection.

17. The method of claim 16, wherein the anti-VEGF antibody conjugate comprises: an anti-VEGF-A immunoglobulin G (IgG) bonded to the phosphorylcholine-containing polymer, wherein the sequence of the anti-VEGF-A antibody heavy chain is SEQ ID NO: 1, with or without the C-terminal lysine, and the sequence of the anti-VEGF-A antibody light chain is SEQ ID NO. 2, and wherein the anti-VEGF-A antibody is bonded at C449 in SEQ ID NO:1 to the phosphorylcholine-containing polymer.

18. The method of claim 17, wherein the anti-VEGF antibody conjugate has the following structure:

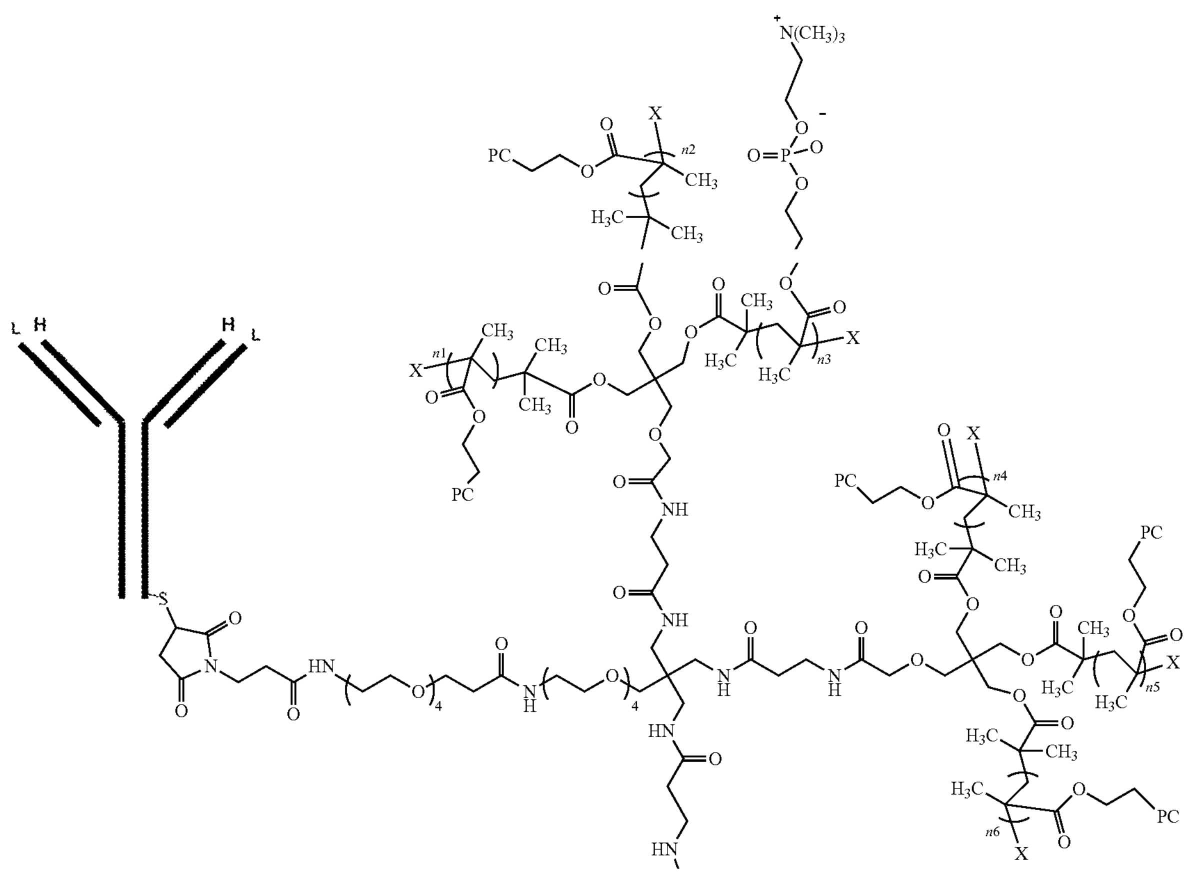

-continued

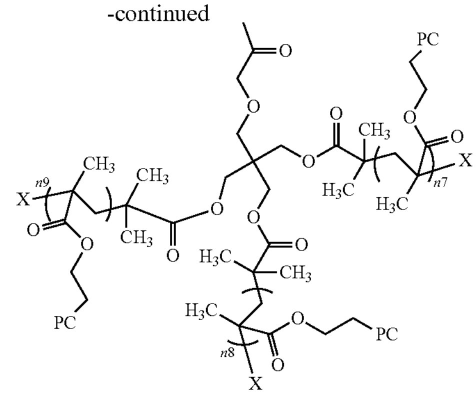

wherein:

each heavy chain of the anti-VEGF-A antibody is denoted by the letter H, and each light chain of the anti-VEGF-A antibody is denoted by the letter L;

the polymer is bonded to the anti-VEGF-A antibody through the sulfhydryl of C443 (EU numbering), which bond is depicted on one of the heavy chains;

PC is

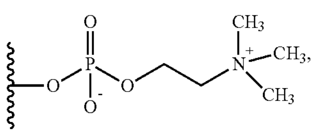

where the curvy line indicates the point of attachment to the rest of the polymer, where X is a) —OR where R is —H, methyl, ethyl, propyl, isopropyl, b) —H, c) any halogen, including —Br, —Cl, or —I, d) —SCN, or e) —NCS; and n1, n2, n3, n4, n5, n6, n7, n8 and n9 are the same or different such that the sum of n1, n2, n3, n4, n5, n6, n7, n8 and n9 is 2500 plus or minus 15%.

19. The method of claim 18, wherein the loading doses are administered with about one month between each loading dose.

20. The method of claim 19, wherein about 2.5 mg of antibody per loading dose is administered to the subject in the form of the anti-VEGF antibody conjugate.

21. The method of claim 20, wherein two loading doses are administered to the subject.

22. The method of claim 20, wherein three loading doses are administered to the subject.

23. The method of claim 19, wherein about 5 mg of antibody per loading dose is administered to the subject in the form of the anti-VEGF antibody conjugate.

24. The method of claim 23, wherein three loading doses are administered to the subject.

25. The method of claim 23, wherein two loading doses are administered to the subject.

26. The method of claim 25, further comprising administering one or more subsequent doses of the anti-VEGF antibody conjugate to the subject after the final loading dose.

27. The method of claim 26, comprising administering the one or more subsequent doses of the anti-VEGF antibody conjugate at a dosing schedule of Q8W.

28. A method of treating retinal vein occlusion (RVO), comprising:

administering intravitreally two loading doses of an anti-VEGF antibody conjugate to a subject in need of treating RVO, wherein the two loading doses are administered about one month apart, wherein about 5 mg of antibody per loading dose is administered to the subject in the form of the anti-VEGF antibody conjugate; and administering intravitreally one or more subsequent doses of the anti-VEGF antibody conjugate to the subject after the second loading dose at a dosing schedule of Q8W, wherein about 5 mg of antibody per subsequent dose is administered to the subject in the form of the anti-VEGF antibody conjugate, thereby treating RVO, wherein the anti-VEGF antibody conjugate comprises:

an anti-VEGF-A antibody comprising a light chain and a heavy chain, wherein the heavy chain comprises $CDR_H1$: GYDFTHYGMN (SEQ ID NO: 9), $CDR_H2$: WINTYTGEPTYAADFKR (SEQ ID NO: 10), and $CDR_H3$:

YPYYYGTSHWYFDV (SEQ ID NO: 11), and the light chain comprises $CDR_L1$:

SASQDISNYLN (SEQ ID NO: 12), $CDR_L2$: FTSSLHS (SEQ ID NO: 13), and $CDR_L3$: QQYSTVPWT (SEQ ID NO: 14); and a phosphorylcholine-containing polymer covalently bonded to the heavy chain, and wherein the anti-VEGF antibody conjugate has the following structure:

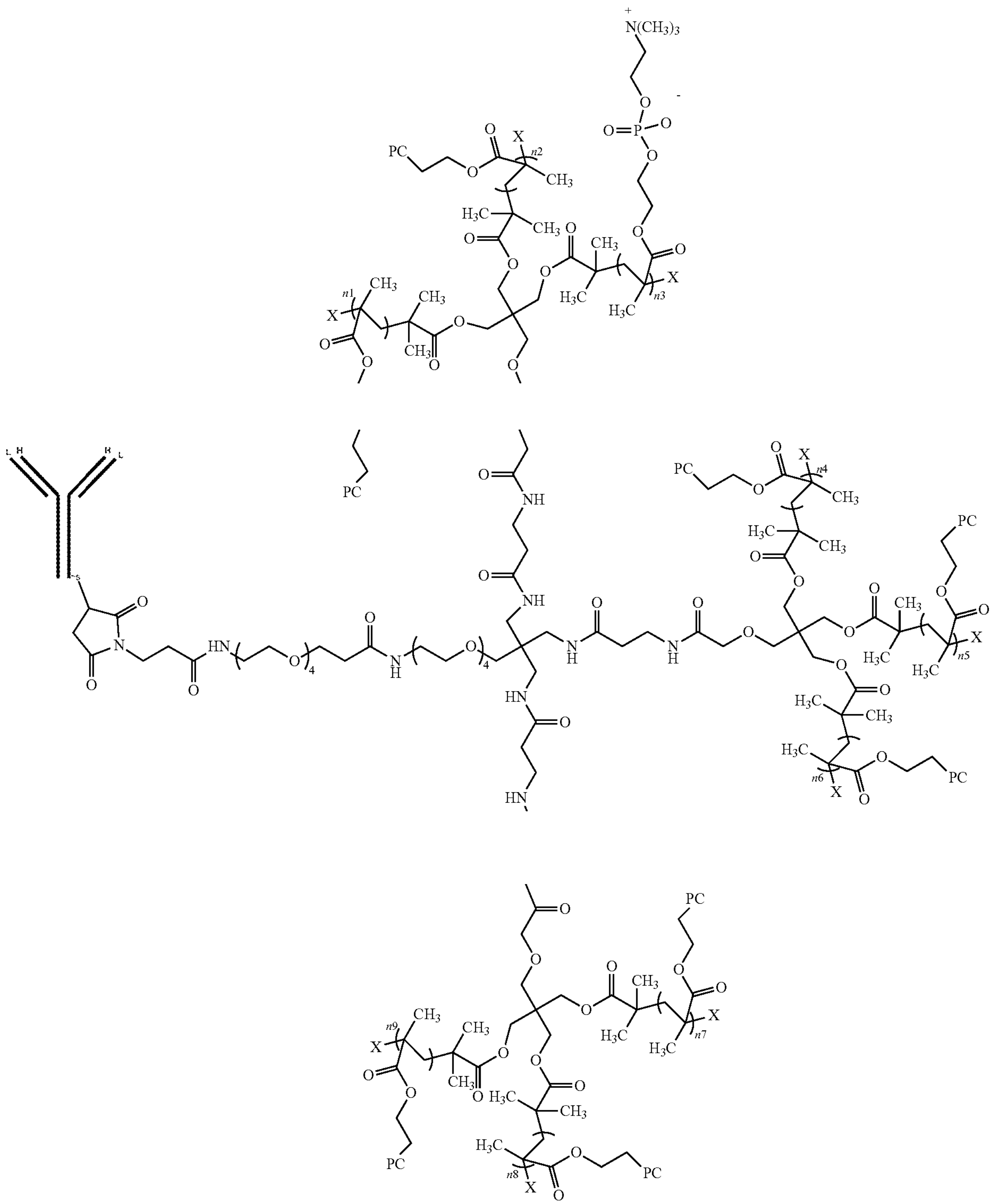
wherein:
each heavy chain of the anti-VEGF-A antibody is denoted by the letter H, and each light chain of the anti-VEGF-A antibody is denoted by the letter L;
the polymer is bonded to the anti-VEGF-A antibody through the sulfhydryl of C443(EU numbering), which bond is depicted on one of the heavy chains;
PC is
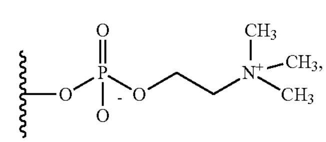 [SMILES: *OP(=O)(O)OCC[N+](C)(C)C]

where the curvy line indicates the point of attachment to the rest of the polymer, where X is a)—OR where R is —H, methyl, ethyl, propyl, isopropyl, b) —H, c) any halogen, including —Br, —Cl, or —I, d) —SCN, or e) —NCS; and n1, n2, n3, n4, n5, n6, n7, n8 and n9 are the same or different such that the sum of n1, n2, n3, n4, n5, n6, n7, n8 and n9 is 2500 plus or minus 15%.

29. A method of treating retinal vein occlusion (RVO), comprising:

administering intravitreally two loading doses of an anti-VEGF antibody conjugate to a subject in need of treating RVO, wherein the two loading doses are administered about one month apart, wherein about 5 mg of antibody per loading dose is administered to the subject in the form of the anti-VEGF antibody conjugate; and administering intravitreally one or more subsequent doses of the anti-VEGF antibody conjugate to the subject after the second loading dose at a dosing schedule of Q8W, wherein about 5 mg of antibody per subsequent dose is administered to the subject in the form of the anti-VEGF antibody conjugate, thereby treating RVO, wherein the anti-VEGF antibody conjugate comprises:

an anti-VEGF-A antibody comprising a light chain and a heavy chain, wherein the sequence of the anti-VEGF-A antibody heavy chain is SEQ ID NO: 1,with or without the C-terminal lysine, and the sequence of the anti-VEGF-A antibody light chain is SEQ ID NO. 2; and a phosphorylcholine-containing polymer covalently bonded to the heavy chain, and wherein the anti-VEGF antibody conjugate has the following structure:

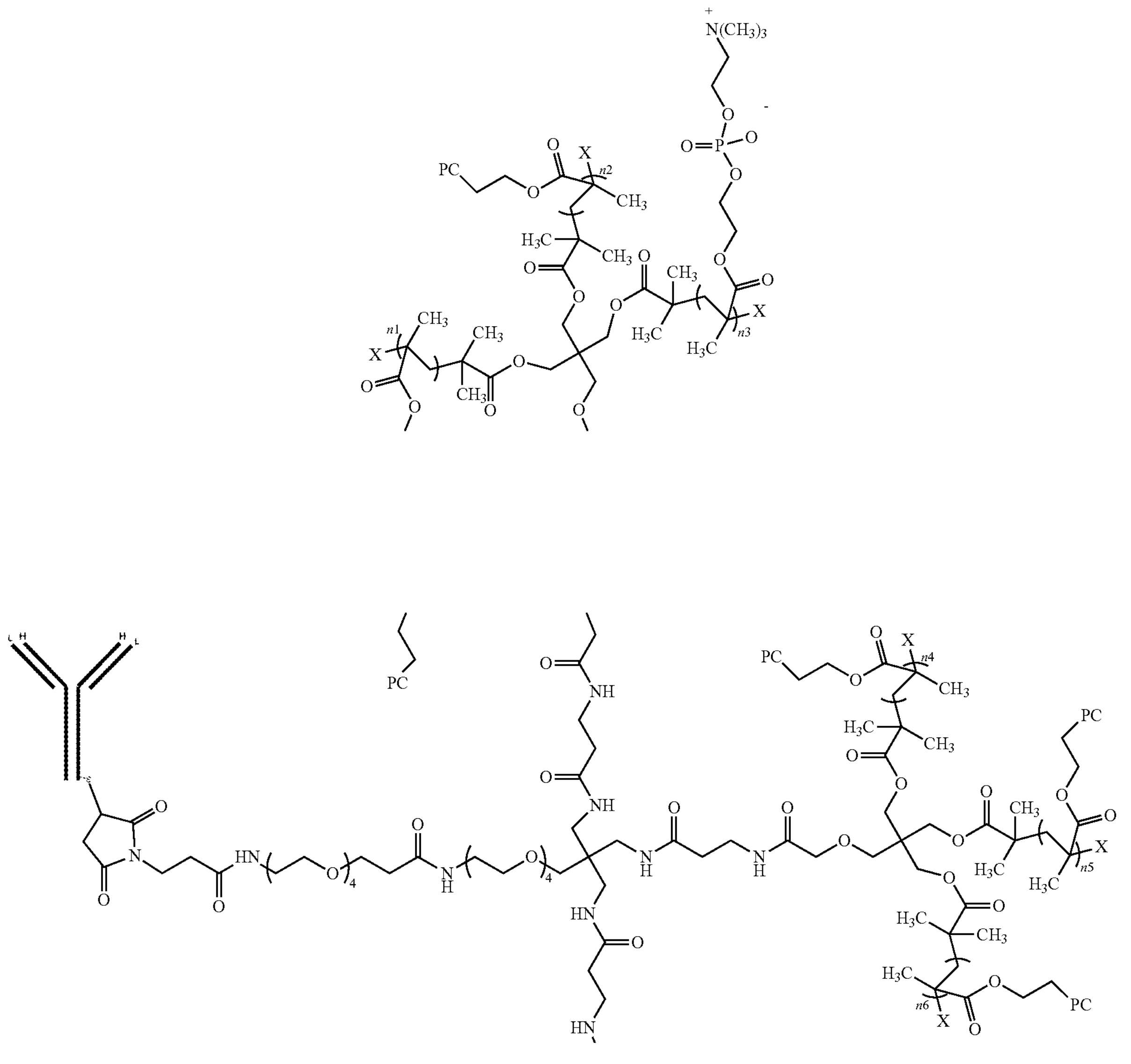

-continued

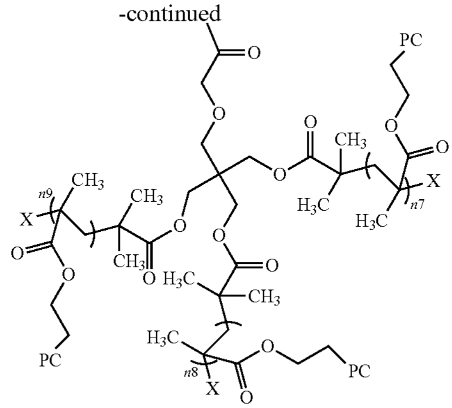

wherein:

each heavy chain of the anti-VEGF-A antibody is denoted by the letter H, and each light chain of the anti-VEGF-A antibody is denoted by the letter L;

the polymer is bonded to the anti-VEGF-A antibody through the sulfhydryl of C443 (EU numbering), which bond is depicted on one of the heavy chains;

PC

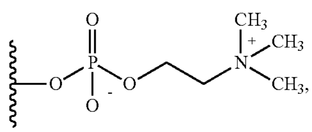

is where the curvy line indicates the point of attachment to the rest of the polymer, where X is a) —OR where R is —H, methyl, ethyl, propyl, isopropyl, b) —H, c) any halogen, including —Br, —Cl, or —I, d) —SCN, or e) —NCS; and n1, n2, n3, n4, n5, n6, n7, n8 and n9 are the same or different such that the sum of n1, n2, n3, n4, n5, n6, n7, n8 and n9 is 2500 plus or minus 15%.

* * * * *